(12) United States Patent
Arney et al.

(10) Patent No.: US 11,977,729 B2
(45) Date of Patent: May 7, 2024

(54) PHYSICAL ACTIVITY INFORMATION USER INTERFACES

(71) Applicant: Apple Inc., Cupertino, CA (US)

(72) Inventors: Julie A. Arney, Los Gatos, CA (US); Chandler S. Bachman, Cupertino, CA (US); Jay K. Blahnik, Venice, CA (US); Edward Chao, Palo Alto, CA (US); David S. Clark, Cupertino, CA (US); Brett L. Lareau, San Jose, CA (US); Emily Pedersen, Los Altos Hills, CA (US); Matthew M. Sun, Cupertino, CA (US); Eduardo Valencia Paz, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/204,217

(22) Filed: May 31, 2023

(65) Prior Publication Data
US 2023/0393723 A1 Dec. 7, 2023

Related U.S. Application Data

(60) Provisional application No. 63/349,104, filed on Jun. 5, 2022.

(51) Int. Cl.
*G06F 3/04847* (2022.01)
(52) U.S. Cl.
CPC ................................ *G06F 3/04847* (2013.01)
(58) Field of Classification Search
CPC .............................................. G06F 3/048–05
See application file for complete search history.

(56) References Cited

U.S. PATENT DOCUMENTS

| | | |
|---|---|---|
| 4,205,628 A | 6/1980 | Null |
| 4,842,266 A | 6/1989 | Sweeney et al. |
| 5,349,962 A | 9/1994 | Lockard et al. |
| 5,423,863 A | 6/1995 | Felblinger et al. |
| 5,458,548 A | 10/1995 | Crossing et al. |
| 5,474,077 A | 12/1995 | Suga |
| 5,642,731 A | 7/1997 | Kehr |
| 5,685,723 A | 11/1997 | Ladin et al. |
| 5,730,141 A | 3/1998 | Fain et al. |
| 5,788,655 A | 8/1998 | Yoshimura et al. |
| 5,845,235 A | 12/1998 | Luukkanen et al. |
| 5,944,633 A | 8/1999 | Wittrock |
| 6,013,008 A | 1/2000 | Fukushima |

(Continued)

FOREIGN PATENT DOCUMENTS

| | | |
|---|---|---|
| AU | 2011302438 A1 | 5/2013 |
| CA | 2815518 A1 | 5/2012 |

(Continued)

OTHER PUBLICATIONS

Adeniyi Samuel, "How to connect a second PS4 controller to a PlayStation 4 console", Online available on: https://www.youtube.com/watch?v=mOZX_SrNISE. May 28. 2017, 2 pages.

(Continued)

*Primary Examiner* — Daniel Rodriguez
(74) *Attorney, Agent, or Firm* — DLA Piper LLP (US)

(57) ABSTRACT

The present disclosure generally relates to user interfaces for navigating and providing physical activity information.

36 Claims, 41 Drawing Sheets

(56) References Cited

U.S. PATENT DOCUMENTS

| | | | |
|---|---|---|---|
| 6,061,592 A | 5/2000 | Nigam | |
| 6,095,949 A | 8/2000 | Arai | |
| 6,095,984 A | 8/2000 | Amano et al. | |
| 6,097,371 A | 8/2000 | Siddiqui et al. | |
| 6,097,385 A | 8/2000 | Robinson | |
| 6,199,012 B1 | 3/2001 | Hasegawa | |
| 6,244,988 B1 | 6/2001 | Delman | |
| 6,302,789 B2 | 10/2001 | Harada et al. | |
| 6,416,471 B1 | 7/2002 | Kumar et al. | |
| 6,603,477 B1 | 8/2003 | Tittle | |
| 6,639,584 B1 | 10/2003 | Li | |
| 6,705,972 B1 | 3/2004 | Takano et al. | |
| 6,837,827 B1 | 1/2005 | Lee | |
| 6,866,613 B1 | 3/2005 | Brown et al. | |
| 7,020,514 B1 | 3/2006 | Wiesel | |
| 7,128,693 B2 | 10/2006 | Brown et al. | |
| 7,251,454 B2 | 7/2007 | White | |
| 7,302,272 B2 | 11/2007 | Ackley | |
| 7,662,065 B1 | 2/2010 | Kahn | |
| 7,695,406 B2 | 4/2010 | Waters | |
| 7,739,148 B2 | 6/2010 | Suzuki et al. | |
| 7,870,013 B1 | 1/2011 | Allemann et al. | |
| 8,060,229 B2 | 11/2011 | Gupta et al. | |
| 8,105,208 B2 | 1/2012 | Oleson et al. | |
| 8,321,006 B1 | 11/2012 | Snyder et al. | |
| 8,341,557 B2 | 12/2012 | Pisula et al. | |
| 8,475,339 B2 | 7/2013 | Hwang et al. | |
| 8,496,563 B2 | 7/2013 | Komatsu et al. | |
| 8,676,170 B2 | 3/2014 | Porrati et al. | |
| 8,734,296 B1 | 5/2014 | Brumback et al. | |
| 8,768,648 B2 | 7/2014 | Panther et al. | |
| 8,784,115 B1 | 7/2014 | Chuang | |
| 8,784,271 B2 | 7/2014 | Brumback et al. | |
| 8,825,445 B2 | 9/2014 | Hoffman et al. | |
| 8,934,963 B1 | 1/2015 | Farazi | |
| 8,947,239 B1 | 2/2015 | Park | |
| 8,990,006 B1 | 3/2015 | Wallace et al. | |
| 9,011,292 B2 | 4/2015 | Weast et al. | |
| 9,020,538 B1 | 4/2015 | White et al. | |
| 9,063,164 B1 | 6/2015 | Yuen et al. | |
| 9,087,234 B2 * | 7/2015 | Hoffman | G09B 19/003 |
| 9,148,483 B1 | 9/2015 | Molettiere et al. | |
| 9,164,663 B1 | 10/2015 | Berard | |
| 9,224,291 B2 | 12/2015 | Moll-Carrillo et al. | |
| 9,230,076 B2 | 1/2016 | King et al. | |
| 9,449,365 B2 | 9/2016 | Roberts | |
| 9,532,734 B2 | 1/2017 | Hoffman et al. | |
| 9,557,881 B1 | 1/2017 | Jain et al. | |
| 9,582,165 B2 | 2/2017 | Wilson et al. | |
| 9,589,445 B2 | 3/2017 | White et al. | |
| 9,712,629 B2 | 7/2017 | Molettiere et al. | |
| 9,723,381 B2 | 8/2017 | Swanson | |
| 9,734,477 B2 | 8/2017 | Weast et al. | |
| 9,798,443 B1 | 10/2017 | Gray | |
| 9,800,525 B1 | 10/2017 | Lerner et al. | |
| 9,813,642 B1 | 11/2017 | Chen et al. | |
| 9,817,481 B2 | 11/2017 | Pantelopoulos et al. | |
| 9,854,653 B1 | 12/2017 | Ackmann et al. | |
| 9,880,805 B1 | 1/2018 | Guralnick | |
| 9,910,571 B2 | 3/2018 | Chen et al. | |
| 9,918,664 B2 * | 3/2018 | Blahnik | A61B 5/1116 |
| 9,931,539 B1 | 4/2018 | De Pablos et al. | |
| 9,940,682 B2 | 4/2018 | Hoffman et al. | |
| 10,056,006 B1 | 8/2018 | Hsu-hoffman et al. | |
| 10,105,573 B2 * | 10/2018 | Park | H04M 1/725 |
| 10,220,258 B2 | 3/2019 | Gu et al. | |
| 10,226,195 B2 | 3/2019 | Briante et al. | |
| 10,272,294 B2 * | 4/2019 | Williams | A61B 5/00 |
| 10,300,334 B1 | 5/2019 | Chuang | |
| 10,304,347 B2 | 5/2019 | Wilson et al. | |
| 10,339,830 B2 | 7/2019 | Han et al. | |
| 10,398,381 B1 | 9/2019 | Heneghan et al. | |
| 10,489,508 B2 | 11/2019 | Zhai et al. | |
| 10,500,441 B2 | 12/2019 | Lagree | |
| 10,639,521 B2 | 5/2020 | Foley et al. | |
| 10,736,543 B2 * | 8/2020 | Chen | A61B 5/1118 |
| 10,777,314 B1 | 9/2020 | Williams et al. | |
| 10,898,132 B2 | 1/2021 | White et al. | |
| 10,978,195 B2 | 4/2021 | Blahnik et al. | |
| 11,103,161 B2 | 8/2021 | Williams et al. | |
| 11,107,567 B2 * | 8/2021 | Blahnik | A61B 5/1123 |
| 11,107,569 B1 | 8/2021 | Devoto | |
| 11,152,100 B2 | 10/2021 | Crowley et al. | |
| 11,202,598 B2 | 12/2021 | Soli et al. | |
| 11,209,957 B2 | 12/2021 | Dryer et al. | |
| 11,216,119 B2 | 1/2022 | De Vries et al. | |
| 11,317,833 B2 | 5/2022 | Williams et al. | |
| 11,446,548 B2 | 9/2022 | Devine et al. | |
| 11,452,915 B2 | 9/2022 | Devine et al. | |
| 11,458,363 B2 * | 10/2022 | Powers | A63B 24/0062 |
| 11,529,074 B2 * | 12/2022 | Vaterlaus | G16H 20/70 |
| 11,801,423 B2 * | 10/2023 | Bissonnette | A63B 23/0417 |
| 2001/0049470 A1 | 12/2001 | Mault et al. | |
| 2002/0045960 A1 | 4/2002 | Phillips et al. | |
| 2002/0086774 A1 | 7/2002 | Warner | |
| 2002/0118121 A1 | 8/2002 | Lehrman et al. | |
| 2003/0023178 A1 | 1/2003 | Bischoff et al. | |
| 2003/0064860 A1 | 4/2003 | Yamashita et al. | |
| 2003/0134714 A1 | 7/2003 | Oishi et al. | |
| 2003/0179229 A1 | 9/2003 | Van et al. | |
| 2003/0181291 A1 | 9/2003 | Ogawa | |
| 2003/0182628 A1 | 9/2003 | Lira | |
| 2003/0216971 A1 | 11/2003 | Sick et al. | |
| 2003/0226695 A1 | 12/2003 | Mault | |
| 2004/0014567 A1 | 1/2004 | Mendel | |
| 2004/0077462 A1 | 4/2004 | Brown et al. | |
| 2004/0128286 A1 | 7/2004 | Yasushi et al. | |
| 2004/0236189 A1 | 11/2004 | Hawthorne et al. | |
| 2005/0015803 A1 | 1/2005 | Macrae et al. | |
| 2005/0075214 A1 | 4/2005 | Brown et al. | |
| 2005/0079905 A1 | 4/2005 | Martens | |
| 2005/0113650 A1 | 5/2005 | Pacione et al. | |
| 2005/0124324 A1 | 6/2005 | Thomas et al. | |
| 2005/0130802 A1 | 6/2005 | Kinnunen et al. | |
| 2005/0139852 A1 | 6/2005 | Chen et al. | |
| 2005/0165627 A1 | 7/2005 | Fotsch et al. | |
| 2005/0171410 A1 | 8/2005 | Hjelt et al. | |
| 2005/0172311 A1 | 8/2005 | Hjelt et al. | |
| 2005/0197063 A1 | 9/2005 | White et al. | |
| 2005/0215848 A1 | 9/2005 | Lorenzato et al. | |
| 2005/0216867 A1 | 9/2005 | Marvit et al. | |
| 2005/0228735 A1 | 10/2005 | Duquette | |
| 2005/0272564 A1 | 12/2005 | Pyles et al. | |
| 2006/0020174 A1 | 1/2006 | Matsumura et al. | |
| 2006/0047208 A1 * | 3/2006 | Yoon | A61B 5/02438 600/500 |
| 2006/0048076 A1 | 3/2006 | Vronay et al. | |
| 2006/0052727 A1 | 3/2006 | Palestrant | |
| 2006/0098109 A1 | 5/2006 | Ooki | |
| 2006/0106741 A1 | 5/2006 | Janarthanan | |
| 2006/0117014 A1 | 6/2006 | Qi | |
| 2006/0160090 A1 | 7/2006 | Macina et al. | |
| 2006/0184800 A1 | 8/2006 | Rosenberg | |
| 2006/0240959 A1 | 10/2006 | Huang | |
| 2006/0250524 A1 | 11/2006 | Roche | |
| 2007/0016091 A1 | 1/2007 | Butt et al. | |
| 2007/0021269 A1 | 1/2007 | Shum | |
| 2007/0032733 A1 | 2/2007 | Burton | |
| 2007/0033069 A1 | 2/2007 | Rao et al. | |
| 2007/0056727 A1 | 3/2007 | Newman | |
| 2007/0071256 A1 | 3/2007 | Ito | |
| 2007/0113726 A1 | 5/2007 | Oliver et al. | |
| 2007/0136093 A1 | 6/2007 | Rankin et al. | |
| 2007/0143433 A1 | 6/2007 | Daigle | |
| 2007/0169614 A1 | 7/2007 | Sasaki et al. | |
| 2007/0249949 A1 | 10/2007 | Hadley | |
| 2007/0271065 A1 | 11/2007 | Gupta et al. | |
| 2008/0020803 A1 | 1/2008 | Rios et al. | |
| 2008/0027673 A1 | 1/2008 | Trumm | |
| 2008/0051919 A1 | 2/2008 | Sakai et al. | |
| 2008/0052945 A1 | 3/2008 | Matas et al. | |
| 2008/0058626 A1 | 3/2008 | Miyata et al. | |
| 2008/0076637 A1 | 3/2008 | Gilley et al. | |
| 2008/0077026 A1 | 3/2008 | Banet et al. | |

(56) References Cited

U.S. PATENT DOCUMENTS

| | | |
|---|---|---|
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0141135 A1 | 6/2008 | Mason et al. |
| 2008/0150731 A1 | 6/2008 | Laukkanen et al. |
| 2008/0161161 A1 | 7/2008 | Pipinich et al. |
| 2008/0161707 A1 | 7/2008 | Farringdon et al. |
| 2008/0200312 A1 | 8/2008 | Tagliabue |
| 2008/0229226 A1 | 9/2008 | Rowbottom et al. |
| 2008/0254767 A1 | 10/2008 | Jin |
| 2008/0262946 A1 | 10/2008 | Wren |
| 2008/0278333 A1 | 11/2008 | Fennell et al. |
| 2008/0300110 A1 | 12/2008 | Smith et al. |
| 2009/0007017 A1 | 1/2009 | Anzures et al. |
| 2009/0012821 A1 | 1/2009 | Besson et al. |
| 2009/0012988 A1 | 1/2009 | Brown |
| 2009/0047645 A1 | 2/2009 | Dibenedetto et al. |
| 2009/0075782 A1 | 3/2009 | Joubert et al. |
| 2009/0106685 A1 | 4/2009 | Care et al. |
| 2009/0118100 A1 | 5/2009 | Oliver et al. |
| 2009/0144639 A1 | 6/2009 | Nims et al. |
| 2009/0149299 A1 | 6/2009 | Tchao et al. |
| 2009/0158167 A1 | 6/2009 | Wang et al. |
| 2009/0164567 A1 | 6/2009 | Hara |
| 2009/0170532 A1 | 7/2009 | Lee et al. |
| 2009/0192823 A1 | 7/2009 | Hawkins et al. |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0222761 A1 | 9/2009 | Hayashi |
| 2009/0233771 A1 | 9/2009 | Quatrochi et al. |
| 2009/0249076 A1 | 10/2009 | Reed et al. |
| 2009/0259134 A1 | 10/2009 | Levine |
| 2009/0262088 A1 | 10/2009 | Moll-Carrillo et al. |
| 2009/0268949 A1 | 10/2009 | Ueshima et al. |
| 2009/0287103 A1 | 11/2009 | Pillai |
| 2009/0291805 A1 | 11/2009 | Blum et al. |
| 2009/0292561 A1 | 11/2009 | Itoh |
| 2009/0319243 A1 | 12/2009 | Suarez-rivera et al. |
| 2010/0030094 A1 | 2/2010 | Lundback |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0060586 A1 | 3/2010 | Pisula et al. |
| 2010/0062818 A1 | 3/2010 | Haughay et al. |
| 2010/0062905 A1* | 3/2010 | Rottler .............. H04M 1/72403 482/9 |
| 2010/0064255 A1 | 3/2010 | Rottler et al. |
| 2010/0076331 A1 | 3/2010 | Chan et al. |
| 2010/0079291 A1 | 4/2010 | Kroll et al. |
| 2010/0103101 A1 | 4/2010 | Song et al. |
| 2010/0121700 A1 | 5/2010 | Wigder et al. |
| 2010/0130890 A1 | 5/2010 | Matsumura et al. |
| 2010/0137106 A1 | 6/2010 | Oshima et al. |
| 2010/0145209 A1 | 6/2010 | Lee et al. |
| 2010/0152600 A1 | 6/2010 | Droitcour et al. |
| 2010/0179832 A1 | 7/2010 | Van et al. |
| 2010/0179833 A1 | 7/2010 | Roizen et al. |
| 2010/0184564 A1 | 7/2010 | Molyneux et al. |
| 2010/0194692 A1 | 8/2010 | Orr et al. |
| 2010/0197463 A1 | 8/2010 | Haughay et al. |
| 2010/0198453 A1 | 8/2010 | Dorogusker et al. |
| 2010/0222859 A1 | 9/2010 | Govari et al. |
| 2010/0231612 A1 | 9/2010 | Chaudhri et al. |
| 2010/0264097 A1 | 10/2010 | Sun et al. |
| 2010/0269055 A1 | 10/2010 | Daikeler et al. |
| 2010/0269157 A1 | 10/2010 | Experton |
| 2010/0273610 A1 | 10/2010 | Johnson |
| 2010/0281374 A1 | 11/2010 | Schulz et al. |
| 2010/0292599 A1 | 11/2010 | Oleson et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0309149 A1 | 12/2010 | Blumenberg et al. |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0032105 A1 | 2/2011 | Hoffman et al. |
| 2011/0052005 A1 | 3/2011 | Selner |
| 2011/0066051 A1 | 3/2011 | Moon et al. |
| 2011/0071869 A1 | 3/2011 | Obrien et al. |
| 2011/0074699 A1 | 3/2011 | Marr et al. |
| 2011/0087076 A1 | 4/2011 | Brynelsen et al. |
| 2011/0098928 A1 | 4/2011 | Hoffman et al. |
| 2011/0106553 A1 | 5/2011 | Tanaka et al. |
| 2011/0112418 A1 | 5/2011 | Feild et al. |
| 2011/0113430 A1 | 5/2011 | Fuse |
| 2011/0125041 A1 | 5/2011 | Fischell et al. |
| 2011/0137678 A1* | 6/2011 | Williams .............. G16H 20/30 705/3 |
| 2011/0137836 A1 | 6/2011 | Kuriyama et al. |
| 2011/0159469 A1 | 6/2011 | Hwang et al. |
| 2011/0167369 A1 | 7/2011 | Van |
| 2011/0201911 A1 | 8/2011 | Johnson et al. |
| 2011/0213276 A1 | 9/2011 | Sarussi et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0246509 A1 | 10/2011 | Migita et al. |
| 2011/0257638 A1 | 10/2011 | Boukhny et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2012/0015778 A1 | 1/2012 | Lee et al. |
| 2012/0015779 A1 | 1/2012 | Powch et al. |
| 2012/0022884 A1 | 1/2012 | Chillemi |
| 2012/0030623 A1 | 2/2012 | Hoellwarth |
| 2012/0034897 A1 | 2/2012 | Kreitzer et al. |
| 2012/0041767 A1 | 2/2012 | Hoffman et al. |
| 2012/0042039 A1 | 2/2012 | Mark |
| 2012/0046784 A1 | 2/2012 | Malina et al. |
| 2012/0059664 A1 | 3/2012 | Georgiev et al. |
| 2012/0071770 A1 | 3/2012 | Grey et al. |
| 2012/0092379 A1 | 4/2012 | Tsuji et al. |
| 2012/0092383 A1 | 4/2012 | Hysek et al. |
| 2012/0105225 A1 | 5/2012 | Valtonen |
| 2012/0116550 A1 | 5/2012 | Hoffman et al. |
| 2012/0116684 A1 | 5/2012 | Ingrassia et al. |
| 2012/0119911 A1 | 5/2012 | Jeon et al. |
| 2012/0143094 A1 | 6/2012 | Jallon |
| 2012/0143095 A1 | 6/2012 | Nakamura |
| 2012/0150759 A1 | 6/2012 | Tarjan |
| 2012/0159380 A1 | 6/2012 | Kocienda et al. |
| 2012/0169882 A1 | 7/2012 | Millar et al. |
| 2012/0171649 A1 | 7/2012 | Wander et al. |
| 2012/0179319 A1 | 7/2012 | Gilman et al. |
| 2012/0215328 A1 | 8/2012 | Schmelzer |
| 2012/0232414 A1 | 9/2012 | Mollicone et al. |
| 2012/0251079 A1 | 10/2012 | Meschter et al. |
| 2012/0253485 A1 | 10/2012 | Weast et al. |
| 2012/0253488 A1 | 10/2012 | Shaw et al. |
| 2012/0254263 A1 | 10/2012 | Hiestermann et al. |
| 2012/0274508 A1 | 11/2012 | Brown et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0302843 A1 | 11/2012 | Otsubo et al. |
| 2012/0310389 A1 | 12/2012 | Martin |
| 2012/0313776 A1 | 12/2012 | Utter |
| 2012/0317167 A1 | 12/2012 | Rahman et al. |
| 2012/0317430 A1 | 12/2012 | Rahman et al. |
| 2012/0323129 A1 | 12/2012 | Fujita et al. |
| 2012/0326873 A1 | 12/2012 | Utter, II |
| 2013/0053990 A1 | 2/2013 | Ackland |
| 2013/0054150 A1 | 2/2013 | Sacks et al. |
| 2013/0054720 A1 | 2/2013 | Kang et al. |
| 2013/0067050 A1 | 3/2013 | Kotteri et al. |
| 2013/0081083 A1 | 3/2013 | Yu et al. |
| 2013/0093715 A1 | 4/2013 | Marsden et al. |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0115583 A1 | 5/2013 | Gordon et al. |

(56) References Cited

U.S. PATENT DOCUMENTS

| | | |
|---|---|---|
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0151285 A1 | 6/2013 | Mclaren et al. |
| 2013/0158367 A1 | 6/2013 | Pacione et al. |
| 2013/0184613 A1 | 7/2013 | Homsi et al. |
| 2013/0185097 A1 | 7/2013 | Saria et al. |
| 2013/0187923 A1 | 7/2013 | Yoshimoto et al. |
| 2013/0188322 A1 | 7/2013 | Lowe et al. |
| 2013/0191034 A1 | 7/2013 | Weast et al. |
| 2013/0197679 A1 | 8/2013 | Balakrishnan et al. |
| 2013/0198672 A1 | 8/2013 | Yoon et al. |
| 2013/0203475 A1 | 8/2013 | Shin et al. |
| 2013/0215119 A1 | 8/2013 | Vanhoecke |
| 2013/0217253 A1 | 8/2013 | Golko et al. |
| 2013/0217979 A1 | 8/2013 | Blackadar et al. |
| 2013/0223707 A1 | 8/2013 | Stephenson |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0238287 A1 | 9/2013 | Hoffman et al. |
| 2013/0245966 A1 | 9/2013 | Burroughs et al. |
| 2013/0262155 A1 | 10/2013 | Hinkamp |
| 2013/0263719 A1 | 10/2013 | Watterson et al. |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0325758 A1 | 12/2013 | Alphin et al. |
| 2013/0330694 A1 | 12/2013 | Watterson |
| 2013/0332286 A1 | 12/2013 | Medelius et al. |
| 2013/0345978 A1 | 12/2013 | Lush et al. |
| 2014/0035761 A1 | 2/2014 | Burton et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0067096 A1 | 3/2014 | Aibara |
| 2014/0081666 A1 | 3/2014 | Teller et al. |
| 2014/0089836 A1 | 3/2014 | Damani et al. |
| 2014/0107524 A1 | 4/2014 | Brull et al. |
| 2014/0108998 A1 | 4/2014 | Chaudhri et al. |
| 2014/0135955 A1 | 5/2014 | Burroughs |
| 2014/0139637 A1 | 5/2014 | Mistry et al. |
| 2014/0143678 A1 | 5/2014 | Mistry et al. |
| 2014/0156292 A1 | 6/2014 | Kozicki et al. |
| 2014/0176346 A1 | 6/2014 | Brumback et al. |
| 2014/0176475 A1 | 6/2014 | Myers et al. |
| 2014/0180786 A1 | 6/2014 | Sullivan |
| 2014/0189584 A1 | 7/2014 | Weng et al. |
| 2014/0197946 A1 | 7/2014 | Park et al. |
| 2014/0200691 A1 | 7/2014 | Lee et al. |
| 2014/0213415 A1 | 7/2014 | Parker et al. |
| 2014/0218369 A1 | 8/2014 | Yuen et al. |
| 2014/0221790 A1 | 8/2014 | Pacione et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0266731 A1 | 9/2014 | Malhotra |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278229 A1 | 9/2014 | Hong et al. |
| 2014/0280498 A1 | 9/2014 | Frankel et al. |
| 2014/0282153 A1 | 9/2014 | Christiansen et al. |
| 2014/0288680 A1 | 9/2014 | Hoffman et al. |
| 2014/0310598 A1 | 10/2014 | Sprague et al. |
| 2014/0310643 A1 | 10/2014 | Karmanenko et al. |
| 2014/0331314 A1 | 11/2014 | Fujioka |
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0344693 A1 | 11/2014 | Reese et al. |
| 2014/0344723 A1 | 11/2014 | Malik et al. |
| 2014/0344951 A1 | 11/2014 | Brewer |
| 2014/0358473 A1 | 12/2014 | Goel et al. |
| 2014/0358584 A1 | 12/2014 | Worden et al. |
| 2014/0371887 A1 | 12/2014 | Hoffman et al. |
| 2015/0004578 A1 | 1/2015 | Gilley et al. |
| 2015/0018632 A1 | 1/2015 | Khair |
| 2015/0033149 A1 | 1/2015 | Kuchoor |
| 2015/0046814 A1 | 2/2015 | Haughay et al. |
| 2015/0057942 A1 | 2/2015 | Self et al. |
| 2015/0057943 A1 | 2/2015 | Self et al. |
| 2015/0057945 A1 | 2/2015 | White et al. |
| 2015/0058093 A1 | 2/2015 | Jakobs |
| 2015/0058263 A1 | 2/2015 | Landers |
| 2015/0065095 A1 | 3/2015 | Seo et al. |
| 2015/0065302 A1 | 3/2015 | Ou et al. |
| 2015/0066172 A1 | 3/2015 | Yi |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0081060 A1 | 3/2015 | Hwang et al. |
| 2015/0081529 A1 | 3/2015 | Lee et al. |
| 2015/0082167 A1* | 3/2015 | Yeh .............. G08B 25/016 715/716 |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0112990 A1 | 4/2015 | Van Os et al. |
| 2015/0113553 A1 | 4/2015 | Pan |
| 2015/0118657 A1 | 4/2015 | Shrake et al. |
| 2015/0124067 A1 | 5/2015 | Bala et al. |
| 2015/0130830 A1 | 5/2015 | Nagasaki et al. |
| 2015/0133748 A1 | 5/2015 | Edmonds et al. |
| 2015/0142689 A1 | 5/2015 | Squires |
| 2015/0153943 A1 | 6/2015 | Wang |
| 2015/0164349 A1 | 6/2015 | Gopalakrishnan et al. |
| 2015/0180746 A1 | 6/2015 | Day et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0193805 A1 | 7/2015 | Filipiak |
| 2015/0196804 A1 | 7/2015 | Koduri et al. |
| 2015/0196805 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0217163 A1 | 8/2015 | Amis et al. |
| 2015/0220523 A1 | 8/2015 | Lagree |
| 2015/0220883 A1 | 8/2015 | Bfar et al. |
| 2015/0248535 A1* | 9/2015 | Cho .............. G16Z 99/00 705/2 |
| 2015/0251053 A1 | 9/2015 | Hoffman et al. |
| 2015/0262497 A1 | 9/2015 | Landau et al. |
| 2015/0269848 A1 | 9/2015 | Yuen et al. |
| 2015/0293592 A1 | 10/2015 | Cheong et al. |
| 2015/0294440 A1 | 10/2015 | Roberts |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0343709 A1 | 12/2015 | Gerstle et al. |
| 2015/0347711 A1 | 12/2015 | Soli et al. |
| 2015/0350861 A1 | 12/2015 | Soli et al. |
| 2015/0351655 A1 | 12/2015 | Coleman |
| 2015/0364057 A1 | 12/2015 | Catani et al. |
| 2015/0374267 A1 | 12/2015 | Laughlin |
| 2015/0374310 A1 | 12/2015 | Lee |
| 2016/0000379 A1 | 1/2016 | Pougatchev et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0027282 A1 | 1/2016 | Lee |

(56) References Cited

U.S. PATENT DOCUMENTS

| | | |
|---|---|---|
| 2016/0034148 A1 | 2/2016 | Wilson et al. |
| 2016/0048298 A1 | 2/2016 | Choi et al. |
| 2016/0058331 A1 | 3/2016 | Keen et al. |
| 2016/0058336 A1 | 3/2016 | Blahnik et al. |
| 2016/0058337 A1 | 3/2016 | Blahnik et al. |
| 2016/0062464 A1 | 3/2016 | Moussette et al. |
| 2016/0062582 A1 | 3/2016 | Wilson et al. |
| 2016/0062589 A1 | 3/2016 | Wan et al. |
| 2016/0065505 A1 | 3/2016 | Iskander |
| 2016/0070275 A1 | 3/2016 | Anderson et al. |
| 2016/0072896 A1 | 3/2016 | Petersen et al. |
| 2016/0085937 A1 | 3/2016 | Dettinger et al. |
| 2016/0107031 A1 | 4/2016 | Palatsi et al. |
| 2016/0135731 A1 | 5/2016 | Drennan |
| 2016/0140828 A1 | 5/2016 | Deforest |
| 2016/0156584 A1 | 6/2016 | Hum et al. |
| 2016/0193500 A1* | 7/2016 | Webster ............ G09B 19/0038 434/247 |
| 2016/0196635 A1 | 7/2016 | Cho et al. |
| 2016/0203691 A1 | 7/2016 | Arnold et al. |
| 2016/0210099 A1 | 7/2016 | Hampapuram et al. |
| 2016/0210568 A1 | 7/2016 | Krupa et al. |
| 2016/0220225 A1 | 8/2016 | Wang et al. |
| 2016/0235374 A1 | 8/2016 | Miller et al. |
| 2016/0246880 A1 | 8/2016 | Battiah et al. |
| 2016/0249864 A1 | 9/2016 | Kang et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0296798 A1 | 10/2016 | Balakrishnan et al. |
| 2016/0301794 A1 | 10/2016 | Schlakman et al. |
| 2016/0302680 A1 | 10/2016 | Narusawa et al. |
| 2016/0302717 A1 | 10/2016 | Tawa et al. |
| 2016/0321932 A1 | 11/2016 | Mitchell et al. |
| 2016/0324457 A1 | 11/2016 | Dagum |
| 2016/0328736 A1 | 11/2016 | Wang et al. |
| 2016/0332025 A1 | 11/2016 | Repka |
| 2016/0346607 A1 | 12/2016 | Rapfogel |
| 2016/0371464 A1 | 12/2016 | Bricker |
| 2016/0373631 A1 | 12/2016 | Titi et al. |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0007882 A1 | 1/2017 | Werner |
| 2017/0011210 A1 | 1/2017 | Cheong et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0045866 A1 | 2/2017 | Hou et al. |
| 2017/0046108 A1 | 2/2017 | Kang et al. |
| 2017/0053542 A1 | 2/2017 | Wilson et al. |
| 2017/0056722 A1 | 3/2017 | Singh et al. |
| 2017/0065224 A1 | 3/2017 | Rahko et al. |
| 2017/0087469 A1 | 3/2017 | Hardee et al. |
| 2017/0095695 A1 | 4/2017 | Mangusson et al. |
| 2017/0124276 A1 | 5/2017 | Tee |
| 2017/0140143 A1 | 5/2017 | Ahmad et al. |
| 2017/0143262 A1 | 5/2017 | Kurunmäki et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0161462 A1 | 6/2017 | Parker et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0239525 A1 | 8/2017 | Kim et al. |
| 2017/0243508 A1 | 8/2017 | Cheng et al. |
| 2017/0249417 A1 | 8/2017 | Gosieski et al. |
| 2017/0266494 A1 | 9/2017 | Crankson et al. |
| 2017/0266531 A1 | 9/2017 | Elford et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0301039 A1 | 10/2017 | Dyer et al. |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0333752 A1 | 11/2017 | Korkala et al. |
| 2017/0337033 A1 | 11/2017 | Duyan et al. |
| 2017/0348562 A1 | 12/2017 | Jung et al. |
| 2017/0354845 A1 | 12/2017 | Williams et al. |
| 2017/0357520 A1 | 12/2017 | De Vries et al. |
| 2017/0359623 A1 | 12/2017 | Folse et al. |
| 2018/0000426 A1 | 1/2018 | Li |
| 2018/0001184 A1 | 1/2018 | Tran et al. |
| 2018/0032234 A1 | 2/2018 | Michalske |
| 2018/0036591 A1 | 2/2018 | King et al. |
| 2018/0053200 A1 | 2/2018 | Cronin et al. |
| 2018/0056132 A1 | 3/2018 | Foley et al. |
| 2018/0065025 A1 | 3/2018 | Toda et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0085058 A1* | 3/2018 | Chakravarthi ......... G16H 40/67 |
| 2018/0126248 A1 | 5/2018 | Dion et al. |
| 2018/0133537 A1* | 5/2018 | Montantes ............... H02J 7/32 |
| 2018/0137937 A1 | 5/2018 | Gass et al. |
| 2018/0140211 A1 | 5/2018 | Nakazawa et al. |
| 2018/0140903 A1 | 5/2018 | Poure et al. |
| 2018/0140927 A1 | 5/2018 | Kito et al. |
| 2018/0150709 A1 | 5/2018 | Ha |
| 2018/0177437 A1 | 6/2018 | Yoshioka |
| 2018/0182491 A1 | 6/2018 | Belliveau et al. |
| 2018/0189077 A1 | 7/2018 | Gupta et al. |
| 2018/0206766 A1 | 7/2018 | Blahnik et al. |
| 2018/0247706 A1 | 8/2018 | Riley et al. |
| 2018/0272190 A1 | 9/2018 | Miura et al. |
| 2018/0294053 A1 | 10/2018 | Runyon et al. |
| 2018/0300037 A1 | 10/2018 | Takeda et al. |
| 2018/0316964 A1 | 11/2018 | Dillon et al. |
| 2018/0318647 A1 | 11/2018 | Foley et al. |
| 2018/0329584 A1 | 11/2018 | Williams et al. |
| 2018/0339195 A1 | 11/2018 | Bernotas |
| 2018/0345078 A1 | 12/2018 | Blahnik et al. |
| 2018/0367484 A1 | 12/2018 | Rodriguez et al. |
| 2019/0008467 A1 | 1/2019 | Averina et al. |
| 2019/0025995 A1 | 1/2019 | Williams |
| 2019/0026011 A1 | 1/2019 | Wang et al. |
| 2019/0034049 A1 | 1/2019 | Williams et al. |
| 2019/0034050 A1 | 1/2019 | Williams et al. |
| 2019/0089701 A1 | 3/2019 | Mercury et al. |
| 2019/0102049 A1 | 4/2019 | Anzures et al. |
| 2019/0104951 A1 | 4/2019 | Valys et al. |
| 2019/0126099 A1 | 5/2019 | Hoang |
| 2019/0143194 A1 | 5/2019 | Evancha et al. |
| 2019/0184234 A1 | 6/2019 | Packles et al. |
| 2019/0209777 A1 | 7/2019 | O'Connell et al. |
| 2019/0232110 A1 | 8/2019 | Williams et al. |
| 2019/0232111 A1 | 8/2019 | Williams et al. |
| 2019/0274565 A1 | 9/2019 | Soli et al. |
| 2019/0279520 A1 | 9/2019 | Wilson et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339849 A1 | 11/2019 | Williams et al. |
| 2019/0339860 A1 | 11/2019 | Chen et al. |
| 2019/0342616 A1 | 11/2019 | Domm et al. |
| 2019/0364120 A1 | 11/2019 | Bandela et al. |
| 2019/0387982 A1 | 12/2019 | Buller |
| 2020/0014967 A1 | 1/2020 | Putnam |
| 2020/0026398 A1 | 1/2020 | Kim |
| 2020/0054931 A1 | 2/2020 | Martin et al. |
| 2020/0098278 A1 | 3/2020 | Doti et al. |
| 2020/0101365 A1 | 4/2020 | Wilson et al. |

(56) References Cited

U.S. PATENT DOCUMENTS

| | | | |
|---|---|---|---|
| 2020/0110814 A1 | 4/2020 | Abuelsaad et al. | |
| 2020/0149921 A1 | 5/2020 | Hoffman et al. | |
| 2020/0160961 A1 | 5/2020 | Wadhawan et al. | |
| 2020/0261763 A1 | 8/2020 | Park et al. | |
| 2020/0289919 A1* | 9/2020 | Gruben | G06F 3/0346 |
| 2020/0297249 A1 | 9/2020 | Williams et al. | |
| 2020/0356242 A1 | 11/2020 | Wilson et al. | |
| 2020/0357522 A1 | 11/2020 | Pahwa et al. | |
| 2020/0381100 A1 | 12/2020 | Williams et al. | |
| 2020/0382613 A1 | 12/2020 | Sundstrom et al. | |
| 2021/0001226 A1* | 1/2021 | Suzuki | A63F 13/212 |
| 2021/0007632 A1 | 1/2021 | Blahnik et al. | |
| 2021/0007633 A1 | 1/2021 | Blahnik et al. | |
| 2021/0008413 A1* | 1/2021 | Asikainen | G06F 3/0304 |
| 2021/0042132 A1 | 2/2021 | Park et al. | |
| 2021/0093919 A1 | 4/2021 | Lyke et al. | |
| 2021/0110908 A1 | 4/2021 | Blahnik et al. | |
| 2021/0113116 A1 | 4/2021 | Chen et al. | |
| 2021/0113137 A1 | 4/2021 | Soli et al. | |
| 2021/0145321 A1 | 5/2021 | Chen et al. | |
| 2021/0191584 A1 | 6/2021 | Williams et al. | |
| 2021/0193293 A1 | 6/2021 | Blahnik et al. | |
| 2021/0236903 A1* | 8/2021 | Briel | A63B 71/0622 |
| 2021/0252337 A1 | 8/2021 | Devine et al. | |
| 2021/0252341 A1 | 8/2021 | Devine et al. | |
| 2021/0252369 A1 | 8/2021 | Devine et al. | |
| 2021/0255747 A1 | 8/2021 | Devine et al. | |
| 2021/0255758 A1 | 8/2021 | Devine et al. | |
| 2021/0255826 A1 | 8/2021 | Devine et al. | |
| 2021/0294438 A1 | 9/2021 | Yang et al. | |
| 2021/0316185 A1 | 10/2021 | Mckenna et al. | |
| 2021/0350900 A1 | 11/2021 | Blahnik et al. | |
| 2021/0352118 A1 | 11/2021 | Ahn et al. | |
| 2021/0379447 A1 | 12/2021 | Lee | |
| 2021/0394020 A1 | 12/2021 | Killen et al. | |
| 2022/0047918 A1 | 2/2022 | Williams et al. | |
| 2022/0062707 A1 | 3/2022 | Bedekar et al. | |
| 2022/0066902 A1 | 3/2022 | Narra et al. | |
| 2022/0121299 A1 | 4/2022 | De Vries et al. | |
| 2022/0157184 A1 | 5/2022 | Wilson et al. | |
| 2022/0160258 A1 | 5/2022 | Williams et al. | |
| 2022/0262485 A1 | 8/2022 | Meschter et al. | |
| 2022/0262509 A1 | 8/2022 | Pahwa et al. | |
| 2022/0328161 A1 | 10/2022 | Gilravi et al. | |
| 2022/0336077 A1 | 10/2022 | Chen et al. | |
| 2022/0386901 A1 | 12/2022 | Chen et al. | |
| 2023/0012755 A1 | 1/2023 | D'Auria et al. | |
| 2023/0013809 A1 | 1/2023 | D'Auria et al. | |
| 2023/0013932 A1 | 1/2023 | Blahnik et al. | |
| 2023/0014053 A1 | 1/2023 | Devine et al. | |
| 2023/0014290 A1 | 1/2023 | Davydov et al. | |
| 2023/0017793 A1 | 1/2023 | Williams et al. | |
| 2023/0019337 A1 | 1/2023 | D'Auria et al. | |
| 2023/0024084 A1 | 1/2023 | D'Auria et al. | |
| 2023/0025724 A1 | 1/2023 | Gilravi et al. | |
| 2023/0027358 A1 | 1/2023 | Williams et al. | |
| 2023/0066552 A1 | 3/2023 | Van Os et al. | |
| 2023/0107803 A1 | 4/2023 | Dugan | |
| 2023/0119253 A1 | 4/2023 | Sundstrom et al. | |
| 2023/0136700 A1 | 5/2023 | Williams et al. | |
| 2023/0191198 A1 | 6/2023 | Lee et al. | |
| 2023/0260416 A1 | 8/2023 | Wilson et al. | |
| 2023/0390606 A1 | 12/2023 | Bolton et al. | |
| 2023/0390626 A1 | 12/2023 | Bolton et al. | |
| 2023/0390627 A1 | 12/2023 | Bolton et al. | |
| 2024/0077309 A1 | 3/2024 | Felton et al. | |
| 2024/0081751 A1* | 3/2024 | Murphy | G06F 3/0482 |

FOREIGN PATENT DOCUMENTS

| | | |
|---|---|---|
| CA | 2826239 C | 1/2017 |
| CN | 1337638 A | 2/2002 |
| CN | 1397904 A | 2/2003 |
| CN | 1523500 A | 8/2004 |
| CN | 1585943 A | 2/2005 |
| CN | 1628609 A | 6/2005 |
| CN | 1767789 A | 5/2006 |
| CN | 1824358 A | 8/2006 |
| CN | 101150810 A | 3/2008 |
| CN | 101219046 A | 7/2008 |
| CN | 101444419 A | 6/2009 |
| CN | 101541387 A | 9/2009 |
| CN | 101651870 A | 2/2010 |
| CN | 101658423 A | 3/2010 |
| CN | 101668482 A | 3/2010 |
| CN | 101836894 A | 9/2010 |
| CN | 101890217 A | 11/2010 |
| CN | 101910992 A | 12/2010 |
| CN | 101978374 A | 2/2011 |
| CN | 102339201 A | 2/2012 |
| CN | 102438521 A | 5/2012 |
| CN | 102448555 | 5/2012 |
| CN | 102449560 A | 5/2012 |
| CN | 102449566 A | 5/2012 |
| CN | 102549590 A | 7/2012 |
| CN | 102804238 A | 11/2012 |
| CN | 102814037 A | 12/2012 |
| CN | 102834079 A | 12/2012 |
| CN | 102989159 A | 3/2013 |
| CN | 103154954 A | 6/2013 |
| CN | 103182175 A | 7/2013 |
| CN | 103210355 A | 7/2013 |
| CN | 103212197 A | 7/2013 |
| CN | 103270540 A | 8/2013 |
| CN | 103294124 A | 9/2013 |
| CN | 103370924 A | 10/2013 |
| CN | 103403627 A | 11/2013 |
| CN | 203276086 U | 11/2013 |
| CN | 103646570 A | 3/2014 |
| CN | 103682785 A | 3/2014 |
| CN | 103701504 A | 4/2014 |
| CN | 104288983 A | 1/2015 |
| CN | 104501043 A | 4/2015 |
| CN | 104508426 A | 4/2015 |
| CN | 104815428 A | 8/2015 |
| CN | 105187282 A | 12/2015 |
| CN | 105320454 A | 2/2016 |
| CN | 105681328 A | 6/2016 |
| CN | 106310638 A | 1/2017 |
| CN | 106510719 A | 3/2017 |
| CN | 106537397 A | 3/2017 |
| CN | 106709235 A | 5/2017 |
| CN | 106878550 A | 6/2017 |
| CN | 107469327 A | 12/2017 |
| EP | 0943290 A1 | 9/1999 |
| EP | 1559372 A1 | 8/2005 |
| EP | 1935339 A1 | 6/2008 |
| EP | 2025368 A2 | 2/2009 |
| EP | 2529663 A1 | 12/2012 |
| EP | 2631830 A2 | 8/2013 |
| EP | 2728680 A1 | 5/2014 |
| EP | 3117767 A1 | 1/2017 |
| EP | 3122038 A1 | 1/2017 |
| EP | 3130997 A1 | 2/2017 |
| JP | 5-288869 A | 11/1993 |
| JP | 6-187118 A | 7/1994 |
| JP | 8-126632 A | 5/1996 |
| JP | 11-84030 A | 3/1999 |
| JP | 2001-76078 A | 3/2001 |
| JP | 2002-190007 A | 7/2002 |
| JP | 2002-346013 A | 12/2002 |
| JP | 2003-102868 A | 4/2003 |
| JP | 2003-157323 A | 5/2003 |
| JP | 2003-248721 A | 9/2003 |
| JP | 2003-319912 A | 11/2003 |
| JP | 2003-337863 A | 11/2003 |
| JP | 2004-102609 A | 4/2004 |
| JP | 2004-113466 A | 4/2004 |
| JP | 2004-174006 A | 6/2004 |
| JP | 2005-79814 A | 3/2005 |
| JP | 3635663 B2 | 4/2005 |
| JP | 2006-155104 A | 6/2006 |
| JP | 2006-180899 A | 7/2006 |
| JP | 2006-230679 A | 9/2006 |

(56) References Cited

FOREIGN PATENT DOCUMENTS

| | | |
|---|---|---|
| JP | 2007-260288 A | 10/2007 |
| JP | 2007-330513 A | 12/2007 |
| JP | 2008-104758 A | 5/2008 |
| JP | 2008-183339 A | 8/2008 |
| JP | 2009-78134 A | 4/2009 |
| JP | 2009-088989 A | 4/2009 |
| JP | 2009-112731 A | 5/2009 |
| JP | 2009-211241 A | 9/2009 |
| JP | 2009-282670 A | 12/2009 |
| JP | 2010-12335 A | 1/2010 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2010-182287 A | 8/2010 |
| JP | 2010-186249 A | 8/2010 |
| JP | 2010-206668 A | 9/2010 |
| JP | 2011-514192 A | 5/2011 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011210119 | 10/2011 |
| JP | 2011-229141 A | 11/2011 |
| JP | 2011-259253 A | 12/2011 |
| JP | 2012-20134 A | 2/2012 |
| JP | 2012-35071 A | 2/2012 |
| JP | 2012-59264 A | 3/2012 |
| JP | 2012-86088 A | 5/2012 |
| JP | 2012-524640 A | 10/2012 |
| JP | 2012-230503 A | 11/2012 |
| JP | 2012-232114 A | 11/2012 |
| JP | 2013-103020 A | 5/2013 |
| JP | 2013-117690 A | 6/2013 |
| JP | 2013-146557 A | 8/2013 |
| JP | 2013-530776 A | 8/2013 |
| JP | 2013-543156 A | 11/2013 |
| JP | 5346115 B1 | 11/2013 |
| JP | 2013-544140 A | 12/2013 |
| JP | 2014-500740 A | 1/2014 |
| JP | 2014-045782 A | 3/2014 |
| JP | 2014-104139 A | 6/2014 |
| JP | 2014-143473 A | 8/2014 |
| JP | 2014-168685 A | 9/2014 |
| JP | 2014-171831 A | 9/2014 |
| JP | 2015-58218 A | 3/2015 |
| JP | 2015-507811 A | 3/2015 |
| JP | 2015-509019 A | 3/2015 |
| JP | 2015-509755 A | 4/2015 |
| JP | 2016-17331 A | 2/2016 |
| JP | 2016-502875 A | 2/2016 |
| JP | 2016-52512 A | 4/2016 |
| JP | 2016-517329 A | 6/2016 |
| JP | 2016-158867 A | 9/2016 |
| JP | 2016-528016 A | 9/2016 |
| JP | 2016-177151 A | 10/2016 |
| JP | 2016-185288 A | 10/2016 |
| JP | 2016-202751 A | 12/2016 |
| JP | 2017-83978 A | 5/2017 |
| JP | 2017-134689 A | 8/2017 |
| JP | 2017-156267 A | 9/2017 |
| JP | 2017-531235 A | 10/2017 |
| JP | 2017-211994 A | 11/2017 |
| JP | 2017-532069 A | 11/2017 |
| JP | 2018-102908 A | 7/2018 |
| JP | 2018-202174 A | 12/2018 |
| JP | 2019-3670 A | 1/2019 |
| KR | 10-2006-0117570 A | 11/2006 |
| KR | 10-2011-0017076 A | 2/2011 |
| KR | 10-2011-0121394 A | 11/2011 |
| KR | 10-2012-0023657 A | 3/2012 |
| KR | 10-2012-0076559 A | 7/2012 |
| KR | 10-2012-0098854 A | 9/2012 |
| KR | 10-2012-0132732 A | 12/2012 |
| KR | 10-2013-0043698 A | 5/2013 |
| KR | 10-2013-0111569 A | 10/2013 |
| KR | 10-2013-0111570 A | 10/2013 |
| KR | 10-2013-0135282 A | 12/2013 |
| KR | 10-2015-0026635 A | 3/2015 |
| KR | 10-2016-0027943 A | 3/2016 |
| KR | 10-2016-0105129 A | 9/2016 |
| KR | 10-2016-0142418 A | 12/2016 |
| KR | 10-2017-0003608 A | 1/2017 |
| KR | 10-2017-0020085 A | 2/2017 |
| KR | 10-2017-0029014 A | 3/2017 |
| KR | 10-2017-0032471 A | 3/2017 |
| KR | 10-2019-0022883 A | 3/2019 |
| KR | 10-2019-0141702 A | 12/2019 |
| WO | 1997/38626 A1 | 10/1997 |
| WO | 1999/41682 A2 | 8/1999 |
| WO | 2002/27530 A2 | 4/2002 |
| WO | 2005/029242 A2 | 3/2005 |
| WO | 2005/070289 A1 | 8/2005 |
| WO | 2006/103965 A1 | 10/2006 |
| WO | 2007/081629 A2 | 7/2007 |
| WO | 2009/129402 A1 | 10/2009 |
| WO | 2009/152608 A1 | 12/2009 |
| WO | 2010/126821 A1 | 11/2010 |
| WO | 2010/126825 A1 | 11/2010 |
| WO | 2011/072111 A2 | 6/2011 |
| WO | 2011/108335 A1 | 9/2011 |
| WO | 2012/021507 A2 | 2/2012 |
| WO | 2012/036891 A2 | 3/2012 |
| WO | 2012/061438 A2 | 5/2012 |
| WO | 2012/061440 A2 | 5/2012 |
| WO | 2012/078079 A2 | 6/2012 |
| WO | 2012/086910 A1 | 6/2012 |
| WO | 2012/095712 A1 | 7/2012 |
| WO | 2013/052789 A1 | 4/2013 |
| WO | 2013/109762 A1 | 7/2013 |
| WO | 2013/109776 A1 | 7/2013 |
| WO | 2013/109777 A1 | 7/2013 |
| WO | 2013/109916 A1 | 7/2013 |
| WO | 2013/157307 A1 | 10/2013 |
| WO | 2013/169870 A1 | 11/2013 |
| WO | 2013/173838 A2 | 11/2013 |
| WO | 2014/059259 A1 | 4/2014 |
| WO | 2014/105276 A1 | 7/2014 |
| WO | 2014/200730 A1 | 12/2014 |
| WO | 2014/207294 A1 | 12/2014 |
| WO | 2015/027133 A1 | 2/2015 |
| WO | 2015/179592 A1 | 11/2015 |
| WO | 2015/198488 A1 | 12/2015 |
| WO | 2016/022203 A1 | 2/2016 |
| WO | 2016/025036 A1 | 2/2016 |
| WO | 2016/036472 A1 | 3/2016 |
| WO | 2016/036582 A2 | 3/2016 |
| WO | 2017/037242 A1 | 3/2017 |
| WO | 2018/048510 A1 | 3/2018 |
| WO | 2018/213066 A1 | 11/2018 |
| WO | 2018/222313 A1 | 12/2018 |
| WO | 2018/236291 A1 | 12/2018 |
| WO | 2019/017508 A1 | 1/2019 |
| WO | 2019/024383 A1 | 2/2019 |
| WO | 2019/024603 A1 | 2/2019 |
| WO | 2019/183422 A1 | 9/2019 |
| WO | 2019/190001 A1 | 10/2019 |
| WO | 2019/217249 A2 | 11/2019 |
| WO | 2019/231982 A1 | 12/2019 |

OTHER PUBLICATIONS

Advisory Action received for U.S. Appl. No. 15/144,364, mailed on Jul. 29, 2019, 6 pages.

Advisory Action received for U.S. Appl. No. 14/732,773, mailed on Aug. 23, 2019, 6 pages Advisory Action received for U.S.Appl. No. 14/732,773, mailed on Nov. 9, 2018, 6 pages.

Advisory Action received for U.S. Appl. No. 14/839,922, mailed on Mar. 24, 2017, 4 pages.

Advisory Action received for U.S. Appl. No. 16/144,849, mailed on Aug. 12, 2019, 5 pages.

(56) References Cited

OTHER PUBLICATIONS

Advisory Action received for U.S. Appl. No. 16/144,864, mailed on Jul. 6, 2020, 6 pages.
Advisory Action received for U.S. Appl. No. 16/337,892, mailed on Apr. 9, 2021, 4 pages.
Advisory Action received for U.S. Appl. No. 16/378,136, mailed on Apr. 12, 2021, 4 pages.
Advisory Action received for U.S. Appl. No, 17/381,570, mailed on May 23, 2023, 5 pages.
Allen Ray, "Join the Nike Training Club and let your iPhone be your fitness instructor", Apr. 19, 2011, 26 pages.
Allison Conor, "Working out with Fiit's wearable-powered boutique fitness classes", Online available at: <https://www.wareable.com/wearable-tech/fiit-fitness-classes-review-3849>, May 14, 2018, 8 pages.
AndroidAndYuk, "Endomondo Android App Review", Available online at: https://www.youtube.com/watch?v=Wyjyrza-P1E, Jan. 9, 2013, 17 pages.
Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Applicant-Initiated Interview Summary received for U.S. Appl. No. 16/994,352, mailed on Nov. 2, 2021, 4 pages.
Applicant-Initiated Interview Summary received for U.S. Appl. No. 15/608,848, mailed on Apr. 13, 2021, 4 pages.
Applicant-Initiated Interview Summary received for U.S. Appl. No. 15/608,848, mailed on May 12, 2020, 4 pages.
Applicant-Initiated Interview Summary received for U.S. Appl. No. 15/608,848, mailed on Oct. 26, 2020, 3 pages.
Applicant-Initiated Interview Summary received for U.S. Appl. No. 15/627,069, mailed on Nov. 4, 2019, 6 pages.
Applicant-Initiated Interview Summary received for U.S. Appl. No. 16/144,735, mailed on Jun. 18, 2020, 3 pages.
Applicant-Initiated Interview Summary received for U.S. Appl. No. 16/144,753, mailed on Jun. 18, 2020, 3 pages.
Applicant-Initiated Interview Summary received for U.S. Appl. No. 16/144,849, mailed on Jan. 21, 2020, 6 pages.
Applicant-Initiated Interview Summary received for U.S. Appl. No. 16/144,864, mailed on Apr. 29, 2020, 4 pages.
Applicant-Initiated Interview Summary received for U.S. Appl. No. 16/894,309, mailed on Jan. 26, 2021, 3 pages.
Applicant-Initiated Interview Summary received for U.S. Appl. No. 17/030,318, mailed on Jul. 30, 2021, 4 pages.
Applicant-Initiated Interview Summary received for U.S. Appl. No. 17/030,321, mailed on Jul. 30, 2021, 2 pages.
Applicant-Initiated Interview Summary received for U.S. Appl. No. 17/381,570, mailed on Apr. 26, 2022, 5 pages.
Applicant-Initiated Interview Summary received for U.S. Appl. No. 15/600,243, mailed on Nov. 1, 2019, 6 pages.
Applicant-Initiated Interview Summary received for U.S. Appl. No. 15/608,848, mailed on Nov. 1, 2019, 3 pages.
Applicant-Initiated Interview Summary received for U.S. Appl. No. 15/627,069, mailed on Jan. 22, 2021, 4 pages.
Applicant-Initiated Interview Summary received for U.S. Appl. No. 15/627,069, mailed on Jul. 20, 2020, 5 pages.
Applicant-Initiated Interview Summary received for U.S. Appl. No. 15/705,849, mailed on Feb. 14, 2020, 3 pages.
Applicant-Initiated Interview Summary received for U.S. Appl. No. 15/705,849, mailed on Jun. 29, 2020, 3 pages.
Applicant-Initiated Interview Summary received for U.S. Appl. No. 15/925,652, mailed on Nov. 3, 2020, 4 pages.
Applicant-Initiated Interview Summary received for U.S. Appl. No. 16/138,809, mailed on Dec. 16, 2020, 7 pages.
Applicant-Initiated Interview Summary received for U.S. Appl. No. 16/138,809, mailed on Jun. 9, 2020, 4 pages.
Applicant-Initiated Interview Summary received for U.S. Appl. No. 16/144,753, mailed on Nov. 4, 2020, 3 pages.
Applicant-Initiated Interview Summary received for U.S. Appl. No. 16/144,864, mailed on Jun. 22, 2020, 3 pages.
Applicant-Initiated Interview Summary received for U.S. Appl. No. 16/377,892, mailed on Mar. 26, 2021, 2 pages.
Applicant-Initiated Interview Summary received for U.S. Appl. No. 16/377,892, mailed on Oct. 13, 2020, 5 pages.
Applicant-Initiated Interview Summary received for U.S. Appl. No. 16/378,136, mailed on Mar. 26, 2021, 2 pages.
Applicant-Initiated Interview Summary received for U.S. Appl. No. 16/378,136, mailed on Oct. 13, 2020, 4 pages.
Applicant-Initiated Interview Summary received for U.S. Appl. No. 16/418,786, mailed on Mar. 30, 2021, 4 pages.
Applicant-Initiated Interview Summary received for U.S. Appl. No. 16/418,786, mailed on May 9, 2022, 2 pages.
Applicant-Initiated Interview Summary received for U.S. Appl. No. 16/418,786, mailed on Sep. 23, 2022, 2 pages.
Applicant-Initiated Interview Summary received for U.S. Appl. No. 16/820,383, mailed on Aug. 12, 2022, 2 pages.
Applicant-Initiated Interview Summary received for U.S. Appl. No. 16/820,383, mailed on Mar. 11, 2021, 2 pages.
Applicant-Initiated Interview Summary received for U.S. Appl. No. 16/820,383, mailed on May 10, 2022, 2 pages.
Applicant-Initiated Interview Summary received for U.S. Appl. No. 16/888,629, mailed on Aug. 4, 2021, 5 pages.
Applicant-Initiated Interview Summary received for U.S. Appl. No. 16/894,309, mailed on Jun. 25, 2021, 4 pages.
Applicant-Initiated Interview Summary received for U.S. Appl. No. 16/987,275, mailed on Feb. 3, 2022, 4 pages.
Applicant-Initiated Interview Summary received for U.S. Appl. No. 17/030,337, mailed on Jul. 27, 2022, 2 pages.
Applicant-Initiated Interview Summary received for U.S. Appl. No. 17/031,543, mailed on Apr. 21, 2022, 2 pages.
Applicant-Initiated Interview Summary received for U.S. Appl. No. 17/031,854, mailed on Apr. 6, 2023, 5 pages.
Applicant-Initiated Interview Summary received for U.S. Appl. No. 17/031,854, mailed on Feb. 25, 2022, 5 pages.
Applicant-Initiated Interview Summary received for U.S. Appl. No. 17/031,854, mailed on Jan. 24, 2023, 6 pages.
Applicant-Initiated Interview Summary received for U.S. Appl. No. 17/031,854, mailed on Jul. 27, 2022, 5 pages.
Applicant-Initiated Interview Summary received for U.S. Appl. No. 17/031,859, mailed on Dec. 27, 2022, 5 pages.
Applicant-Initiated Interview Summary received for U.S. Appl. No. 17/031,859, mailed on Feb. 25, 2022, 4 pages.
Applicant-Initiated Interview Summary received for U.S. Appl. No. 17/031,859, mailed on Feb. 26, 2021, 4 pages.
Applicant-Initiated Interview Summary received for U.S. Appl. No. 17/031,859, mailed on Jul. 28, 2022, 3 pages.
Applicant-Initiated Interview Summary received for U.S. Appl. No. 17/031,859, mailed on Jun. 30, 2021, 4 pages.
Applicant-Initiated Interview Summary received for U.S. Appl. No. 17/031,859, mailed on Mar. 3, 2023, 5 pages.
Applicant-Initiated Interview Summary received for U.S. Appl. No. 17/031,874, mailed on Feb. 25, 2022, 4 pages.
Applicant-Initiated Interview Summary received for U.S. Appl. No. 17/031,874, mailed on Feb. 26, 2021, 4 pages.
Applicant-Initiated Interview Summary received for U.S. Appl. No. 17/031,874, mailed on Jan. 24, 2023, 5 pages.
Applicant-Initiated Interview Summary received for U.S. Appl. No. 17/031,874, mailed on Jul. 27, 2022, 5 pages.
Applicant-Initiated Interview Summary received for U.S. Appl. No. 17/031,874, mailed on Jun. 30, 2021, 4 pages.
Applicant-Initiated Interview Summary received for U.S. Appl. No. 17/157,728, mailed on Feb. 3, 2022, 5 pages.
Applicant-Initiated Interview Summary received for U.S. Appl. No. 17/192,161, mailed on Dec. 24, 2021, 4 pages.
Applicant-Initiated Interview Summary received for U.S. Appl. No. 17/192,161, mailed on Jun. 29, 2021, 4 pages.
Applicant-Initiated Interview Summary received for U.S. Appl. No. 17/192,161, mailed on Sep. 29, 2021, 3 pages.
Applicant-Initiated Interview Summary received for U.S. Appl. No. 17/381,570, mailed on Aug. 24, 2022, 5 pages.
Applicant-Initiated Interview Summary received for U.S. Appl. No. 17/381,570, mailed on Nov. 28, 2022, 5 pages.

(56) References Cited

OTHER PUBLICATIONS

Applicant-Initiated Interview Summary received for U.S. Appl. No. 17/516,537, mailed on Jul. 5, 2022, 4 pages.
Applicant-Initiated Interview Summary received for U.S. Appl. No. 17/516,537, mailed on Nov. 22, 2022, 2 pages.
Applicant-Initiated Interview Summary received for U.S. Appl. No. 17/591,184, mailed on Feb. 27, 2023, 2 pages.
Applicant-Initiated Interview Summary received for U.S. Appl. No. 17/591,184, mailed on Sep. 23, 2022, 2 pages.
Applicant-Initiated Interview Summary received for U.S. Appl. No. 17/666,301, mailed on Mar. 28, 2023, 4 pages.
Applicant-Initiated Interview Summary received for U.S. Appl. No. 17/735,395, mailed on Apr. 28, 2023, 2 pages.
Applicant-Initiated Interview Summary received for U.S. Appl. No. 17/744,500, mailed on May 30, 2023, 4 pages.
Applicant-Initiated Interview Summary received for U.S. Appl. No. 17/892,534, mailed on Feb. 6, 2023, 2 pages.
Applicant-Initiated Interview Summary received for U.S. Appl. No. 17/892,534, mailed on Feb. 10, 2023, 2 pages.
Applicant-Initiated Interview Summary received for U.S. Appl. No. 17/951,875, mailed on Feb. 28, 2023, 2 pages.
Applicant-Initiated Interview Summary received for U.S. Appl. No. 17/951,945, mailed on Apr. 28, 2023, 2 pages.
Applicant-Initiated Interview Summary received for U.S. Appl. No. 17/952,027, mailed on May 30, 2023, 4 pages.
Applicant-Initiated Interview Summary received for U.S. Appl. No. 17/381,570, mailed on Apr. 6, 2023, 4 pages.
Bagala et al., "Evaluation of Accelerometer-Based Fall Detection Algorithms on Real-World Falls", PLoS ONE, vol. 7, No. 5, May 16, 2012, 9 pages.
Board Decision received for Chinese Patent Application No. 201380081349.6, mailed on Nov. 23, 2020, 2 pages (1 page of English Translation and 1 page of Official Copy).
Brief Communication Regarding Oral Proceedings received for European Patent Application No. 18727543.3, mailed on Mar. 23, 2023. 1 page.
Brief Communication Regarding Oral Proceedings received for European Patent Application No. 20182116.2, mailed on Apr. 13, 2022. 3 pages.
Brief Communication Regarding Oral Proceedings received for European Patent Application No. 20203526.7, mailed on Dec. 23, 2022, 4 pages.
Brief Communication Regarding Oral Proceedings received for European Patent Application No. 20203526.7, mailed on Jan. 18, 2023, 1 page.
Brief Communication Regarding Oral Proceedings received for European Patent Application No. 20721342.2, mailed on Oct. 18, 2022, 1 page.
CBS This Morning, "This smart mirror puts a personal trainer in your reflection". Available on: https://www.youtube.com/watch?v=nSmTTZcpVGg, Oct. 13, 2018, 4 pages.
Certificate of Examination received for Australian Patent Application No. 2018101855, mailed on Aug. 6, 2019, 2 pages.
Certification of Examination received for Australian Patent Application No. 2018100158, mailed on Oct. 23, 2018, 2 pages.
Cho H.S., "Satisfactory Innovative Smartwatch (fitbit force) . . . review after seven days of use, such as the amount of sleep and movement (improving sleep is the object of X-Blue", Online Available at: <https://x-blueuv.blogspot.com/2013/12/fitbit-force.html>, Dec. 3, 2013, 8 pages (2 pages of English Translation and 6 pages of Official Copy).
CNET, "Google Fit's automatic activity tracking is getting smarter on Android Wear", Available online at: https://www.youtube.com/watch?v=IttzlCid_d8, May 18, 2016, 1 page.
Codrington Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.

Communication of the Board of Appeal received for European Patent Application No. 13811085.3, mailed on Jul. 28, 2022, 13 pages.
Communication of the Board of Appeal received for European Patent Application No. 15771747.1, mailed on Aug. 25, 2021, 9 pages.
Corrected Notice of Allowance received for U.S. Appl. No. 14/732,773, mailed on Feb. 10, 2020, 3 pages.
Corrected Notice of Allowance received for U.S. Patent Application No. 14/732,773, mailed on Mar. 24, 2020, 3 pages.
Corrected Notice of Allowance received for U.S. Appl. No. 15/183,663, mailed on Feb. 25, 2019, 3 pages.
Corrected Notice of Allowance received for U.S. Appl. No. 15/183,663, mailed on Mar. 27, 2019, 2 pages.
Corrected Notice of Allowance received for U.S. Appl. No. 15/600,243, mailed on Feb. 5, 2020, 3 pages.
Corrected Notice of Allowance received for U.S. Appl. No. 15/600,243, mailed on Mar. 13, 2020, 3 pages.
Corrected Notice of Allowance received for U.S. Appl. No. 15/600,243, mailed on Mar. 31, 2020, 5 pages.
Corrected Notice of Allowance received for U.S. Appl. No. 16/377,892, mailed on Aug. 11, 2021, 3 pages.
Corrected Notice of Allowance received for U.S. Appl. No. 16/378,136, mailed on Aug. 11, 2021, 2 pages.
Corrected Notice of Allowance received for U.S. Appl. No. 16/378,136, mailed on Jun. 11, 2021, 2 pages.
Corrected Notice of Allowance received for U.S. Appl. No. 16/418,786, mailed on Jan. 5, 2022, 3 pages.
Corrected Notice of Allowance received for U.S. Appl. No. 16/418,786, mailed on Jun. 23, 2022, 2 pages.
Corrected Notice of Allowance received for U.S. Appl. No. 16/820,383, mailed on Apr. 28, 2023, 2 pages.
Corrected Notice of Allowance received for U.S. Appl. No. 16/820,383, mailed on Aug. 13, 2021, 2 pages.
Corrected Notice of Allowance received for U.S. Appl. No. 16/820,383, mailed on Aug. 19, 2021, 2 pages.
Corrected Notice of Allowance received for U.S. Appl. No. 16/820,383, mailed on Oct. 5, 2021, 2 pages.
Corrected Notice of Allowance received for U.S. Appl. No. 16/888,629, mailed on Jan. 21, 2022, 2 pages.
Corrected Notice of Allowance received for U.S. Appl. No. 16/987,275, mailed on Jun. 8, 2022, 3 pages.
Corrected Notice of Allowance received for U.S. Appl. No. 17/030,318, mailed on Jan. 24, 2022, 2 pages.
Corrected Notice of Allowance received for U.S. Appl. No. 17/030,318, mailed on Jun. 1, 2023, 3 pages.
Corrected Notice of Allowance received for U.S. Appl. No. 17/030,321, mailed on Aug. 15, 2022, 3 pages.
Corrected Notice of Allowance received for U.S. Appl. No. 17/030,337, mailed on Aug. 31, 2022, 2 pages.
Corrected Notice of Allowance received for U.S. Appl. No. 17/030,337, mailed on Feb. 10, 2023, 2 pages.
Corrected Notice of Allowance received for U.S. Appl. No. 17/030,337, mailed on Feb. 17, 2023, 2 pages.
Corrected Notice of Allowance received for U.S. Appl. No. 17/030,337, mailed on Nov. 3, 2022, 2 pages.
Corrected Notice of Allowance received for U.S. Appl. No. 17/030,337, mailed on Nov. 15, 2022, 2 pages.
Corrected Notice of Allowance received for U.S. Appl. No. 17/030,337, mailed on Oct. 18, 2022, 2 pages.
Corrected Notice of Allowance received for U.S. Appl. No. 17/030,337, mailed on Sep. 21, 2022, 2 pages.
Corrected Notice of Allowance received for U.S. Appl. No. 17/031,543, mailed on Aug. 22, 2022, 2 pages.
Corrected Notice of Allowance received for U.S. Appl. No. 17/031,543, mailed on Jul. 18, 2022, 2 pages.
Corrected Notice of Allowance received for U.S. Appl. No. 17/031,543, mailed on Jun. 8, 2022, 3 pages.
Corrected Notice of Allowance received for U.S. Appl. No. 17/157,728, mailed on Apr. 4, 2022, 3 pages.
Corrected Notice of Allowance received for U.S. Appl. No. 17/157,728, mailed on Apr. 14, 2022, 6 pages.

(56) References Cited

OTHER PUBLICATIONS

Corrected Notice of Allowance received for U.S. Appl. No. 17/192,161, mailed on Apr. 22, 2022, 2 pages.
Corrected Notice of Allowance received for U.S. Appl. No. 17/192,161, mailed on Mar. 23, 2022, 2 pages.
Corrected Notice of Allowance received for U.S. Appl. No. 17/197,628, mailed on Apr. 27, 2022, 3 pages.
Corrected Notice of Allowance received for U.S. Appl. No. 17/197,628, mailed on Jul. 29, 2022, 2 pages.
CycleSpeed Tours, "The Most Useful Data Fields to Display on Your Garmin", Online Available at: https://www.youtube.com/watch?v=AN0Eo50yxdg, Nov. 16, 2016, 3 pages.
DC Rainmaker, "Garmin Fenix3 New Auto Climb Functionality". Available online at: https://www.youtube.com/watch?v=iuavOSNpVRc, Feb. 19, 2015, 1 page.
Decision of Appeal received for European Patent Application No. 15771747.1, mailed on Dec. 14, 2021, 21 pages.
Decision on Appeal received for Korean Patent Application No. 10-2019-7025538, mailed on Feb. 24, 2021, 20 pages (4 pages of English Translation and 16 pages of Official Copy).
Decision to Grant received for Danish Patent Application No. PA201670656, mailed on Jun. 21, 2021, 2 pages.
Decision to Grant received for Danish Patent Application No. PA201870379, mailed on Jul. 5, 2019, 2 pages.
Decision to Grant received for Danish Patent Application No. PA202070614, mailed on Nov. 10, 2022, 2 pages.
Decision to Grant received for Danish Patent Application No. PA202070615, mailed on Jul. 29, 2022, 2 pages.
Decision to Grant received for Danish Patent Application No. PA202070815, mailed on Dec. 23, 2022, 1 page.
Decision to Grant received for European Patent Application No. 20182116.2, mailed on Mar. 23, 2023, 3 pages.
Decision to Grant received for German Patent Application No. 112015002326.7, mailed on Jun. 15, 2021, 10 pages (1 page of English Translation and 9 pages of Official Copy).
Decision to Refuse received for European Patent Application No. 13811085.3, mailed on Sep. 11, 2018, 21 pages.
Decision to Refuse received for European Patent Application No. 15771747.1, mailed on Aug. 10, 2018, 22 pages.
Decision to Refuse received for European Patent Application No. 17810749.6, mailed on Jan. 29, 2021, 24 pages.
Decision to Refuse received for European Patent Application No. 18154145.9, mailed on Feb. 17, 2021, 20 pages.
Decision to Refuse received for European Patent Application No. 20721342.2, mailed on Nov. 10, 2022, 14 pages.
dwProgressBar v2: Stepping and Events, davidwalsh.name/dwprogressbar-2-stepping-events-mootools-progress-bar, retrieved from the Wayback Machine, Aug. 31, 2008, 4 pages.
European Search Report received for European Patent Application No. 20182116.2, mailed on Oct. 21, 2020, 4 pages.
European Search Report received for European Patent Application No. 21165295.3, mailed on Jun. 18, 2021, 4 pages.
European Search Report received for European Patent Application No. 21168916.1, mailed on Jul. 14, 2021, 5 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 16837432.0, mailed on Mar. 11, 2019, 10 pages.
Extended European Search Report received for European Patent Application No. 18154145.9, mailed on Mar. 2, 2018, 8 pages.
Extended European Search Report received for European Patent Application No. 20203526.7, mailed on Jan. 29, 2021, 13 pages.
Extended European Search Report received for European Patent Application No. 22194355.8, mailed on Dec. 23, 2022, 10 pages.
Extended European Search Report received for European Patent Application No. 23150297.2, mailed on Mar. 28, 2023, 8 pages.
Extended European Search Report received for European Patent Application No. 23153898.4, mailed on May 4, 2023, 11 pages.
Extended European Search Report received for European Patent Application No. 23153899.2, mailed on May 4, 2023, 10 pages.
Extended European Search Report received for European Patent Application No. 23153900.8, mailed on May 4, 2023, 10 pages.
Final Office Action received for U.S. Appl. No. 16/994,352, mailed on Dec. 6, 2021, 14 pages.
Final Office Action received for U.S. Appl. No. 12/205,847, mailed on Apr. 25, 2012, 42 pages.
Final Office Action received for U.S. Appl. No. 14/732,773, mailed on Jul. 13, 2018, 48 pages.
Final Office Action received for U.S. Appl. No. 14/732,773, mailed on Jun. 21, 2019, 32 pages.
Final Office Action received for U.S. Appl. No. 14/839,922, mailed on Dec. 14, 2016, 22 pages.
Final Office Action received for U.S. Appl. No. 15/608,848, mailed on Aug. 21, 2020, 15 pages.
Final Office Action received for U.S. Appl. No. 15/608,848, mailed on Jun. 26, 2019, 27 pages.
Final Office Action received for U.S. Appl. No. 15/627,069, mailed on Mar. 2, 2020, 22 pages.
Final Office Action received for U.S. Appl. No. 15/627,069, mailed on Oct. 20, 2020, 25 pages.
Final Office Action received for U.S. Appl. No. 15/705,849, mailed on May 1, 2020, 17 pages.
Final Office Action received for U.S. Appl. No. 15/925,652, mailed on Aug. 1, 2019, 30 Pages.
Final Office Action received for U.S. Appl. No. 16/138,809, mailed on Aug. 27, 2020, 24 pages.
Final Office Action received for U.S. Appl. No. 16/144,735, mailed on May 4, 2020, 12 pages.
Final Office Action received for U.S. Appl. No. 16/144,753, mailed on Sep. 22, 2020, 9 pages.
Final Office Action received for U.S. Appl. No. 16/144,849, mailed on Jun. 7, 2019, 29 pages.
Final Office Action received for U.S. Appl. No. 16/144,864, mailed on May 17, 2019, 24 pages.
Final Office Action received for U.S. Appl. No. 16/144,864, mailed on May 28, 2020, 29 pages.
Final Office Action received for U.S. Appl. No. 16/377,892, mailed on Jan. 28, 2021, 11 pages.
Final Office Action received for U.S. Appl. No. 16/378,136, mailed on Jan. 28, 2021, 9 pages.
Final Office Action received for U.S. Appl. No. 16/418,786, mailed on Jan. 13, 2021, 14 pages.
Final Office Action received for U.S. Appl. No. 16/820,383, mailed on Jun. 22, 2022, 21 pages.
Final Office Action received for U.S. Appl. No. 16/894,309, mailed on Feb. 24, 2021, 30 pages.
Final Office Action received for U.S. Appl. No. 17/030,318, mailed on Nov. 28, 2022, 13 pages.
Final Office Action received for U.S. Appl. No. 17/030,318, mailed on Sep. 30, 2021, 28 pages.
Final Office Action received for U.S. Appl. No. 17/030,321, mailed on Apr. 2, 2021, 28 pages.
Final Office Action received for U.S. Appl. No. 17/031,854, mailed on Feb. 23, 2023, 19 pages.
Final Office Action received for U.S. Appl. No. 17/031,854, mailed on Jun. 10, 2022, 15 pages.
Final Office Action received for U.S. Appl. No. 17/031,859, mailed on Apr. 16. 2021, 14 pages.
Final Office Action received for U.S. Appl. No. 17/031,859, mailed on Feb. 8, 2023, 15 pages.
Final Office Action received for U.S. Appl. No. 17/031,859, mailed on Jun. 10, 2022, 13 pages.
Final Office Action received for U.S. Appl. No. 17/031,874, mailed on Apr. 16. 2021, 17 pages.
Final Office Action received for U.S. Appl. No. 17/031,874, mailed on Jun. 2, 2022, 19 pages.
Final Office Action received for U.S. Appl. No. 17/031,874, mailed on Mar. 17, 2023, 24 pages.
Final Office Action received for U.S. Appl. No. 17/192,161, mailed on Aug. 16, 2021, 22 pages.

(56) References Cited

OTHER PUBLICATIONS

Final Office Action received for U.S. Appl. No. 17/192,161, mailed on Oct. 18, 2021, 22 pages.
Final Office Action received for U.S. Appl. No. 17/381,570, mailed on Feb. 10, 2023, 22 pages.
Final Office Action received for U.S. Appl. No. 17/381,570, mailed on Jul. 20, 2022, 22 pages.
Final Office Action received for U.S. Appl. No. 17/516,537, mailed on Oct. 11, 2022, 9 pages.
Final Office Action received for U.S. Appl. No. 17/591,184, mailed on Dec. 23, 2022, 10 pages.
Final Office Action received for U.S. Appl. No. 17/735,395, mailed on May 17, 2023, 31 pages.
Final Office Action received for U.S. Appl. No. 17/951,875, mailed on May 30, 2023, 12 pages.
Final Office Action received for U.S. Appl. No. 17/951,945, mailed on May 18, 2023. 18 pages.
Fitbit App, Available online at: <http://web.archive.org/web/20180114083150/https://www.fitbit.com/au/app>, Jan. 14, 2018, 8 pages.
Garmin Edge 520, Owner's Manual, Online available at: https://www8.garmin.com/manuals/webhelp/edge520/EN-US/Edge_520_OM_EN-US.pdf. 2015, 24 pages.
Garmin, "EDGE 520 Plus Owner's Manual", Online Available at: https://www8.garmin.com/manuals/webhelp/edge520plus/EN-US/Edge_520_Plus_OM_EN-US.pdf, 2018, 30 pages.
Garmin, "Fenix 5x Owner's Manual", Online Available at: https://web.archive.org/web/20180127170640/https://static.garmin.com/pumac/fenix5x_OM_EN.pdf, Jan. 27, 2018, 42 pages.
Gpscity, "Garmin Connect 2.0 Overview with GPS City", Available online at: https://www.youtube.com/watch?v=EJ6U10y_8y0, Feb. 28, 2014, 8 pages.
Graphs and Charts, Online available at: <https://www.teachervision.com/lesson-planning/graph-chart-teacher-resources, retrieved on Dec. 12, 2018, 4 pages.
Gym Book—Strength Training Planner, Logger and Analyzer, GymBookApp, Available Online at: https://web.archive.org/web/20160401104508/https://gymbookapp.com/, Apr. 1, 2016, 10 pages.
Hamilton Jim, "Peloton Tips", Online available on: <https://www.youtube.com/watch?app=desktop&v=OneXtB0kaD4>, Oct. 22, 2015, 3 pages.
Heinrich Peter, "More Player Engagement Potential: GameCircle Now Rewards Player Experience across Games", Available online at: https://www.developer.amazon.com/es-mx/blogs/home/tag/badges, Apr. 11, 2014, 9 pages.
Intention to Grant received for Danish Patent Application No. PA201570668, mailed on Mar. 27, 2017, 2 pages.
Intention to Grant received for Danish Patent Application No. PA201670656, mailed on Jan. 18, 2021, 2 pages.
Intention to Grant received for Danish Patent Application No. PA201870379, mailed on May 2, 2019, 2 pages.
Intention to Grant received for Danish Patent Application No. PA202070614, mailed on Aug. 8, 2022, 2 pages.
Intention to Grant received for Danish Patent Application No. PA202070615, mailed on Jan. 27, 2022, 2 pages.
Intention to Grant received for Danish Patent Application No. PA202070815, mailed on Sep. 13, 2022, 2 pages.
Intention to Grant received for European Patent Application No. 16837432.0, mailed on Apr. 14, 2023, 8 pages.
Intention to Grant received for European Patent Application No. 18727543.3, mailed on Apr. 12, 2023, 9 pages.
Intention to Grant received for European Patent Application No. 19721883.7, mailed on May 11, 2023, 9 pages.
Intention to Grant received for European Patent Application No. 20182116.2, mailed on Jun. 2, 2022, 8 pages.
Intention to Grant received for European Patent Application No. 20182116.2, mailed on Nov. 11, 2022, 9 pages.
Intention to Grant received for European Patent Application No. 20203526.7, mailed on Feb. 10, 2023, 9 pages.
International Preliminary Report on Patentability received for PCT Application No. PCT/US2016/037686, mailed on Mar. 1, 2018, 12 pages.
International Preliminary Report on Patentability received for PCT Patent Application No. PCT/US2020/035199, mailed on Dec. 16, 2021, 14 pages.
International Preliminary Report on Patentability received for PCT Patent Application No. PCT/US2013/073195, mailed on Jun. 16, 2016, 10 pages.
International Preliminary Report on Patentability received for PCT Patent Application No. PCT/US2015/047282, mailed on Mar. 16, 2017, 26 pages.
International Preliminary Report on Patentability received for PCT Patent Application No. PCT/US2017/035554, mailed on Dec. 20, 2018, 39 pages.
International Preliminary Report on Patentability received for PCT Patent Application No. PCT/US2018/031662, mailed on Nov. 28, 2019, 12 pages.
International Preliminary Report on Patentability received for PCT Patent Application No. PCT/US2019/024570, mailed on Nov. 19, 2020, 10 pages.
International Preliminary Report on Patentability received for PCT Patent Application No. PCT/US2020/025997, mailed on Nov. 18, 2021, 10 pages.
International Preliminary Report on Patentability received for PCT Patent Application No. PCT/US2021/017736, mailed on Aug. 25, 2022, 19 pages.
International Search Report and Written Opinion received for PCT Patent Application No. PCT/US2015/047282, mailed on May 9, 2016, 33 pages.
International Search Report and Written Opinion received for PCT Patent Application No. PCT/US2016/037686, mailed on Sep. 9, 2016, 19 pages.
International Search Report and Written Opinion received for PCT Patent Application No. PCT/US2017/035554, mailed on Sep. 22, 2017, 42 pages.
International Search Report and Written Opinion received for PCT Patent Application No. PCT/US2018/031662, mailed on Sep. 27, 2018, 17 pages.
International Search Report and Written Opinion received for PCT Patent Application No. PCT/US2019/024570, mailed on Aug. 8, 2019, 18 pages.
International Search Report and written Opinion received for PCT Patent Application No. PCT/US2020/025997, mailed on Jul. 1, 2020, 16 pages.
International Search Report and Written Opinion received for PCT Patent Application No. PCT/US2020/025997, mailed on Jul. 14, 2020, 15 pages.
International Search Report and Written Opinion received for PCT Patent Application No. PCT/US2020/035199, mailed on Oct. 30, 2020, 20 pages.
International Search Report and Written Opinion received for PCT Patent Application No. PCT/US2021/017736, mailed on Sep. 2, 2021, 25 pages.
International Search Report and Written Opinion received for PCT Patent Application No. PCT/US2022/029297, mailed on Aug. 11, 2022, 13 pages.
International Search Report received for PCT Patent Application No. PCT/US2013/073195, mailed on Jun. 23, 2014, 3 pages.
International Written Opinion received for PCT Patent Application No. PCT/US2013/073195, mailed on Jun. 23, 2014, 8 pages.
Invitation to Pay Addition Fees and Partial International Search Report received for PCT Patent Application No. PCT/US2018/031662, mailed on Jul. 16, 2018, 13 pages.
Invitation to Pay Additional Fees received for PCT Patent Application No. PCT/US2015/047282, mailed on Dec. 22, 2015, 7 pages.
Invitation to Pay Additional Fees received for PCT Patent Application No. PCT/US2017/035554, mailed on Jul. 20, 2017, 2 pages.
Invitation to Pay Additional Fees received for PCT Patent Application No. PCT/US2020/035199, mailed on Sep. 8, 2020, 12 pages.
Invitation to Pay Additional Fees received for PCT Patent Application No. PCT/US2021/017736, mailed on Jun. 15, 2021, 14 pages.

(56) References Cited

OTHER PUBLICATIONS

Jenbsjourney, "Wondering About a Fitbit?", Available at: https://jenbsjourney.blogspot.kr/2013/08/wondering-about-fitbit.html, Aug. 6, 2013, 12 pages.

Li-Yu et al., "Influence of exercise prescription on body composition of college students", Clinical Rehabilitation in China, vol. 9 Issue 24, Jun. 28, 2005, pp. 147-149. (Official Copy only). {See Communication Under 37 CFR § 1.98(a) (3)}.

Minutes of Oral Proceedings received for European Patent Application No. 13811085.3, mailed on Sep. 11, 2018, 3 pages.

Minutes of Oral Proceedings received for European Patent Application No. 15771747.1, mailed on Aug. 10, 2018, 11 pages.

Minutes of Oral Proceedings received for European Patent Application No. 20721342.2, mailed on Nov. 8, 2022, 5 pages.

Minutes of the Oral Proceedings received for European Patent Application No. 15771747.1, mailed on Dec. 1, 2021, 4 pages.

Minutes of the Oral Proceedings received for European Patent Application No. 17810749.6, mailed on Jan. 26, 2021, 8 pages.

Minutes of the Oral Proceedings received for European Patent Application No. 18154145.9, mailed on Feb. 12, 2021, 8 pages.

Minutes of the Oral Proceedings received for European Patent Application No. 20182116.2, mailed on May 24, 2022, 7 pages.

Mugs, Online Available at: https://web.archive.org/web/20151029034349/http://le-mugs.com/, Oct. 29, 2015, 14 pages.

Multi-Set Bar Chart, The Data Visualization Catalogue, Available Online at: https://datavizcatalogue.com/methods/multiset_barchart.html, Feb. 8, 2014, 3 pages.

My CalStep, http://www.surprisesoftware.com/mycalstep/, retrieved from the Wayback Machine, May 9, 2007, 2 pages.

Nakasuji Yoshito, "Apple Watch", First Edition 1st Printing, Japan, Incorporated Company Technical Hyoronsha, Jun. 15, 2015, 4 pages (Official copy only). {See Communication Under 37 CFR § 1.98(a) (3)}.

Non-Final Office Action received for U.S. Appl. No. 14/839,916, mailed on Feb. 4, 2016, 19 pages.

Non-Final Office Action received for U.S. Appl. No. 14/839,922, mailed on Feb. 25, 2016, 20 pages.

Non-Final Office Action Received for U.S. Appl. No. 16/144,864, mailed on Dec. 18, 2018, 19 pages.

Non-Final Office Action received for U.S. Appl. No. 16/994,352, mailed on Jul. 30, 2021, 11 pages.

Non-Final Office Action received for U.S. Appl. No. 12/205,847, mailed on Oct. 3, 2011, 59 pages.

Non-Final Office Action received for U.S. Appl. No. 14/732,773, mailed on Feb. 8, 2019, 32 pages.

Non-Final Office Action received for U.S. Appl. No. 14/732,773, mailed on Jan. 19, 2018., 45 pages.

Non-Final Office Action received for U.S. Appl. No. 14/839,916, mailed on May 1, 2017, 18 pages.

Non-Final Office Action received for U.S. Appl. No. 14/839,922, mailed on Aug. 17, 2016, 25 pages.

Non-Final Office Action received for U.S. Appl. No. 15/183,663, mailed on Jul. 9, 2018, 13 pages.

Non-Final Office Action received for U.S. Appl. No. 15/600,243, mailed on Jun. 27, 2019, 17 Pages.

Non-Final Office Action received for U.S. Appl. No. 15/608,848, mailed on Feb. 6, 2020, 12 pages.

Non-Final Office Action received for U.S. Appl. No. 15/608,848, mailed on Feb. 12, 2021, 14 pages.

Non-Final Office Action received for U.S. Appl. No. 15/608,848, mailed on Nov. 2, 2018, 21 pages.

Non-Final Office Action received for U.S. Appl. No. 15/627,069, mailed on Jun. 21, 2019, 22 pages.

Non-Final Office Action received for U.S. Appl. No. 15/627,069, mailed on May 26, 2020, 25 pages.

Non-Final Office Action received for U.S. Appl. No. 15/705,849, mailed on Nov. 12, 2019, 15 pages.

Non-Final Office Action received for U.S. Appl. No. 15/925,652, mailed on Apr. 5, 2019, 28 pages.

Non-Final Office Action received for U.S. Appl. No. 15/925,652, mailed on Aug. 7, 2020, 39 pages.

Non-Final Office Action received for U.S. Appl. No. 16/138,809, mailed on Feb. 28, 2020, 22 pages.

Non-Final Office Action received for U.S. Appl. No. 16/144,735, mailed on Feb. 19, 2020, 10 pages.

Non-Final Office Action received for U.S. Appl. No. 16/144,753, mailed on Mar. 5, 2020, 9 pages.

Non-Final Office Action received for U.S. Appl. No. 16/144,849, mailed on Dec. 31, 2018, 28 pages.

Non-Final Office Action received for U.S. Appl. No. 16/144,849, mailed on Sep. 17, 2019, 9 pages.

Non-Final Office Action received for U.S. Appl. No. 16/144,864, mailed on Jan. 31, 2020, 29 pages.

Non-Final Office Action received for U.S. Appl. No. 16/377,892, mailed on May 21, 2020, 9 pages.

Non-Final Office Action received for U.S. Appl. No. 16/378,136, mailed on Jun. 2, 2020, 8 pages.

Non-Final Office Action received for U.S. Appl. No. 16/418,786, mailed on Apr. 24, 2020, 16 pages.

Non-Final Office Action received for U.S. Appl. No. 16/418,786, mailed on Aug. 1, 2022, 18 pages.

Non-Final Office Action received for U.S. Appl. No. 16/418,786, mailed on Mar. 28, 2022, 14 pages.

Non-Final Office Action received for U.S. Appl. No. 16/418,786, mailed on Oct. 4, 2021, 10 pages.

Non-Final Office Action received for U.S. Appl. No. 16/820,383, mailed on Dec. 14, 2020, 11 pages.

Non-Final Office Action received for U.S. Appl. No. 16/820,383, mailed on Jan. 10, 2022, 18 pages.

Non-Final Office Action received for U.S. Appl. No. 16/888,629, mailed on Mar. 31, 2021, 14 pages.

Non-Final Office Action received for U.S. Appl. No. 16/894,309, mailed on Oct. 15, 2020, 24 pages.

Non-Final Office Action received for U.S. Appl. No. 16/987,275, mailed on Nov. 23, 2021, 17 pages.

Non-Final Office Action received for U.S. Appl. No. 17/030,318, mailed on Apr. 2, 2021, 28 pages.

Non-Final Office Action received for U.S. Appl. No. 17/030,318, mailed on Dec. 3, 2020, 22 pages.

Non-Final Office Action received for U.S. Appl. No. 17/030,318, mailed on Jun. 14, 2022, 9 pages.

Non-Final Office Action received for U.S. Appl. No. 17/030,321, mailed on Dec. 15, 2020, 25 pages.

Non-Final Office Action received for U.S. Appl. No. 17/030,321, mailed on Oct. 18, 2021, 28 pages.

Non-Final Office Action received for U.S. Appl. No. 17/030,337, mailed on Jun. 14, 2022, 13 pages.

Non-Final Office Action received for U.S. Appl. No. 17/030,340, mailed on Jun. 14, 2022, 15 pages.

Non-Final Office Action received for U.S. Appl. No. 17/031,543, mailed on Apr. 1, 2022, 9 pages.

Non-Final Office Action received for U.S. Appl. No. 17/031,854, mailed on Dec. 27, 2021, 13 pages.

Non-Final Office Action received for U.S. Appl. No. 17/031,854, mailed on Sep. 26, 2022, 17 pages.

Non-Final Office Action received for U.S. Appl. No. 17/031,859, mailed on Dec. 15, 2020, 13 pages.

Non-Final Office Action received for U.S. Appl. No. 17/031,859, mailed on Dec. 24, 2021, 16 pages.

Non-Final Office Action received for U.S. Appl. No. 17/031,859, mailed on Sep. 12, 2022, 17 pages.

Non-Final Office Action received for U.S. Appl. No. 17/031,874, mailed on Dec. 28, 2020, 14 pages.

Non-Final Office Action received for U.S. Appl. No. 17/031,874, mailed on Jan. 24, 2022, 18 pages.

Non-Final Office Action received for U.S. Appl. No. 17/031,874, mailed on Oct. 4, 2022, 20 pages.

Non-Final Office Action received for U.S. Appl. No. 17/041,438, mailed on May 25, 2023, 47 pages.

Non-Final Office Action received for U.S. Appl. No. 17/157,728, mailed on Nov. 26, 2021, 18 pages.

(56) References Cited

OTHER PUBLICATIONS

Non-Final Office Action received for U.S. Appl. No. 17/192,161, mailed on May 13, 2021, 28 pages.
Non-Final Office Action received for U.S. Appl. No. 17/381,570, mailed on Apr. 1, 2022, 29 pages.
Non-Final Office Action received for U.S. Appl. No. 17/381,570, mailed on Sep. 28, 2022, 20 pages.
Non-Final Office Action received for U.S. Appl. No. 17/516,537, mailed on May 5, 2022, 8 pages.
Non-Final Office Action received for U.S. Appl. No. 17/566,521, mailed on May 15, 2023, 12 pages.
Non-Final Office Action received for U.S. Appl. No. 17/591,184, mailed on Apr. 21, 2023, 15 pages.
Non-Final Office Action received for U.S. Appl. No. 17/591,184, mailed on Aug. 4, 2022, 18 pages.
Non-Final Office Action received for U.S. Appl. No. 17/666,301, mailed on Feb. 16, 2023, 24 pages.
Non-Final Office Action received for U.S. Appl. No. 17/735,395, mailed on Feb. 10, 2023, 28 pages.
Non-Final Office Action received for U.S. Appl. No. 17/744,500, mailed on Apr. 19, 2023, 30 pages.
Non-Final Office Action received for U.S. Appl. No. 17/892,534, mailed on Dec. 19, 2022, 20 pages.
Non-Final Office Action received for U.S. Appl. No. 17/892,534, mailed on May 10, 2023, 17 pages.
Non-Final Office Action received for U.S. Appl. No. 17/951,875, mailed on Jan. 23, 2023, 12 pages.
Non-Final Office Action received for U.S. Appl. No. 17/951,945, mailed on Mar. 24, 2023, 14 pages.
Non-Final Office Action received for U.S. Appl. No. 17/952,027, mailed on Apr. 28, 2023, 46 pages.
Non-Final Office Action received for U.S. Appl. No. 17/952,133, mailed on Jun. 2, 2023, 28 pages.
Notice of Acceptance received for Australian Patent Application No. 2015312215, mailed on Oct. 9, 2017, 3 pages.
Notice of Acceptance received for Australian Patent Application No. 2017277971, mailed on Feb. 17, 2021, 3 pages.
Notice of Acceptance received for Australian Patent Application No. 2018268972, mailed on Dec. 18, 2020, 3 pages.
Notice of Acceptance received for Australian Patent Application No. 2019201583, mailed on Jul. 15, 2019, 3 pages.
Notice of Acceptance received for Australian Patent Application No. 2019222943, mailed on May 5, 2020, 3 pages.
Notice of Acceptance received for Australian Patent Application No. 2019250251, mailed on Feb. 18, 2021, 3 pages.
Notice of Acceptance received for Australian Patent Application No. 2020204153, mailed on Jul. 6, 2020, 3 pages.
Notice of Acceptance received for Australian Patent Application No. 2020239743, mailed on Jan. 13, 2022, 3 pages.
Notice of Acceptance received for Australian Patent Application No. 2020239752, mailed on Jan. 31, 2022, 3 pages.
Notice of Acceptance received for Australian Patent Application No. 2020256383, mailed on Aug. 3, 2021, 3 pages.
Notice of Acceptance received for Australian Patent Application No. 2020288139, mailed on Feb. 2, 2023, 3 pages.
Notice of Acceptance received for Australian Patent Application No. 2021200787, mailed on Mar. 19, 2021, 3 pages.
Notice of Acceptance received for Australian Patent Application No. 2021201130, mailed on Mar. 28, 2022, 3 pages.
Notice of Acceptance received for Australian Patent Application No. 2021203636, mailed on Apr. 14, 2022, 3 pages.
Notice of Acceptance received for Australian Patent Application No. 2021204422, mailed on Aug. 15, 2022, 3 pages.
Notice of Acceptance received for Australian Patent Application No. 2021266294, mailed on Mar. 3, 2023, 3 pages.
Notice of Acceptance received for Australian Patent Application No. 2022209277, mailed on Apr. 28, 2023, 3 pages.
Notice of Allowance received for Australian Patent Application No. 2020256383, mailed on Mar. 7, 2022, 3 pages.
Notice of Allowance received for Chinese Patent Application No. 201380081349.6, mailed on Dec. 17, 2021, 2 pages (1 page of English Translation and 1 page of Official Copy).
Notice of Allowance received for Chinese Patent Application No. 201580037927.5, mailed on Oct. 17, 2019, 3 pages (1 page of English Translation and 2 pages of Official Copy).
Notice of Allowance received for Chinese Patent Application No. 201680047983.1, mailed on Apr. 28, 2021, 3 pages (1 page of English Translation and 2 pages of Official Copy).
Notice of Allowance received for Chinese Patent Application No. 201710439448.7, mailed on Jan. 26, 2021, 2 pages (1 page of English Translation and 1 page of Official Copy).
Notice of Allowance received for Chinese Patent Application No. 201780034203.4, mailed on Jan. 17, 2022, 2 pages (1 page of English Translation and 1 page of Official Copy).
Notice of Allowance received for Chinese Patent Application No. 201810105846.X, mailed on Feb. 18, 2020, 2 pages (1 page of English Translation and 1 page of Official Copy).
Notice of Allowance received for Chinese Patent Application No. 201911401161.0, mailed on Apr. 24, 2023, 11 pages (5 pages of English Translation and 6 pages of Official Copy).
Notice of Allowance received for Chinese Patent Application No. 202010606407.4, mailed on Jan. 24, 2022, 2 pages (1 page of English Translation and 1 page of Official Copy).
Notice of Allowance received for Chinese Patent Application No. 202210238202.4, mailed on Jan. 13, 2023, 7 pages (3 pages of English Translation and 4 pages of Official Copy).
Notice of Allowance received for Danish Patent Application No. PA201570666, mailed on Sep. 15, 2016, 1 page.
Notice of Allowance received for Danish Patent Application No. PA201570668, mailed on Oct. 30, 2017, 2 pages.
Notice of Allowance received for Japanese Patent Application No. 2016-535045, mailed on Mar. 2, 2018, 4 pages (1 page of English Translation and 3 pages of Official Copy).
Notice of Allowance received for Japanese Patent Application No. 2016-557650, mailed on Apr. 9, 2019, 4 pages (1 page of English Translation and 3 pages of Official Copy).
Notice of Allowance received for Japanese Patent Application No. 2018-014096, mailed on Jan. 5, 2021, 3 pages (1 page of English Translation and 2 pages of Official Copy).
Notice of Allowance received for Japanese Patent Application No. 2018-068846, mailed on Dec. 9, 2019, 4 pages (1 page of English Translation and 3 pages of Official Copy).
Notice of Allowance received for Japanese Patent Application No. 2018-184532, mailed on Jan. 17, 2022, 4 pages (1 page of English Translation and 3 pages of Official Copy).
Notice of Allowance received for Japanese Patent Application No. 2019-044107, mailed on Jul. 11, 2022, 31 pages (1 page of English Translation and 30 pages of Official Copy).
Notice of Allowance received for Japanese Patent Application No. 2019-162293, mailed on Apr. 9, 2021, 4 pages (1 page of English Translation and 3 pages of Official Copy).
Notice of Allowance received for Japanese Patent Application No. 2019-563407, mailed on Aug. 20, 2021, 4 pages (1 page of English Translation and 3 pages of Official Copy).
Notice of Allowance received for Japanese Patent Application No. 2020-000492, mailed on Jul. 16, 2021, 4 pages (1 page of English Translation and 3 pages of Official Copy).
Notice of Allowance received for Japanese Patent Application No. 2020-104679, mailed on Jan. 4, 2021, 4 pages (1 page of English Translation and 3 pages of Official Copy).
Notice of Allowance received for Japanese Patent Application No. 2020-115940, mailed on Oct. 22, 2021, 4 pages (1 page of English Translation and 3 pages of Official Copy).
Notice of Allowance received for Japanese Patent Application No. 2020-160052, mailed on Jun. 3, 2022, 4 pages (1 page of English Translation and 3 pages of Official Copy).
Notice of Allowance received for Japanese Patent Application No. 2020-160053, mailed on Jan. 16, 2023, 4 pages (1 page of English Translation and 3 pages of Official Copy).
Notice of Allowance received for Japanese Patent Application No. 2020-160054, mailed on Apr. 4, 2022, 4 pages (1 page of English Translation and 3 pages of Official Copy).

(56) References Cited

OTHER PUBLICATIONS

Notice of Allowance received for Japanese Patent Application No. 2021-131726, mailed on Mar. 17, 2023, 4 pages (1 page of English Translation and 3 pages of Official Copy).
Notice of Allowance received for Japanese Patent Application No. 2021-188824, mailed on Feb. 13, 2023, 4 pages (1 page of English Translation and 3 pages of Official Copy).
Notice of Allowance received for Japanese Patent Application No. 2021-571468, mailed on May 19, 2023, 4 pages (1 page of English Translation and 3 pages of Official Copy).
Notice of Allowance received for Japanese Patent Application No. 2022-107902, mailed on Aug. 26, 2022, 4 pages (1 page of English Translation and 3 pages of Official Copy).
Notice of Allowance received for Korean Patent Application No. 10-2016-7014577, mailed on May 30, 2019, 5 pages (2 pages of English Translation and 3 pages of Official Copy).
Notice of Allowance received for Korean Patent Application No. 10-2016-7033638, issued on May 31, 2017, 5 pages (2 pages of English Translation and 3 pages of Official Copy).
Notice of Allowance received for Korean Patent Application No. 10-2019-7025538, mailed on Mar. 10, 2021, 5 pages (2 pages of English Translation and 3 pages of Official Copy).
Notice of Allowance received for Korean Patent Application No. 10-2019-7025781, mailed on Jun. 29, 2021, 5 pages (2 pages of English Translation and 3 pages of Official Copy).
Notice of Allowance received for Korean Patent Application No. 10-2019-7033834, mailed on Jul. 3, 2021, 4 pages (2 pages of English Translation and 2 pages of Official Copy).
Notice of Allowance received for Korean Patent Application No. 10-2020-0123815, mailed on Aug. 26, 2022, 7 pages (2 pages of English Translation and 5 pages of Official Copy).
Notice of Allowance received for Korean Patent Application No. 10-2020-0123821, mailed on Mar. 28, 2023, 8 pages (2 pages of English Translation and 6 pages of Official Copy).
Notice of Allowance received for Korean Patent Application No. 10-2020-7026035, mailed on Aug. 23, 2021, 4 pages (2 pages of English Translation and 2 pages of Official Copy).
Notice of Allowance received for Korean Patent Application No. 10-2021-7026284, mailed on Jul. 28, 2022, 6 pages (2 pages of English Translation and 4 pages of Official Copy).
Notice of Allowance received for Korean Patent Application No. 10-2021-7031939, mailed on Apr. 5, 2022, 4 pages (1 page of English Translation and 3 pages of Official Copy).
Notice of Allowance received for Korean Patent Application No. 10-2021-7038005, mailed on Dec. 14, 2021, 4 pages (2 pages of English Translation and 2 pages of Official Copy).
Notice of Allowance received for Korean Patent Application No. 10-2022-0061486, mailed on Nov. 22, 2022, 7 pages (2 pages of English Translation and 5 pages of Official Copy).
Notice of Allowance received for Korean Patent Application No. 10-2022-7008569, mailed on May 19, 2022, 5 pages (2 pages of English Translation and 3 pages of Official Copy).
Notice of Allowance received for Korean Patent Application No. 10-2022-7017918, mailed on Jun. 13, 2022, 6 pages (2 pages of English Translation and 4 pages of Official Copy).
Notice of Allowance received for Korean Patent Application No. 10-2022-7031866, mailed on May 1, 2023, 7 pages (2 pages of English Translation and 5 pages of Official Copy).
Notice of Allowance received for Korean Patent Application No. 10-2023-0023706, mailed on Mar. 27, 2023, 8 pages (2 pages of English Translation and 6 pages of Official Copy).
Notice of Allowance received for Taiwanese Application No. 104128685, mailed on May 3, 2017, 3 pages (Official Copy only). {See Communication Under 37 § 1.98(a) (3)}.
Notice of Allowance received for U.S. Appl. No. 12/205,847, mailed on Aug. 20, 2012, 13 pages.
Notice of Allowance received for U.S. Appl. No. 14/732,773, mailed on Dec. 18, 2019, 21 pages.
Notice of Allowance received for U.S. Appl. No. 14/839,916, mailed on Aug. 31, 2016, 11 pages.
Notice of Allowance received for U.S. Appl. No. 14/839,916, mailed on Jan. 10, 2018, 19 pages.
Notice of Allowance received for U.S. Appl. No. 14/839,922, mailed on Jan. 26, 2018, 2 pages.
Notice of Allowance received for U.S. Appl. No. 14/839,922, mailed on Jul. 6, 2017, 8 pages.
Notice of Allowance received for U.S. Appl. No. 14/839,922, mailed on Nov. 2, 2017, 8 pages.
Notice of Allowance received for U.S. Appl. No. 15/183,663, mailed on Jan. 17, 2019, 6 pages.
Notice of Allowance received for U.S. Appl. No. 15/600,243, mailed on Dec. 12, 2019, 7 pages.
Notice of Allowance received for U.S. Appl. No. 15/608,848, mailed on Aug. 25, 2021, 9 pages.
Notice of Allowance received for U.S. Appl. No. 15/608,848, mailed on Oct. 29, 2021, 7 pages.
Notice of Allowance received for U.S. Appl. No. 15/616,480, mailed on Jan. 3, 2019, 8 pages.
Notice of Allowance received for U.S. Appl. No. 15/627,069, mailed on Jun. 17, 2021, 14 pages.
Notice of Allowance received for U.S. Appl. No. 15/705,849, mailed on Jul. 28, 2020, 10 pages.
Notice of Allowance received for U.S. Appl. No. 15/705,849, mailed on Oct. 16, 2020, 14 pages.
Notice of Allowance received for U.S. Appl. No. 15/925,652, mailed on Mar. 9, 2021, 9 pages.
Notice of Allowance received for U.S. Appl. No. 15/925,652, mailed on Nov. 20, 2020, 9 pages.
Notice of Allowance received for U.S. Appl. No. 16/138,809, mailed on Apr. 16, 2021, 11 pages.
Notice of Allowance received for U.S. Appl. No. 16/138,809, mailed on Jul. 20, 2021, 6 pages.
Notice of Allowance received for U.S. Appl. No. 16/144,671, mailed on Feb. 10, 2020, 17 pages.
Notice of Allowance received for U.S. Appl. No. 16/144,735, mailed on Jul. 21, 2020, 13 pages.
Notice of Allowance received for U.S. Appl. No. 16/144,735, mailed on Oct. 28, 2020, 13 pages.
Notice of Allowance received for U.S. Appl. No. 16/144,753, mailed on Dec. 4, 2020, 22 pages.
Notice of Allowance received for U.S. Appl. No. 16/144,753, mailed on Feb. 10, 2021, 8 pages.
Notice of Allowance received for U.S. Appl. No. 16/144,849, mailed on Apr. 17, 2020, 2 pages.
Notice of Allowance received for U.S. Appl. No. 16/144,849, mailed on Mar. 6, 2020, 9 pages.
Notice of Allowance received for U.S. Appl. No. 16/144,864, mailed on Feb. 9, 2021, 13 pages.
Notice of Allowance received for U.S. Appl. No. 16/144,864, mailed on Jul. 28, 2020, 27 pages.
Notice of Allowance received for U.S. Appl. No. 16/144,864, mailed on Mar. 12, 2021, 2 pages.
Notice of Allowance received for U.S. Appl. No. 16/144,864, mailed on Mar. 30, 2021, 2 pages.
Notice of Allowance received for U.S. Appl. No. 16/144,864, mailed on Sep. 10, 2020, 3 pages.
Notice of Allowance received for U.S. Appl. No. 16/144,864, mailed on Sep. 16, 2020, 2 pages.
Notice of Allowance received for U.S. Appl. No. 16/144,864, mailed on Sep. 29, 2020, 2 pages.
Notice of Allowance received for U.S. Appl. No. 16/377,892, mailed on May 24, 2021, 9 pages.
Notice of Allowance received for U.S. Appl. No. 16/377,892, mailed on Sep. 9, 2021, 9 pages.
Notice of Allowance received for U.S. Appl. No. 16/378,136, mailed on Jun. 3, 2021, 7 pages.
Notice of Allowance received for U.S. Appl. No. 16/378,136, mailed on Sep. 22, 2021, 7 pages.
Notice of Allowance received for U.S. Appl. No. 16/418,786, mailed on Dec. 9, 2021, 9 pages.
Notice of Allowance received for U.S. Appl. No. 16/418,786, mailed on Jun. 14, 2022, 9 pages.

(56) References Cited

OTHER PUBLICATIONS

Notice of Allowance received for U.S. Appl. No. 16/418,786, mailed on Nov. 22, 2022, 6 pages.
Notice of Allowance received for U.S. Appl. No. 16/556,023, mailed on Jan. 13, 2021, 8 pages.
Notice of Allowance received for U.S. Appl. No. 16/556,023, mailed on Oct. 15, 2020, 8 pages.
Notice of Allowance received for U.S. Appl. No. 16/588,950, mailed on Feb. 10, 2020, 9 pages.
Notice of Allowance received for U.S. Appl. No. 16/588,950, mailed on May 5, 2020, 9 pages.
Notice of Allowance received for U.S. Appl. No. 16/820,383, mailed on Jul. 21, 2021, 11 pages.
Notice of Allowance received for U.S. Appl. No. 16/820,383, mailed on Mar. 8, 2023, 13 pages.
Notice of Allowance received for U.S. Appl. No. 16/820,383, mailed on Mar. 31, 2021, 11 pages.
Notice of Allowance received for U.S. Appl. No. 16/820,383, mailed on Nov. 22, 2022, 16 pages.
Notice of Allowance received for U.S. Appl. No. 16/888,629, mailed on Nov. 9, 2021, 11 pages.
Notice of Allowance received for U.S. Appl. No. 16/894,309, mailed on Feb. 25, 2022, 9 pages.
Notice of Allowance received for U.S. Appl. No. 16/894,309, mailed on Nov. 5, 2021, 12 pages.
Notice of Allowance received for U.S. Appl. No. 16/987,275, mailed on Jul. 27, 2022, 6 pages.
Notice of Allowance received for U.S. Appl. No. 16/987,275, mailed on May 16, 2022, 7 pages.
Notice of Allowance received for U.S. Appl. No. 16/994,352, mailed on Jun. 3, 2022, 9 pages.
Notice of Allowance received for U.S. Appl. No. 16/994,352, mailed on Mar. 2, 2022, 14 pages.
Notice of Allowance received for U.S. Appl. No. 17/030,318, mailed on Jan. 5, 2022, 8 pages.
Notice of Allowance received for U.S. Appl. No. 17/030,318, mailed on Jan. 25, 2023, 10 pages.
Notice of Allowance received for U.S. Appl. No. 17/030,318, mailed on May 16, 2023, 5 pages.
Notice of Allowance received for U.S. Appl. No. 17/030,321, mailed on Apr. 1, 2022, 8 pages.
Notice of Allowance received for U.S. Appl. No. 17/030,337, mailed on Aug. 22, 2022, 10 pages.
Notice of Allowance received for U.S. Appl. No. 17/030,337, mailed on Dec. 23, 2022, 9 pages.
Notice of Allowance received for U.S. Appl. No. 17/030,340, mailed on Sep. 28, 2022, 7 pages.
Notice of Allowance received for U.S. Appl. No. 17/030,343, mailed on Dec. 15, 2022, 9 pages.
Notice of Allowance received for U.S. Appl. No. 17/030,343, mailed on Sep. 16, 2022, 11 pages.
Notice of Allowance received for U.S. Appl. No. 17/031,543, mailed on May 11, 2022, 6 pages.
Notice of Allowance received for U.S. Appl. No. 17/157,728, mailed on Feb. 24, 2022, 7 pages.
Notice of Allowance received for U.S. Appl. No. 17/192,161, mailed on Feb. 16, 2022, 8 pages.
Notice of Allowance received for U.S. Appl. No. 17/192,161, mailed on May 27, 2022, 8 pages.
Notice of Allowance received for U.S. Appl. No. 17/197,628, mailed on Jun. 24, 2022, 8 pages.
Notice of Allowance received for U.S. Appl. No. 17/197,628, mailed on Mar. 23, 2022, 35 pages.
Notice of Allowance received for U.S. Appl. No. 17/516,537, mailed on Apr. 17, 2023, 8 pages.
Notice of Allowance received for U.S. Appl. No. 17/516,537, mailed on Dec. 27, 2022, 7 pages.
Notice of Allowance received for U.S. Appl. No. 17/591,184, mailed on Feb. 22, 2023, 5 pages.
Notice of Allowance received for U.S. Appl. No. 17/666,301, mailed on May 4, 2023, 10 pages.
Office Action received for Australian Patent Application No. 2015312215, mailed on Oct. 13, 2016, 3 pages.
Office Action received for Australian Patent Application No. 2017100667, mailed on Aug. 3, 2017, 9 pages.
Office Action received for Australian Patent Application No. 2017277971, mailed on Aug. 12, 2020, 3 pages.
Office Action received for Australian Patent Application No. 2017277971, mailed on Jun. 3, 2020, 3 pages.
Office Action received for Australian Patent Application No. 2018100158, mailed on Apr. 23, 2018, 5 pages.
Office Action received for Australian Patent Application No. 2018101855, mailed on Feb. 22, 2019, 4 pages.
Office Action received for Australian Patent Application No. 2018200428, mailed on Mar. 7, 2018, 4 pages.
Office Action received for Australian Patent Application No. 2018200428, mailed on Nov. 15, 2018, 4 pages.
Office Action received for Australian Patent Application No. 2018268972, mailed on Jul. 9, 2020, 4 pages.
Office Action received for Australian Patent Application No. 2019100495, mailed on Mar. 6, 2020, 3 pages.
Office Action received for Australian Patent Application No. 2019100495, mailed on Mar. 16, 2020, 3 pages.
Office Action received for Australian Patent Application No. 2019100495, mailed on Sep. 17, 2019, 7 pages.
Office Action received for Australian Patent Application No. 2019222943, mailed on Oct. 3, 2019, 3 pages.
Office Action received for Australian Patent Application No. 2019250251, mailed on Aug. 6, 2020, 3 pages.
Office Action received for Australian Patent Application No. 2020239743, mailed on Mar. 25, 2021, 8 pages.
Office Action received for Australian Patent Application No. 2020239743, mailed on Sep. 3, 2021, 4 pages.
Office Action received for Australian Patent Application No. 2020239748, mailed on Apr. 21, 2021, 6 pages.
Office Action received for Australian Patent Application No. 2020239748, mailed on Feb. 11, 2022, 2 pages.
Office Action received for Australian Patent Application No. 2020239748, mailed on Sep. 1, 2021, 4 pages.
Office Action received for Australian Patent Application No. 2020239752. mailed on Jun. 4, 2021, 8 pages.
Office Action received for Australian Patent Application No. 2020239752, mailed on Oct. 25, 2021, 5 pages.
Office Action received for Australian Patent Application No. 2020256383, mailed on Jun. 4, 2021, 3 pages.
Office Action received for Australian Patent Application No. 2020268150, mailed on Feb. 6, 2023, 5 pages.
Office Action received for Australian Patent Application No. 2020268150, mailed on May 8, 2023, 4 pages.
Office Action received for Australian Patent Application No. 2020268150, mailed on Nov. 3, 2022, 4 pages.
Office Action received for Australian Patent Application No. 2020288139, mailed on Oct. 31, 2022, 3 pages.
Office Action received for Australian Patent Application No. 2021201130, mailed on Jan. 27, 2022, 2 pages.
Office Action received for Australian Patent Application No. 2021203636, mailed on Mar. 23, 2022, 3 pages.
Office Action received for Australian Patent Application No. 2021204422, mailed on May 31, 2022, 2 pages.
Office Action received for Australian Patent Application No. 2021266294, mailed on Nov. 11, 2022, 3 pages.
Office Action received for Australian Patent Application No. 2022201761, mailed on Feb. 28, 2023, 5 pages.
Office Action received for Australian Patent Application No. 2022202977, mailed on May 2, 2023, 5 pages.
Office Action received for Australian Patent Application No. 2022209277, mailed on Mar. 10, 2023, 6 pages.
Office Action received for Australian Patent Application No. 2022235614, mailed on May 9, 2023, 2 pages.
Office Action received for Chinese Patent Application No. 201380081349.6, mailed on Feb. 26, 2019, 12 pages (6 pages of English Translation and 6 pages of Official Copy).

(56) References Cited

OTHER PUBLICATIONS

Office Action received for Chinese Patent Application No. 201380081349.6, mailed on Jan. 5, 2021, 16 pages (7 pages of English Translation and 9 pages of Official Copy).
Office Action received for Chinese Patent Application No. 201380081349.6, mailed on Jan. 16, 2020, 11 pages (6 pages of English Translation and 5 pages of Official Copy).
Office Action received for Chinese Patent Application No. 201380081349.6. mailed on Jul. 15, 2019, 10 pages (5 pages of English Translation and 5 pages of Official copy).
Office Action received for Chinese Patent Application No. 201380081349.6, mailed on Jul. 15, 2020, 9 pages (4 pages of English Translation and 5 pages of Official Copy).
Office Action received for Chinese Patent Application No. 201380081349.6, mailed on Jun. 2, 2021, 17 pages (8 pages of English Translation and 9 pages of Official Copy).
Office Action received for Chinese Patent Application No. 201580037927.5, mailed on Apr. 22, 2019, 9 pages (4 pages of English Translation and 5 pages of Official Copy).
Office Action received for Chinese Patent Application No. 201580037927.5, mailed on Jul. 20, 2018, 21 pages (6 pages of English Translation and 15 pages of Official copy).
Office Action received for Chinese Patent Application No. 201680047983.1, mailed on Feb. 1, 2021, 6 pages (3 pages of English Translation and 3 pages of Official Copy).
Office Action received for Chinese Patent Application No. 201680047983.1, mailed on Jul. 1, 2020, 6 pages (3 pages of English Translation and 3 pages of Official Copy).
Office Action received for Chinese Patent Application No. 201680047983.1, mailed on Mar. 18, 2019, 18 pages (6 pages of English Translation and 12 pages of Official Copy).
Office Action received for Chinese Patent Application No. 201680047983.1, mailed on Nov. 28, 2019, 9 pages (4 pages of English Translation and 5 pages of Official Copy).
Office Action received for Chinese Patent Application No. 201710439448.7, mailed on Mar. 27, 2020, 13 pages (7 pages of English Translation and 6 pages of Official Copy).
Office Action received for Chinese Patent Application No. 201710439448.7, mailed on Oct. 10, 2020, 19 pages (8 pages of English Translation and 11 pages of Official Copy).
Office Action received for Chinese Patent Application No. 201780034203.4, mailed on Jul. 14, 2021, 12 pages (5 pages of English Translation and 7 pages of Official Copy).
Office Action received for Chinese Patent Application No. 201780034203.4, mailed on Sep. 24, 2021, 7 pages (3 pages of English Translation and 4 pages of Official Copy).
Office Action received for Chinese Patent Application No. 201810105846.X, mailed on Aug. 27, 2019, 12 pages (5 pages of English Translation and 7 pages of Official Copy).
Office Action received for Chinese Patent Application No. 201810105846.X, mailed on Feb. 25, 2019, 10 pages (5 pages of English Translation and 5 pages of Official copy).
Office Action received for Chinese Patent Application No. 201810105846.X, mailed on Nov. 28, 2019, 9 pages (5 pages of English Translation and 4 pages of Official Copy).
Office Action received for Chinese Patent Application No. 201811303556.2, mailed on Nov. 28, 2022, 18 pages (7 pages of English Translation and 11 pages of Official Copy).
Office Action received for Chinese Patent Application No. 201880032190.1, mailed on Nov. 14, 2022, 23 pages (12 pages of English Translation and 11 pages of Official Copy).
Office Action received for Chinese Patent Application No. 201910858933.7, mailed on Aug. 18, 2020, 14 pages (7 pages of English Translation and 7 pages of Official Copy).
Office Action received for Chinese Patent Application No. 201910858933.7, mailed on Dec. 30, 2021, 9 pages (4 pages of English Translation and 5 pages of Official Copy).
Office Action received for Chinese Patent Application No. 201910858933.7, mailed on Jun. 29, 2021, 8 pages (3 pages of English Translation and 5 pages of Official Copy).
Office Action received for Chinese Patent Application No. 201911396643.1, mailed on Apr. 6, 2023, 26 pages (15 pages of English Translation and 11 pages of official copy).
Office Action received for Chinese Patent Application No. 201911396744.9, mailed on Apr. 6, 2023, 19 pages (7 pages of English Translation and 12 pages of Official Copy).
Office Action received for Chinese Patent Application No. 201911396819.3, mailed on Apr. 6, 2023, 21 pages (10 pages of English Translation and 11 pages of Official copy).
Office Action received for Chinese Patent Application No. 201911401161.0, mailed on Aug. 9, 2022, 17 pages (9 pages of English Translation and 8 pages of Official Copy).
Office Action received for Chinese Patent Application No. 201911401161.0, mailed on Dec. 15, 2022, 14 pages (7 pages of English Translation and 7 pages of Official Copy).
Office Action received for Chinese Patent Application No. 201911401161.0, mailed on Jan. 24, 2022, 6 pages (3 pages of English Translation and 3 pages of Official Copy).
Office Action received for Chinese Patent Application No. 201911401375.8, mailed on Apr. 7, 2023, 10 pages (5 pages of English Translation and 5 pages of Official Copy).
Office Action received for Chinese Patent Application No. 202010606407.4, mailed on Jan. 27, 2021, 16 pages (7 pages of English Translation and 9 pages of Official Copy).
Office Action received for Chinese Patent Application No. 202010606407.4, mailed on Jun. 2, 2021, 12 pages (5 pages of English Translation and 7 pages of Official Copy).
Office Action received for Chinese Patent Application No. 202010606407.4, mailed on Nov. 18, 2021, 6 pages (3 pages of English Translation and 3 pages of Official Copy).
Office Action received for Chinese Patent Application No. 202110363565.6, mailed on May 7, 2022, 12 pages (7 pages of English Translation and 5 pages of Official Copy).
Office Action received for Chinese Patent Application No. 202110363565.6, mailed on Nov. 16, 2021, 16 pages (9 pages of English Translation and 7 pages of Official Copy).
Office Action received for Chinese Patent Application No. 202110783860.7, mailed on Mar. 10, 2022, 15 pages (5 pages of English Translation and 10 pages of Official Copy).
Office Action received for Chinese Patent Application No. 202110783860.7, mailed on Nov. 15, 2022, 8 pages (2 pages of English Translation and 6 pages of Official Copy).
Office Action Received for Danish Patent Application No. PA201670656, mailed on Nov. 3, 2016, 8 pages.
Office Action received for Danish Patent Application No. PA 2020 70612, mailed on Mar. 1, 2022, 2 pages.
Office Action received for Danish Patent Application No. PA201570666, mailed on Feb. 2, 2016, 9 pages.
Office Action received for Danish Patent Application No. PA201570666, mailed on Jun. 27, 2016, 4 pages.
Office Action received for Danish Patent Application No. PA201570668, mailed on Apr. 8, 2016, 8 pages.
Office Action received for Danish Patent Application No. PA201570668, mailed on Sep. 9, 2016, 3 pages.
Office Action Received for Danish Patent Application No. PA201670656, mailed on Jul. 1, 2020, 4 pages.
Office Action received for Danish Patent Application No. PA201670656, mailed on Jun. 14, 2017, 3 pages.
Office Action Received for Danish Patent Application No. PA201670656, mailed on May 2, 2019, 4 pages.
Office Action Received for Danish Patent Application No. PA201670656, mailed on May 30, 2018, 5 pages.
Office Action received for Danish Patent Application No. PA201770191, mailed on Jan. 25, 2018, 3 pages.
Office Action received for Danish Patent Application No. PA201770191, mailed on Nov. 21, 2018, 4 pages.
Office Action received for Danish Patent Application No. PA201770191, mailed on Oct. 25, 2019, 4 pages.
Office Action received for Danish Patent Application No. PA201770423, mailed on Jun. 12, 2018, 7 pages.
Office Action received for Danish Patent Application No. PA201770423, mailed on Mar. 29, 2019, 6 pages.

(56) References Cited

OTHER PUBLICATIONS

Office Action received for Danish Patent Application No. PA201870378, mailed on Feb. 25, 2019, 3 pages.
Office Action received for Danish Patent Application No. PA201870378, mailed on Jan. 6, 2020, 3 pages.
Office Action received for Danish Patent Application No. PA201870379, mailed on Feb. 28, 2019, 3 pages.
Office Action received for Danish Patent Application No. PA201870380, mailed on Mar. 5, 2020, 2 pages.
Office Action received for Danish Patent Application No. PA201870380, mailed on Mar. 27, 2019, 4 pages.
Office Action received for Danish Patent Application No. PA201870380, mailed on Sep. 11, 2018, 9 pages.
Office Action received for Danish Patent Application No. PA201970532, mailed on May 29, 2020, 3 pages.
Office Action received for Danish Patent Application No. PA202070612, mailed on May 10, 2022, 2 pages.
Office Action received for Danish Patent Application No. PA202070612, mailed on Sep. 12, 2022, 3 pages.
Office Action received for Danish Patent Application No. PA202070613, mailed on May 10, 2022, 2 pages.
Office Action received for Danish Patent Application No. PA202070613, mailed on Oct. 13, 2022, 7 pages.
Office Action received for Danish Patent Application No. PA202070613, mailed on Sep. 30, 2021, 4 pages.
Office Action received for Danish Patent Application No. PA202070614, mailed on Apr. 28, 2022, 4 pages.
Office Action received for Danish Patent Application No. PA202070614, mailed on Sep. 28, 2021, 4 pages.
Office Action received for Danish Patent Application No. PA202070615, mailed on Nov. 16, 2021, 4 pages.
Office Action received for Danish Patent Application No. PA202070616, mailed on Jan. 27, 2022, 2 pages.
Office Action received for Danish Patent Application No. PA202070616, mailed on May 5, 2022, 3 pages.
Office Action received for Danish Patent Application No. PA202070815, mailed on Jun. 14, 2022, 3 pages.
Office Action received for Danish Patent Application No. PA202070815, mailed on Oct. 18, 2021, 2 pages.
Office Action received for Danish Patent Application No. PA202170113, mailed on Apr. 15, 2021, 2 pages.
Office Action received for Danish Patent Application No. PA202170113, mailed on Aug. 18, 2022, 2 pages.
Office Action received for Danish Patent Application No. PA202170113, mailed on May 3, 2022, 2 pages.
Office Action received for European Patent Application No. 13811085.3, mailed on Apr. 20, 2018, 15 pages.
Office Action received for European Patent Application No. 16837432.0, mailed on Jan. 10, 2020, 7 pages.
Office Action received for European Patent Application No. 16837432.0, mailed on Jan. 27, 2021, 7 pages.
Office Action received for European Patent Application No. 17810749.6, mailed on Aug. 20, 2019, 9 pages.
Office Action received for European Patent Application No. 18154145.9, mailed on Apr. 3, 2018, 6 pages.
Office Action received for European Patent Application No. 18727543.3, mailed on Mar. 26, 2021, 7 pages.
Office Action received for European Patent Application No. 19721883.7, mailed on Jan. 10, 2020, 4 pages.
Office Action received for European Patent Application No. 19721883.7, mailed on Jun. 15, 2021, 9 pages.
Office Action received for European Patent Application No. 19721883.7, mailed on May 28, 2020, 11 pages.
Office Action received for European Patent Application No. 20182116.2, mailed on May 25, 2021, 9 pages.
Office Action received for European Patent Application No. 20182116.2, mailed on Nov. 6, 2020, 9 pages.
Office Action received for European Patent Application No. 20203526.7, mailed on Nov. 23, 2021, 9 pages.
Office Action received for European Patent Application No. 20721342.2, mailed on Nov. 4, 2021, 9 pages.
Office Action received for European Patent Application No. 21165295.3, mailed on Jul. 1, 2021, 10 pages.
Office Action received for European Patent Application No. 21168916.1, mailed on Aug. 23, 2021, 8 pages.
Office Action received for European Patent Application No. 15771747.1, mailed on Oct. 31, 2017, 7 pages.
Office Action received for German Patent Application No. 112015002326.7, mailed on Feb. 20, 2019, 7 pages (2 pages of English Translation and 5 pages of Official Copy).
Office Action received for German Patent Application No. 112015007285.3, mailed on Mar. 7, 2023, 15 pages (5 pages of English Translation and 10 pages of Official Copy).
Office Action received for Indian Patent Application No. 202014041563, mailed on Dec. 30, 2021, 6 pages.
Office Action received for Indian Patent Application No. 202014041571, mailed on Dec. 17, 2021, 5 pages.
Office Action received for Japanese Patent Application No. 2016-535045, mailed on May 12, 2017, 10 pages (5 pages of English Translation and 5 pages of Official Copy).
Office Action received for Japanese Patent Application No. 2016-557650, mailed on Apr. 13, 2018, 9 pages (5 pages of English Translation and 4 pages of Official Copy).
Office Action received for Japanese Patent Application No. 2016-557650, mailed on Aug. 10, 2017, 10 pages (5 pages of English Translation and 5 pages of Official Copy).
Office Action received for Japanese Patent Application No. 2016-557650, mailed on Nov. 9, 2018, 6 pages (3 pages of English Translation and 3 pages of Official copy).
Office Action received for Japanese Patent Application No. 2018-014096, mailed on Aug. 28, 2020, 4 pages (2 pages of English Translation and 2 pages of Official Copy).
Office Action received for Japanese Patent Application No. 2018-014096, mailed on Jan. 6, 2020, 17 pages (8 pages of English Translation and 9 pages of Official Copy).
Office Action received for Japanese Patent Application No. 2018-014096, mailed on Jun. 29, 2018, 20 pages (11 pages of English Translation and 9 pages of Official Copy).
Office Action received for Japanese Patent Application No. 2018-014096, mailed on May 8, 2019, 14 pages (7 pages of English Translation and 7 pages of Official Copy).
Office Action received for Japanese Patent Application No. 2018-014096, mailed on Nov. 6, 2018, 15 pages (7 pages of English Translation and 8 pages of Official Copy).
Office Action received for Japanese Patent Application No. 2018-068846, mailed on Jan. 8, 2019, 6 pages (3 pages of English Translation and 3 pages of Official Copy).
Office Action received for Japanese Patent Application No. 2018-184532, mailed on Mar. 1, 2021, 11 pages (6 pages of English Translation and 5 pages of Official Copy).
Office Action received for Japanese Patent Application No. 2019-044107, mailed on Jul. 30, 2021, 9 pages (5 pages of English Translation and 4 pages of Official Copy).
Office Action received for Japanese Patent Application No. 2019-044107, mailed on May 29, 2020, 6 pages (3 pages of English Translation and 3 pages of Official Copy).
Office Action received for Japanese Patent Application No. 2019-162293, mailed on Jan. 31, 2020, 8 pages (4 pages of English Translation and 4 pages of Official Copy).
Office Action received for Japanese Patent Application No. 2019-162293, mailed on Jul. 27, 2020, 9 pages (5 pages of English Translation and 4 pages of Official Copy).
Office Action received for Japanese Patent Application No. 2019-563407, mailed on Feb. 5, 2021, 5 pages (2 pages of English Translation and 3 pages of Official Copy).
Office Action received for Japanese Patent Application No. 2019-000492, mailed on Dec. 11, 2020, 6 pages (3 pages of English Translation and 3 pages of Official Copy).
Office Action received for Japanese Patent Application No. 2019-104679, mailed on Sep. 18, 2020, 13 pages (7 pages of English Translation and 6 pages of Official Copy).

(56) References Cited

OTHER PUBLICATIONS

Office Action received for Japanese Patent Application No. 2020-115940, mailed on May 7, 2021, 3 pages (1 page of English Translation and 2 pages of Official Copy).
Office Action received for Japanese Patent Application No. 2020-160052, mailed on Dec. 17, 2021, 10 pages (5 pages of English Translation and 5 pages of Official Copy).
Office Action received for Japanese Patent Application No. 2020-160053, mailed on Aug. 1, 2022, 8 pages (4 pages of English Translation and 4 pages of Official Copy).
Office Action received for Japanese Patent Application No. 2020-160053, mailed on Jan. 31, 2022, 8 pages (4 pages of English Translation and 4 pages of Official Copy).
Office Action received for Japanese Patent Application No. 2020-160054, mailed on Jan. 21, 2022, 8 pages (4 pages of English Translation and 4 pages of Official Copy).
Office Action received for Japanese Patent Application No. 2021-131726, mailed on Aug. 22, 2022, 8 pages (4 pages of English Translation and 4 pages of Official Copy).
Office Action received for Japanese Patent Application No. 2021-131726, mailed on Dec. 2, 2022, 4 pages (2 pages of English Translation and 2 pages of Official Copy).
Office Action received for Japanese Patent Application No. 2021-153558, mailed on Nov. 21, 2022, 8 pages (4 pages of English Translation and 4 pages of Official Copy).
Office Action received for Japanese Patent Application No. 2021-565912, mailed on Jan. 12, 2023, 9 pages (5 pages of English Translation and 4 pages of Official Copy).
Office Action received for Japanese Patent Application No. 2021-571468, mailed on Jan. 5, 2023, 14 pages (7 pages of English Translation & 7 pages of Official Copy).
Office Action received for Japanese Patent Application No. 2022-022159, mailed on Feb. 20, 2023, 10 pages (5 pages of English Translation and 5 pages of Official Copy).
Office Action received for Japanese Patent Application No. 2022-076722, mailed on Mar. 13, 2023, 6 pages (3 pages of English Translation and 3 pages of Official Copy).
Office Action received for Korean Patent Application No. 10-2016-7014577, mailed on Dec. 26, 2017, 14 pages (6 pages of English Translation and 8 pages of Official Copy).
Office Action received for Korean Patent Application No. 10-2016-7014577, mailed on Oct. 31, 2018, 11 pages (5 pages of English Translation and 6 pages of Official Copy).
Office Action received for Korean Patent Application No. 10-2016-7033638, mailed on Jan. 31, 2017, 6 pages (2 pages of English Translation and 4 pages of Official Copy).
Office Action received for Korean Patent Application No. 10-2019-7025538, mailed on Aug. 15, 2020, 8 pages (4 pages of English Translation and 4 pages of Official Copy).
Office Action received for Korean Patent Application No. 10-2019-7025538, mailed on Feb. 17, 2020, 12 pages (6 pages of English Translation and 6 pages of Official Copy).
Office Action received for Korean Patent Application No. 10-2019-7025781, mailed on Nov. 26, 2019, 10 pages (4 pages of English Translation and 6 pages of Official Copy).
Office Action received for Korean Patent Application No. 10-2019-7025781, mailed on Oct. 30, 2020, 10 pages (4 pages of English Translation and 6 pages of Official Copy).
Office Action received for Korean Patent Application No. 10-2019-7033834, mailed on Jan. 22, 2021, 13 pages (6 pages of English Translation and 7 pages of Official Copy).
Office Action received for Korean Patent Application No. 10-2020-0123815, mailed on May 31, 2022, 10 pages (5 pages of English Translation and 5 pages of Official Copy).
Office Action received for Korean Patent Application No. 10-2020-0123821, mailed on Sep. 20, 2022, 11 pages (5 pages of English Translation and 6 pages of Official Copy).
Office Action received for Korean Patent Application No. 10-2020-0123840, mailed on Nov. 21, 2022, 18 pages (8 pages of English Translation and 10 pages of Official Copy).
Office Action received for Korean Patent Application No. 10-2020-7026035, mailed on Feb. 19, 2021, 13 pages (6 pages of English Translation and 7 pages of Official Copy).
Office Action received for Korean Patent Application No. 10-2021-7026284, mailed on Aug. 31, 2021, 10 pages (4 pages of English Translation and 6 pages of Official Copy).
Office Action received for Korean Patent Application No. 10-2021-7031939, mailed on Oct. 19 2021, 11 pages (5 pages of English Translation and 6 pages of Official Copy).
Office Action received for Korean Patent Application No. 10-2022-0061486, mailed on Aug. 29, 2022, 5 pages (2 pages of English Translation and 3 pages of Official Copy).
Office Action received for Korean Patent Application No. 10-2022-7031866, mailed on Nov. 18, 2022, 11 pages (5 pages of English Translation and 6 pages of Official Copy).
Office Action received for Taiwanese Patent Application No. 104128685, mailed on Jan. 4, 2017, 40 pages (15 pages of English Translation and 25 pages of Official Copy).
Partial Supplementary European Search Report received for European Patent Application No. 17810749.6, mailed on Apr. 25, 2019, 8 pages.
RAZYKDREVIEWS, "In Depth Review of Apple Watch Activity and Workout App", available at <URL: https://www.youtube.com/watch?v=GkKl3qlK0ow>,, Category: X Claims: 1-5Category: L Reason: Internet citation/video, May 11, 2015, 1 page.
Result of Consultation received for European Patent Application No. 17810749.6, mailed on Dec. 15, 2020, 3 pages.
Result of Consultation received for European Patent Application No. 17810749.6, mailed on Jan. 18, 2021, 3 pages.
Result of Consultation received for European Patent Application No. 17810749.6, mailed on Jan. 21, 2021, 18 pages.
Result of Consultation received for European Patent Application No. 18154145.9, mailed on Nov. 30, 2020, 17 pages.
Result of Consultation received for European Patent Application No. 18154145.9, mailed on Sep. 4, 2020, 3 pages.
Result of Consultation received for European Patent Application No. 18727543.3, mailed on Mar. 15, 2023, 6 pages.
Result of Consultation received for European Patent Application No. 19721883.7, mailed on Oct. 7, 2020, 3 pages.
Result of Consultation received for European Patent Application No. 20203526.7, mailed on Jan. 13, 2023, 3 pages.
Result of Consultation received for European Patent Application No. 20721342.2, mailed on Oct. 18, 2022, 3 pages.
RIZKNOWS, "Garmin Connect Mobile App—REVIEW #2", https://www.youtube.com/watch?v=7my3wMpeRbE, Category: X Claims: 1-5 Category: L Reason: Internet citation/video, Oct. 22, 2015, 1 page.
RIZKNOWS, "TomTom Multisport Cardio Review", Online available at: https://www.youtube.com/watch?v=WoVCzLrSN9A, Sep. 4, 2015, 1 page.
Search Report and opinion received for Danish Patent Application No. PA201770191, mailed on Jun. 30, 2017, 9 pages.
Search Report and Opinion received for Danish Patent Application No. PA201770423, mailed on Oct. 4, 2017, 10 pages.
Search Report and Opinion received for Danish Patent Application No. PA201870378, mailed on Sep. 10, 2018, 9 pages.
Search Report and Opinion received for Danish Patent Application No. PA201870379, mailed on Sep. 14, 2018, 9 pages.
Search Report and Opinion received for Danish Patent Application No. PA201970532, mailed on Nov. 8, 2019, 9 pages.
Search Report and Opinion received for Danish Patent Application No. PA202070612, mailed on Jun. 7, 2021, 9 pages.
Search Report and Opinion received for Danish Patent Application No. PA202070613, mailed on Jan. 22, 2021, 9 pages.
Search Report and Opinion received for Danish Patent Application No. PA202070614, mailed on Jan. 14, 2021, 9 pages.
Search Report and Opinion received for Danish Patent Application No. PA202070615, mailed on Jan. 22, 2021, 9 pages.
Search Report and Opinion received for Danish Patent Application No. PA202070616, mailed on Feb. 3, 2021, 8 pages.
Search Report and Opinion received for Danish Patent Application No. PA202070815, mailed on Mar. 16, 2021, 8 pages.

(56) References Cited

OTHER PUBLICATIONS

Search Report and Opinion received for Danish Patent Application No. PA202170113, mailed on Nov. 30, 2021, 9 pages.
Smith, "Garmin Fenix 5 Activity/Smart Watch Review", Online Available at: https://www.youtube.com/watch?v=6PkQxXQxpoU, Sep. 2, 2017, 1 page.
SPORTSTECHGUIDES, "Garmin Fenix 5: How to Add Power Data Fields", Online Available at: https://www.youtube.com/watch?v=ZkPptnnXEiQ. Apr. 29, 2017, 2 pages.
SPORTSTECHGUIDES, "Garmin Fenix 5: How to Set Up Run Alerts", Online Available at: https://www.youtube.com/watch?v=gSMwv8vlhB4, May 13, 2017, 2 pages.
Summons to attend oral proceedings received for European Patent Application No. 13811085.3, mailed on Jan. 26, 2018., 14 pages.
Summons to Attend Oral Proceedings received for European Patent Application No. 13811085.3, mailed on Mar. 3, 2022, 3 pages.
Summons to Attend Oral Proceedings received for European Patent Application No. 17810749.6, mailed on Aug. 12, 2020, 11 pages.
Summons to Attend Oral Proceedings received for European Patent Application No. 18154145.9, mailed on Sep. 17, 2020, 11 pages.
Summons to Attend Oral Proceedings received for European Patent Application No. 18727543.3, mailed on Oct. 25, 2022, 8 pages.
Summons to Attend Oral Proceedings received for European Patent Application No. 20182116.2, mailed on Dec. 21, 2021, 7 pages.
Summons to Attend Oral Proceedings received for European Patent Application No. 20203526.7, mailed on Jun. 23, 2022, 9 pages.
Summons to Attend Oral Proceedings received for European Patent Application No. 20721342.2, mailed on May 20, 2022, 11 pages.
Summons to Attend Oral Proceedings received for European Patent Application No. 15771747.1, mailed on May 25, 2018, 17 pages.
Summons to Oral Proceedings received for European Patent Application No. 15771747.1, mailed on Apr. 29, 2021, 8 pages.
Supplemental Notice of Allowance received for U.S. Appl. No. 15/616,480, mailed on Mar. 28, 2019, 2 pages.
Supplemental Notice of Allowance received for U.S. Appl. No. 15/627,069, mailed on Jul. 12, 2021, 2 pages.
Supplemental Notice of Allowance received for U.S. Appl. No. 15/925,652, mailed on Feb. 17, 2021, 3 pages.
Supplemental Notice of Allowance received for U.S. Appl. No. 15/925,652, mailed on Jan. 6, 2021, 3 pages.
Supplemental Notice of Allowance received for U.S. Appl. No. 15/925,652, mailed on Jan. 26, 2021, 3 pages.
Supplemental Notice of Allowance received for U.S. Appl. No. 16/144,849, mailed on Mar. 31, 2020, 2 pages.
Supplemental Notice of Allowance received for U.S. Appl. No. 16/566,023, mailed on Feb. 3, 2021, 2 pages.
Supplemental Notice of Allowance received for U.S. Appl. No. 16/588,950, mailed on Apr. 1, 2020, 2 pages.
Supplemental Notice of Allowance received for U.S. Appl. No. 16/588,950, mailed on Jul. 29, 2020, 2 pages.
Supplemental Notice of Allowance received for U.S. Appl. No. 16/588,950, mailed on Jun. 18, 2020, 2 pages.
Supplemental Notice of Allowance received for U.S. Appl. No. 16/894,309, mailed on Apr. 8, 2022, 3 pages.
Supplemental Notice of Allowance received for U.S. Appl. No. 16/894,309, mailed on Dec. 24, 2021, 2 pages.
Supplemental Notice of Allowance received for U.S. Appl. No. 16/894,309, mailed on Jan. 25, 2022, 2 pages.
Supplemental Notice of Allowance received for U.S. Appl. No. 16/994,352, mailed on Jun. 20, 2022, 2 pages.
Supplemental Notice of Allowance received for U.S. Appl. No. 17/030,318, mailed on Apr. 4, 2022, 2 pages.
Supplemental Notice of Allowance received for U.S. Appl. No. 17/030,318, mailed on Feb. 22, 2022, 2 pages.
Supplemental Notice of Allowance received for U.S. Appl. No. 17/030,318, mailed on Mar. 16, 2022, 2 pages.
Supplemental Notice of Allowance received for U.S. Appl. No. 17/030,321, mailed on Apr. 15, 2022, 2 pages.
Supplemental Notice of Allowance received for U.S. Appl. No. 17/030,321, mailed on Jul. 27, 2022, 2 pages.
Supplemental Notice of Allowance received for U.S. Appl. No. 17/030,321, mailed on Jun. 10, 2022, 2 pages.
Supplemental Notice of Allowance received for U.S. Appl. No. 17/030,321, mailed on May 27, 2022, 2 pages.
Supplemental Notice of Allowance received for U.S. Appl. No. 17/030,343, mailed on Jan. 6, 2023, 2 pages.
Supplemental Notice of Allowance received for U.S. Appl. No. 17/030,343, mailed on Nov. 9, 2022, 2 pages.
Supplemental Notice of Allowance received for U.S. Appl. No. 17/030,343, mailed on Oct. 5, 2022, 2 pages.
Supplemental Notice of Allowance received for U.S. Appl. No. 17/192,161, mailed on Jun. 13, 2022, 2 pages.
Supplemental Notice of Allowance received for U.S. Appl. No. 17/192,161, mailed on May 13, 2022, 2 pages.
Supplemental Notice of Allowance received for U.S. Appl. No. 17/666,301, mailed on Jun. 5, 2023, 2 pages.
Supplemental Notice of Allowance received for U.S. Appl. No. 17/666,301, mailed on May 17, 2023, 2 pages.
Supplementary European Search Report received for European Patent Application No. 17810749.6, mailed on Aug. 6, 2019, 6 pages.
Suunto Spartan Trainer Wrist HR 1.12, Online Available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Availabie at: https://www.youtube.com/watch?v=aixfoCnS0OU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TomTom, "TomTom Runner & Multi-Sport Reference Guide", Online available at: https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Updated Notice of Allowance received for U.S. Appl. No. 17/030,318, mailed on Feb. 23, 2023, 3 pages.
Updated Notice of Allowance received for U.S. Appl. No. 17/030,340, mailed on Dec. 2, 2022, 2 pages.
Updated Notice of Allowance received for U.S. Appl. No. 17/030,340, mailed on Nov. 2, 2022, 2 pages.
Updated Notice of Allowance received for U.S. Appl. No. 17/030,340, mailed on Nov. 10, 2022, 2 pages.
Utilization of GalaxyS4- S Health, ChatOn and Samsung Hub, Available at: http://seeit.kr/1263, Jun. 12, 2013, 25 pages (Official Copy only). {See Communication Under 37 CFR § 1.98(a) (3)}.
Venusivenus, "Nike Training Club", Available online at: https://www.youtube.com/watch?v =_pe6fqJPA04, Mar. 28, 2011, 6 pages.
Vicky's Blog, "How to Log in to PS4 Automatically with Particular User?", Online available on: https://www.youtube.com/watch?v=kqdlzXAvOkY, May 30, 2018, 3 pages.
Visual Pace Alarm app, Available Online at: https://apps.garmin.com/en-US/apps/3940f3a2-4847-4078-a911-d77422966c82, Oct. 19, 2016, 1 page.
Wesley, "Apple Watch Series 1", online available at: http://toolbox.info/blog/archives/1737-unknown.html, May 28, 2015, 5 pages (Official copy only). {See Communication Under 37 CFR § 1.98(a) (3)}.
Youtube, "Apple Watch Series 3", Online available at: https://www.youtube.com/watch?v=iBPr9gEfkK8, Nov. 21, 2017, 15 pages (Official copy only). {See Communication Under 37 CFR § 1.98(a) (3)}.
YoyoDavid, "How to Use Multiple Accounts on the Playstation 4", Online available at: https://www.youtube.com/watch?v=5V21obRMeKE, Jan. 9, 2014, 3 pages.
Zlelik, "Garmin Fenix 5 Open Water Swimming Activity Demo", Online Available at: https://www.youtube.com/watch?v=iSVhdvw2dcs, Jun. 9, 2017, 1 page.
"Influence of exercise prescription on body composition of college students", 3 pages, Cited by Chinese Patent Office in an Office Action for related Patent Application No. 201911401161.0 on Dec. 15, 2022.

(56) References Cited

OTHER PUBLICATIONS

"Apple Watch", 4 pages, Cited by Japanese Patent Office in Office Action for related Patent Application No. 2022-022159 on Feb. 20, 2023.
Issued by the Taiwanese Patent Office in related Patent Application No. 104128685, on May 3, 2017.
Advisory Action received for U.S. Appl. No. 17/591,184, mailed on Nov. 14, 2023, 5 pages.
Advisory Action received for U.S. Appl. No. 17/744,500, mailed on Nov. 14, 2023, 5 pages.
Advisory Action received for U.S. Appl. No. 17/952,133, mailed on Oct. 20, 2023, 7 pages.
Applicant-Initiated Interview Summary received for U.S. Appl. No. 17/031,854, mailed on Dec. 21, 2023, 5 pages.
Applicant-Initiated Interview Summary received for U.S. Appl. No. 17/031,859, mailed on Aug. 1, 2023, 4 pages.
Applicant-Initiated Interview Summary received for U.S. Appl. No. 17/041,438, mailed on Jun. 23, 2023, 4 pages.
Applicant-Initiated Interview Summary received for U.S. Appl. No. 17/591,184, mailed on Jun. 28, 2023, 2 pages.
Applicant-Initiated Interview Summary received for U.S. Appl. No. 17/591,184, mailed on Oct. 30, 2023, 2 pages.
Applicant-Initiated Interview Summary received for U.S. Appl. No. 17/735,395, mailed on Aug. 1, 2023, 2 pages.
Applicant-Initiated Interview Summary received for U.S. Appl. No. 17/735,395, mailed on Nov. 15, 2023, 2 pages.
Applicant-Initiated Interview Summary received for U.S. Appl. No. 17/744,500, mailed on Oct. 17, 2023, 4 pages.
Applicant-Initiated Interview Summary received for U.S. Appl. No. 17/892,534, mailed on Aug. 3, 2023, 3 pages.
Applicant-Initiated Interview Summary received for U.S. Appl. No. 17/896,791, mailed on Oct. 12, 2023, 2 pages.
Applicant-Initiated Interview Summary received for U.S. Appl. No. 17/951,613, mailed on Sep. 8, 2023, 5 pages.
Applicant-Initiated Interview Summary received for U.S. Appl. No. 17/951,624, mailed on Nov. 16, 2023, 3 pages.
Applicant-Initiated Interview Summary received for U.S. Appl. No. 17/951,875, mailed on Jun. 27, 2023, 2 pages.
Applicant-Initiated Interview Summary received for U.S. Appl. No. 17/951,945, mailed on Aug. 1, 2023, 2 pages.
Applicant-Initiated Interview Summary received for U.S. Appl. No. 17/951,945, mailed on Nov. 15, 2023, 2 pages.
Applicant-Initiated Interview Summary received for U.S. Appl. No. 17/951,976, mailed on Aug. 23, 2023, 2 pages.
Applicant-Initiated Interview Summary received for U.S. Appl. No. 17/952,027, mailed on Sep. 11, 2023, 3 pages.
Applicant-Initiated Interview Summary received for U.S. Appl. No. 17/952,133, mailed on Jul. 3, 2023, 4 pages.
Applicant-Initiated Interview Summary received for U.S. Appl. No. 17/952,233, mailed on May 24, 2023, 5 pages.
Applicant-Initiated Interview Summary received for U.S. Appl. No. 17/952,233, mailed on Sep. 7, 2023, 4 pages.
Applicant-Initiated Interview Summary received for U.S. Appl. No. 17/952,239, mailed on May 31, 2023, 2 pages.
Corrected Notice of Allowance received for U.S. Appl. No. 17/041,438, mailed on Dec. 1, 2023, 2 pages.
Corrected Notice of Allowance received for U.S. Appl. No. 17/041,438, mailed on Sep. 27, 2023, 3 pages.
Corrected Notice of Allowance received for U.S. Appl. No. 17/896,791, mailed on Jan. 2, 2024, 2 pages.
Corrected Notice of Allowance received for U.S. Appl. No. 17/951,613, mailed on Jan. 2, 2024, 2 pages.
Corrected Notice of Allowance received for U.S. Appl. No. 17/952,239, mailed on Jul. 12, 2023, 2 pages.
Corrected Notice of Allowance received for U.S. Appl. No. 17/952,239, mailed on Nov. 15, 2023, 2 pages.
Decision to Grant received for European Patent Application No. 16837432.0, mailed on Dec. 21, 2023, 2 pages.
Decision to Grant received for European Patent Application No. 18727543.3, mailed on Aug. 18, 2023, 2 pages.
Decision to Grant received for European Patent Application No. 19721883.7, mailed on Aug. 31, 2023, 4 pages.
Decision to Grant received for European Patent Application No. 20203526.7, mailed on Jun. 22, 2023, 4 pages.
Decision to Grant received for German Patent Application No. 112015007285.3, mailed on Jul. 25, 2023, 11 pages (1 page of English Translation and 10 pages of Official Copy).
Examiner-Initiated Interview received for U.S. Appl. No. 17/896,791, mailed on Sep. 1, 2023, 2 pages.
Extended European Search Report received for European Patent Application No. 23189089.8, mailed on Nov. 23, 2023, 11 pages.
Final Office Action received for U.S. Appl. No. 17/031,859, mailed on Nov. 13, 2023, 15 pages.
Final Office Action received for U.S. Appl. No. 17/591,184, mailed on Sep. 22, 2023, 19 pages.
Final Office Action received for U.S. Appl. No. 17/735,395, mailed on Dec. 7, 2023, 29 pages.
Final Office Action received for U.S. Appl. No. 17/744,500, mailed on Sep. 19, 2023, 35 pages.
Final Office Action received for U.S. Appl. No. 17/892,534, mailed on Nov. 9, 2023, 17 pages.
Final Office Action received for U.S. Appl. No. 17/951,945, mailed on Dec. 7, 2023, 20 pages.
Final Office Action received for U.S. Appl. No. 17/952,027, mailed on Aug. 21, 2023, 47 pages.
Final Office Action received for U.S. Appl. No. 17/952,133, mailed on Sep. 26, 2023, 20 pages.
Final Office Action received for U.S. Appl. No. 17/952,233, mailed on Jun. 26, 2023, 18 pages.
Intention to Grant received for European Patent Application No. 16837432.0, mailed on Sep. 7, 2023, 9 pages.
International Preliminary Report on Patentability received for PCT Patent Application No. PCT/US2022/029297, mailed on Nov. 30, 2023, 10 pages.
International Search Report and Written Opinion received for PCT Patent Application No. PCT/US2023/024104, mailed on Oct. 18, 2023, 18 pages.
International Search Report and Written Opinion received for PCT Patent Application No. PCT/US2023/024185, mailed on Sep. 18, 2023, 12 pages.
Invitation to Pay Search Fees received for European Patent Application No. 21714460.9, mailed on Aug. 8, 2023, 3 pages.
Non-Final Office Action received for U.S. Appl. No. 17/031,854, mailed on Oct. 18, 2023, 22 pages.
Non-Final Office Action received for U.S. Appl. No. 17/031,859, mailed on Jul. 10, 2023, 15 pages.
Non-Final Office Action received for U.S. Appl. No. 17/735,395, mailed on Sep. 20, 2023, 29 pages.
Non-Final Office Action received for U.S. Appl. No. 17/896,791, mailed on Aug. 30, 2023, 11 pages.
Non-Final Office Action received for U.S. Appl. No. 17/951,613, mailed on Aug. 2, 2023, 42 pages.
Non-Final Office Action received for U.S. Appl. No. 17/951,624, mailed on Sep. 19, 2023, 41 pages.
Non-Final Office Action received for U.S. Appl. No. 17/951,945, mailed on Sep. 20, 2023, 19 pages.
Non-Final Office Action received for U.S. Appl. No. 17/951,976, mailed on Aug. 3, 2023, 16 pages.
Non-Final Office Action received for U.S. Appl. No. 17/952,181, mailed on Aug. 7, 2023, 18 pages.
Non-Final Office Action received for U.S. Appl. No. 17/952,233, mailed on Apr. 28, 2023, 21 pages.
Non-Final Office Action received for U.S. Appl. No. 17/952,239, mailed on Apr. 4, 2023, 45 pages.
Non-Final Office Action received for U.S. Appl. No. 18/135,056, mailed on Dec. 7, 2023, 16 pages.
Notice of Acceptance received for Australian Patent Application No. 2022201761, mailed on Jun. 15, 2023, 3 pages.
Notice of Acceptance received for Australian Patent Application No. 2022202977, mailed on Sep. 26, 2023, 3 pages.
Notice of Acceptance received for Australian Patent Application No. 2022235614, mailed on Jul. 6, 2023, 3 pages.

(56) References Cited

OTHER PUBLICATIONS

Notice of Acceptance received for Australian Patent Application No. 2023203050, mailed on Oct. 24, 2023, 3 pages.
Notice of Acceptance received for Australian Patent Application No. 2023203776, mailed on Dec. 12, 2023, 3 pages.
Notice of Allowance received for Chinese Patent Application No. 201811303558.2, mailed on Jul. 28, 2023, 2 pages (1 page of English Translation and 1 page of Official Copy).
Notice of Allowance received for Chinese Patent Application No. 201880032190.1, mailed on Oct. 7, 2023, 4 pages (1 page of English Translation and 3 pages of Official Copy).
Notice of Allowance received for Chinese Patent Application No. 201911396643.1, mailed on Jun. 15, 2023, 8 pages (4 pages of English Translation and 4 pages of Official Copy).
Notice of Allowance received for Chinese Patent Application No. 201911396744.9, mailed on Aug. 3, 2023, 5 pages (1 page of English Translation and 4 pages of Official Copy).
Notice of Allowance received for Chinese Patent Application No. 201911396819.3, mailed on Aug. 3, 2023, 5 pages (1 page of English Translation and 4 pages of Official Copy).
Notice of Allowance received for Chinese Patent Application No. 201911396876.1, mailed on Sep. 6, 2023, 5 pages (1 page of English Translation and 4 pages of Official Copy).
Notice of Allowance received for Chinese Patent Application No. 201911401375.8, mailed on Nov. 26, 2023, 2 pages (1 page of English Translation and 1 page of Official Copy).
Notice of Allowance received for Japanese Patent Application No. 2021-153558, mailed on Jun. 9, 2023, 4 pages (1 page of English Translation and 3 pages of Official Copy).
Notice of Allowance received for Japanese Patent Application No. 2022-022159, mailed on Aug. 10, 2023, 4 pages (1 page of English Translation and 3 pages of Official Copy).
Notice of Allowance received for Japanese Patent Application No. 2022-076722, mailed on Jul. 28, 2023, 4 pages (1 page of English Translation and 3 pages of Official Copy).
Notice of Allowance received for Japanese Patent Application No. 2022-107903, mailed on Sep. 1, 2023, 4 pages (1 page of English Translation and 3 pages of Official Copy).
Notice of Allowance received for Korean Patent Application No. 10-2020-0123840, mailed on May 26, 2023, 9 pages (2 pages of English Translation and 7 pages of Official Copy).
Notice of Allowance received for U.S. Appl. No. 16/820,383, mailed on Aug. 2, 2023, 14 pages.
Notice of Allowance received for U.S. Appl. No. 16/820,383, mailed on Dec. 7, 2023, 13 pages.
Notice of Allowance received for U.S. Appl. No. 17/041,438, mailed on Oct. 19, 2023, 2 pages.
Notice of Allowance received for U.S. Appl. No. 17/041,438, mailed on Sep. 20, 2023, 11 pages.
Notice of Allowance received for U.S. Appl. No. 17/381,570, mailed on Jul. 26, 2023, 14 pages.
Notice of Allowance received for U.S. Appl. No. 17/591,184, mailed on Dec. 11, 2023, 9 pages.
Notice of Allowance received for U.S. Appl. No. 17/744,500, mailed on Dec. 22, 2023, 38 pages.
Notice of Allowance received for U.S. Appl. No. 17/852,020, mailed on Jul. 12, 2023, 9 pages.
Notice of Allowance received for U.S. Appl. No. 17/896,791, mailed on Dec. 15, 2023, 9 pages.
Notice of Allowance received for U.S. Appl. No. 17/951,613, mailed on Dec. 8, 2023, 13 pages.
Notice of Allowance received for U.S. Appl. No. 17/951,875, mailed on Dec. 26, 2023, 7 pages.
Notice of Allowance received for U.S. Appl. No. 17/951,875, mailed on Jul. 26, 2023, 7 pages.
Notice of Allowance received for U.S. Appl. No. 17/951,875, mailed on Oct. 20, 2023, 8 pages.
Notice of Allowance received for U.S. Appl. No. 17/951,976, mailed on Nov. 17, 2023, 9 pages.
Notice of Allowance received for U.S. Appl. No. 17/952,027, mailed on Dec. 29, 2023, 6 pages.
Notice of Allowance received for U.S. Appl. No. 17/952,027, mailed on Oct. 4, 2023, 13 pages.
Notice of Allowance received for U.S. Appl. No. 17/952,181, mailed on Sep. 27, 2023, 9 pages.
Notice of Allowance received for U.S. Appl. No. 17/952,185, mailed on Aug. 30, 2023, 12 pages.
Notice of Allowance received for U.S. Appl. No. 17/952,185, mailed on Dec. 13, 2023, 9 pages.
Notice of Allowance received for U.S. Appl. No. 17/952,239, mailed on Jun. 23, 2023, 5 pages.
Notice of Allowance received for U.S. Appl. No. 17/952,239, mailed on Oct. 20, 2023, 5 pages.
Office Action received for Australian Patent Application No. 2020268150, mailed on Aug. 24, 2023, 5 pages.
Office Action received for Australian Patent Application No. 2022202977, mailed on Jul. 21, 2023, 3 pages.
Office Action received for Australian Patent Application No. 2023203050, mailed on Sep. 1, 2023, 3 pages.
Office Action received for Australian Patent Application No. 2023203776, mailed on Nov. 7, 2023, 2 pages.
Office Action received for Australian Patent Application No. 2023237090, mailed on Oct. 18, 2023, 3 pages.
Office Action received for Chinese Patent Application No. 201811303556.2, mailed on May 19, 2023, 6 pages (3 pages on English Translation and 3 pages of Official Copy).
Office Action received for Chinese Patent Application No. 201880032190.1, mailed on May 31, 2023, 20 pages (12 pages on English Translation and 8 pages of Official Copy).
Office Action received for Chinese Patent Application No. 201911396876.1, mailed on Apr. 7, 2023, 16 pages (9 pages on English Translation and 7 pages of Official Copy).
Office Action received for Chinese Patent Application No. 201911401375.8, mailed on Sep. 26, 2023, 13 pages (6 pages on English Translation and 7 pages of Official Copy).
Office Action received for Chinese Patent Application No. 202211193170.7, mailed on Jun. 30, 2023, 19 pages (9 pages on English Translation and 10 pages of Official Copy).
Office Action received for European Patent Application No. 20733174.5, mailed on Dec. 18, 2023, 9 pages.
Office Action received for European Patent Application No. 21714460.9, mailed on Oct. 24, 2023, 13 pages.
Office Action received for Japanese Patent Application No. 2021-565912, mailed on Jun. 26, 2023, 3 pages (1 page on English Translation and 2 pages of Official Copy).
Office Action received for Japanese Patent Application No. 2022-130087, mailed on Oct. 2, 2023, 12 pages (6 pages on English Translation and 6 pages of Official Copy).
Office Action received for Japanese Patent Application No. 2023-110196, mailed on Nov. 6, 2023, 4 pages (2 page on English Translation and 2 pages of Official Copy).
Office Action received for Korean Patent Application No. 10-2021-7036242, mailed on Sep. 19, 2023, 13 pages (6 page on English Translation and 7 pages of Official Copy).
Office Action received for Korean Patent Application No. 10-2022-7036278, mailed on Jun. 30, 2023, 10 pages (4 page on English Translation and 6 pages of Official Copy).
Pre-Appeal Review Report received for Japanese Patent Application No. 2021-565912, mailed on Oct. 12, 2023, 5 pages (2 pages of English Translation and 3 pages of Official Copy).
Result of Consultation received for European Patent Application No. 21168916.1, mailed on Dec. 11, 2023, 25 pages.
Summons to Attend Oral Proceedings received for European Patent Application No. 21165295.3, mailed on Jul. 25, 2023, 14 pages.
Summons to Attend Oral Proceedings received for European Patent Application No. 21168916.1, mailed on Jul. 14, 2023, 12 pages.
Supplemental Notice of Allowance received for U.S. Appl. No. 17/381,570, mailed on Aug. 11, 2023, 2 pages.
Supplemental Notice of Allowance received for U.S. Appl. No. 17/381,570, mailed on Sep. 13, 2023, 2 pages.
Supplemental Notice of Allowance received for U.S. Appl. No. 17/850,020, mailed on Aug. 4, 2023, 2 pages.

(56) References Cited

OTHER PUBLICATIONS

Supplemental Notice of Allowance received for U.S. Appl. No. 17/951,875, mailed on Aug. 25, 2023, 2 pages.
Supplemental Notice of Allowance received for U.S. Appl. No. 17/952,181, mailed on Dec. 20, 2023, 2 pages.
Supplemental Notice of Allowance received for U.S. Appl. No. 17/952,181, mailed on Oct. 6, 2023, 2 pages.
Supplemental Notice of Allowance received for U.S. Appl. No. 17/952,181, mailed on Oct. 27, 2023, 2 pages.
Supplemental Notice of Allowance received for U.S. Appl. No. 17/952,185, mailed on Nov. 30, 2023, 2 pages.
Supplemental Notice of Allowance received for U.S. Appl. No. 17/952,185, mailed on Oct. 2, 2023, 2 pages.
ChengCheng et al., "Platform of Development of Motion Control Systems Experimental Software", Experimental and Management, vol. 30, No. 1, Jan. 2013, 3 pages (Official Copy Only) (See Communication Under Rule CFR § 1.98(a) (3)).
DiCristina John, "Fitness Monitoring Equipment Goes Wireless", Frontier Technology, China Academic journal Electronic Publishing House, Online Available at: http://www.cnki.net, Dec. 2012, pp. 44-45 (Official Copy Only) (See Communication Under Rule 37 CFR § 1.98(a) (3)).
GPSCITY, "Garmin Connect Mobile App iOS Overview with GPS City", Available on: https://www.youtube.com/watch?v=rD-KPOJgmOA, 2014, 9 pages.
Yuling et al., "Research on Motion Modeling of Virtual Gear Measuring Center", Tool Technology, vol. 43, No. 2, 2009, pp. 85-87 (Official Copy Only) (See Communication Under Rule 37 CFR § 1.98(a) (3)).
Brief Communication Regarding Oral Proceedings received for European Patent Application No. 21165295.3, mailed on Feb. 27, 2024, 1 page.
Extended European Search Report received for European Patent Application No. 23192409.3, mailed on Feb. 20, 2024, 13 pages.
Non-Final Office Action received for U.S. Appl. No. 17/952,133, mailed on Feb. 28, 2024, 22 pages.
Notice of Acceptance received for Australian Patent Application No. 2023237090, mailed on Feb. 23, 2024, 3 pages.
Applicant-Initiated Interview Summary received for U.S. Appl. No. 17/735,395, mailed on Jan. 31, 2024, 2 pages.
Applicant-Initiated Interview Summary received for U.S. Appl. No. 17/892,534, mailed on Feb. 1, 2024, 4 pages.
Applicant-Initiated Interview Summary received for U.S. Appl. No. 17/951,945, mailed on Jan. 31, 2024, 2 pages.
Applicant-Initiated Interview Summary received for U.S. Appl. No. 18/135,056, mailed on Jan. 3, 2024, 2 pages.
Corrected Notice of Allowance received for U.S. Appl. No. 17/744,500, mailed on Jan. 12, 2024, 3 pages.
Corrected Notice of Allowance received for U.S. Appl. No. 17/952,027, mailed on Jan. 22, 2024, 3 pages.
Final Office Action received for U.S. Appl. No. 17/951,624, mailed on Jan. 25, 2024, 48 pages.
Intention to Grant received for European Patent Application No. 21714460.9, mailed on Feb. 8, 2024, 12 pages.
Minutes of the Oral Proceedings received for European Patent Application No. 21168916.1, mailed on Jan. 3, 2024, 5 pages.
Non-Final Office Action received for U.S. Appl. No. 17/952,075, mailed on Jan. 16, 2024, 27 pages.
Non-Final Office Action received for U.S. Appl. No. 17/952,233, mailed on Feb. 2, 2024, 18 pages.
Notice of Allowance received for Japanese Patent Application No. 2023-110196, mailed on Feb. 13, 2024, 4 pages (1 page of English Translation and 3 pages of Official Copy).
Notice of Allowance received for Korean Patent Application No. 10-2022-7036278, mailed on Jan. 30, 2024, 8 pages (2 pages of English Translation and 6 pages of Official Copy).
Notice of Allowance received for U.S. Appl. No. 17/041,438, mailed on Jan. 22, 2024, 10 pages.
Notice of Allowance received for U.S. Appl. No. 17/892,534, mailed on Feb. 21, 2024, 7 pages.
Notice of Allowance received for U.S. Appl. No. 17/951,613, mailed on Feb. 2, 2024, 5 pages.
Office Action received for Japanese Patent Application No. 2023-041035, mailed on Feb. 9, 2024, 13 pages (6 pages of English Translation and 7 pages of Official Copy).
International Search Report and Written Opinion received for PCT Patent Application No. PCT/US2023/030718, mailed on Jan. 9, 2024, 12 pages.
Notice of Allowance received for U.S. Appl. No. 17/896,791, mailed on Mar. 13, 2024, 8 pages.
Notice of Allowance received for U.S. Appl. No. 17/951,976, mailed on Mar. 12, 2024, 5 pages.
Office Action received for Chinese Patent Application No. 202211193170.7, mailed on Jan. 6, 2024, 13 pages (6 pages of English Translation and 7 pages of Official Copy).

* cited by examiner

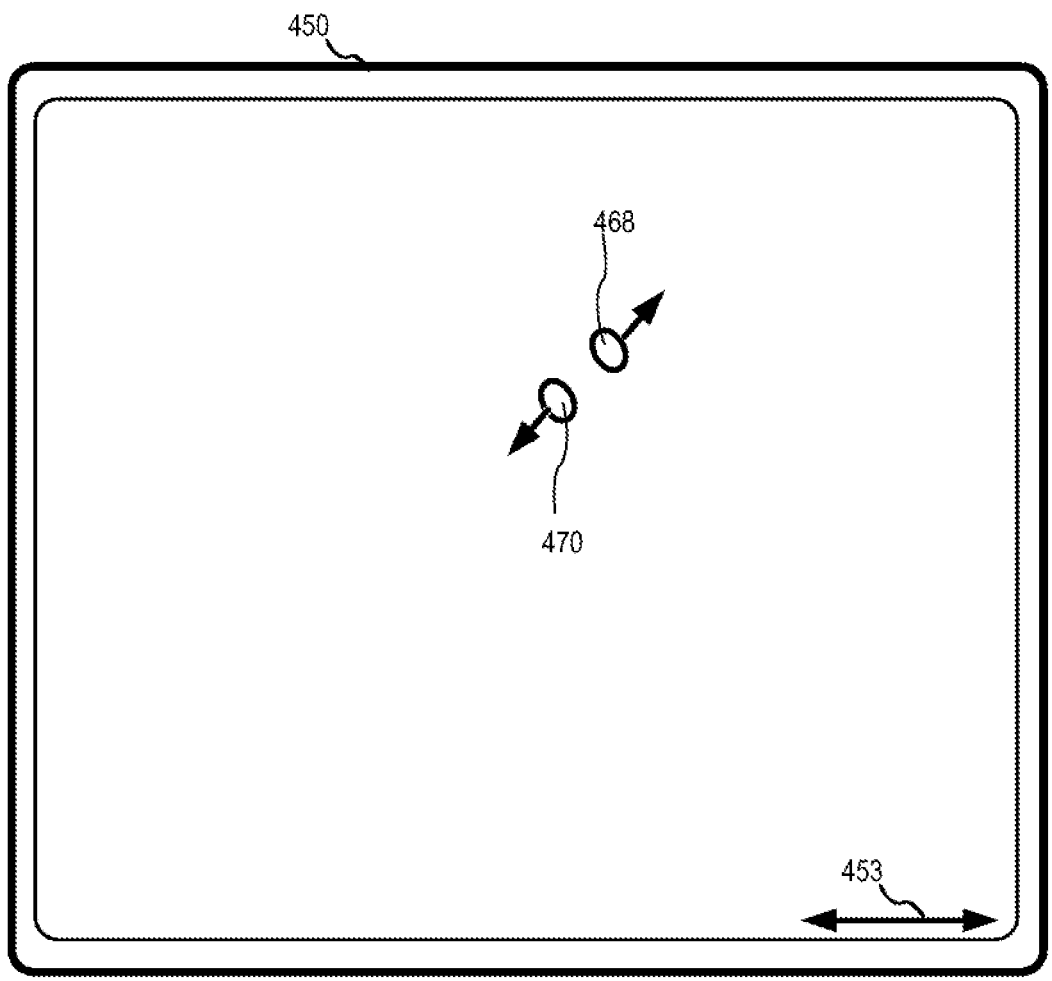
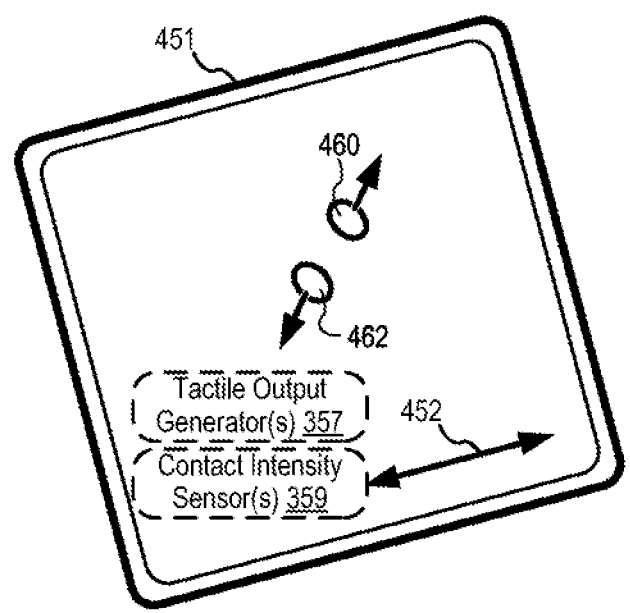
FIG. 4B

700 ⟶

702
Receive, via the one or more input devices, a first user input corresponding to a request to initiate a workout session corresponding to a first workout.

704
In response to receiving the first user input:

706
In accordance with a determination that a user participating in the workout session is associated with an external device of a first type, display, via the display generation component, a first workout session user interface, wherein displaying the first workout session user interface includes concurrently displaying:

708
Visual content corresponding to the first workout.

710
A representation of a first physical activity metric.

712
A representation of a second physical activity metric different from the first physical activity metric.

714
In accordance with a determination that the user participating in the workout session is not associated with an external device of the first type, display, via the display generation component, a second workout session user interface different from first workout session user interface, wherein displaying the second workout session user interface includes concurrently displaying:

716
The visual content corresponding to the first workout.

718
The representation of the first physical activity metric, without displaying the representation of the second physical activity metric.

*FIG. 7*

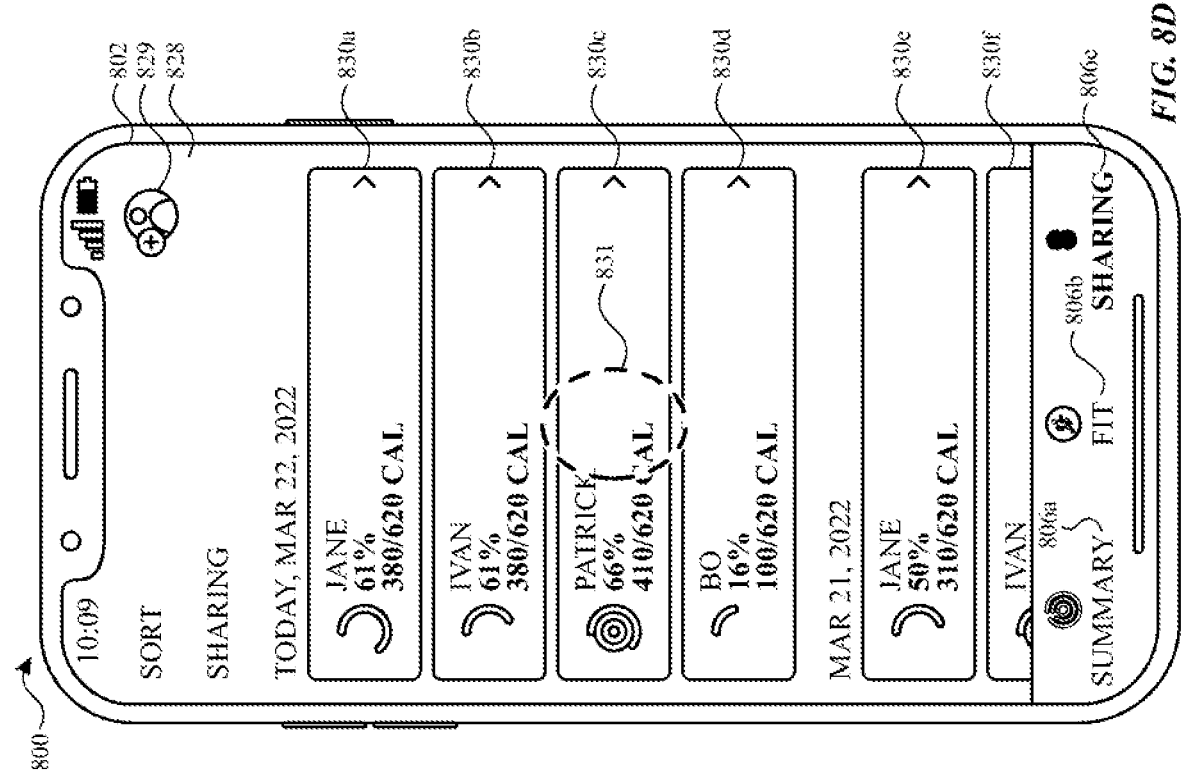
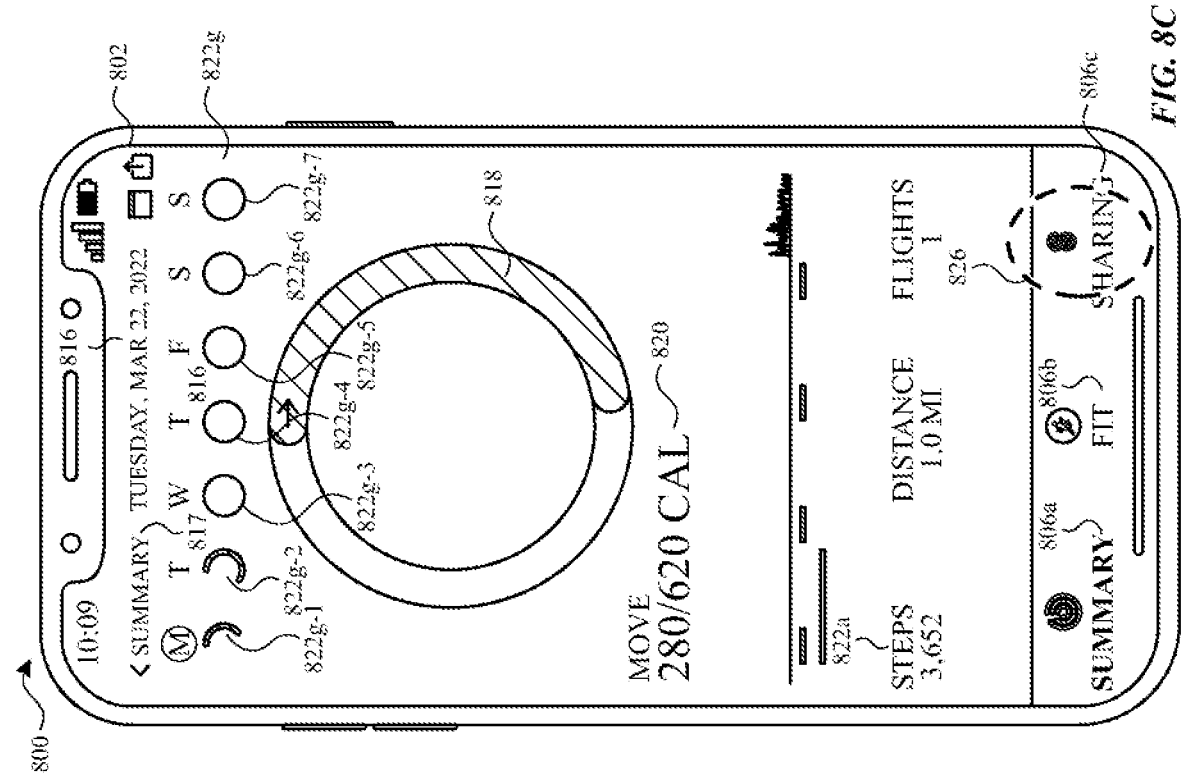

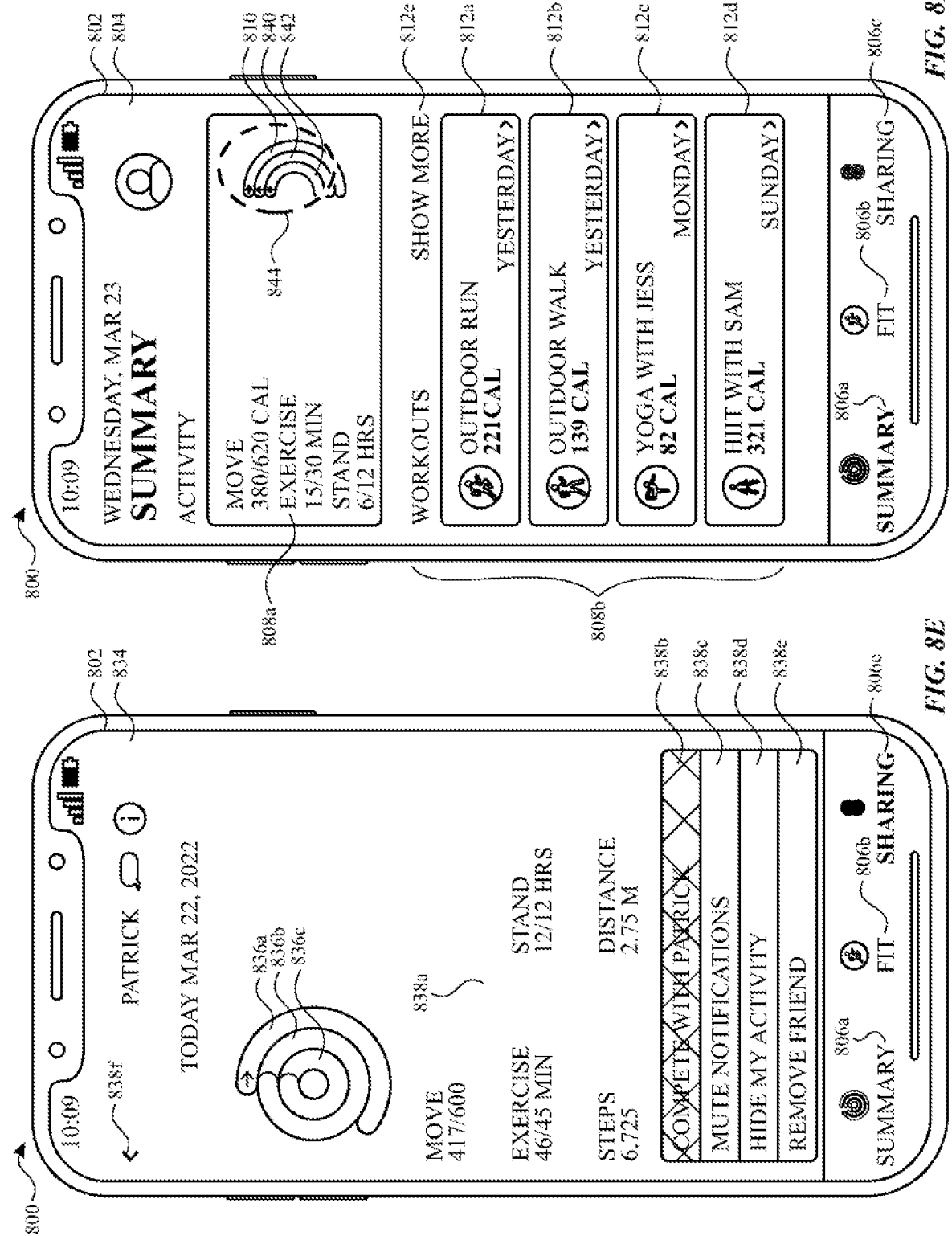

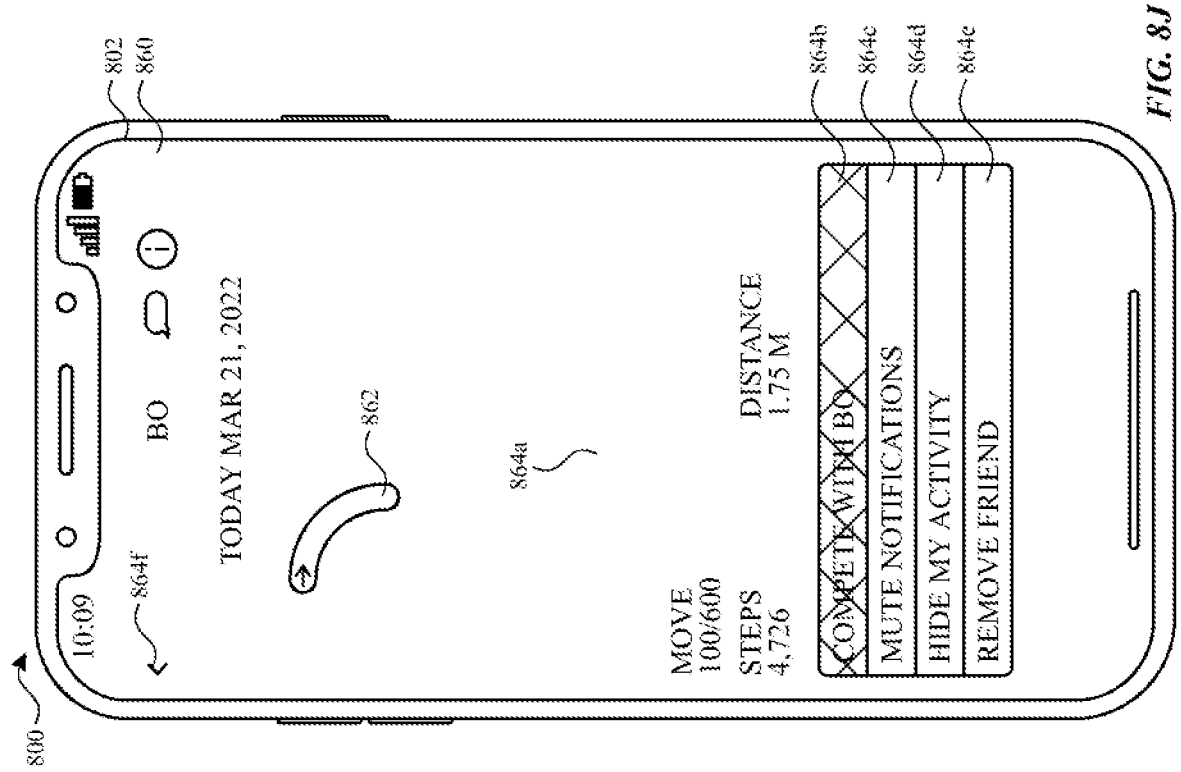

900

902
Receive, via the one or more input devices, a first user input corresponding to a request to view a daily activity user interface, wherein the daily activity user interface displays one or more physical activity metrics corresponding to a plurality of days.

904
In response to receiving the first user input, display, via the display generation component, the daily activity user interface, including displaying a first set of physical activity metrics corresponding to a first day, wherein:

906
In accordance with a determination that external device criteria are satisfied for the first day, displaying the first set of physical activity metrics corresponding to the first day includes concurrently displaying:

908
A representation of a first physical activity metric corresponding to the first day

910
A representation of a second physical activity metric corresponding to the first day

912
In accordance with a determination that external device criteria are not satisfied for the first day, display the first set of physical activity metrics corresponding to the first day includes displaying the representation of the first physical activity metric corresponding to the first day without displaying the representation of the second physical activity metric corresponding to the first day.

*FIG. 9*

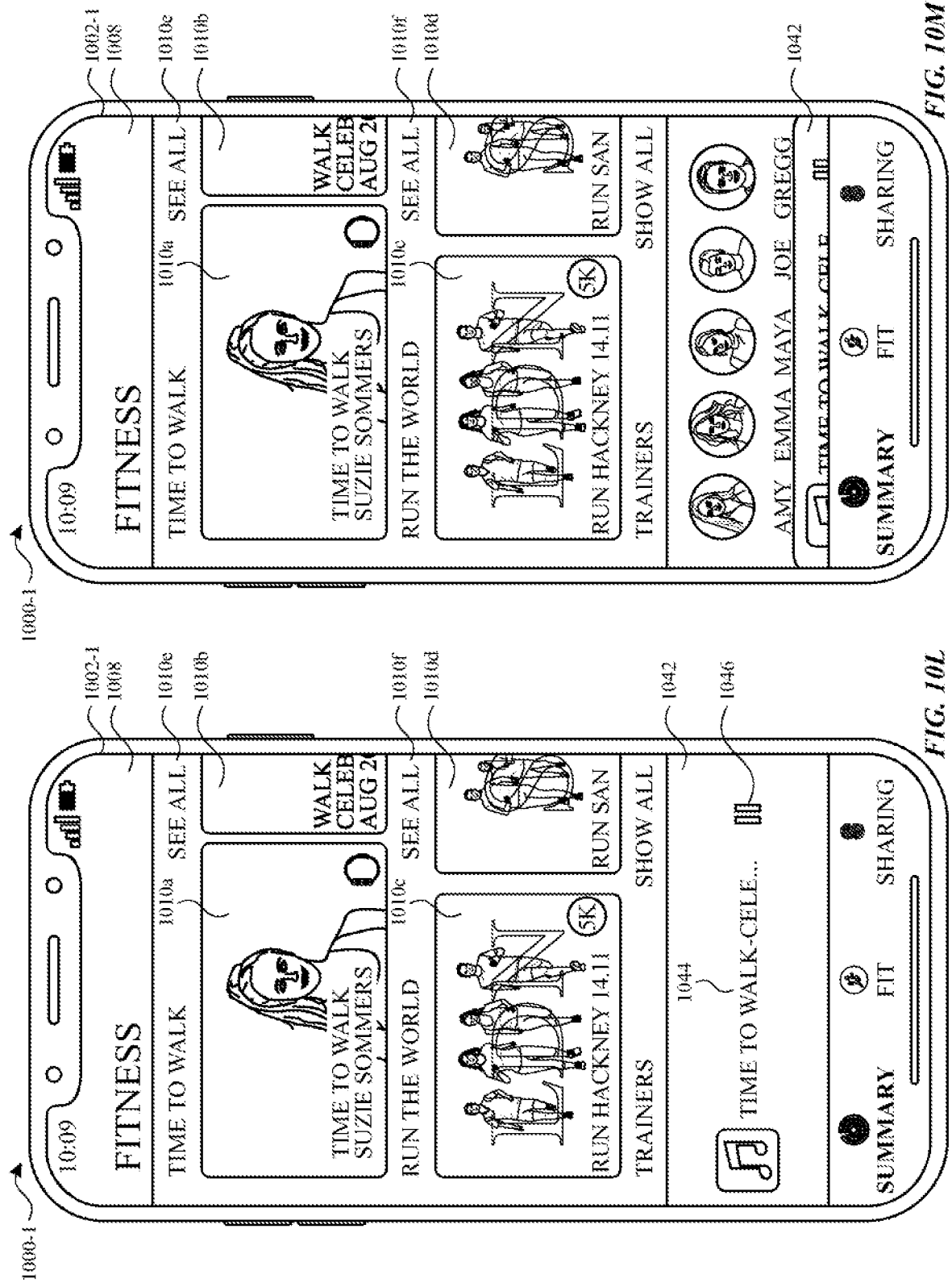

PHYSICAL ACTIVITY INFORMATION USER INTERFACES

CROSS-REFERENCE TO RELATED APPLICATIONS

This application claims priority to U.S. provisional patent application 63/349,104, entitled "PHYSICAL ACTIVITY INFORMATION USER INTERFACES", filed on Jun. 5, 2022, the content of which is hereby incorporated by reference in its entirety.

FIELD

The present disclosure relates generally to computer user interfaces, and more specifically to techniques for navigating and outputting physical activity information.

BACKGROUND

As electronic devices, such as smartphones, have become more widely used, their functions have grown beyond phone calls and text messaging. Providing an efficient method for using and implementing the various functions on these electronic devices can be complex and time-consuming.

BRIEF SUMMARY

Some techniques for navigating and outputting physical activity information using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for navigating and outputting physical activity information. Such methods and interfaces optionally complement or replace other methods for navigating and outputting physical activity information. Such methods and interfaces reduce the cognitive burden on a user and produce a more efficient human-machine interface. For battery-operated computing devices, such methods and interfaces conserve power and increase the time between battery charges.

In accordance with some embodiments, a method, performed at a computer system that is in communication with a display generation component and one or more input devices is described. The method includes: receiving, via the one or more input devices, a first user input corresponding to a request to initiate a workout session corresponding to a first workout; and in response to receiving the first user input: in accordance with a determination that a user participating in the workout session is associated with an external device of a first type, displaying, via the display generation component, a first workout session user interface, wherein displaying the first workout session user interface includes concurrently displaying: visual content corresponding to the first workout; a representation of a first physical activity metric; and representation of a second physical activity metric different from the first physical activity metric; and in accordance with a determination that the user participating in the workout session is not associated with an external device of the first type, displaying, via the display generation component, a second workout session user interface different from first workout session user interface, wherein displaying the second workout session user interface includes concurrently displaying: the visual content corresponding to the first workout, and the representation of the first physical activity metric, without displaying the representation of the second physical activity metric.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: receiving, via the one or more input devices, a first user input corresponding to a request to initiate a workout session corresponding to a first workout; and in response to receiving the first user input: in accordance with a determination that a user participating in the workout session is associated with an external device of a first type, displaying, via the display generation component, a first workout session user interface, wherein displaying the first workout session user interface includes concurrently displaying: visual content corresponding to the first workout; a representation of a first physical activity metric; and representation of a second physical activity metric different from the first physical activity metric; and in accordance with a determination that the user participating in the workout session is not associated with an external device of the first type, displaying, via the display generation component, a second workout session user interface different from first workout session user interface, wherein displaying the second workout session user interface includes concurrently displaying: the visual content corresponding to the first workout, and the representation of the first physical activity metric, without displaying the representation of the second physical activity metric.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: receiving, via the one or more input devices, a first user input corresponding to a request to initiate a workout session corresponding to a first workout; and in response to receiving the first user input: in accordance with a determination that a user participating in the workout session is associated with an external device of a first type, displaying, via the display generation component, a first workout session user interface, wherein displaying the first workout session user interface includes concurrently displaying: visual content corresponding to the first workout; a representation of a first physical activity metric; and representation of a second physical activity metric different from the first physical activity metric; and in accordance with a determination that the user participating in the workout session is not associated with an external device of the first type, displaying, via the display generation component, a second workout session user interface different from first workout session user interface, wherein displaying the second workout session user interface includes concurrently displaying: the visual content corresponding to the first workout, and the representation of the first physical activity metric, without displaying the representation of the second physical activity metric.

In accordance with some embodiments, a computer system that is in communication with a display generation component and one or more input devices, comprising: one or more processors; and memory storing one or more programs configured to be executed by the one or more processors is described. The one or more programs include instructions for: receiving, via the one or more input devices, a first user input corresponding to a request to initiate a workout session corresponding to a first workout; and in response to receiving the first user input: in accordance with a determination that a user participating in the workout session is associated with an external device of a first type, displaying, via the display generation component, a first workout session user interface, wherein displaying the first workout session user interface includes concurrently displaying: visual content corresponding to the first workout; a representation of a first physical activity metric; and representation of a second physical activity metric different from the first physical activity metric; and in accordance with a determination that the user participating in the workout session is not associated with an external device of the first type, displaying, via the display generation component, a second workout session user interface different from first workout session user interface, wherein displaying the second workout session user interface includes concurrently displaying: the visual content corresponding to the first workout, and the representation of the first physical activity metric, without displaying the representation of the second physical activity metric.

In accordance with some embodiments, a computer system that is in communication with a display generation component and one or more input devices is described. The computer system comprises: means for receiving, via the one or more input devices, a first user input corresponding to a request to initiate a workout session corresponding to a first workout; and means for, in response to receiving the first user input: in accordance with a determination that a user participating in the workout session is associated with an external device of a first type, displaying, via the display generation component, a first workout session user interface, wherein displaying the first workout session user interface includes concurrently displaying: visual content corresponding to the first workout; a representation of a first physical activity metric; and representation of a second physical activity metric different from the first physical activity metric; and in accordance with a determination that the user participating in the workout session is not associated with an external device of the first type, displaying, via the display generation component, a second workout session user interface different from first workout session user interface, wherein displaying the second workout session user interface includes concurrently displaying: the visual content corresponding to the first workout, and the representation of the first physical activity metric, without displaying the representation of the second physical activity metric.

In accordance with some embodiments, a computer program product, comprising one or more programs configured to be executed by one or more processors of a computer system that is in communication with a display generation component and one or more input devices is described. The one or more programs include instructions for: receiving, via the one or more input devices, a first user input corresponding to a request to initiate a workout session corresponding to a first workout; and in response to receiving the first user input: in accordance with a determination that a user participating in the workout session is associated with an external device of a first type, displaying, via the display generation component, a first workout session user interface, wherein displaying the first workout session user interface includes concurrently displaying: visual content corresponding to the first workout; a representation of a first physical activity metric; and representation of a second physical activity metric different from the first physical activity metric; and in accordance with a determination that the user participating in the workout session is not associated with an external device of the first type, displaying, via the display generation component, a second workout session user interface different from first workout session user interface, wherein displaying the second workout session user interface includes concurrently displaying: the visual content corresponding to the first workout, and the representation of the first physical activity metric, without displaying the representation of the second physical activity metric.

In accordance with some embodiments, a method performed at a computer system that is in communication with a display generation component and one or more input devices is described. The method includes: receiving, via the one or more input devices, a first user input corresponding to a request to initiate a workout session corresponding to a first workout; and in response to receiving the first user input: in accordance with a determination that a first set of criteria are met, displaying, via the display generation component, a first workout session user interface, corresponding to the first workout; and in accordance with a determination that external device criteria are met with respect to a first external device, causing the first external device to display a second workout session user interface corresponding to the first workout.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: receiving, via the one or more input devices, a first user input corresponding to a request to initiate a workout session corresponding to a first workout; and in response to receiving the first user input: in accordance with a determination that a first set of criteria are met, displaying, via the display generation component, a first workout session user interface, corresponding to the first workout; and in accordance with a determination that external device criteria are met with respect to a first external device, causing the first external device to display a second workout session user interface corresponding to the first workout.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: receiving, via the one or more input devices, a first user input corresponding to a request to initiate a workout session corresponding to a first workout; and in response to receiving the first user input: in accordance with a determination that a first set of criteria are met, displaying, via the display generation component, a first workout session user interface, corresponding to the first workout; and in accordance with a determination that external device criteria are met with respect to a first external device, causing the first external device to display a second workout session user interface corresponding to the first workout.

In accordance with some embodiments, a computer system that is in communication with a display generation component and one or more input devices, comprising: one or more processors; and memory storing one or more programs configured to be executed by the one or more processors is described. The one or more programs include instructions for: receiving, via the one or more input devices, a first user input corresponding to a request to initiate a workout session corresponding to a first workout; and in response to receiving the first user input: in accordance with a determination that a first set of criteria are met, displaying, via the display generation component, a first workout session user interface, corresponding to the first workout; and in accordance with a determination that external device criteria are met with respect to a first external device, causing the first external device to display a second workout session user interface corresponding to the first workout.

In accordance with some embodiments, a computer system that is in communication with a display generation component and one or more input devices is described. The computer system comprises: means for receiving, via the one or more input devices, a first user input corresponding to a request to initiate a workout session corresponding to a first workout; and means for, in response to receiving the first user input: in accordance with a determination that a first set of criteria are met, displaying, via the display generation component, a first workout session user interface, corresponding to the first workout; and in accordance with a determination that external device criteria are met with respect to a first external device, causing the first external device to display a second workout session user interface corresponding to the first workout.

In accordance with some embodiments, a computer program product, comprising one or more programs configured to be executed by one or more processors of a computer system that is in communication with a display generation component and one or more input devices is described. The one or more programs include instructions for: receiving, via the one or more input devices, a first user input corresponding to a request to initiate a workout session corresponding to a first workout; and in response to receiving the first user input: in accordance with a determination that a first set of criteria are met, displaying, via the display generation component, a first workout session user interface, corresponding to the first workout; and in accordance with a determination that external device criteria are met with respect to a first external device, causing the first external device to display a second workout session user interface corresponding to the first workout.

In accordance with some embodiments, a method, performed at a computer system that is in communication with a display generation component and one or more input devices is described. The method includes: receiving, via the one or more input devices, a first user input corresponding to a request to view a daily activity user interface, wherein the daily activity user interface displays one or more physical activity metrics corresponding to a plurality of days; and in response to receiving the first user input, displaying, via the display generation component, the daily activity user interface, including displaying a first set of physical activity metrics corresponding to a first day, wherein: in accordance with a determination that external device criteria are satisfied for the first day, displaying the first set of physical activity metrics corresponding to the first day includes concurrently displaying: a representation of a first physical activity metric corresponding to the first day; and a representation of a second physical activity metric corresponding to the first day; and in accordance with a determination that external device criteria are not satisfied for the first day, displaying the first set of physical activity metrics corresponding to the first day includes displaying the representation of the first physical activity metric corresponding to the first day without displaying the representation of the second physical activity metric corresponding to the first day.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: receiving, via the one or more input devices, a first user input corresponding to a request to view a daily activity user interface, wherein the daily activity user interface displays one or more physical activity metrics corresponding to a plurality of days; and in response to receiving the first user input, displaying, via the display generation component, the daily activity user interface, including displaying a first set of physical activity metrics corresponding to a first day, wherein: in accordance with a determination that external device criteria are satisfied for the first day, displaying the first set of physical activity metrics corresponding to the first day includes concurrently displaying: a representation of a first physical activity metric corresponding to the first day; and a representation of a second physical activity metric corresponding to the first day; and in accordance with a determination that external device criteria are not satisfied for the first day, displaying the first set of physical activity metrics corresponding to the first day includes displaying the representation of the first physical activity metric corresponding to the first day without displaying the representation of the second physical activity metric corresponding to the first day.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: receiving, via the one or more input devices, a first user input corresponding to a request to view a daily activity user interface, wherein the daily activity user interface displays one or more physical activity metrics corresponding to a plurality of days; and in response to receiving the first user input, displaying, via the display generation component, the daily activity user interface, including displaying a first set of physical activity metrics corresponding to a first day, wherein: in accordance with a determination that external device criteria are satisfied for the first day, displaying the first set of physical activity metrics corresponding to the first day includes concurrently displaying: a representation of a first physical activity metric corresponding to the first day; and a representation of a second physical activity metric corresponding to the first day; and in accordance with a determination that external device criteria are not satisfied for the first day, displaying the first set of physical activity metrics corresponding to the first day includes displaying the representation of the first physical activity metric corresponding to the first day without displaying the representation of the second physical activity metric corresponding to the first day.

In accordance with some embodiments, a computer system that is in communication with a display generation component and one or more input devices, comprising: one or more processors; and memory storing one or more programs configured to be executed by the one or more processors is described. The one or more programs include instructions for: receiving, via the one or more input devices, a first user input corresponding to a request to view a daily activity user interface, wherein the daily activity user interface displays one or more physical activity metrics corresponding to a plurality of days; and in response to receiving the first user input, displaying, via the display generation component, the daily activity user interface, including displaying a first set of physical activity metrics corresponding to a first day, wherein: in accordance with a determination that external device criteria are satisfied for the first day, displaying the first set of physical activity metrics corresponding to the first day includes concurrently displaying: a representation of a first physical activity metric corresponding to the first day; and a representation of a second physical activity metric corresponding to the first day; and in accordance with a determination that external device criteria are not satisfied for the first day, displaying the first set of physical activity metrics corresponding to the first day includes displaying the representation of the first physical activity metric corresponding to the first day without displaying the representation of the second physical activity metric corresponding to the first day.

In accordance with some embodiments, a computer system that is in communication with a display generation component and one or more input devices is described. The computer system comprises: means for receiving, via the one or more input devices, a first user input corresponding to a request to view a daily activity user interface, wherein the daily activity user interface displays one or more physical activity metrics corresponding to a plurality of days; and means for, in response to receiving the first user input, displaying, via the display generation component, the daily activity user interface, including displaying a first set of physical activity metrics corresponding to a first day, wherein: in accordance with a determination that external device criteria are satisfied for the first day, displaying the first set of physical activity metrics corresponding to the first day includes concurrently displaying: a representation of a first physical activity metric corresponding to the first day; and a representation of a second physical activity metric corresponding to the first day; and in accordance with a determination that external device criteria are not satisfied for the first day, displaying the first set of physical activity metrics corresponding to the first day includes displaying the representation of the first physical activity metric corresponding to the first day without displaying the representation of the second physical activity metric corresponding to the first day.

In accordance with some embodiments, a computer program product, comprising one or more programs configured to be executed by one or more processors of a computer system that is in communication with a display generation component and one or more input devices is described. The one or more programs include instructions for: receiving, via the one or more input devices, a first user input corresponding to a request to view a daily activity user interface, wherein the daily activity user interface displays one or more physical activity metrics corresponding to a plurality of days; and in response to receiving the first user input, displaying, via the display generation component, the daily activity user interface, including displaying a first set of physical activity metrics corresponding to a first day, wherein: in accordance with a determination that external device criteria are satisfied for the first day, displaying the first set of physical activity metrics corresponding to the first day includes concurrently displaying: a representation of a first physical activity metric corresponding to the first day; and a representation of a second physical activity metric corresponding to the first day; and in accordance with a determination that external device criteria are not satisfied for the first day, displaying the first set of physical activity metrics corresponding to the first day includes displaying the representation of the first physical activity metric corresponding to the first day without displaying the representation of the second physical activity metric corresponding to the first day.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for navigating and outputting physical activity information, thereby increasing the effectiveness, efficiency, and user satisfaction with such devices. Such methods and interfaces may complement or replace other methods for navigating and outputting physical activity information.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIG. 7 illustrates a flow diagram depicting a method for navigating and displaying physical activity information, in accordance with some embodiments.

FIGS. 8A-8J illustrate exemplary user interfaces for navigating and displaying physical activity information, in accordance with some embodiments.

FIG. 9 illustrates a flow diagram depicting a method for navigating and displaying physical activity information, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for navigating and outputting physical activity information. For example, a user would benefit from being shown certain physical activity information if the user does not have an external device or accessory, such as a smart watch or fitness band, and being shown other physical activity information (e.g., additional physical activity information) if the user does have an external device or accessory. Such techniques can reduce the cognitive burden on a user who navigates and views physical activity information, thereby enhancing productivity. Further, such techniques can reduce processor and battery power otherwise wasted on redundant user inputs.

Figure 10A:
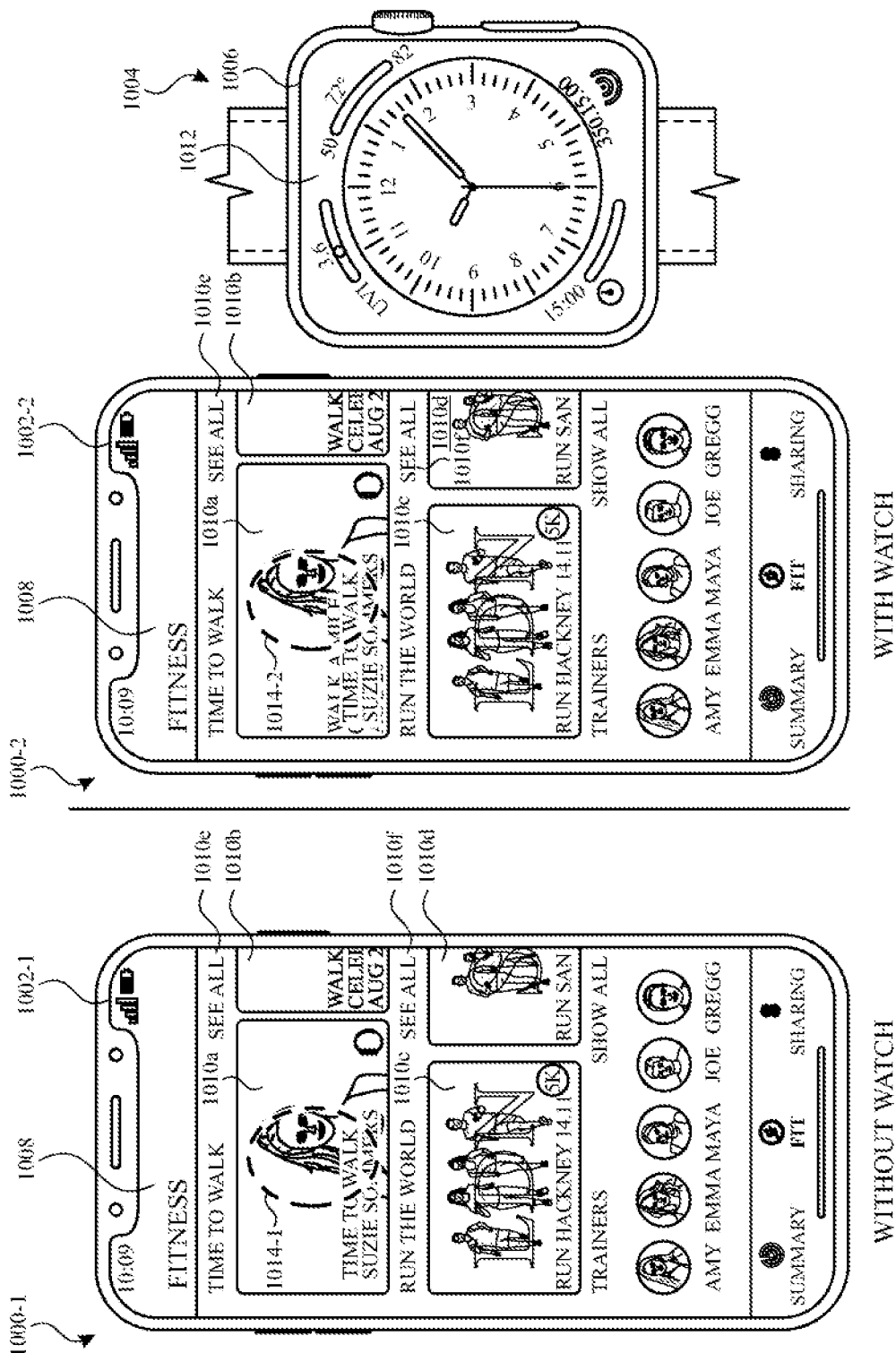
FIGS. 10A-10N illustrate exemplary user interfaces for providing physical activity information including workout content, in accordance with some embodiments.
Figure 10N:
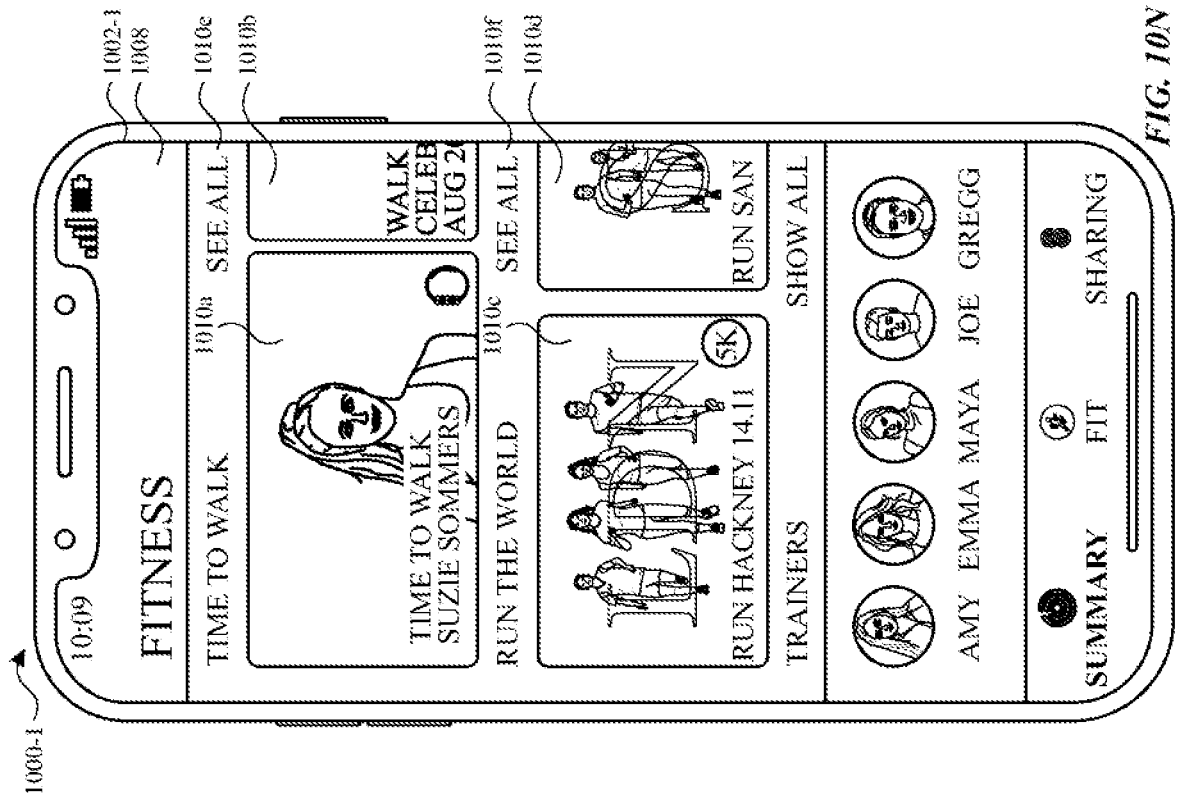
Figure 11:
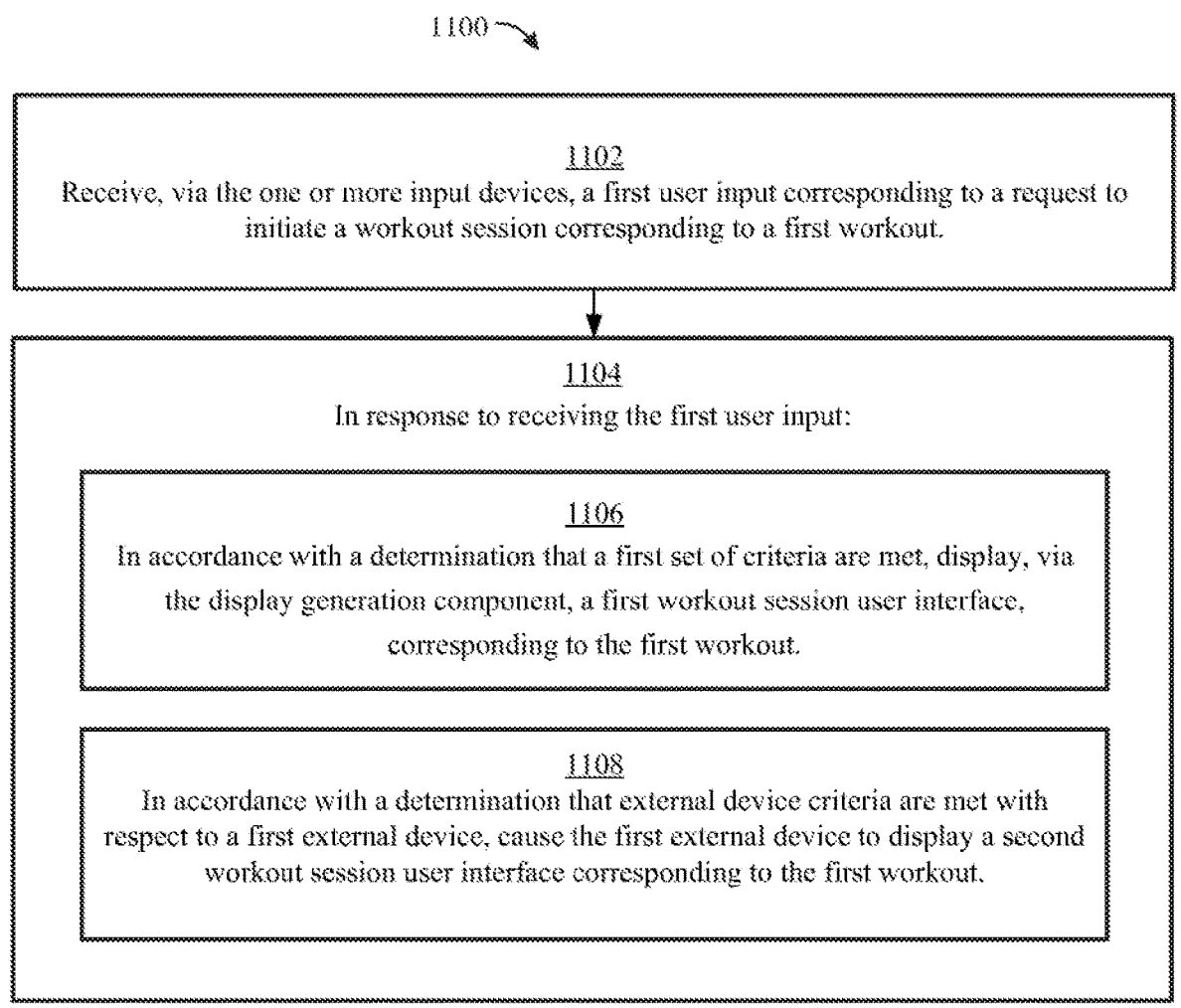
FIG. 11 illustrates a flow diagram depicting a method for providing physical activity information including workout content, in accordance with some embodiments.

Below, FIGS. 1A-1B, 2, 3, 4A-4B, and 5A-5B provide a description of exemplary devices for performing the techniques for navigating and outputting physical activity information. FIGS. 6A-6J illustrate exemplary user interfaces for navigating and displaying physical activity information. FIG. 7 is a flow diagram illustrating methods of navigating and displaying physical activity information in accordance with some embodiments. The user interfaces in FIGS. 6A-6J are used to illustrate the processes described below, including the processes in FIG. 7. FIGS. 8A-8J illustrate exemplary user interfaces for navigating and displaying physical activity information. FIG. 9 is a flow diagram illustrating methods of navigating and displaying physical activity information in accordance with some embodiments. The user interfaces in FIGS. 8A-8J are used to illustrate the processes described below, including the processes in FIG. 9. FIGS. 10A-10N illustrate exemplary user interfaces for providing physical activity information including workout content. FIG. 11 is a flow diagram illustrating methods for providing physical activity information including workout content in accordance with some embodiments. The user interfaces in FIGS. 10A-10N are used to illustrate the processes described below, including the processes in FIG. 11.

The processes described below enhance the operability of the devices and make the user-device interfaces more efficient (e.g., by helping the user to provide proper inputs and reducing user mistakes when operating/interacting with the device) through various techniques, including by providing improved visual feedback to the user, reducing the number of inputs needed to perform an operation, providing additional control options without cluttering the user interface with additional displayed controls, performing an operation when a set of conditions has been met without requiring further user input, and/or additional techniques. These techniques also reduce power usage and improve battery life of the device by enabling the user to use the device more quickly and efficiently.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms "first," "second," etc. to describe various elements, these elements should not be limited by the terms. In some embodiments, these terms are used to distinguish one element from another. For example, a first touch could be termed a second touch, and, similarly, a second touch could be termed a first touch, without departing from the scope of the various described embodiments. In some embodiments, the first touch and the second touch are two separate references to the same touch. In some embodiments, the first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
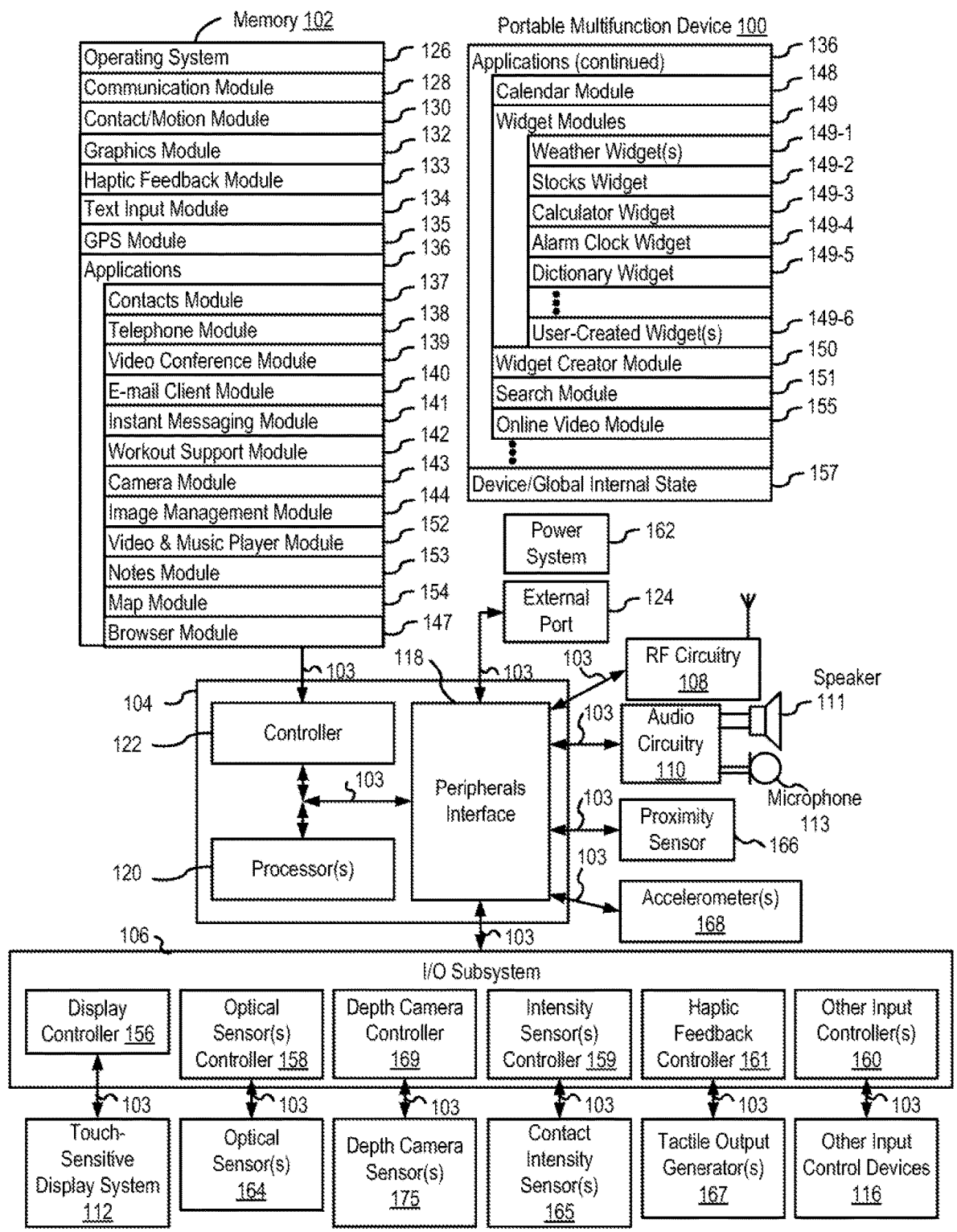
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures and/or air gestures) as input. In some embodiments, the one or more input devices are integrated with the computer system. In some embodiments, the one or more input devices are separate from the computer system. In some embodiments, an air gesture is a gesture that is detected without the user touching an input element that is part of the device (or independently of an input element that is a part of the device) and is based on detected motion of a portion of the user's body through the air including motion of the user's body relative to an absolute reference (e.g., an angle of the user's arm relative to the ground or a distance of the user's hand relative to the ground), relative to another portion of the user's body (e.g., movement of a hand of the user relative to a shoulder of the user, movement of one hand of the user relative to another hand of the user, and/or movement of a finger of the user relative to another finger or portion of a hand of the user), and/or absolute motion of a portion of the user's body (e.g., a tap gesture that includes movement of a hand in a predetermined pose by a predetermined amount and/or speed, or a shake gesture that includes a predetermined speed or amount of rotation of a portion of the user's body).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
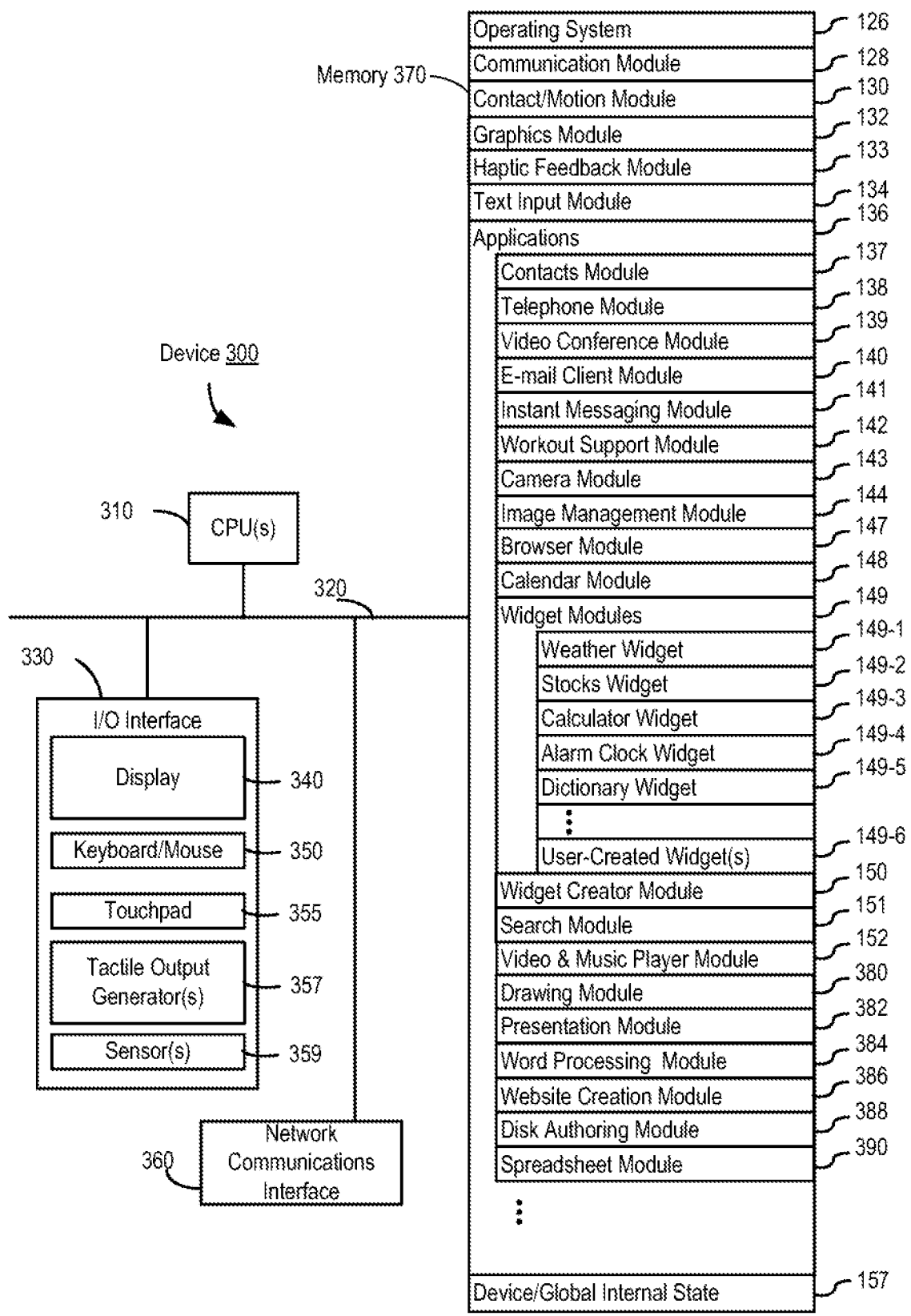
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts module 137, e-mail client module 140, IM module 141, browser module 147, and any other application that needs text input).

GPS module 135 determines the location of the device and provides this information for use in various applications (e.g., to telephone module 138 for use in location-based dialing; to camera module 143 as picture/video metadata; and to applications that provide location-based services such as weather widgets, local yellow page widgets, and map/navigation widgets).

Applications 136 optionally include the following modules (or sets of instructions), or a subset or superset thereof:

Contacts module 137 (sometimes called an address book or contact list);

Telephone module 138;
Video conference module 139;
E-mail client module 140;
Instant messaging (IM) module 141;
Workout support module 142;
Camera module 143 for still and/or video images;
Image management module 144;
Video player module;
Music player module;
Browser module 147;
Calendar module 148;
Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
Widget creator module 150 for making user-created widgets 149-6;
Search module 151;
Video and music player module 152, which merges video player module and music player module;
Notes module 153;
Map module 154; and/or
Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone module 138, video conference module 139, e-mail client module 140, or IM module 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
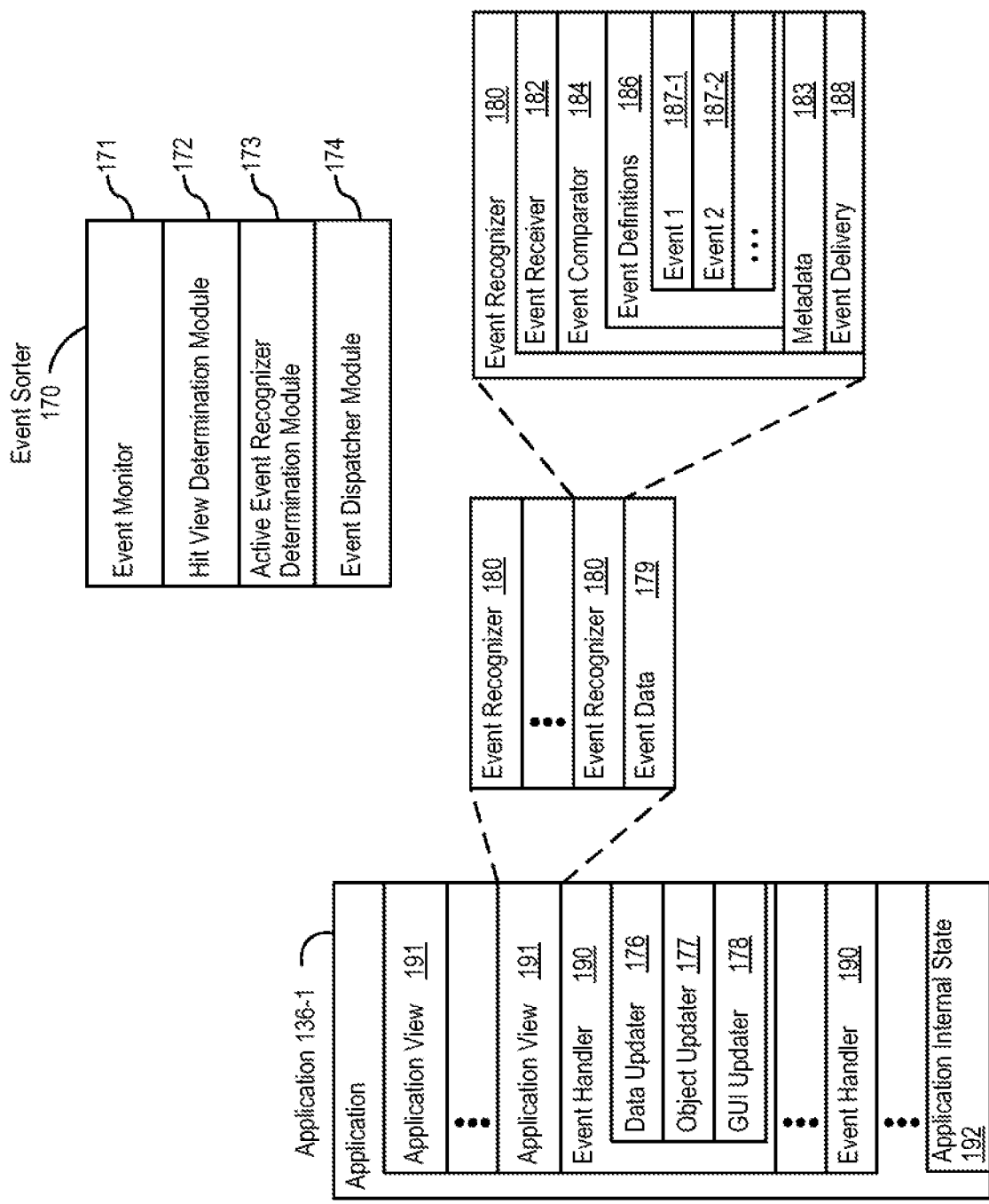
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (e.g., 187-1 and/or 187-2) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definitions 186 include a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
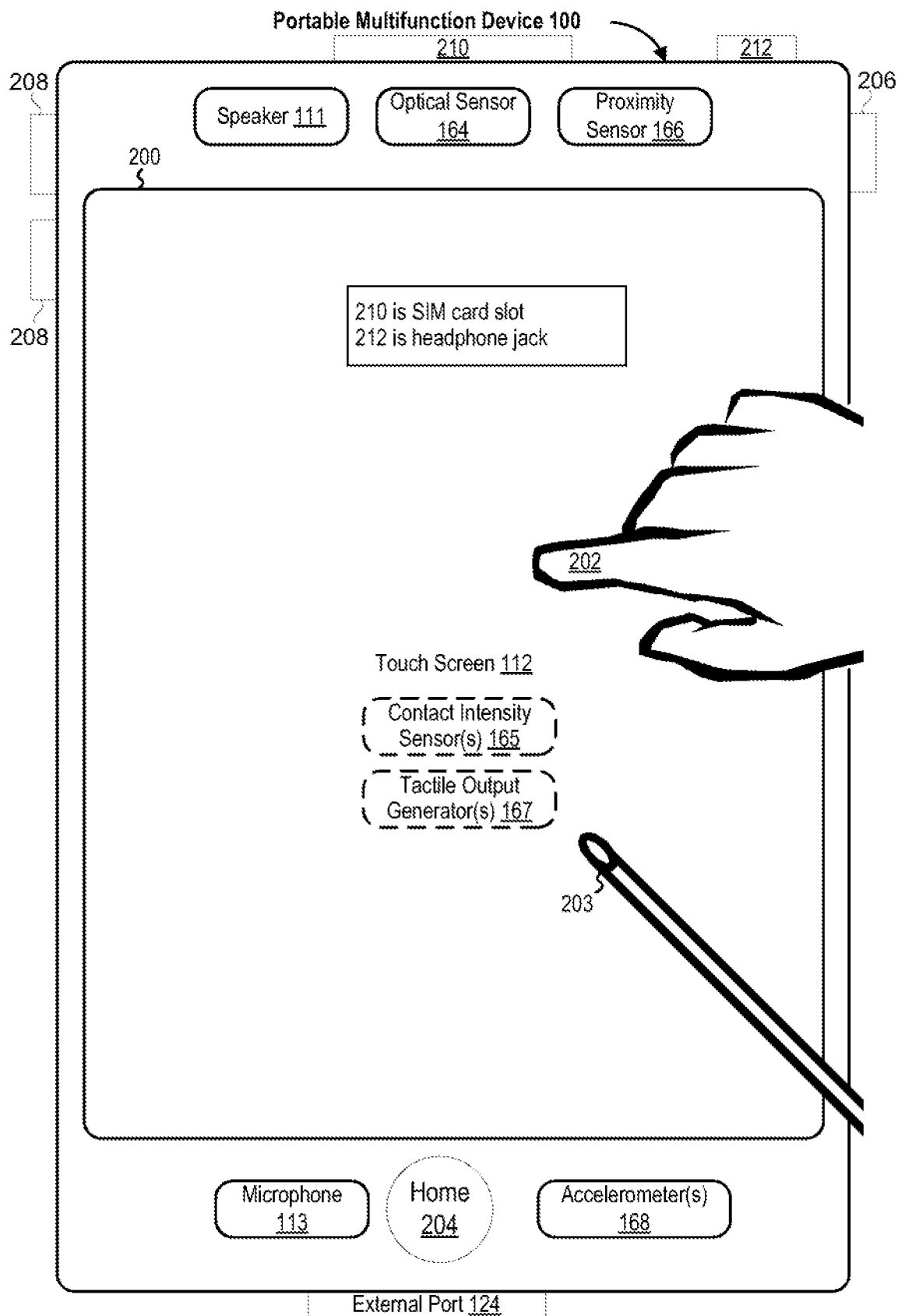
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
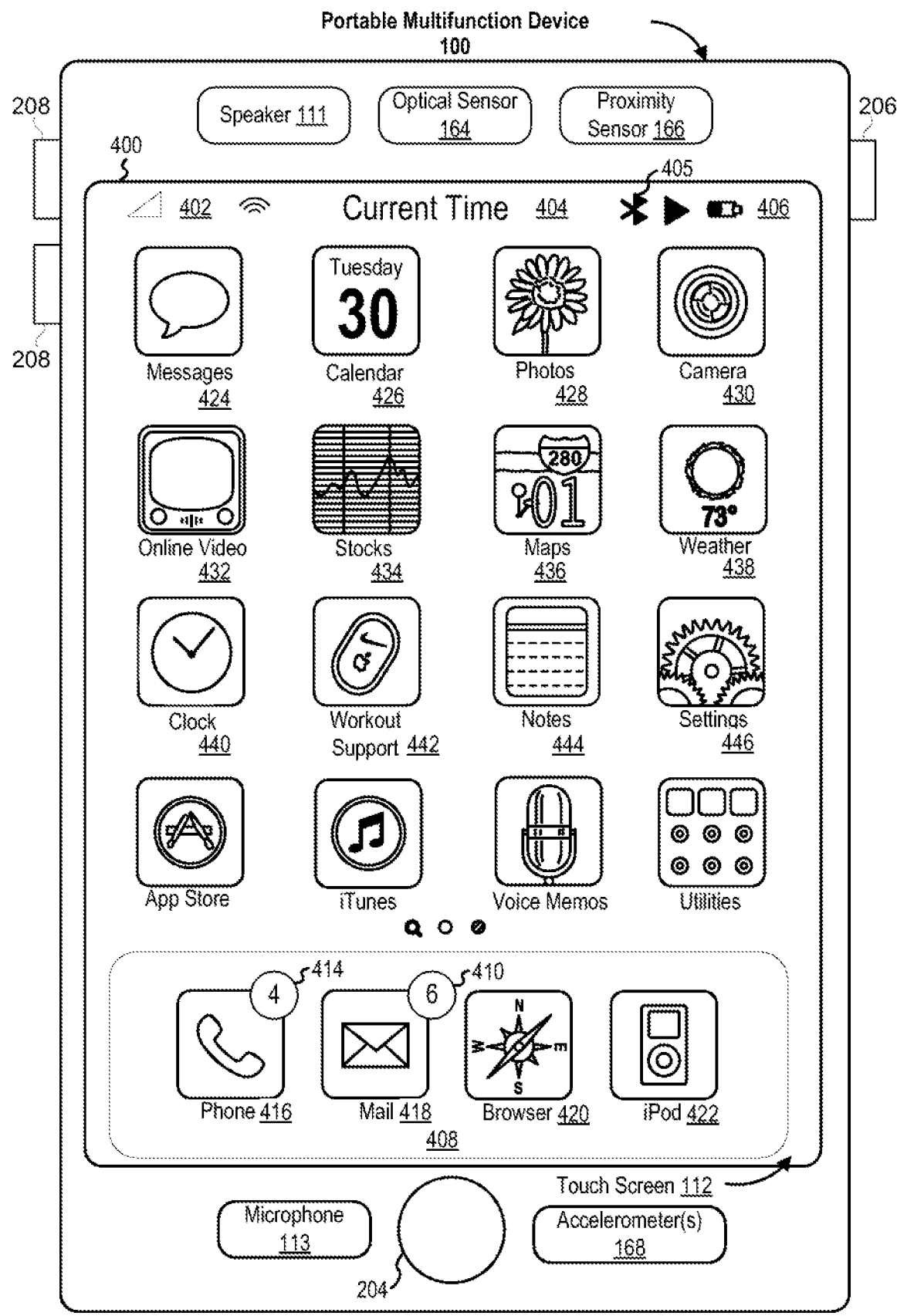
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
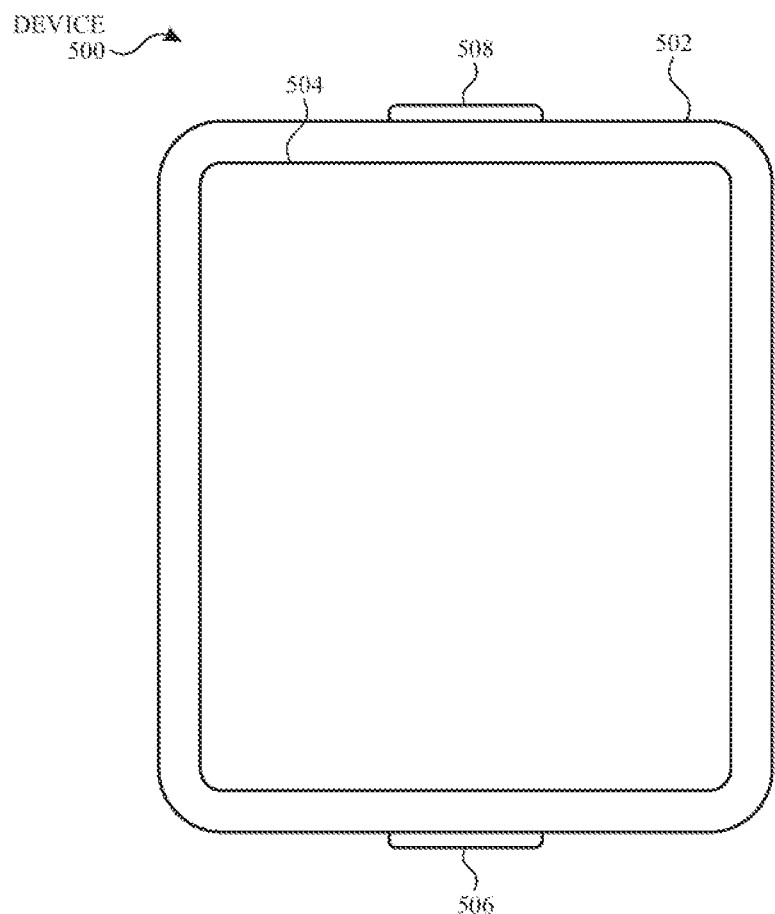
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
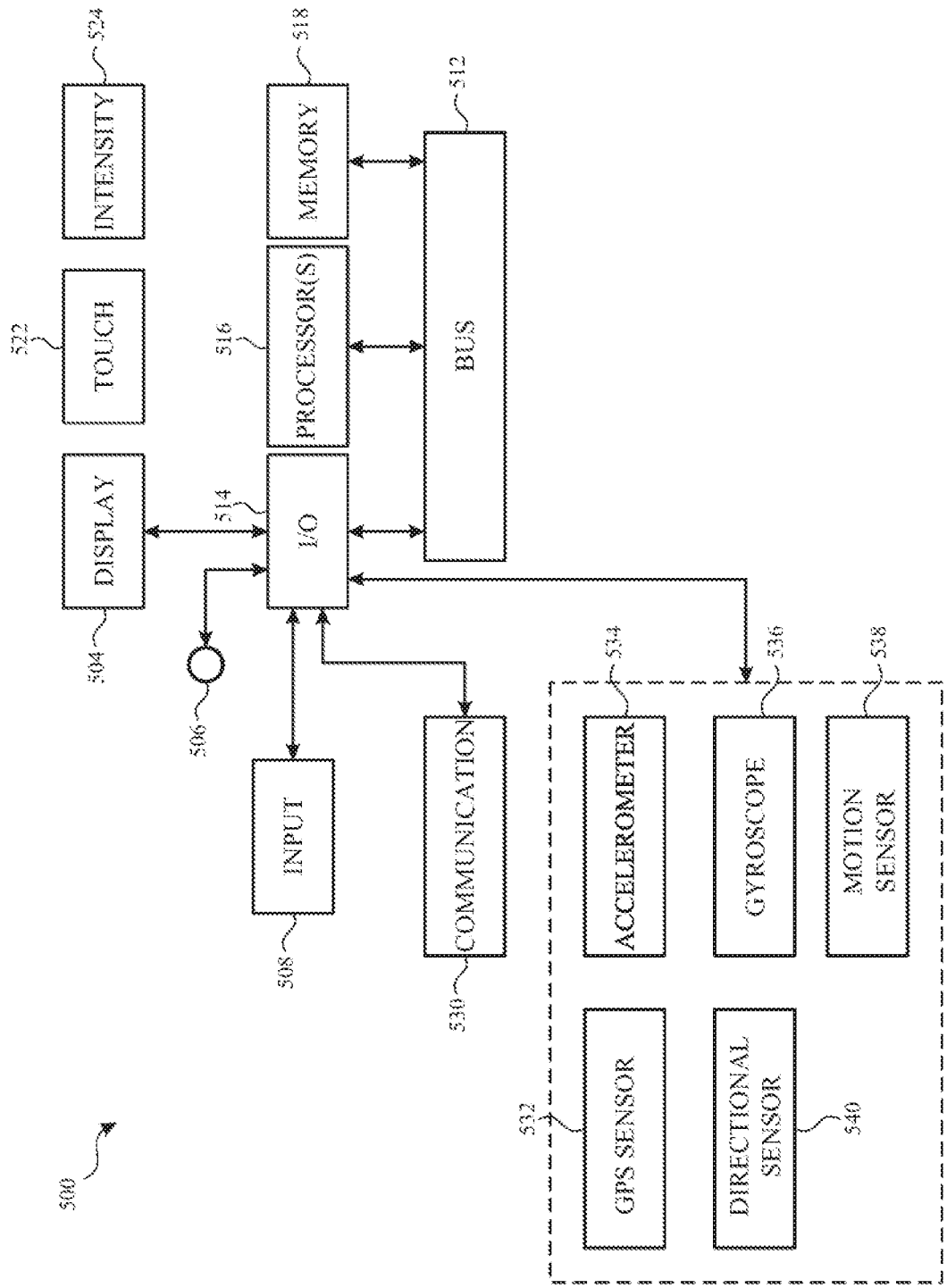
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 900, and 1100 (FIGS. 7, 9, and 11). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

- an active application, which is currently displayed on a display screen of the device that the application is being used on;
- a background application (or background processes), which is not currently displayed, but one or more processes for the application are being processed by one or more processors; and
- a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

In some embodiments, the computer system is in a locked state or an unlocked state. In the locked state, the computer system is powered on and operational but is prevented from performing a predefined set of operations in response to user input. The predefined set of operations optionally includes navigation between user interfaces, activation or deactivation of a predefined set of functions, and activation or deactivation of certain applications. The locked state can be used to prevent unintentional or unauthorized use of some functionality of the computer system or activation or deactivation of some functions on the computer system. In some embodiments, in the unlocked state, the computer system is powered on and operational and is not prevented from performing at least a portion of the predefined set of operations that cannot be performed while in the locked state. When the computer system is in the locked state, the computer system is said to be locked. When the computer system is in the unlocked state, the computer is said to be unlocked. In some embodiments, the computer system in the locked state optionally responds to a limited set of user inputs, including input that corresponds to an attempt to transition the computer system to the unlocked state or input that corresponds to powering the computer system off.

Attention is now directed towards embodiments of user interfaces ("UI") and associated processes that are implemented on an electronic device, such as portable multifunction device 100, device 300, or device 500.

FIGS. 6A-6J illustrate exemplary user interfaces for navigating and outputting physical activity information, in accordance with some embodiments. The user interfaces in these figures are used to illustrate the processes described below, including the processes in FIG. 7.

Figure 6A:
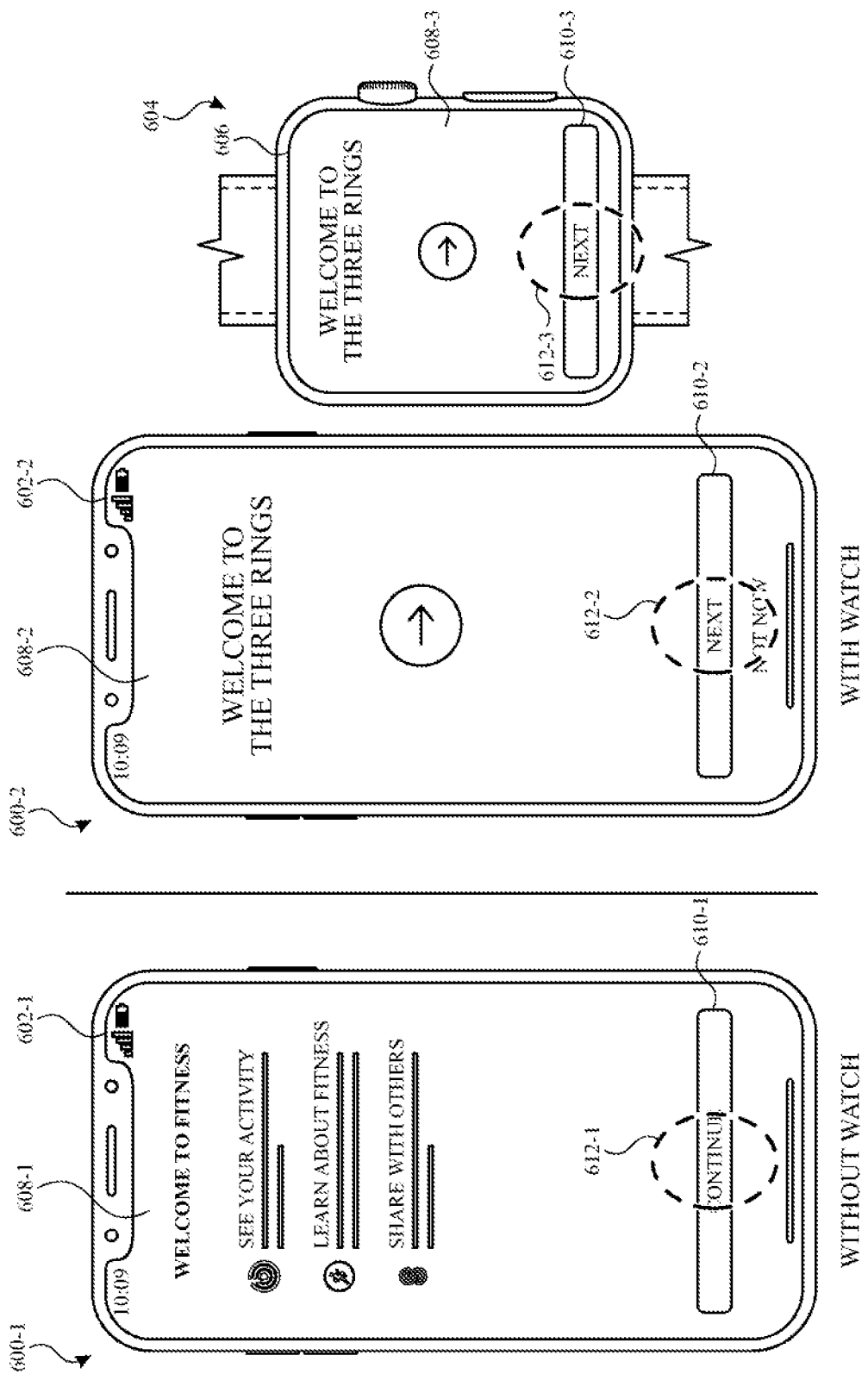
FIGS. 6A-6J illustrate exemplary user interfaces for navigating and displaying physical activity information including workout content, in accordance with some embodiments.

FIG. 6A illustrates electronic device 600-1 with touch-sensitive display 602-1, and electronic device 600-2 with touch-sensitive display 602-2. In the depicted examples, electronic device 600-1 and electronic device 600-2 are the same electronic device but in different states and displayed at two different times (e.g., on a first day and on a second day). Electronic device 600-1 is an electronic device that does not have a smartwatch or other wearable device associated with it (e.g., registered on it and/or paired with it), while electronic device 600-2 is an electronic device that does have a smartwatch or other wearable device associated with it (e.g., registered on it and/or paired with it). In FIG. 6A, electronic device 604, which is a smartwatch with touch-sensitive display 606, is paired to electronic device 600-2. In FIGS. 6A-6J, electronic device 600-1 and electronic device 600-2 will be displayed adjacent to one another in order to demonstrate various user interfaces and how they are displayed differently based on whether or not an electronic device (e.g., 600-1, 600-2) is associated with and/or paired to an external device of a particular type (e.g., a smartwatch (e.g., electronic device 604)). While the depicted embodiments show the external device of the particular type as a smartwatch, in other embodiments, the external device is a different type of device (e.g., a wearable device, a fitness band, or other external electronic device).

On the left side of FIG. 6A, a user has begun using a fitness application for the first time on electronic device 600-1 (e.g., the user has tapped on an application icon corresponding to the fitness application to open the fitness application). In response, electronic device 600-1 displays welcome user interface 608-1, which includes option 610-1 that is selectable to initiate a watchless onboarding process. On the right side of FIG. 6A, a user has paired electronic device 604 with electronic device 600-2, and in response to this pairing (and/or in accordance with this pairing), electronic device 600-2 displays welcome user interface 608-2, which includes option 610-2 that is selectable to initiate a watch onboarding process, and electronic device 604 displays corresponding welcome user interface 608-3 that includes option 610-3 that is also selectable to initiate a watch onboarding process. While both electronic device 600-2 and electronic device 604 are shown displaying a welcome user interface, in some embodiments, only one of these devices displays a welcome user interface (e.g., only electronic device 600-2 displays welcome user interface 608-2 without electronic device 604 displaying welcome user interface 608-3 and/or only electronic device 604 displays welcome user interface 608-2 without electronic device 600-2 displaying welcome user interface 608-2). At FIG. 6A, electronic device 600-1 detects user input 612-1 (e.g., a tap input) corresponding to selection of option 610-1, electronic device 600-2 detects user input 612-2 (e.g., a tap input) corresponding to selection of option 610-2, and electronic device 604 detects user input 612-3 (e.g., a tap input) corresponding to selection of option 610-3.

Figure 6B:
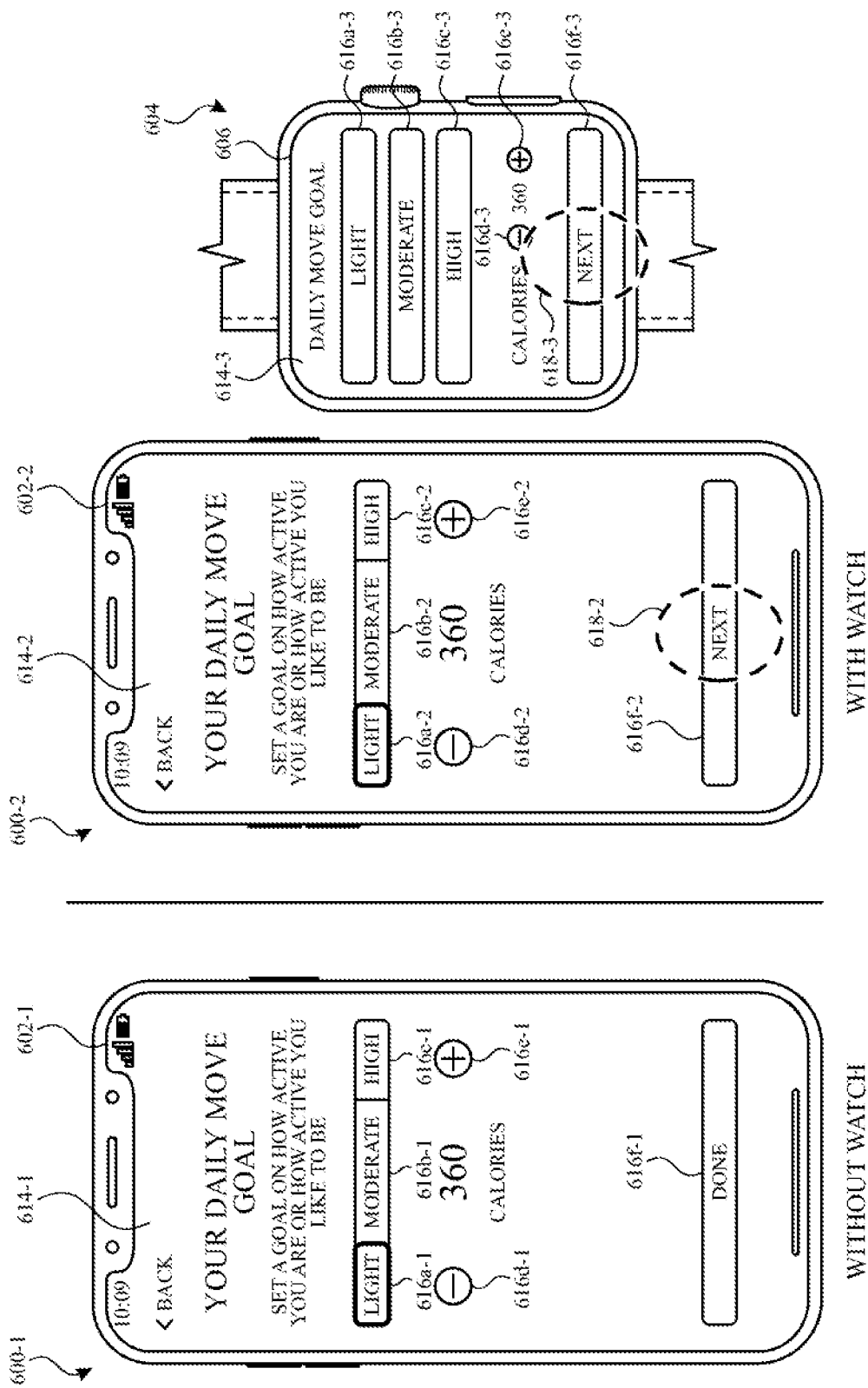

At FIG. 6B, in response to user input 612-1, electronic device 600-1 displays move goal user interface 614-1, which includes one or more controls for the user to define a daily move goal (e.g., a goal for number of calories burned during each calendar day). Move goal user interface 614-1 includes options 616a-1, 616b-1, 616c-1 that correspond to three predefined move goal values (e.g., a lowest predefined move goal value, a middle predefined move goal value, and a highest predefined move goal value) and are each selectable to set the daily move goal value at the corresponding predefined value. Move goal user interface 614-1 also includes control 616d-1 and control 616e-1 to manually increase or decrease the daily move goal value. Finally, move goal user interface 614-1 includes option 616f-1 that is selectable to conclude the watchless onboarding process.

At FIG. 6B, in response to user input 612-2, electronic device 600-2 displays move goal user interface 614-2, and in response to user input 612-3, electronic device 600-3 displays move goal user interface 614-3. Move goal user interface 614-2 and move goal user interface 614-3 are essentially identical to move goal user interface 614-1, with the exception that move goal user interface 614-2 includes option 616f-2 and move goal user interface 614-3 includes option 616f-3 which are each selectable to continue the watch onboarding process, whereas move goal user interface 614-1 included option 616f-1 to end/complete the watchless onboarding process. In the depicted embodiments, when a smartwatch has not been paired to an electronic device (e.g., as with electronic device 600-1), a user of the electronic device is able to track a daily move goal, whereas if a smartwatch has been paired to the electronic device (e.g., as with electronic device 600-2), a user of the electronic device is able to track additional physical activity metrics, including a daily exercise goal and a daily stand goal, as will be discussed below. Accordingly, the watchless onboarding process asks a user to set only the daily move goal while the watch onboarding process asks the user to set additional physical activity metric goals, in addition to the daily move goal. At FIG. 6B, electronic device 600-2 detects user input 618-2 (e.g., a tap input) corresponding to selection of option 616f-2, and electronic device 604 detects user input 618-3 (e.g., a tap input) corresponding to selection of option 616f-3.

Figure 6C:
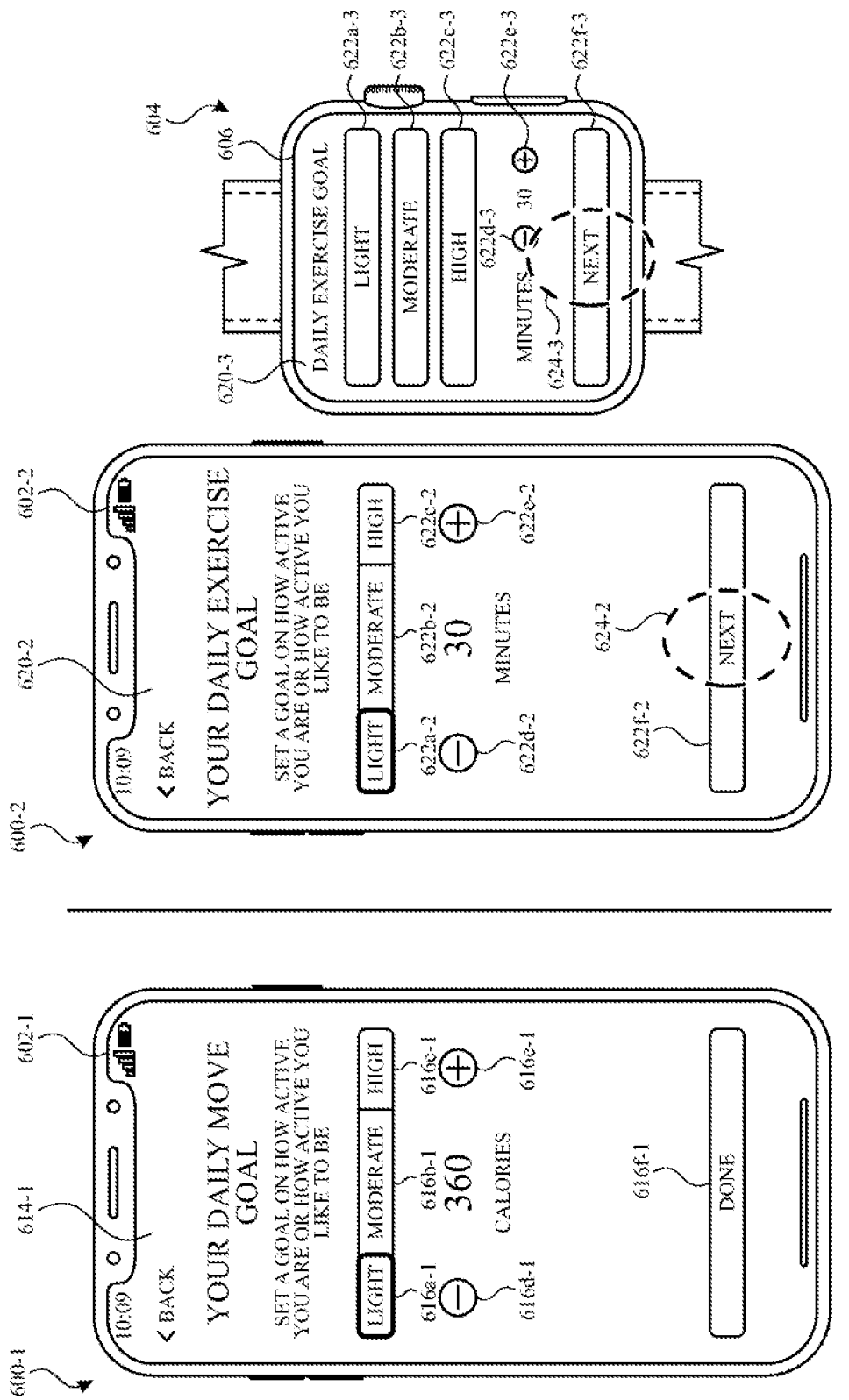

At FIG. 6C, in response to user input 618-2, electronic device 600-2 displays exercise goal user interface 620-2, which includes one or more controls for the user to define a daily exercise goal (e.g., a target number of minutes of exercise for each calendar day). Exercise goal user interface 620-2 includes options 622a-2, 622b-2, and 622c-2 that correspond to three predefined exercise goal values (e.g., a lowest predefined exercise goal value, a middle predefined exercise goal value, and a highest predefined exercise goal value) and are each selectable to set the daily exercise goal value at the corresponding predefined value. Exercise goal user interface 620-2 also includes control 622d-2 and control 622e-2 to manually increase or decrease the daily exercise goal value. Finally, exercise goal user interface 620-2 includes option 622f-2 that is selectable to continue the watch onboarding process.

At FIG. 6C, in response to user input 618-3, electronic device 604 displays exercise goal user interface 620-3, which includes controls that are largely identical to exercise goal user interface 620-2. At FIG. 6C, electronic device 600-2 detects user input 624-2 (e.g., a tap input) corresponding to selection of option 622f-2, and electronic device 604 detects user input 624-3 (e.g., a tap input) corresponding to selection of option 622f-3.

Figure 6D:
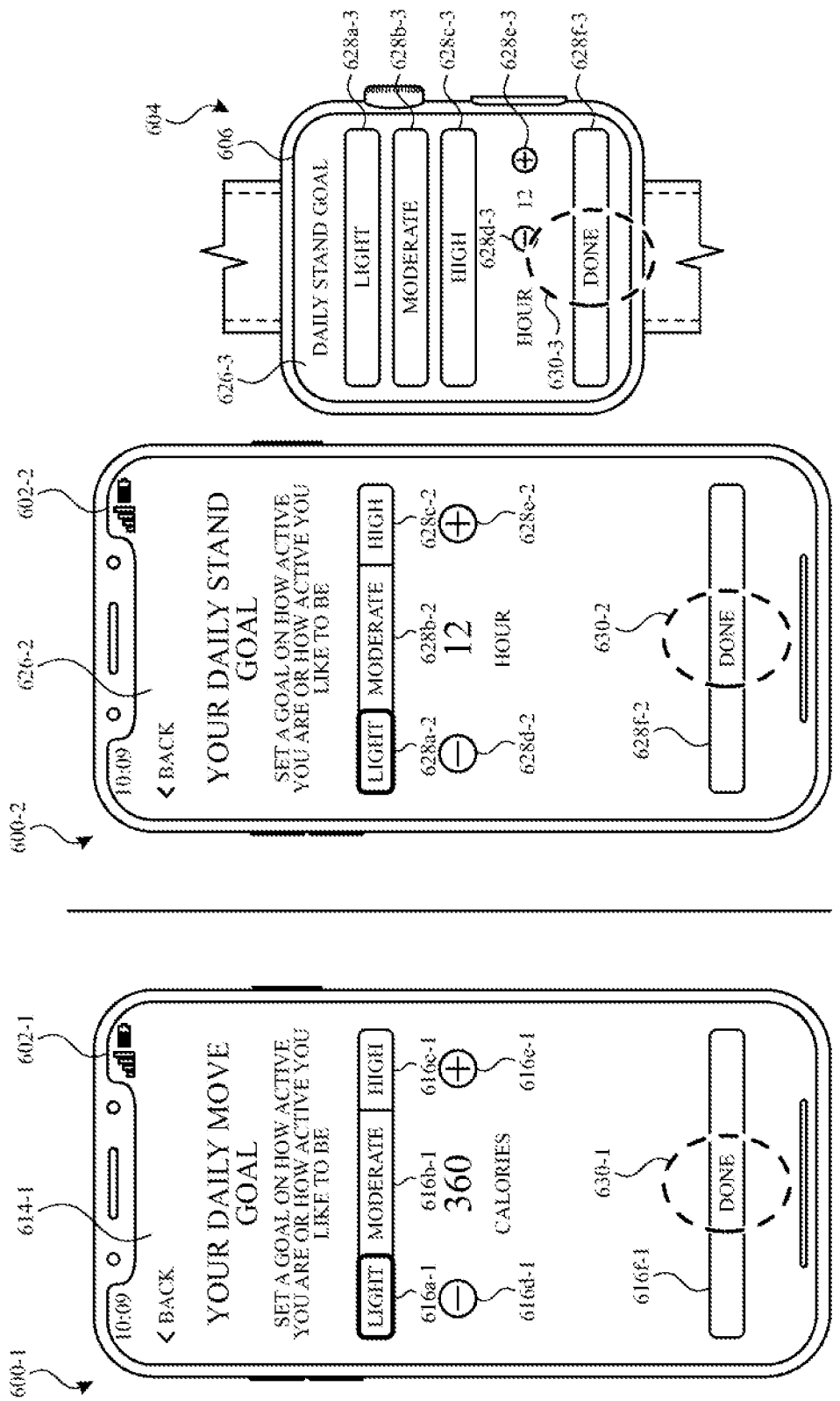

At FIG. 6D, in response to user input 624-2, electronic device 600-2 display stand goal user interface 626-2, which includes one or more controls for the user to define a daily stand goal (e.g., a target number of hours each calendar day for the user to stand for a threshold duration of time during each hour (e.g., for the user to stand for at least 2 minutes per hour for 12 hours a day)). Stand goal user interface 626-2 includes options 628a-2, 628b-2, and 628c-2 that correspond to three predefined stand goal values (e.g., a lowest predefined stand goal value, a middle predefined stand goal value, and a highest predefined stand goal value) and are each selectable to set the daily stand goal value at the corresponding predefined value. Stand goal user interface 626-2 also includes control 628d-2 and control 628e-2 to manually increase or decrease the daily stand goal value. Finally, stand goal user interface 626-2 includes option 628f-2 that is selectable to conclude the watch onboarding process.

At FIG. 6D, in response to user input 624-3, electronic device 604 displays stand goal user interface 626-3, which includes controls that are largely identical to stand goal user interface 626-2. At FIG. 6D, electronic device 600-2 detects user input 630-2 (e.g., a tap input) corresponding to selection of option 628f-2 to conclude the watch onboarding process, and electronic device 604 detects user input 630-3 (e.g., a tap input) corresponding to selection of option 628f-3 to conclude the watch onboarding process. Similarly, electronic device 600-1 detects user input 630-1 (e.g., a tap input) corresponding to selection of option 616f-1 to conclude the watchless onboarding process.

Figure 6E:
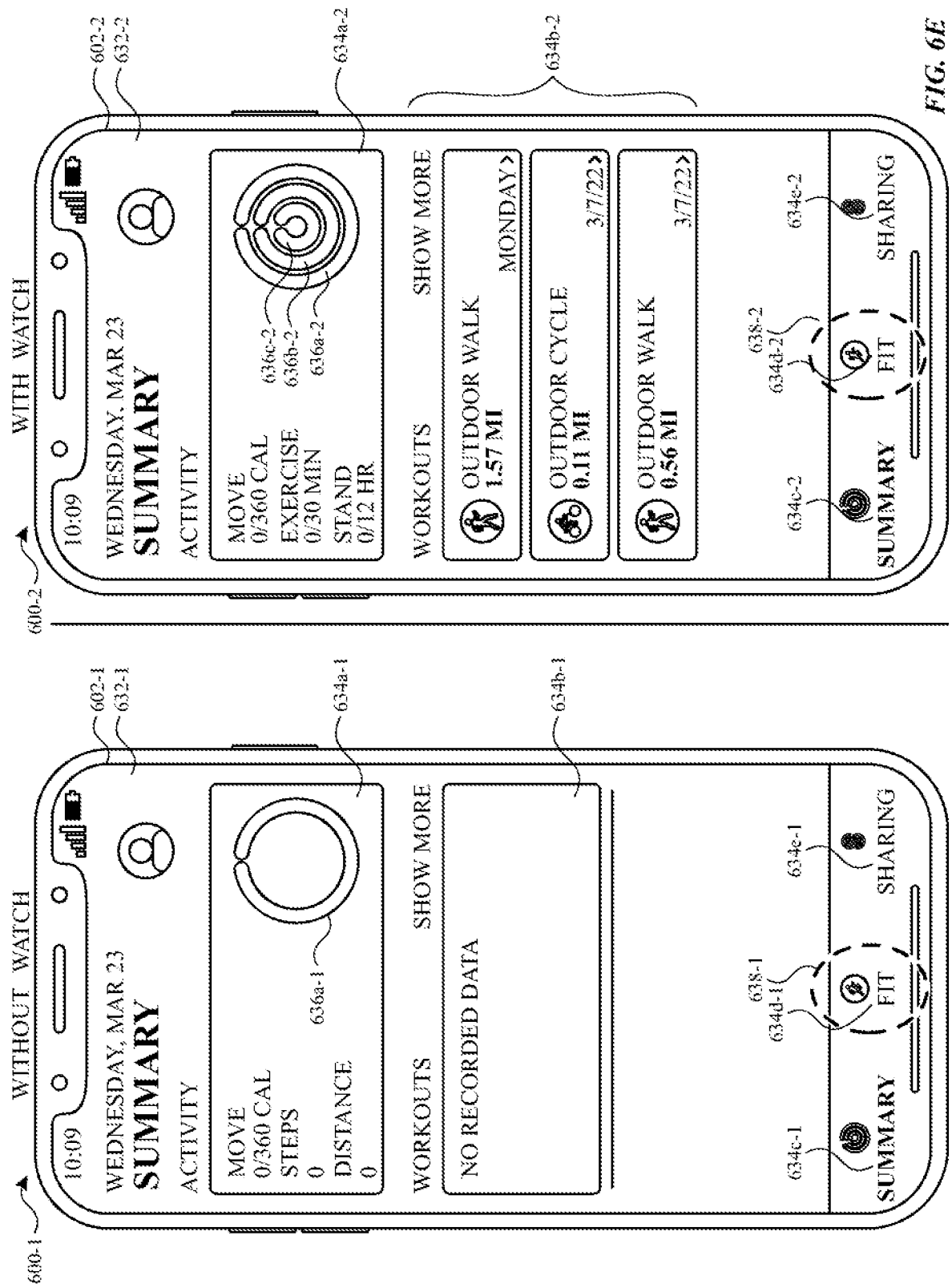

At FIG. 6E, in response to user input 630-1, electronic device 600-1 displays physical activity summary user interface 632-1, and in response to user input 630-2, electronic device 600-2 displays physical activity summary user interface 632-2. Physical activity summary user interface 632-1 includes physical activity information 634a-1 for a current calendar day, including move goal representation 636a-1 that is indicative of the user's progress in the current calendar day towards their move goal. Physical activity summary user interface 632-2 on electronic device 600-2 also includes physical activity information 634a-2, which includes move goal representation 636a-2, and also includes exercise goal representation 636b-2 (indicative of the user's progress towards their daily exercise goal for the current calendar day) and stand goal representation 636c-2 (indicative of the user's progress towards their daily stand goal for the current calendar day). As discussed above, in the depicted embodiments, when a smartwatch has not been paired to an electronic device (e.g., as with electronic device 600-1), a user of the electronic device is able to track a daily move goal, whereas if a smartwatch has been paired to the electronic device (e.g., as with electronic device 600-2), a user of the electronic device is able to track additional physical activity metrics, including a daily exercise goal and a daily stand goal, as will be discussed below.

Physical activity summary user interfaces 632-1, 632-2 also include past workout information 634b-1, 634b-2, which display workout information for previous workouts performed by the user. Past workout information 634b-1 does not display any past workouts for the user of electronic device 600-1 because this is the first time the user is using the fitness application. Physical activity summary user interfaces 632-1, 632-2 also include options 634c-1, 634c-2, which are selectable to display physical activity summary user interfaces 632-1, 632-2, options 634d-1, 634d-2 which are selectable to display a workout selection user interface, which we will be discussed below, and options 634e-1, 634e-2 which are selectable to display a sharing user interface, which will also be described in greater detail below. At FIG. 6E, electronic device 600-1 detects user input 638-1 (e.g., a tap input) corresponding to selection of option 634d-1, and electronic device 600-2 detects user input 638-2 (e.g., a tap input) corresponding to selection of option 638-2.

Figure 6F:
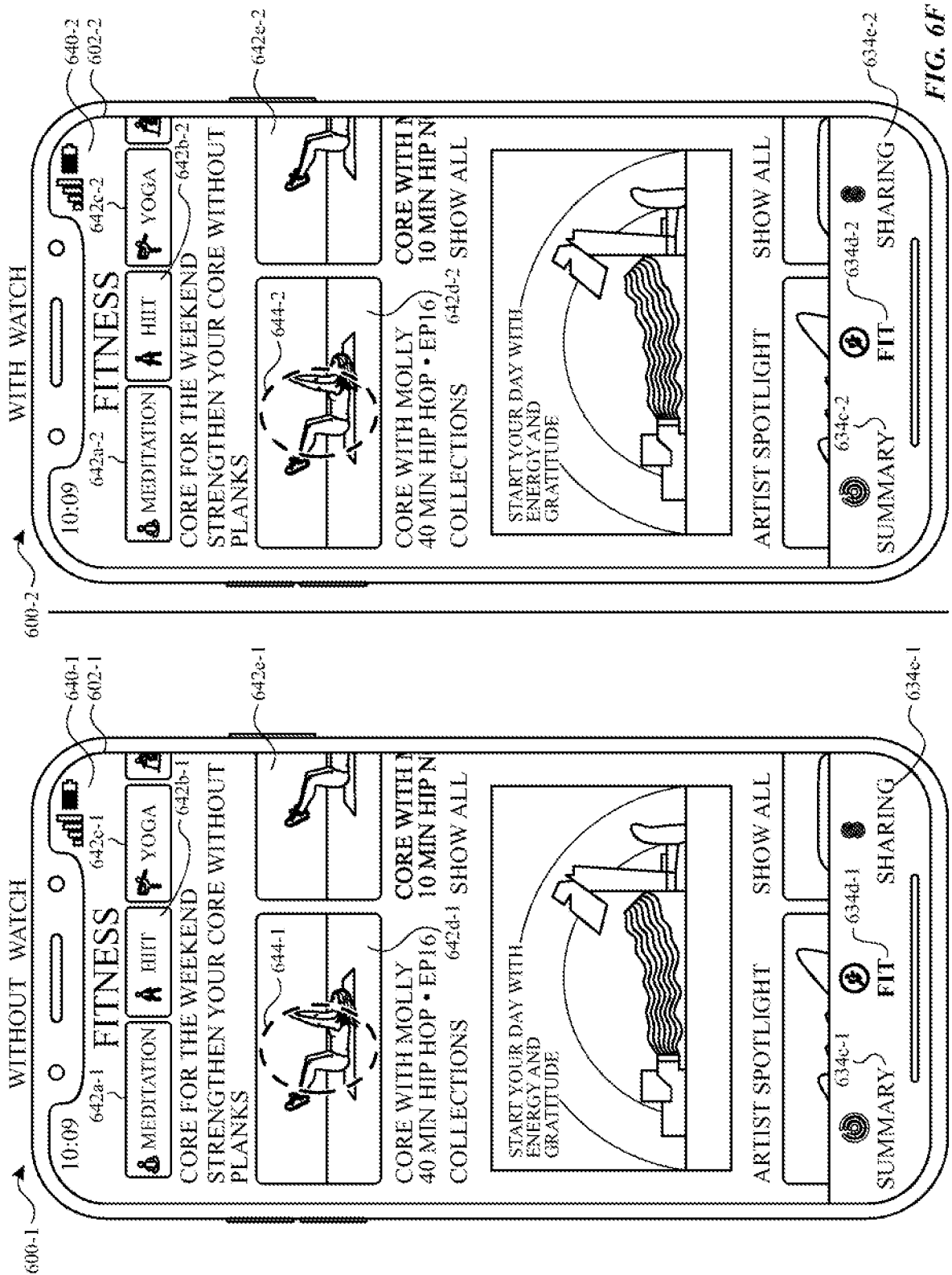

At FIG. 6F, in response to user input 638-1, electronic device 600-1 displays workout selection user interface 640-1, and in response to user input 638-2, electronic device 600-2 displays workout selection user interface 640-1 that is identical to workout selection user interface 640-1. Workout selection user interface 640-1 includes selectable options 642d-1, 642e-1 that each correspond to a respective workout, and are each selectable to initiate a process for initiating a workout session corresponding to the respective workout. Workout selection user interface 640-1 also includes selectable options 642a-1, 642b-1, 642c-1, that each correspond to a respective workout modality (e.g., meditation, HIIT, and/or yoga), and are each selectable to display one or more workout suggestions that correspond to the selected workout modality. At FIG. 6F, electronic device 600-1 detects user input 644-1 (e.g., a tap input) corresponding to selection of option 642d-1, and electronic device 600-2 detects user input 644-2 (e.g., a tap input) corresponding to selection of option 642d-2.

Figure 6G:
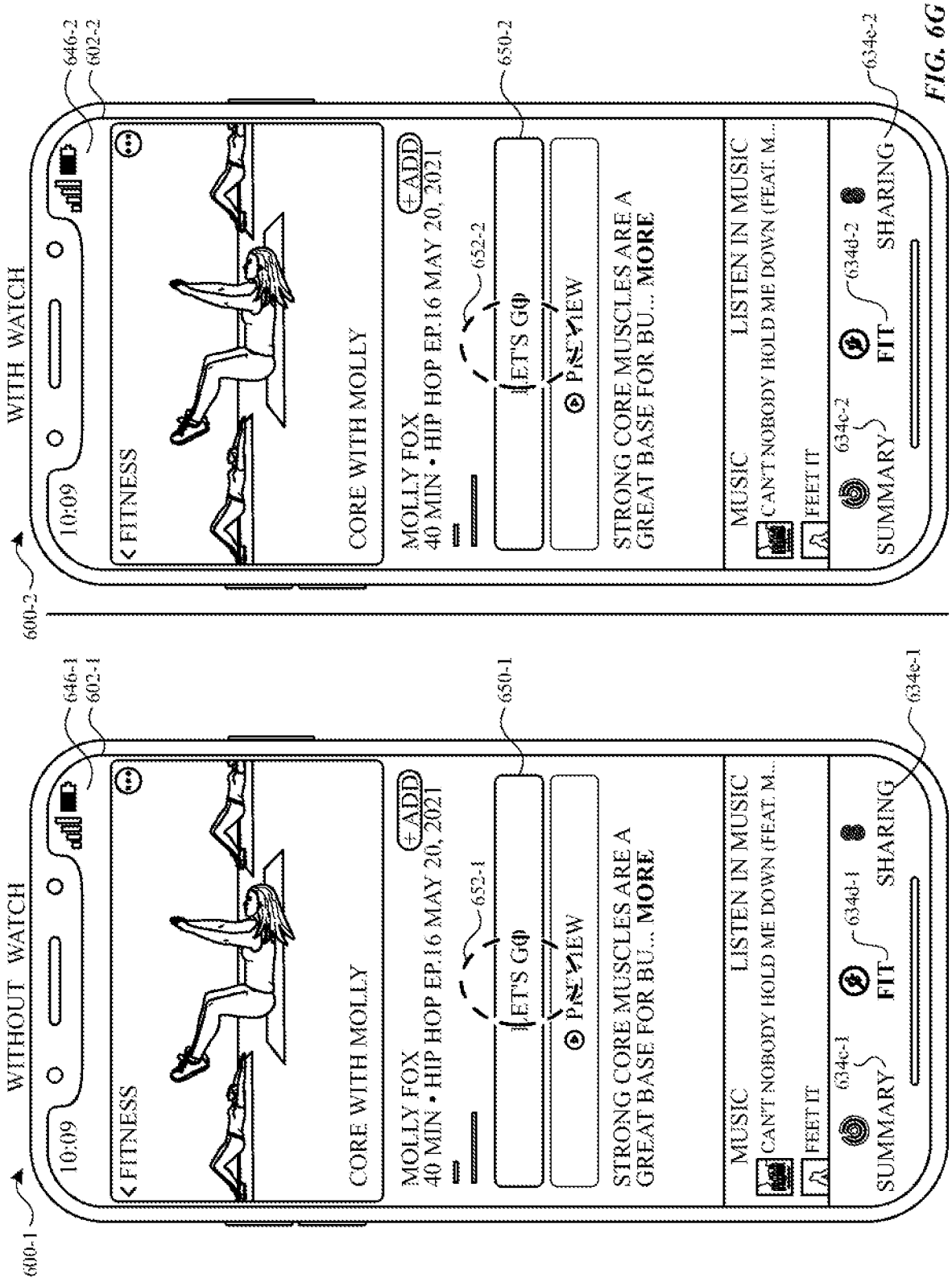

At FIG. 6G, in response to user input 642d-1, electronic device 600-1 displays user interface 646-1, which corresponds to a particular workout (in this case, "CORE WITH MOLLY" that was recorded on May 20, 2021), and in response to user input 642d-2, electronic device 600-2 displays user interface 646-2, which corresponds to the same workout. User interface 646-1 includes option 650-1 that is selectable to initiate a workout session for the particular workout, and user interface 646-2 includes option 650-2 that is selectable to initiate a workout session for the particular workout. At FIG. 6G, electronic device 600-1 detects user input 652-1 (e.g., a tap input) corresponding to selection of option 650-1, and electronic device 600-2 detects user input 652-2 (e.g., a tap input) corresponding to selection of option 650-2.

Figure 6H:
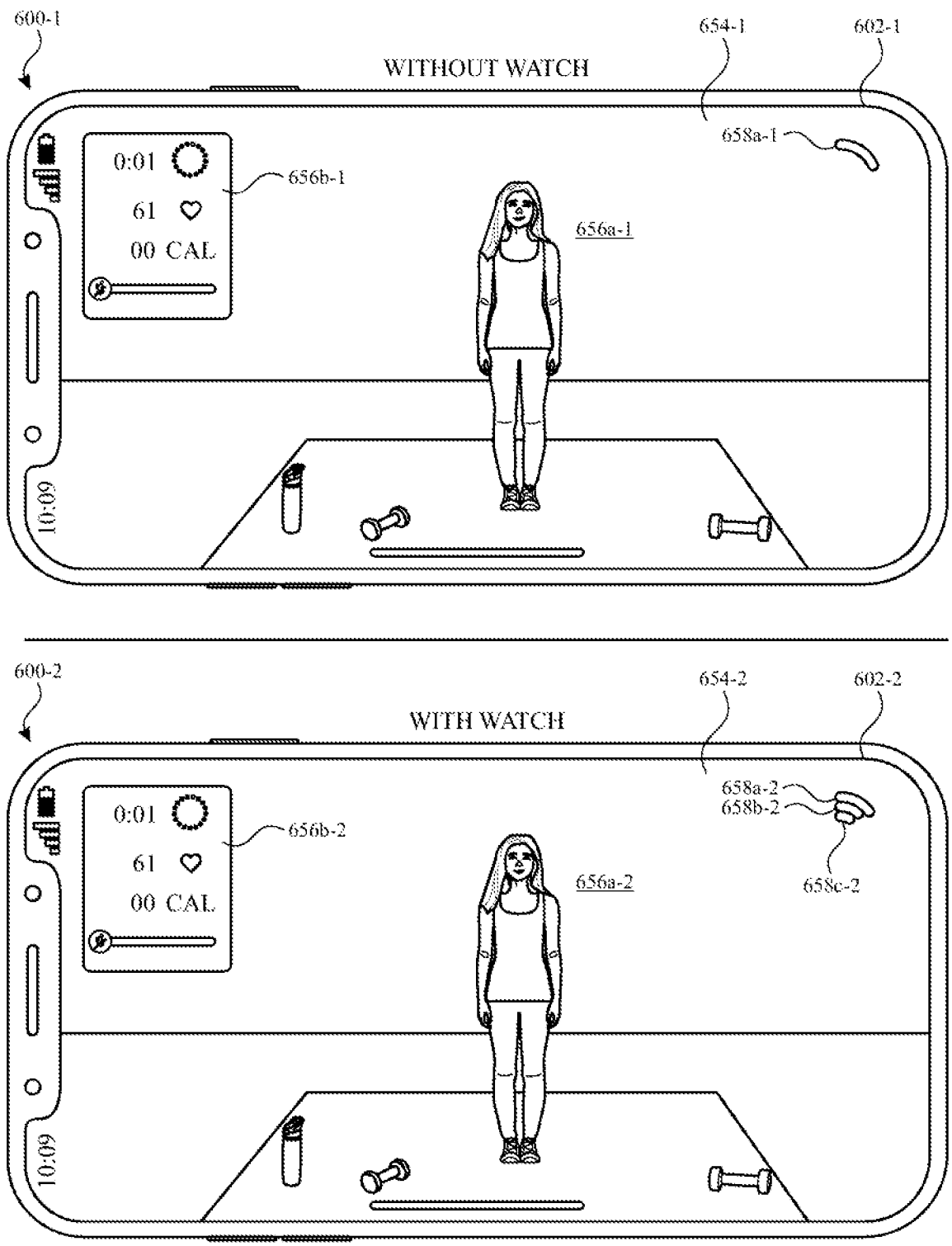

At FIG. 6H, in response to user input 646-1, electronic device 600-1 initiates a workout session for the particular workout, and displays workout user interface 654-1. Similarly, in response to user input 646-2, electronic device 600-2 initiates a workout session for the particular workout and displays workout user interface 654-2.

Workout user interface 654-1 includes workout physical activity metrics 656b-1, and video content 656a-1 corresponding to the workout (e.g., video content demonstrating the workout). Workout user interface 654-2 includes workout physical activity metrics 654b-2 that are identical to workout physical activity metrics 654b-1, and video content 656a-2 that is identical to video content 656a-1. Workout user interface 654-1 includes move goal representation 658a-1, whereas workout user interface 654-2 includes move goal representation 658a-2 as well as exercise goal representation 658b-2, and stand goal representation 658c-2. Move goal representations 658a-1, 658a-2 is indicative of the user's progress towards their daily move goal for the current calendar day, including time preceding the user's current workout session. Similarly, exercise goal representation 658b-2 is indicative of the user's progress towards their daily exercise goal for the current day (including time preceding the user's current workout session) and stand goal representation 658c-2 is indicative of the user's progress towards their daily stand goal for the current day (including time preceding the user's current workout session).

Figure 6I:
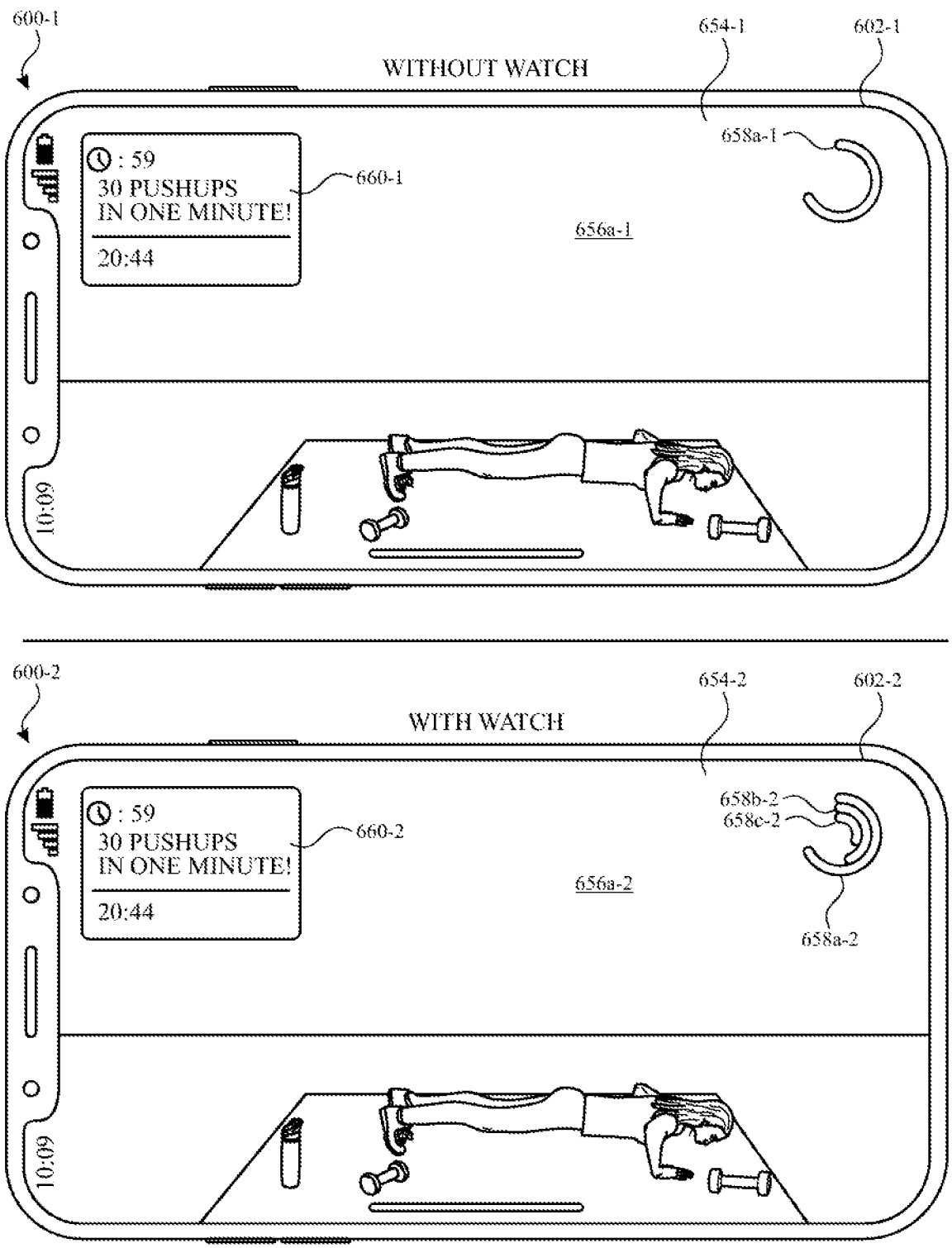

At FIG. 6I, the user in both scenarios has been working out for 20 minutes and 44 seconds, and both electronic device 600-1 and electronic device 600-2 detect a first type of event, which in FIG. 6I is a trainer callout instructing the user to up their intensity for a duration of time. In response to detecting the first type of event, electronic device 600-1 replaces display of workout physical activity metrics 656b-1 with callout indication 660-1, which instructs the user to perform 30 pushups in one minute, and displays a one minute timer. Similarly, in response to detecting the first type of event, electronic device 600-1 replaces display of workout physical activity metrics 656b-2 with callout indication 66-2, which is identical to callout indication 660-1. It can be seen in FIG. 6I that during the workout, the user has gotten closer to their daily move goal (as demonstrated by move goal representations 658a-1, 658a-2), and the user of electronic device 600-2 has gotten closer to their daily exercise and stand goals.

Figure 6J:
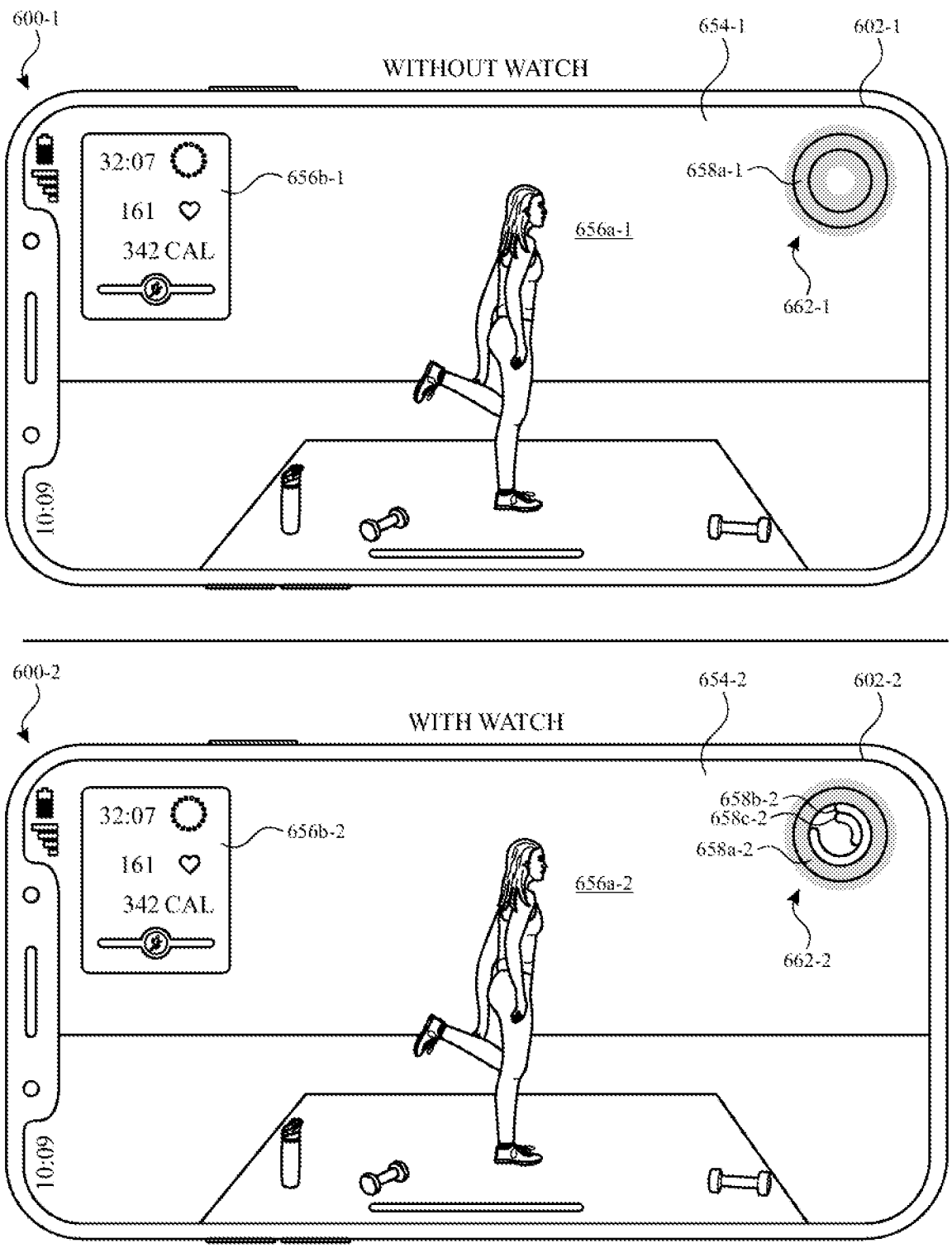

At FIG. 6J, both electronic devices 600-1, 600-2 detect a second type of event, which in FIG. 6J is the user accomplishing their daily move goal. In FIG. 6J, in response to detecting that the user of electronic device 600-1 has accomplished their daily move goal, electronic device 600-1 displays a first animation 662-1 of move goal representation 658a-1. In response to detecting that the user of electronic device 600-2 has accomplished their daily move goal, electronic device 600-2 displays a second animation 662-2 of move goal representation 658a-2. In the depicted embodiment, the first animation 662-1 is different from second animation 662-2. For example, first animation 662-1 does not include display of any additional rings, whereas animation 662-2 does include display of exercise goal representation 658b-2 and stand goal representation 658c-2.

FIG. 7 is a flow diagram illustrating a method for navigating and outputting physical activity information using a computer system in accordance with some embodiments. Method 700 is performed at a computer system (e.g., 100, 300, 500) (e.g., a wearable device, a smart watch, a smart phone, a tablet, a head-mounted device (HMD), and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 700 are, optionally, combined, the orders of some operations are, optionally, changed, and some operations are, optionally, omitted.

As described below, method 700 provides an intuitive way for navigating and providing physical activity information. The method reduces the cognitive burden on a user for navigating and accessing physical activity information, thereby creating a more efficient human-machine interface. For battery-operated computing devices, enabling a user to navigate and access physical activity information faster and more efficiently conserves power and increases the time between battery charges.

The computer system (e.g., 600-1, 600-2, 604) receives (702), via the one or more input devices, a first user input (e.g., 652-1, 652-2) (e.g., a first set of user inputs and/or one or more user inputs) (e.g., one or more touch inputs, one or more non-touch inputs, and/or one or more gestures) corresponding to a request to initiate a workout session corresponding to a first workout (e.g., a first workout selected (e.g., by a user) from a plurality of available workouts). In some embodiments, initiating the workout session includes initiating recording of one or more physical activity metrics (e.g., heartrate and/or calories burned) for the workout session (e.g., via one or more sensors in communication with the computer system). In some embodiments, initiating the workout session includes recording one or more physical activity metrics at a greater frequency than prior to initiation of the workout session.

In some embodiments, in response to receiving the first user input (706) (e.g., 652-1, 652-2) and in accordance with a determination that a user participating in the workout session is associated with an external device of a first type (e.g., 604) (e.g., a wearable device, a smart watch, and/or a physical activity metrics monitoring device) (e.g., in accordance with a determination that the user has paired an external device of the first type (e.g., 604) with the computer system (e.g., 600-2) and/or registered an external device of the first type on the computer system (in some embodiments, regardless of whether the user is wearing the external device); in accordance with a determination that the user participating in the workout session is wearing an external device of the first type (e.g., wearing an external device of the first type when the first user input is received and/or while the workout session is in progress); and/or in accordance with a determination that the user participating in the workout session is wearing an external device of the first type and that the external device of the first type is paired with the computer system and/or has been previously registered with the computer system)), the computer system (e.g., 600-2) displays (706), via the display generation component (e.g., 602-2) (e.g., a display controller, a touch-sensitive display system; and/or a display (e.g., integrated and/or connected)), a first workout session user interface (e.g., 654-2) (e.g., a user interface indicative of an active and/or in-progress workout session).

In some embodiments displaying the first workout session user interface includes concurrently displaying: visual content (708) corresponding to the first workout (e.g., 656a-2) (e.g., video content) (e.g., visual content demonstrating the first workout); a representation of a first physical activity metric (710) (e.g., 658a-2, 658b-2, 658c-2) (e.g., hours in which a user has stood for at least some predetermined amount of time, minutes of activity above a certain threshold activity level, active calories, calories burned, heart rate, distanced traveled, stairs climbed either based on passive background activity monitoring or activity data recorded during specific workouts) (in some embodiments, the representation of the first physical activity metric corresponds to a predetermined amount of time that includes a period of time preceding the workout session (e.g., the number of hours in the current day during which the user has stood for at least some predetermined amount of time, minutes of activity above a certain threshold activity level during the current day, calories burned during the current day) (in some embodiments, data for the first activity metric is collected (e.g., primarily or solely collected) using one or more sensors of the computer system); and a representation of a second physical activity metric (712) (e.g., 658*a*-2, 658*b*-2, 658*c*-2) different from the first physical activity metric (e.g., hours in which a user has stood for at least some predetermined amount of time, minutes of activity above a certain threshold activity level, active calories, calories burned, heart rate, distanced traveled, stairs climbed either based on passive background activity monitoring or activity data recorded during specific workouts). In some embodiments, the representation of the first physical activity metric corresponds to a predetermined amount of time that includes a period of time preceding the workout session (e.g., the number of hours in the current day during which the user has stood for at least some predetermined amount of time, minutes of activity above a certain threshold activity level during the current day, calories burned during the current day). In some embodiments, data for the second activity metric is collected (e.g., primarily or solely collected) using one or more sensors of the external device the first type.

In some embodiments, in response to receiving the first user input (704) (e.g., 652-1, 652-2) and in accordance with a determination that the user participating in the workout session is not associated with an external device of the first type (e.g., is not wearing an external device of the first type (e.g., is not wearing an external device of the first type when the first user input is received and/or while the workout session is in progress) and/or has not previously registered and/or paired an external device of the first type (e.g., has not previously registered and/or paired an external device of the first type with the computer system and/or with any computer system associated with the user)), the computer system (e.g., 600-1) displays (714), via the display generation component (e.g., 602-1), a second workout session user interface (e.g., 654-1) (e.g., a user interface indicative of an active and/or in-progress workout session) different from first workout session user interface (e.g., 654-2).

In some embodiments, displaying the second workout session user interface (e.g., 654-1) includes concurrently displaying the visual content (716) corresponding to the first workout (e.g., 656*a*-1, 656*a*-2), and the representation of the first physical activity metric (718) (e.g., 658*a*-1), without displaying the representation of the second physical activity metric (e.g., 658*b*-2, 658*c*-2). Displaying the first workout session user interface if the user participating in the workout is associated with an external device of the first type, and displaying the second workout session user interface if the user is not associated with an external device of the first type provides the user with feedback about the state of the device (e.g., that the device has determined that the user is associated with an external device of the first type or that the user is not associated with an external device of the first type). Doing so also performs an operation (e.g., displaying the relevant interface) when a set of conditions (e.g., whether the user is associated with an external device of the first type) has been met without requiring further user input. Furthermore, displaying the second workout session user interface if the user is not associated with an external device interface avoids cluttering the display with user interface elements that are not relevant to the particular user.

In some embodiments, the representation of the first physical activity metric (e.g., 658*a*-1, 658*a*-2) and the representation of the second physical activity metric (e.g., 658*b*-2, 658*c*-2) correspond to a predetermined amount of time (e.g., the current calendar day and/or the current 24 hour period) that includes a period of time preceding playback of the content. In some embodiments, the representation of the first physical activity metric is indicative of progress towards a first goal value for the first physical activity metric during the predetermined amount of time (e.g., a target number of hours during the current calendar day during which the user has stood for a predetermined amount of time; a target number of minutes of activity above a threshold activity level (e.g., above a target heart rate and/or within a workout session) during the current calendar day; a target number of total calories burned during the current calendar day; a target number of active calories burned during the current calendar day; a target distance traveled during the current calendar day; and/or a target number of stairs climbed during the current calendar day). In some embodiments, the representation of the second physical activity metric is indicative of progress towards a second goal value for the second physical activity metric during the predetermined amount of time. Displaying the representation of the first physical activity metric and/or the representation of the second physical activity metric provides the user with feedback about the state of the device (e.g., that the device has detected a certain amount of progress towards the goal value for the first physical activity metric and/or towards the goal value for the second physical activity metric). Doing so also performs an operation (e.g., displaying the relevant interface) when a set of conditions (e.g., whether the user is associated with an external device of the first type) has been met without requiring further user input. Furthermore, displaying the second workout session user interface if the user is not associated with an external device interface avoids cluttering the display with user interface elements that are not relevant to the particular user.

In some embodiments, during a process for setting activity goals for one or more physical activity metrics (e.g., FIGS. 6A-6D), the computer system (e.g., 600-1, 600-2) displays a set of selectable options (e.g., FIGS. 6B-6D) for setting activity goal values. In some embodiments, in accordance with a determination that a user of the computer system (e.g., 600-2) is associated with an external device of the first type (e.g., 604) (e.g., a wearable device, a smart watch, and/or a physical activity metrics monitoring device) (e.g., in accordance with a determination that the user has paired an external device of the first type with the computer system and/or registered an external device of the first type on the computer system (in some embodiments, regardless of whether the user is wearing the external device); in accordance with a determination that the user is wearing an external device of the first type (e.g., wearing an external device of the first type when the first user input is received and/or while the workout session is in progress); and/or in accordance with a determination that the user is wearing an external device of the first type and that the external device of the first type is paired with the computer system and/or has been previously registered with the computer system)), the set of selectable options include a first selectable option (e.g., 616*a*-2, 616*b*-2, 616*c*-1, 616*d*-1, 616*e*-2, 616*f*-2) for setting an activity goal value for the first physical activity metric (e.g., move goal) and a second selectable option (e.g., 622*a*-2, 622*b*-2, 622*c*-2, 622*d*-2, 622*e*-2, 622*f*-2) for setting an activity goal value for the second physical activity metric (e.g., exercise goal). In some embodiments, the first selectable option is displayed in a first goal setting user interface and the second selectable option is displayed in a second goal setting user interface different from the first goal setting user interface. In some embodiments, the first selectable option and the second selectable option are not displayed concurrently (e.g., are displayed in separate user interfaces that are not displayed concurrently). In some embodiments, the first selectable option and the second selectable option are displayed in the same user interface and/or displayed concurrently.

In some embodiments, in accordance with a determination that the user of the computer system (e.g., 600-1) is not associated with an external device of the first type (e.g., is not wearing an external device of the first type (e.g., is not wearing an external device of the first type when the first user input is received and/or while the workout session is in progress) and/or has not previously registered and/or paired an external device of the first type (e.g., has not previously registered and/or paired an external device of the first type with the computer system and/or with any computer system associated with the user)), the set of selectable options include the first selectable option (e.g., 616a-1, 616b-1, 616c-1, 616d-1, 616e-1, 616f-1) for setting an activity goal value for the first physical activity metric (e.g., move goal) without including the second selectable option for setting an activity goal value for the second physical activity metric (e.g., exercise goal). Displaying selectable options for setting goal values for both the first and second physical activity metrics if the user is associated with an external device of the first type, and the selectable option for setting the goal value for the first physical activity metric without displaying the second selectable option for setting the goal value for the second physical activity metric if the user is not associated with an external device of the first type provides the user with feedback about the state of the device (e.g., that the device has determined that the user is associated with an external device of the first type or that the user is not associated with an external device of the first type). Doing so also performs an operation (e.g., displaying the relevant interfaces and/or selectable options) when a set of conditions (e.g., whether the user is associated with an external device of the first type) has been met without requiring further user input. Furthermore, forgoing displaying the second selectable option if the user is not associated with an external device interface avoids cluttering the display with user interface elements that are not relevant to the particular user.

In some embodiments, at a first time and in accordance with a determination that a user of the computer system is not associated with an external device of the first type, the computer system (e.g., 600-1) displays, via the display generation component (e.g., 602-1), the second workout session user interface (e.g., 654-1). In some embodiments, at a second time subsequent to the first time, the computer system detects that the user of the computer system (e.g., 600-1, 600-2) is now associated with a first external device of the first type (e.g., 604) (e.g., detecting that the user of the computer system has connected an external device of the first type to the computer system and/or that the user of the computer system has registered an external device of the first type with the computer system). In some embodiments, after detecting that the user of the computer system (e.g., 600-1, 600-2) is now associated with the first external device of the first type (e.g., 604) and in accordance with a determination that the user of the computer system is now associated with the first external device of the first type (in some embodiments, in response to detecting that the user of the computer system is now associated with the first external device of the first type, in response to detecting that the user of the computer system has paired the first external device of the first type to the computer system, and/or in response to one or more user inputs (e.g., one or more user inputs corresponding to a request to access and/or open a fitness application) after detecting that the user of the computer system is now associated with the first external device of the first type), the computer system (e.g., 600-2) displays, via the display generation component (e.g., 602-2), a goal setting user interface (e.g., 620-2, 626-2) prompting the user to provide user input to define a goal value (e.g., a daily goal value and/or a weekly goal value) corresponding to the second physical activity metric (e.g., daily exercise goal and/or daily stand goal).

In some embodiments, after detecting that the user of the computer system is now associated with the first external device of the first type and in accordance with a determination that the user of the computer system is now associated with the first external device of the first type, the computer system initiates a process for receiving user input defining a first goal value corresponding to the first physical activity metric (e.g., FIG. 6B) and for receiving user input defining a second goal value corresponding to the second physical activity metric (e.g., FIGS. 6C and/or 6D). In some embodiments, the process for receiving user input defining a first goal value corresponding to the first physical activity metric and for receiving user input defining a second goal value corresponding to the second physical activity metric includes displaying a first goal setting user interface (e.g., 614-2) corresponding to the first physical activity metric and display a second goal setting user interface (e.g., 620-2 and/or 626-2) corresponding to the second physical activity metric. Initiating a process for receiving user input defining a goal value corresponding to the second physical activity metric in accordance with a determination that the user of the computer system is now associated with the first external device of the first type provides the user with feedback about the state of the device (e.g., that the computer system has detected that the user is now associated with an external device of the first type). Doing so also performs an operation (e.g., displaying the relevant interfaces and/or selectable options) when a set of conditions (e.g., whether the user is associated with an external device of the first type) has been met without requiring further user input.

In some embodiments, at a third time and in accordance with a determination that a user of the computer system (e.g., 600-1, 600-2) is not associated with an external device of the first type, the computer system (e.g., 600-1) displays, via the display generation component (e.g., 602-1), the second workout session user interface (e.g., 654-1). In some embodiments, at a fourth time subsequent to the third time, the computer system detects that the user of the computer system (e.g., 600-1, 600-2) is now associated with a second external device of the first type (e.g., 604) (e.g., detecting that the user of the computer system has connected an external device of the first type to the computer system and/or that the user of the computer system has registered an external device of the first type with the computer system). In some embodiments, after detecting that the user of the computer system (e.g., 600-2) is now associated with the second external device of the first type (e.g., 604) and in accordance with a determination that the user of the computer system is now associated with the second external device of the first type (in some embodiments, in response to detecting that the user of the computer system is now associated with the second external device of the first type, in response to detecting that the user of the computer system has paired the second external device of the first type to the computer system, and/or in response to one or more user inputs (e.g., one or more user inputs corresponding to a request to access and/or open a fitness application) after detecting that the user of the computer system is now associated with the second external device of the first type), the computer system (e.g., 600-2) initiates a process to cause the second external device of the first type (e.g., 604) to display (e.g., transmitting, to the second external device of the first type, one or more instructions and/or signals that cause the second external device of the first type to display), via a display generation component (e.g., 606) corresponding to the second external device of the first type (e.g., 604), a third goal setting user interface (e.g., 620-3, 626-3) prompting the user to provide user input to define a goal value corresponding to the second physical activity metric (e.g., daily exercise goal and/or daily stand goal).

In some embodiments, the second external device of the first type displays the third goal setting user interface (e.g., 620-3, 626-3) and also displays (e.g., before and/or after displaying the third goal setting user interface) a fourth goal setting user interface (e.g., 614-3) prompting the user to provide user input to define a goal value corresponding to the first physical activity metric (e.g., daily move goal). Causing the second external device of the first type to display the third goal setting user interface in accordance with a determination that the user of the computer system is now associated with the second external device of the first type provides the user with feedback about the state of the device (e.g., that the computer system has detected that the user is now associated with an external device of the first type). Doing so also performs an operation (e.g., causing the second external device of the first type to display the relevant interfaces and/or selectable options) when a set of conditions (e.g., whether the user is associated with an external device of the first type) has been met without requiring further user input.

In some embodiments, at a fifth time and in accordance with a determination that a user of the computer system is not associated with an external device of the first type, the computer system (e.g., 600-1) displays, via the display generation component (e.g., 602-1), the second workout session user interface (e.g., 654-1). In some embodiments, at a sixth time subsequent to the fifth time, the computer system detects that the user of the computer system (e.g., 600-1, 600-2) is now associated with a third external device of the first type (e.g., 604) (e.g., detecting that the user of the computer system has connected an external device of the first type to the computer system and/or that the user of the computer system has registered an external device of the first type with the computer system). In some embodiments, after detecting that the user of the computer system (e.g., 600-2) is now associated with the third external device of the first type (e.g., 604), the computer system (e.g., 600-2) receives, via the one or more user inputs, a third user input (e.g., 652-2) (e.g., a third set of user inputs and/or one or more user inputs) (e.g., one or more touch inputs, one or more non-touch inputs, and/or one or more gestures) corresponding to a request to initiate a workout session corresponding to the first workout. In some embodiments, in response to receiving the third user input (e.g., 652-2) and in accordance with a determination that the user of the computer system (e.g., 600-2) is now associated with the third external device of the first type (e.g., 604), the computer system (e.g., 600-2) displays, via the display generation component (e.g., 602-2), the first workout session user interface (e.g., 654-2). Displaying the first workout session user interface in accordance with a determination that the user of the computer system is now associated with the third external device of the first type provides the user with feedback about the state of the device (e.g., that the computer system has detected that the user is now associated with an external device of the first type). Doing so also performs an operation (e.g., displaying the relevant interface) when a set of conditions (e.g., whether the user is associated with an external device of the first type) has been met without requiring further user input.

In some embodiments, the representation of the first physical activity metric (e.g., 658a-1, 658a-2) is indicative of a number of calories burned by the user (e.g., the number of calories burned by the user during a predefined period of time (e.g., the current calendar day and/or the current 24-hour period)) (e.g., an estimated and/or measured number of calories burned by the user). In some embodiments, the representation of the first physical activity metric is indicative of the user's progress towards a target and/or goal number of calories burned (e.g., during a predefined period of time (e.g., during the current calendar day and/or the current 24-hour period)). Displaying a representation of a first physical activity metric that is indicative of the number of calories burned by the user provides the user with feedback about the state of the device (e.g., that the device has measured and/or estimated that the user has burned a certain number of calories).

In some embodiments, the representation of the first physical activity metric (e.g., 658a-1, 658a-2) is indicative of a number of calories burned by the user (e.g., the number of calories burned by the user during a predefined period of time (e.g., the current calendar day and/or the current 24-hour period)) (e.g., an estimated and/or measured number of calories burned by the user). In some embodiments, the representation of the first physical activity metric is indicative of the user's progress towards a target and/or goal number of calories burned (e.g., during a predefined period of time (e.g., during the current calendar day and/or the current 24-hour period)). In some embodiments, the representation of the first physical activity metric (e.g., 658a-1) in the second workout session user interface (e.g., 654-1) is determined without input by an external device of the first type (e.g., 604) (e.g., without sensor data or other data provided by an external device of the first type). In some embodiments, the representation of the first physical activity metric (e.g., 658a-2) in the first workout session user interface (e.g., 654-2) is determined based on at least information received from an external device of the first type (e.g., 604) (e.g., based on sensor data and/or other data provided by an external device of the first type). Displaying a representation of the first physical activity metric that includes input from an external device of the first type when the user is associated with an external device of the first type causes the device to automatically provide more accurate information pertaining to the first physical activity metric when the user is associated with an external device of the first type.

In some embodiments, the representation of the second physical activity metric (e.g., 658b-2, 658c-2) is indicative of a duration of time (e.g., minutes and/or hours (e.g., minutes and/or hours during the current calendar day and/or during a predefined period of time))) during which the user surpassed a threshold physical activity level (e.g., daily exercise goal) (e.g., as determined based on user movement data and/or user heartrate information), wherein the representation of the second physical activity metric is determined based on at least information received from an external device of the first type (e.g., 604) (e.g., based on sensor data (e.g., user movement information and/or heart rate information) and/or other data provided by an external device of the first type). Displaying a representation of the second physical activity metric that includes input from an external device of the first type when the user is associated with an external device of the first type causes the device to automatically provide information pertaining to the second physical activity metric when the user is associated with an external device of the first type.

In some embodiments, the representation of the second physical activity metric (e.g., 658*b*-2, 658*c*-2) is indicative of a duration of time (e.g., number of minutes and/or hours (e.g., minutes and/or hours during the current calendar day and/or during a predefined period of time))) during which the user was in a predetermined posture (e.g., standing up) for at least a threshold duration of time (e.g., daily stand goal) (e.g., stood up for at least a threshold number of minutes in a particular hour, and/or stood up for at least a threshold number of second in a particular minute), wherein the representation of the second physical activity metric is determined based on at least information received from an external device of the first type (e.g., 604) (e.g., based on sensor data (e.g., user movement information, user stand information, and/or heart rate information) and/or other data provided by an external device of the first type). Displaying a representation of the second physical activity metric that includes input from an external device of the first type when the user is associated with an external device of the first type causes the device to automatically provide information pertaining to the second physical activity metric when the user is associated with an external device of the first type.

In some embodiments, while displaying the second workout session user interface (e.g., 654-1), the computer system (e.g., 600-1) detects that a user has satisfied goal criteria pertaining to the first physical activity metric (e.g., FIG. 6J) (e.g., the user has met and/or achieved a goal value for the first physical activity metric). In some embodiments, while displaying the second workout session user interface and in response to detecting that the user has satisfied the goal criteria pertaining to the first physical activity metric, the computer system (e.g., 600-1) displays, via the display generation component (e.g., 602-1), a first animation (e.g., 662-1). In some embodiments, while displaying the first workout session user interface (e.g., 654-2), the computer system (e.g., 600-2) detects that the user has satisfied the goal criteria pertaining to the first physical activity metric (e.g., FIG. 6J) (e.g., the user has met and/or achieved a goal value for the first physical activity metric). In some embodiments, while displaying the first workout session user interface and in response to detecting that the user has satisfied the goal criteria pertaining to the first physical activity metric, the computer system (e.g., 600-2) displays, via the display generation component (e.g., 602-2), a second animation (e.g., 662-2) different from the first animation (e.g., 662-1). Displaying a first animation when the second workout session user interface is being displayed (e.g., when the user is not associated with an external device of the first type), and displaying a second animation when the first workout session user interface is being displayed (e.g., when the user is associated with an external device of the first type) provides the user with feedback about the state of the device (e.g., that the computer system has detected whether or not the user is associated with an external device of the first type). Doing so also performs an operation (e.g., displaying the relevant animation) when a set of conditions (e.g., whether the user is associated with an external device of the first type) has been met without requiring further user input.

In some embodiments, while displaying the second workout session user interface (e.g., 654-1), the computer system (e.g., 600-1) detects a first type of event has occurred (e.g., a predefined milestone has been achieved (e.g., a threshold value has been obtained for a particular physical activity metric), and/or a particular playback position of the video content has been reached). In some embodiments, while displaying the second workout session user interface (e.g., 654-1) and in response to detecting that the first type of event has occurred, the computer system (e.g., 600-1) displays, via the display generation component (e.g., 602-1), a first visual indication (e.g., 660-1, 660-2) that the first type of event has occurred. In some embodiments, while displaying the first workout session user interface (e.g., 654-2), the computer system (e.g., 600-2) detects that the first type of event has occurred. In some embodiments, while displaying the first workout session user interface (e.g., 654-2) and in response to detecting that the first type of event has occurred, the computer system (e.g., 600-2) displays, via the display generation component (e.g., 602-2), the first visual indication (e.g., 660-1, 660-2) that the first type of event has occurred. In some embodiments, when the first type of event occurs (e.g., a trainer callout and/or a trainer instruction), the first visual indication is displayed regardless of whether the second workout session user interface is displayed or the first workout session user interface is displayed (e.g., regardless of whether or not the user is associated with an external device of the first type). Displaying the first visual indication when the first type of event occurs provides the user with feedback about the state of the device (e.g., that the computer system has detected that the first type of event has occurred). Doing so also performs an operation (e.g., displaying the relevant visual indication) when a set of conditions (e.g., detecting the first type of event) has been met without requiring further user input.

In some embodiments, the first workout session user interface (e.g., 654-2) and the second workout session user interface (e.g., 654-1) are indicative of an active (e.g., in-progress) workout session, and the first visual indication (e.g., 660-1, 660-2) includes one or more instructions for the user pertaining to the workout session (e.g., instructions for the user to perform a certain number of repetitions, instructions for the user to perform an action for a particular duration of time, and/or instructions defining a target intensity value target (e.g., strokes per minute, pedal speed, and/or treadmill incline)). In some embodiments, the first visual indication displays a target value for the user to achieve during the workout session. Displaying the first visual indication when the first type of event occurs provides the user with feedback about the state of the device (e.g., that the computer system has detected that the first type of event has occurred). Doing so also performs an operation (e.g., displaying the relevant visual indication) when a set of conditions (e.g., detecting the first type of event) has been met without requiring further user input.

Note that details of the processes described above with respect to method 700 (e.g., FIG. 7) are also applicable in an analogous manner to the methods described below. For example, methods 1100 and 900 optionally include one or more of the characteristics of the various methods described above with reference to method 700. For example, the computer system in method 700 and the external device of the first type in method 700 are, in some embodiments, the computer system and the external device of the first type in method 900 and method 1100. For brevity, these details are not repeated below.

FIGS. 8A-8J illustrate exemplary user interfaces for navigating and displaying physical activity information, in accordance with some embodiments. The user interfaces in these figures are used to illustrate the processes described below, including the processes in FIG. 9.

Figure 8A:
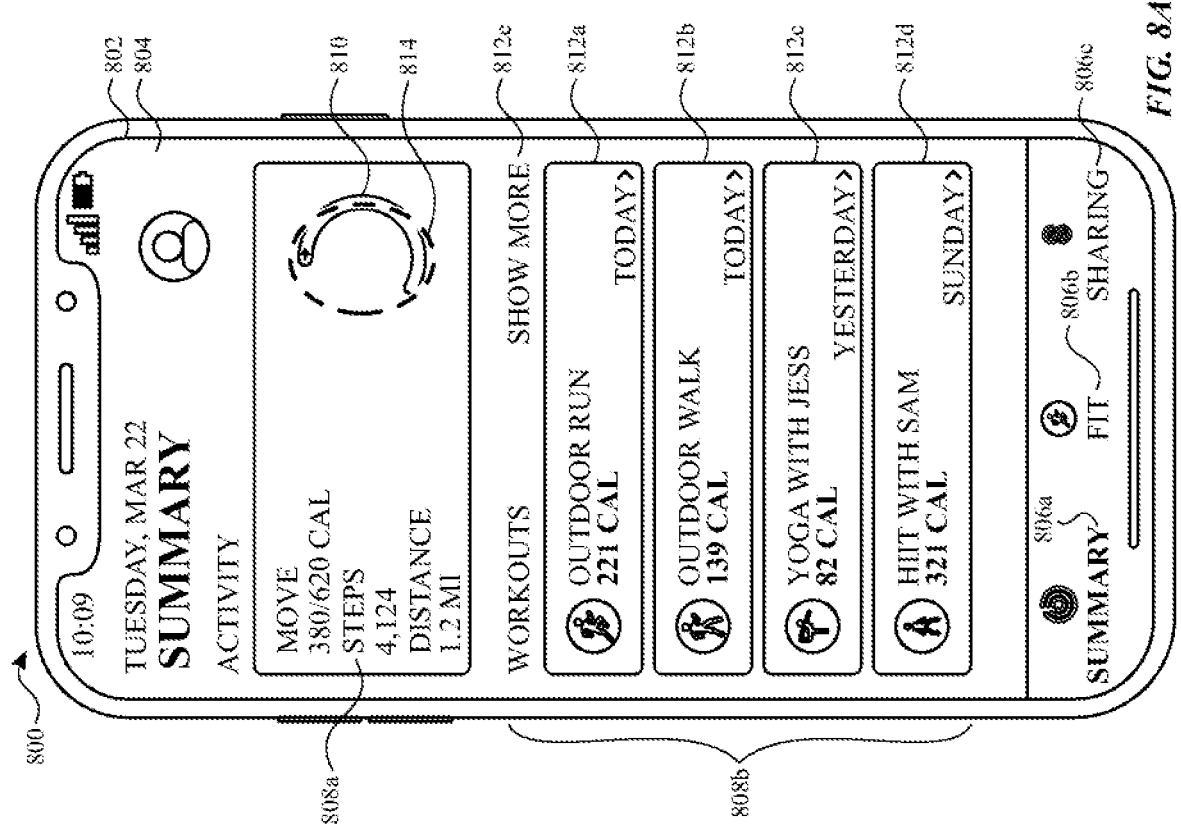

FIG. 8A illustrates electronic device 800, which is a smartphone with a touch-sensitive display 802. In some embodiments, electronic device 800 is electronic device 600-1 and/or electronic device 600-2. At FIG. 8A, electronic device 800 displays, on display 802, physical activity summary user interface 804, which is functionally identical to physical activity summary user interface 632-1 described above with reference to FIG. 6E. As also described above, in the depicted embodiments, if electronic device 800 (and/or a user of electronic device 800) is associated with and/or corresponds to an external device of a particular type (e.g., a wearable device and/or a smartwatch), electronic device 800 maintains and/or displays information pertaining to multiple physical activity metrics and multiple physical activity goals (e.g., move goal, exercise goal, and/or stand goal), whereas if electronic device 800 (and/or a user of electronic device 800) is not associated with and/or corresponds to an external device of the particular type, electronic device 800 maintains and/or display information pertaining to fewer physical activity metrics and/or fewer physical activity goals (e.g., move goal).

In FIG. 8A, electronic device 800 is not associated with and/or paired with an external device of the particular type. Accordingly, physical activity summary user interface 804 displays move goal representation 810 and does not display an exercise goal representation or a stand goal representation. As discussed above with reference to FIG. 6E, physical activity summary user interface 804 (which is similar to physical activity summary user interface 632-1) also includes additional physical activity metrics 808a (e.g., move goal information, steps taken for the day, and distance traversed during the day), and workout information 808b that includes representations 812a-812d of previous workouts performed by the user. At FIG. 8A, electronic device 800 detects user input 814 (e.g., a tap input) corresponding to selection of move goal representation 810.

Figure 8B:
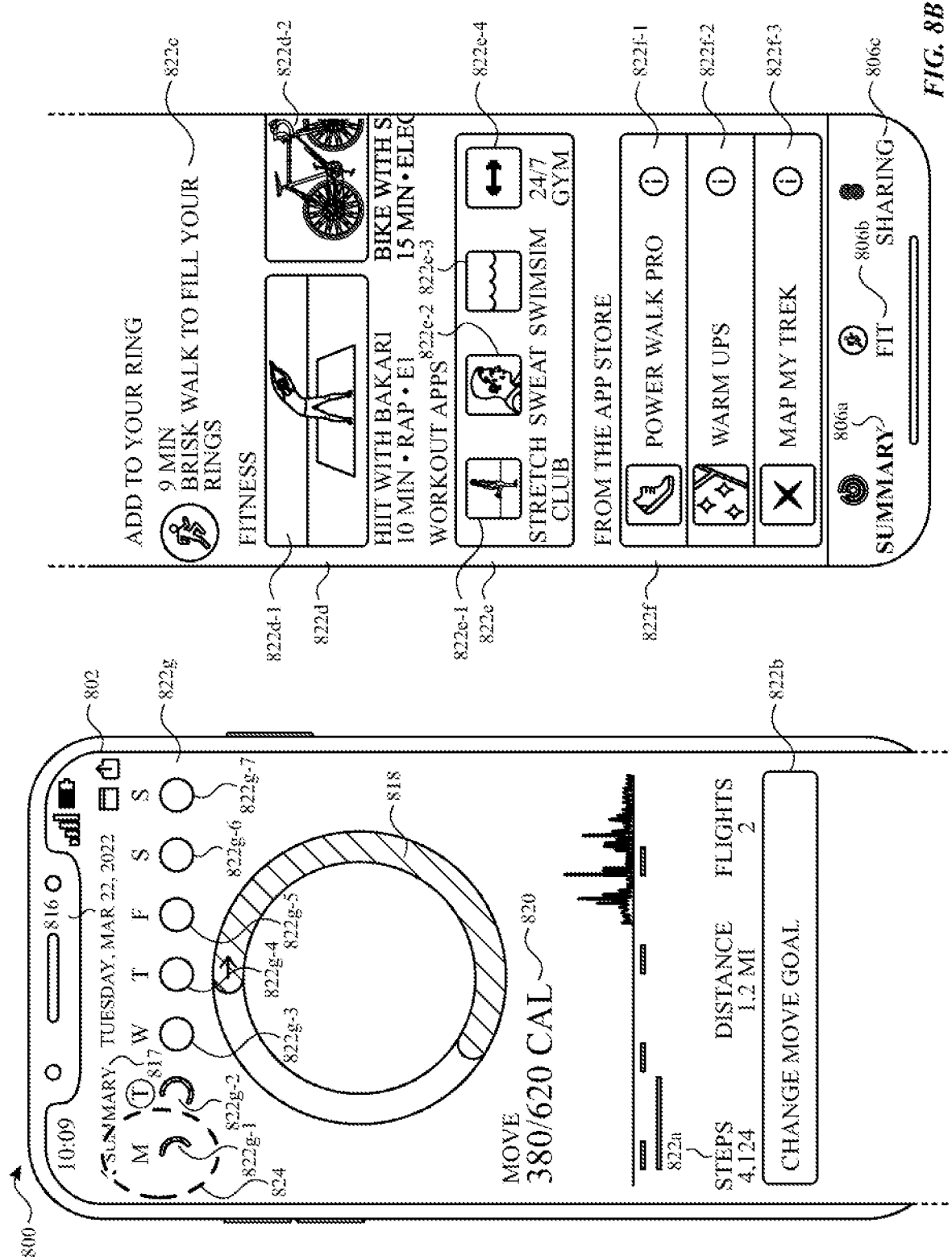

At FIG. 8B, in response to user input 814, electronic device displays user interface 816. User interface 816 includes physical activity goal information which, because electronic device 800 is not associated with an external device of a particular type, includes only move goal information 820 and move goal representation 818 (without including daily exercise goal and/or daily stand goal information). User interface 816 also includes weekly information 822g, which includes a respective representation 822g-1 to 822g-7 for each day of a current week. Representation 822g-1, which corresponds to Monday, shows a move goal representation for that day indicating how close the user got to achieving their move goal for that day. Representation 822g-2, which corresponds to the current day (Tuesday), shows a move goal representation for the current day indicating how close the user is to achieving their move goal for the current day. Representations 822g-3 through 822g-7 represent future days, and do not have any move goal information depicted.

User interface 816 also includes additional physical activity information for the current day (e.g., steps, distance traversed, and flights of stairs traversed), and option 822b that is selectable to initiate a process for changing the user's daily move goal. User interface 816 also includes suggestion 822c which provides a suggestion for the user as to how the user can accomplish their daily move goal for the current day (e.g., by walking for 9 minutes). In some embodiments, suggestion 822c is displayed in user interface 816 only if the user is within a threshold number of walking minutes of accomplishing their daily move goal (e.g., if the user can accomplish their move goal by walking for less than 20 minutes). For example, if the user was further away from accomplishing their daily move goal (e.g., would require walking for 30 minutes to accomplish their daily move goal), in some embodiments, user interface 816 would not include suggestion 822c. User interface 816 also includes workout suggestions 822d (including suggestion 822d-1 and suggestion 822d-2) that are selectable to initiate a process for initiating a workout session corresponding to the selected workout. In some embodiments, workout suggestions 822d are displayed only if the user has previously performed a workout using a particular fitness application (e.g., the fitness application that displays and/or generates user interface 816). User interface 816 also includes workout application representations 822e, 822e-2, 822e-3, and 822e-4 within workout application region 822e. Each workout application representation corresponds to a respective workout application, and is selectable to cause electronic device 800 to open the workout application corresponding to the selected representation. In some embodiments, workout application region 822e is displayed only if the user has previously used one or more workout applications (e.g., one or more workout applications different from the application that displays and/or generated user interface 816 (e.g., third party applications)). User interface 816 also includes workout application recommendations 822f (including recommendation 822f-1, recommendation 822f-2, and recommendation 822f-3), which each correspond to a workout application that the user has not previously used before, and are each selectable to initiate a process for downloading and/or installing the respective workout application to electronic device 800. In some embodiments, user interface 816 displays workout application recommendations 822f only if the user has previously used one or more workout applications and/or one or more third party workout applications.

At FIG. 8B, electronic device 800 detects user input 824 (e.g., a tap input) corresponding to representation 822g-1.

At FIG. 8C, in response to user input 824, electronic device 800 updates user interface 816 to display physical activity metrics corresponding to representation 822g-1 (Monday, Mar. 21, 2022), including updating move goal representation 818, move goal information 820, and physical activity metrics 822a to display information corresponding to the previous Monday, rather than the current day. At FIG. 8C, electronic device 800 detects user input 826 (e.g., a tap input) corresponding to selection of option 806c.

At FIG. 8D, in response to user input 826, electronic device 800 displays sharing user interface 828. Sharing user interface 828 displays representations 830a-830d corresponding to a set of users that have opted into sharing physical activity information with a user of electronic device 800, as well as selectable option 829 that is selectable to initiate a process for sharing physical activity information with a different user (e.g., adding a new user to the list of users that the user of electronic device 800 shares physical activity information with). In FIG. 8D, three of the user representations, 830a, 830b, and 830d, correspond to users that are not associated with an external device of the particular type (e.g., are not associated with a smartwatch or other wearable device) and, as such, user representations 830a, 830b, and 830d display only a move goal representation for each of those users. However, user representation 830c corresponds to a user that is associated with an external device of the particular type (e.g., a smartwatch) and, accordingly, user representation 830c displays a move goal representation, an exercise goal representation, and a stand goal representation for the user (Patrick). At FIG. 8D, electronic device 800 detects user input 831 (e.g., a tap input) corresponding to selection of representation 830c.

At FIG. 8E, in response to user input 831, electronic device 800 displays user interface 834, which displays physical activity information for the current day for Patrick (e.g., a user that has elected to share physical activity information with the user of electronic device 800 and that corresponds to user representation 830c). As mentioned above, Patrick is associated with an external device of the particular type (e.g., a smartwatch and/or wearable device) and, consequently, user interface 834 includes move goal representation 836a indicative of Patrick's progress towards his move goal for the current day, exercise goal representation 836b indicative of Patrick's progress towards his exercise goal for the current day, and stand goal representation 836c indicative of Patrick's progress towards his stand goal for the current day. User interface 834 also includes additional physical activity information 838a for Patrick for the current day. User interface 834 also includes options 838b-838f. Option 838b corresponds to a request to initiate a competition with Patrick. However, in FIG. 8E, option 838b is marked as not selectable because the user of electronic device 800 is not associated with an external device of the particular type. In some embodiments, only users that are both associated with external devices of the particular type (e.g., are both associated with a smartwatch) are able to initiate competitions with one another. Option 838c is selectable to mute notifications pertaining to Patrick and/or pertaining to Patrick's physical activity information. Option 838d is selectable to cease and/or pause sharing of physical activity information with Patrick. Option 838e is selectable to cease sharing of physical activity information with Patrick. Option 838f is selectable to return to user interface 828.

At FIG. 8F, the depicted scenario is one day after the scenario shown in FIGS. 8A-8E, and the user of electronic device 800 has obtained a smartwatch (e.g., become associated with a smartwatch). As such, user interface 804 now displays exercise goal representation 840 and stand goal representation 842 in additional to move goal representation 810. At FIG. 8F, electronic device 800 detects user input 844 corresponding to selection of goal representations 810, 840, 842.

Figure 8G:
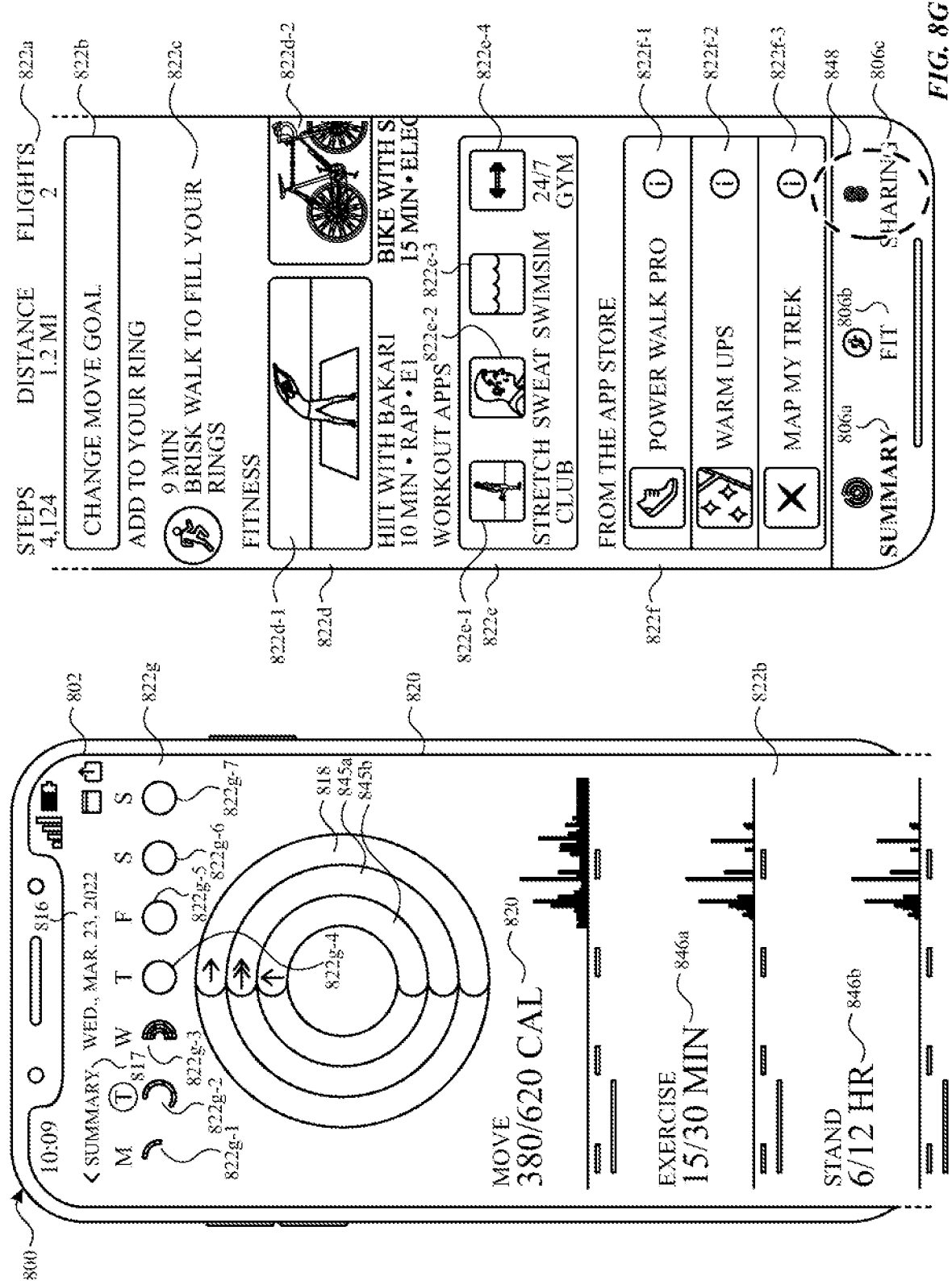

At FIG. 8G, in response to user input 844, electronic device 800 displays user interface 816, which now also displays exercise goal representation 845a and stand goal representation 845b along with move goal representation 818. User interface 816 has also been updated to show physical activity information for what is now the current day, Wednesday, in representation 822g-3. It can be seen that representations 822g-1 and 822g-2 correspond, respectively, to Monday and Tuesday, when the user of electronic device 800 did not have a smartwatch, show only a move goal representation for each of those days. However, representation 822g-3 for Wednesday, when the user became associated with a smartwatch, displays a move goal representation, an exercise goal representation, and a stand goal representation. At FIG. 8G, electronic device 800 detects user input 848 (e.g., a tap input) corresponding to selection of option 806c.

Figure 8I:
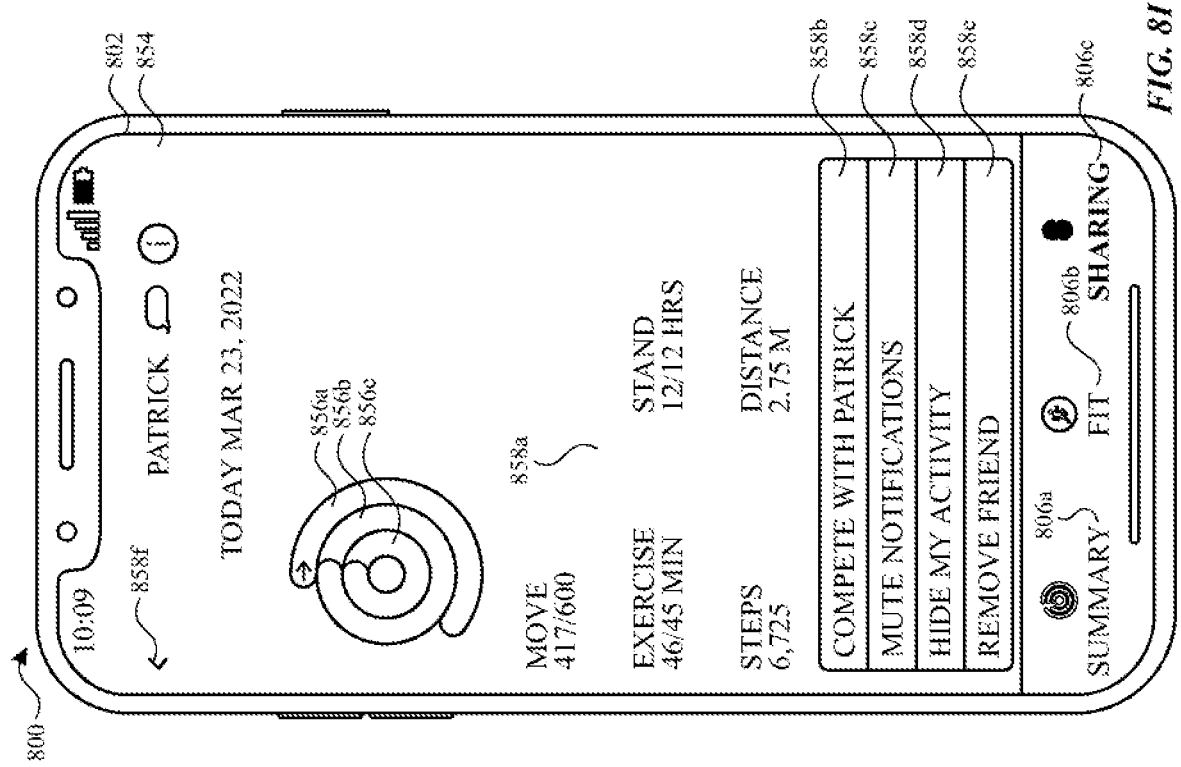
Figure 8H:
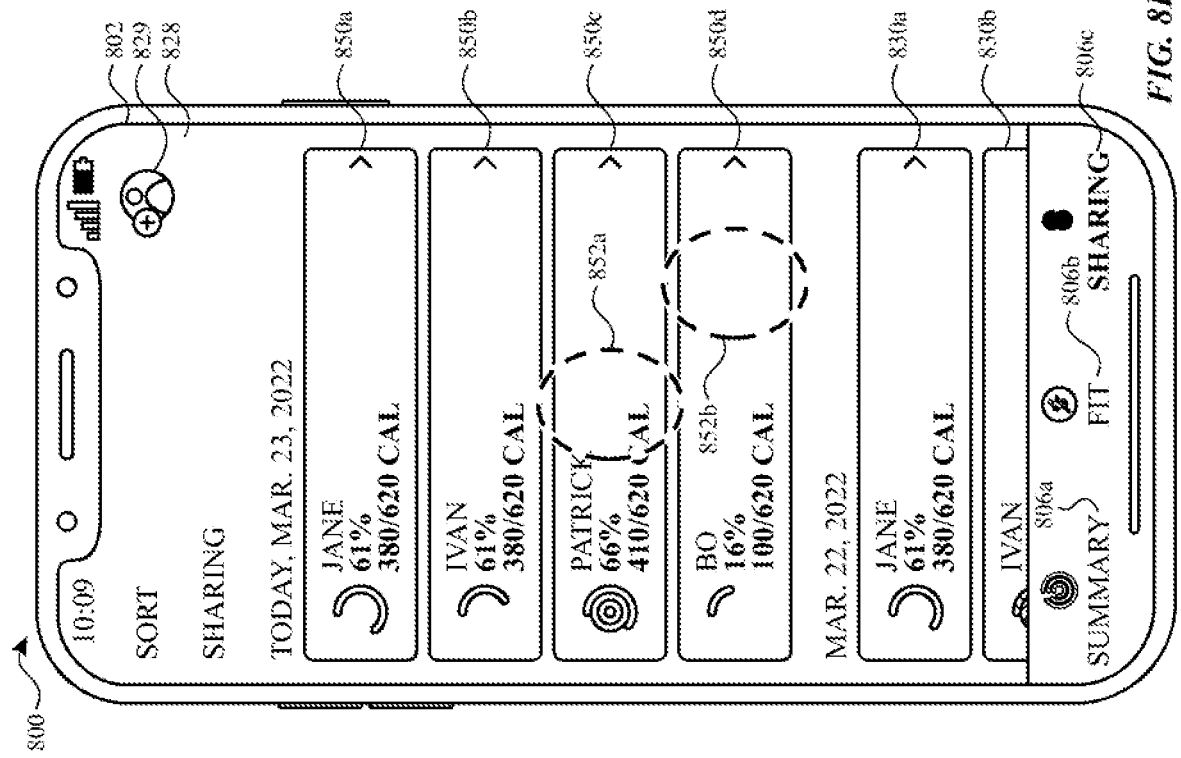

At FIG. 8H, in response to user input 848, electronic device 800 displays sharing user interface 828, which now includes additional representations 850a-850d representative of physical activity metrics for one or more users sharing information with the user of electronic device 800 for the current day. At FIG. 8H, electronic device 800 detects user input 852a (e.g., a tap input) corresponding to selection of representation 850c, and user input 852b (e.g., a tap input) corresponding to selection of representation 850d.

At FIG. 8I, in response to user input 852a, electronic device 800 displays user interface 854, which displays physical activity metrics 856a, 856b, 856c, 858a for Patrick for the current day. As discussed above, Patrick is a user that is associated with a smartwatch and, as such, user interface 854 displays three goal representations 856a-856c. Furthermore, whereas previously the user of electronic device 800 did not have the option to compete with Patrick because the user of electronic device 800 was not associated with a smartwatch (e.g., option 838b in FIG. 8E), option 858b is now available to be selected to initiate a competition with Patrick.

At FIG. 8J, in response to user input 852b, electronic device 800 displays user interface 860, which displays physical activity metrics 862, 864a for a user named Bo, who is sharing physical activity metrics with the user of electronic device 800. Bo is not associated with a smartwatch, and user interface 860 displays only move goal representation 862 without an exercise goal representation or a stand goal representation. Furthermore, because Bo is not associated with a smartwatch, option 864b is not selectable to initiate a competition between the user of electronic device 800 and Bo.

FIG. 9 is a flow diagram illustrating a method for navigating and displaying physical activity information using a computer system in accordance with some embodiments. Method 900 is performed at a computer system (e.g., 100, 300, 500) (e.g., a wearable device, a smart watch, a smart phone, a tablet, a head-mounted device (HMD), and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 900 are, optionally, combined, the orders of some operations are, optionally, changed, and some operations are, optionally, omitted.

As described below, method 900 provides an intuitive way for navigating and displaying physical activity information. The method reduces the cognitive burden on a user for navigating and displaying physical activity information, thereby creating a more efficient human-machine interface. For battery-operated computing devices, enabling a user to navigate and display physical activity information faster and more efficiently conserves power and increases the time between battery charges.

The computer system receives (902), via the one or more input devices, a first user input (e.g., 814, 844) (e.g., a first set of user inputs and/or one or more user inputs) (e.g., one or more touch inputs, one or more non-touch inputs, and/or one or more gestures) corresponding to a request to view a daily activity user interface (816), wherein the daily activity user interface displays one or more physical activity metrics (e.g., 822g-1 through 822g-7) (e.g., one or more metrics indicative of a user's level of physical activity) corresponding to a plurality of days (e.g., displays one or more physical activity metrics for each day of a plurality of days).

In some embodiments, in response to receiving the first user input (e.g., 814, 844), the computer system displays (904), via the display generation component, the daily activity user interface (e.g., 816), including displaying a first set of physical activity metrics (e.g., 822g-1, 822g-2, 822g-3) corresponding to a first day.

In some embodiments, in accordance with a determination that external device criteria are satisfied for the first day (906) (e.g., in accordance with a determination that a first external device of a first type (e.g., a wearable device and/or a smart watch) was connected to and/or paired with the computer system during the first day (e.g., for a threshold duration of time during the first day)), displaying the first set of physical activity metrics corresponding to the first day includes concurrently displaying a representation of a first physical activity metric (908) corresponding to (e.g., measured during) the first day (e.g., move goal representation, exercise goal representation, and/or stand goal representation in representation 822g-3) (e.g., hours during the first day in which a user has stood for at least some predetermined amount of time, minutes of activity above a certain threshold activity level during the first day, active calories, calories burned, heart rate, distanced traveled, stairs climbed either based on passive background activity monitoring or activity data recorded during specific workouts) (in some embodiments, data for the first physical activity metric is collected (e.g., primarily or solely collected) using one or more sensors of the computer system) and a representation of a second physical activity metric (910) (e.g., move goal representation, exercise goal representation, and/or stand goal representation in representation 822g-3) (e.g., different from the first physical activity metric) corresponding to (e.g., measured during) the first day (e.g., hours during the first day in which a user has stood for at least some predetermined amount of time, minutes of activity above a certain threshold activity level during the first day, active calories, calories burned, heart rate, distanced traveled, stairs climbed either based on passive background activity monitoring or activity data recorded during specific workouts). In some embodiments, data for the second physical activity metric is collected (e.g., primarily or solely collected) using one or more sensors of a first external device.

In some embodiments, in accordance with a determination that external device criteria are not satisfied for the first day (e.g., 822g-1, 822g-2) (912) (e.g., in accordance with a determination that a first external device of a first type (e.g., a wearable device and/or a smart watch) was not connected to and/or paired with the computer system during the first day (e.g., for a threshold duration of time during the first day)), displaying the first set of physical activity metrics corresponding to the first day includes displaying the representation of the first physical activity metric (e.g., move goal representation in day representations 822g-1, 822g-2) corresponding to the first day without displaying the representation of the second physical activity metric corresponding to the first day (e.g., day representations 822g-1, 822g-2 do not include exercise goal representations or stand goal representations).

In some embodiments, displaying the daily activity user interface includes concurrently displaying the first set of physical activity metrics corresponding to the first day (e.g., 822g-1, 822g-2, 822g-3), and a second set of physical activity metrics corresponding to a second day different from the first day (e.g., 822g-1, 822g-2, 822g-3), wherein: in accordance with a determination that the external device criteria are satisfied for the second day, displaying the second set of physical activity metrics corresponding to the second day (e.g., 822g-3) includes concurrently displaying: a representation of the first physical activity metric corresponding to (e.g., measured during) the second day; and a representation of the second physical activity metric (e.g., different from the first physical activity metric) corresponding to (e.g., measured during) the second day; and in accordance with a determination that external device criteria are not satisfied for the second day, displaying the second set of physical activity metrics corresponding to the second day (e.g., 822g-1, 822g-2) includes displaying the representation of the first physical activity metric corresponding to the second day without displaying the representation of the second physical activity metric corresponding to the second day. Displaying a representation of the first physical activity metric and representation of the second physical activity metric if external device criteria are satisfied, and displaying the representation of the first physical activity metric without displaying the representation of the second physical activity metric if external device criteria are not satisfied provides the user with feedback about the state of the device (e.g., the computer system has determined either that external device criteria are satisfied or are not satisfied). Doing so also performs an operation (e.g., displaying the relevant interface elements) when a set of conditions (e.g., whether the external device criteria are satisfied) has been met without requiring further user input. Furthermore, displaying the representation of the first physical activity metric without displaying the representation of the second physical activity metric if external device criteria are not satisfied avoids cluttering the display with user interface elements that are not relevant to the particular user.

In some embodiments, the daily activity user interface (e.g., 816) includes (e.g., regardless of whether or not the first set of criteria are satisfied) a first suggestion (e.g., 822c) that provides a suggestion for how a user (e.g., a user corresponding to the computer system and/or the daily activity user interface (e.g., a user for which the daily activity user interface displays physical activity metrics)) can improve upon the first physical activity metric (e.g., a suggestion for an exercise and/or an activity that the user can perform to improve upon the first physical activity metric). In some embodiments, the representation of the first physical activity metric is indicative of the user's progress towards a first goal value corresponding to the first physical activity metric. Displaying the first suggestion and the representation of the first physical activity metric provides the user with feedback about the state of the device (e.g., that the computer system has determined that the user can improve upon the first physical activity metric by taking action consistent with the first suggestion).

In some embodiments, in accordance with a determination that a first set of criteria are satisfied (e.g., in accordance with a determination that a user of the computer system has previously used a first feature, in accordance with a determination that a user of the computer system has previously used a first application and/or a first type of application, and/or in accordance with a determination that a user of the computer system is close to achieving a physical activity goal (e.g., is within a threshold number of calories, steps, and/or minutes of activity from achieving a physical activity goal)), the daily activity user interface (e.g., 816) includes a first set of information (e.g., 822c, 822d, 822e, 822f). In some embodiments, in accordance with a determination that a second set of criteria different from the first set of criteria are satisfied (e.g., in accordance with a determination that a user of the computer system has previously used a first feature, in accordance with a determination that a user of the computer system has previously used a first application and/or a first type of application, and/or in accordance with a determination that a user of the computer system is close to achieving a physical activity goal (e.g., is within a threshold number of calories, steps, and/or minutes of activity from achieving a physical activity goal)), the daily activity user interface (e.g., 816) includes a second set of information (e.g., 822*c*, 822*d*, 822*e*, 822*f*) different from the first set of information. In some embodiments, in accordance with a determination that the first set of criteria are not satisfied, the daily activity user interface does not include the first set of information. In some embodiments, in accordance with a determination that the second set of criteria are not satisfied, the daily activity user interface does not include the second set of information. In some embodiments, in accordance with a determination that the first set of criteria are satisfied and in accordance with a determination that the second set of criteria are satisfied, the daily activity user interface includes the first set of information and the second set of information. Displaying the first set of information if the first set of criteria are satisfied and displaying the second set of information if the second set of criteria are satisfied causes the device to automatically display the first set of information and/or the second set of information without further user input. Furthermore, displaying the first set of information based on a determination that the first set of criteria are satisfied, and displaying the second set of information based on a determination that the set of criteria are satisfied avoids cluttering the display with user interface elements that are not relevant to the particular user.

In some embodiments, the representation of the first physical activity metric (e.g., 818) is indicative of the user's progress towards a first goal value corresponding to the first physical activity metric (e.g., move goal). In some embodiments, the first set of criteria includes a first criterion that is met when a user (e.g., a user corresponding to the computer system and/or the daily activity user interface (e.g., a user for which the daily activity user interface displays physical activity metrics)) satisfies completion threshold criteria with respect to the first goal value (e.g., the user is close to achieving the first goal value (e.g., is within a threshold number of calories, steps, minutes of activity, and/or units from achieving the first goal value for the first physical activity metric)). In some embodiments, the first set of information includes a first suggestion (e.g., 822*c*) for how the user can achieve the first goal value for the first physical activity metric (e.g., a suggestion for an activity and a duration for the activity that would result in the user achieving the first goal value for the first physical activity metric). Displaying the first suggestion if the completion threshold criteria are satisfied provides the user with feedback about the state of the device (e.g., that the device has determined that the user satisfies completion threshold criteria). Doing so also performs an operation (e.g., displaying the first suggestion) when a set of conditions (e.g., whether the completion threshold criteria are satisfied) has been met without requiring further user input. Furthermore, displaying the first suggestion based on a determination as to whether the user satisfies completion threshold criteria with respect to the first goal value avoids cluttering the display with user interface elements that are not relevant to the particular user.

In some embodiments, the first set of criteria includes a second criterion that is met when a user (e.g., a user corresponding to the computer system and/or the daily activity user interface (e.g., a user for which the daily activity user interface displays physical activity metrics)) has previously used a fitness application (e.g., an application pertaining to physical fitness and/or physical exercise and/or an application in which the user can receive instructions for performing one or more workouts) (e.g., has previously used a fitness application on the computer system and/or on a different computer system associated with the user). In some embodiments, the first set of information includes one or more recommendations for fitness applications (e.g., 822*f*, 822*f*-1, 822*f*-2, 822*f*-3) the user has not previously used (e.g., recommendations for one or more fitness applications that are available to be downloaded to and/or installed on the computer system; and/or recommendations for one or more fitness applications that are available within an application database). Displaying the one or more fitness application recommendations if the user has previously used a fitness application provides the user with feedback about the state of the device (e.g., that the device has identified the user as a user of fitness applications). Doing so also performs an operation (e.g., displaying the one or more fitness application recommendation) when a set of conditions (e.g., whether the user has previously used a fitness application) has been met without requiring further user input. Furthermore, displaying the one or more fitness application recommendations based on a determination as to whether the user has previously used a fitness application avoids cluttering the display with user interface elements that are not relevant to the particular user.

In some embodiments, the first set of criteria includes a third criterion that is met when a user (e.g., a user corresponding to the computer system and/or the daily activity user interface (e.g., a user for which the daily activity user interface displays physical activity metrics)) has previously used one or more fitness applications (e.g., an application pertaining to physical fitness and/or physical exercise and/or an application in which the user can receive instructions for performing one or more workouts) (e.g., has previously used a fitness application on the computer system and/or on a different computer system associated with the user) (in some embodiments, the determination that the first set of criteria are satisfied includes a determination that the user has previously used one or more third-party fitness applications (e.g., fitness applications that are not developed by the entity that develops, manufactures, and/or sells the computer system and/or the daily activity user interface)). In some embodiments, the first set of information includes one or more selectable objects (e.g., 822*e*, 822*e*-1, 822*e*-2, 822*e*-3, 822*e*-4) corresponding to the one or more fitness applications including a first selectable object that corresponds to a first fitness application of the one or more fitness applications (e.g., a first selectable object that is selectable to open the first fitness application) (in some embodiments, the first set of information further includes a second selectable object that corresponds to a second fitness application of the one or more fitness applications (e.g., a second selectable object that is selectable to open the second fitness application)). Displaying the one or more selectable objects corresponding to the one or more fitness applications if the user has previously used a fitness application reduces the number of inputs needed to open those fitness applications. Doing so also performs an operation (e.g., displaying the one or more selectable objects) when a set of conditions (e.g., whether the user has previously used a fitness application) has been met without requiring further user input. Furthermore, displaying the one or more selectable objects based on a determination as to whether the user has previously used a fitness application avoids cluttering the display with user interface elements that are not relevant to the particular user.

In some embodiments, the first set of criteria includes a fourth criterion that is met when a user (e.g., a user corresponding to the computer system and/or the daily activity user interface (e.g., a user for which the daily activity user interface displays physical activity metrics)) has previously used a first fitness application (e.g., a specific fitness application) (e.g., an application pertaining to physical fitness and/or physical exercise and/or an application in which the user can receive instructions for performing one or more workouts) (e.g., a first fitness application that is associated with the daily activity user interface (e.g., shares the same developer as the daily activity user interface) and/or a first fitness application that is associated with an entity that manufactures and/or sells the computer system (e.g., a first party fitness application)). In some embodiments, the first set of information (e.g., 822*d*) includes one or more selectable objects corresponding to one or more workouts (e.g., 822*d*-1, 822*d*-2) within the first fitness application including a first selectable object that corresponds to a first workout within the first fitness application and a second selectable object that corresponds to a second workout within the first fitness application (e.g., a first selectable object that is selectable to open the first workout and/or initiate a workout session corresponding to the first workout within the first fitness application; and a second selectable object that is selectable to open the second workout and/or initiate a workout session corresponding to the second workout within the second fitness application), wherein the first workout and the second workout are selected based on one or more workouts completed by the user within the first fitness application (e.g., the first workout and the second workout are similar to one or more workouts completed by the user within the first fitness application (e.g., share the same trainer/instructor, share the same workout modality, are of a similar duration, are of a similar difficulty level, and/or are associated with the same music genre). Displaying the one or more selectable objects corresponding to one or more workouts in the first fitness application if the user has previously used the first fitness application reduces the number of inputs needed to initiate a workout within the first fitness application. Doing so also performs an operation (e.g., displaying the one or more selectable objects) when a set of conditions (e.g., whether the user has previously used the first fitness application) has been met without requiring further user input. Furthermore, displaying the one or more selectable objects based on a determination as to whether the user has previously used the first fitness application avoids cluttering the display with user interface elements that are not relevant to the particular user.

In some embodiments, while displaying the daily activity user interface (e.g., 816), the computer system (e.g., 800) receives, via the one or more input devices, a second user input (e.g., 826, 848) (e.g., a second set of user inputs and/or one or more user inputs) (e.g., one or more touch inputs, one or more non-touch inputs, and/or one or more gestures). In some embodiments, in response to receiving the second user input, the computer system displays, via the display generation component, a sharing user interface (e.g., 828). In some embodiments, displaying the sharing user interface includes concurrently displaying a representation (e.g., 850*a*, 850*b*, 850*c*, 850*d*) of a first user (e.g., a first user that is sharing physical activity metrics with the user of the computer system) and a representation (e.g., 850*a*, 850*b*, 850*c*, 850*d*) of a second user (e.g., a second user that is sharing physical activity metrics with the user of the computer system) different from the first user. In some embodiments, in accordance with a determination that the first user is associated with a device of a first type (e.g., a wearable device and/or a smart watch), displaying the representation of the first user comprises displaying a representation of the first physical activity metric for the first user and a representation of the second physical activity metric for the first user (e.g., representation 850*c* includes move goal representation, exercise goal representation, and stand goal representation). In some embodiments, in accordance with a determination that the second user is not associated with a device of the first type, displaying the representation of the second user comprises displaying a representation of the first physical activity metric for the second user without displaying a representation of the second physical activity metric for the second user (e.g., representation 850*b* includes move goal representation and does not include exercise goal representation or stand goal representation). Displaying the representation of the first user with information about the first and second physical activity metrics and displaying the representation of the second user with information only about the first physical activity metric (without information about the second physical activity metric) provides the user with feedback about the state of the device (e.g., that the device has received information indicating that the first user is associated with a device of the first type and the second user is not associated with a device of the first type). Doing so also performs an operation (e.g., displaying the relevant physical activity metrics) when a set of conditions (e.g., whether the user is associated with a device of the first type) has been met without requiring further user input. Furthermore, forgoing display of the representation of the second physical activity metric if the user is not associated with the device of the first type avoids cluttering the display with user interface elements that are not relevant to the particular user.

In some embodiments, in accordance with a determination that the first user is associated with a device of a first type (e.g., a wearable device and/or a smart watch), the computer system displays, via the display generation component, a selectable object (e.g., 858*b* in FIG. 8I) that is selectable to initiate a competition between a user of the computer system (e.g., 800) and the first user (e.g., "Patrick" in FIG. 8I). In some embodiments, in accordance with a determination that the second user is not associated with a device of the first type, the computer system forgoes display of a selectable object that is selectable to initiate a competition between the user of the computer system and the second user (e.g., 864*b* in FIG. 8J is not selectable). In some embodiments, while displaying the sharing user interface, the computer system receives, via the one or more input devices, a third user input (e.g., 852*a*, 852*b*) (e.g., a third set of user inputs and/or one or more user inputs) (e.g., one or more touch inputs, one or more non-touch inputs, and/or one or more gestures); and in response to receiving the third user input: in accordance with a determination that the third user input corresponds to selection of the representation of the first user (e.g., 850*c*) and in accordance with a determination that the first user is associated with a device of the first type, the computer system displays, via the display generation component, a third selectable object (e.g., 858*b*) that is selectable to initiate a competition between a user of the computer system and the first user; and in accordance with a determination that the third user input (e.g., 852*b*) corresponds to selection of the representation of the second user (e.g., 850*d*) and in accordance with a determination that the second user is not associated with a device of the first type, the computer system (e.g., 800) forgoes display of a selectable object that is selectable to initiate a competition between the user of the computer system and the second user (e.g., 864*b* in FIG. 8J is not selectable). In some embodiments, if a first respective user is associated with a device of a first type, and a second respective user is associated with a device of the first type, the first respective user and the second respective user are able to enter into a competition with one another. In some embodiments, if a user is not associated with a device of the first type, the user is not able to enter into competitions with other users. Displaying the selectable object that is selectable to initiate a competition between a user of the computer system and the first user in accordance with a determination that the first user is associated with a device of the first type, and forgoing display of a similar selectable object in accordance with a determination that the second user is not associated with a device of the first type provides the user with feedback about the state of the device (e.g., that the device has received information indicating that the first user is associated with a device of the first type and the second user is not associated with a device of the first type). Doing so also performs an operation (e.g., displaying the selectable object) when a set of conditions (e.g., if the user is associated with a device of the first type) has been met without requiring further user input. Furthermore, forgoing display of the selectable object if the user is not associated with the device of the first type avoids cluttering the display with user interface elements that are not relevant to the particular user.

In some embodiments, displaying the daily activity user interface (e.g., 816) comprises concurrently displaying a representation of a first day (e.g., 822g-1 through 822g-7) (e.g., a first calendar day) and a representation of a second day (e.g., 822g-1 through 822g-7) (e.g., a second calendar day) different from the first day. In some embodiments, the representation of the first day (e.g., 822g-1, 822g-2) includes a representation of the first physical activity metric corresponding to the first day (e.g., measured during the first day) and does not include a representation of the second physical activity metric corresponding to the first day (e.g., includes move goal representation and does not include exercise goal representation and/or stand goal representation). In some embodiments, the representation of the second day (e.g., 822g-3) includes a representation of the second physical activity metric corresponding to the second day (e.g., measured during the second day) and a representation of the second physical activity metric corresponding to the second day (e.g., measured during the second day). Displaying the representation of the first day with the representation of the first physical activity metric and without the representation of the second physical activity metric, and displaying the representation of the second day with both the representation of the first physical activity metric and the representation of the second physical activity metric provides the user with feedback about the state of the device (e.g., that the device was paired to an external device of the first type on the second day but was not paired to an external device of the first type on the first day). Furthermore, displaying the representation of the first day without the representation of the second physical activity metric avoids cluttering the display with user interface elements that are not relevant to the particular user.

In some embodiments, data pertaining to the first physical activity metric (e.g., move goal) (e.g., data used to calculate, determine, and/or measure the first physical activity metric) is collected by (in some embodiments, exclusively collected by) one or more sensors of the computer system (e.g., 800). Displaying a representation of the first physical activity metric and representation of the second physical activity metric if external device criteria are satisfied, and displaying the representation of the first physical activity metric without displaying the representation of the second physical activity metric if external device criteria are not satisfied provides the user with feedback about the state of the device (e.g., the computer system has determined either that external device criteria are satisfied or are not satisfied). Doing so also performs an operation (e.g., displaying the relevant interface elements) when a set of conditions (e.g., whether the external device criteria are satisfied) has been met without requiring further user input. Furthermore, displaying the representation of the first physical activity metric without displaying the representation of the second physical activity metric if external device criteria are not satisfied avoids cluttering the display with user interface elements that are not relevant to the particular user.

In some embodiments, data pertaining to the second physical activity metric (e.g., exercise goal and/or stand goal) (e.g., data used to calculate, determine, and/or measure the second physical activity metric) is collected by (in some embodiments, exclusively collected by) one or more sensors of an external device separate from the computer system (e.g., an external device of a first type, a wearable device, and/or a smart watch). Displaying a representation of the first physical activity metric and representation of the second physical activity metric if external device criteria are satisfied, and displaying the representation of the first physical activity metric without displaying the representation of the second physical activity metric if external device criteria are not satisfied provides the user with feedback about the state of the device (e.g., the computer system has determined either that external device criteria are satisfied or are not satisfied). Doing so also performs an operation (e.g., displaying the relevant interface elements) when a set of conditions (e.g., whether the external device criteria are satisfied) has been met without requiring further user input. Furthermore, displaying the representation of the first physical activity metric without displaying the representation of the second physical activity metric if external device criteria are not satisfied avoids cluttering the display with user interface elements that are not relevant to the particular user.

Note that details of the processes described above with respect to method 900 (e.g., FIG. 9) are also applicable in an analogous manner to the methods described below and/or above. For example, methods 700 and/or 1100 optionally include one or more of the characteristics of the various methods described above with reference to method 900. For example, the computer system of method 900 can be the computer system of methods 700 and/or 1100, and the external device criteria in method 900 can pertain to the external device recited in methods 700 and/or 1100. For brevity, these details are not repeated below.

FIGS. 10A-10N illustrate exemplary user interfaces for providing physical activity information including workout content, in accordance with some embodiments. The user interfaces in these figures are used to illustrate the processes described below, including the processes in FIG. 11.

FIG. 10A illustrates electronic device 1000-1 with touch-sensitive display 1002-1, and electronic device 1000-2 with touch-sensitive display 1002-2. In the depicted examples, electronic device 1000-1 and electronic device 1000-2 are the same electronic device but in different states. Electronic device 1000-1 is an electronic device that does not have a smartwatch or other wearable device associated with it (e.g., registered on it and/or paired with it), while electronic device 1000-2 is an electronic device that does have a smartwatch or other wearable device associated with it (e.g., registered on it and/or paired with it). In FIG. electronic device 1004, which is a smartwatch with touch-sensitive display 1006, is paired to electronic device 1000-2. In FIGS.

10A-10N, electronic device 1000-1 and electronic device 1000-2 will be displayed adjacent to one another in order to demonstrate various user interfaces and how they are displayed differently based on whether or not an electronic device (e.g., 1000-1, 1000-2) is associated with and/or paired to an external device of a particular type (e.g., a smartwatch (e.g., electronic device 1004)). While the depicted embodiments show the external device of the particular type as a smartwatch, in other embodiments, the external device is a different type of device (e.g., a wearable device, a fitness band, or other external electronic device). In some embodiments, electronic device 1000-1 and/or electronic device 1000-2 are electronic device 600-1, electronic device 600-2, and/or electronic device 800. In some embodiments, electronic device 1004 is electronic device 604.

In FIG. 10A, electronic device 1000-1 and electronic device 1000-2 both display workout selection user interface 1008. Workout selection user interface 1008 includes workout representations 1010a and 1010b, which are each representative of a respective workout of a first workout modality (e.g., "Time to Walk" and/or an outdoor walking modality), and representations 1010c and 1010d, which are each representative of a respective workout of a second workout modality (e.g., "Run the World" and/or an outdoor running modality). Workout selection user interface 1008 also includes option 1010e that is selectable to view additional workouts of the first workout modality, and option 1010f that is selectable to view additional workouts of the second workout modality. In FIG. 10A, electronic device 1004 displays user interface 1012 that includes a watch face that indicates the current time. At FIG. 10A, electronic device 1000-1 detects user input 1014-1 (e.g., a tap input) corresponding to selection of workout representation 1010a, and electronic device 1000-2 detects user input 1014-2 (e.g., a tap input) corresponding to selection of workout representation 1010a.

Figure 10B:
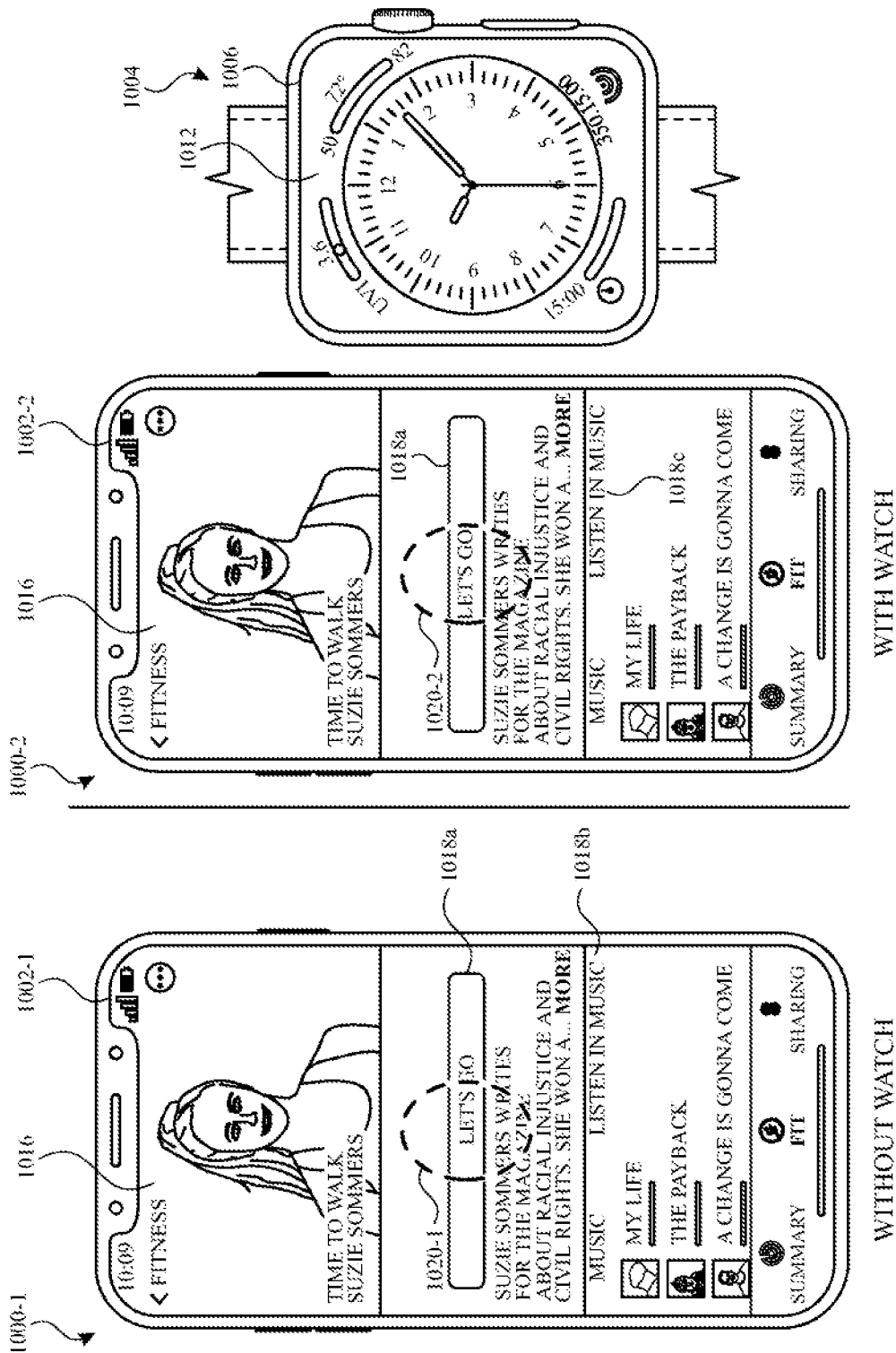

At FIG. 10B, in response to user input 1014-1, electronic device 1000-1 displays user interface 1016, and in response to user input 1014-2, electronic device 1000-2 also displays user interface 1016. User interface 1016 corresponds to a first workout of a first workout type, and includes option 1018a that is selectable to initiate a workout session of the first workout, and option 1018b that is selectable to listen to an audio playlist corresponding to the first workout (e.g., listen to an audio playlist corresponding to the first workout in a music application). At FIG. 10B, electronic device 1000-1 detects user input 1020-1 (e.g., a tap input) corresponding to selection of option 1018a, and electronic device 1000-2 detects user input 1020-2 corresponding to selection of option 1018a.

Figure 10C:
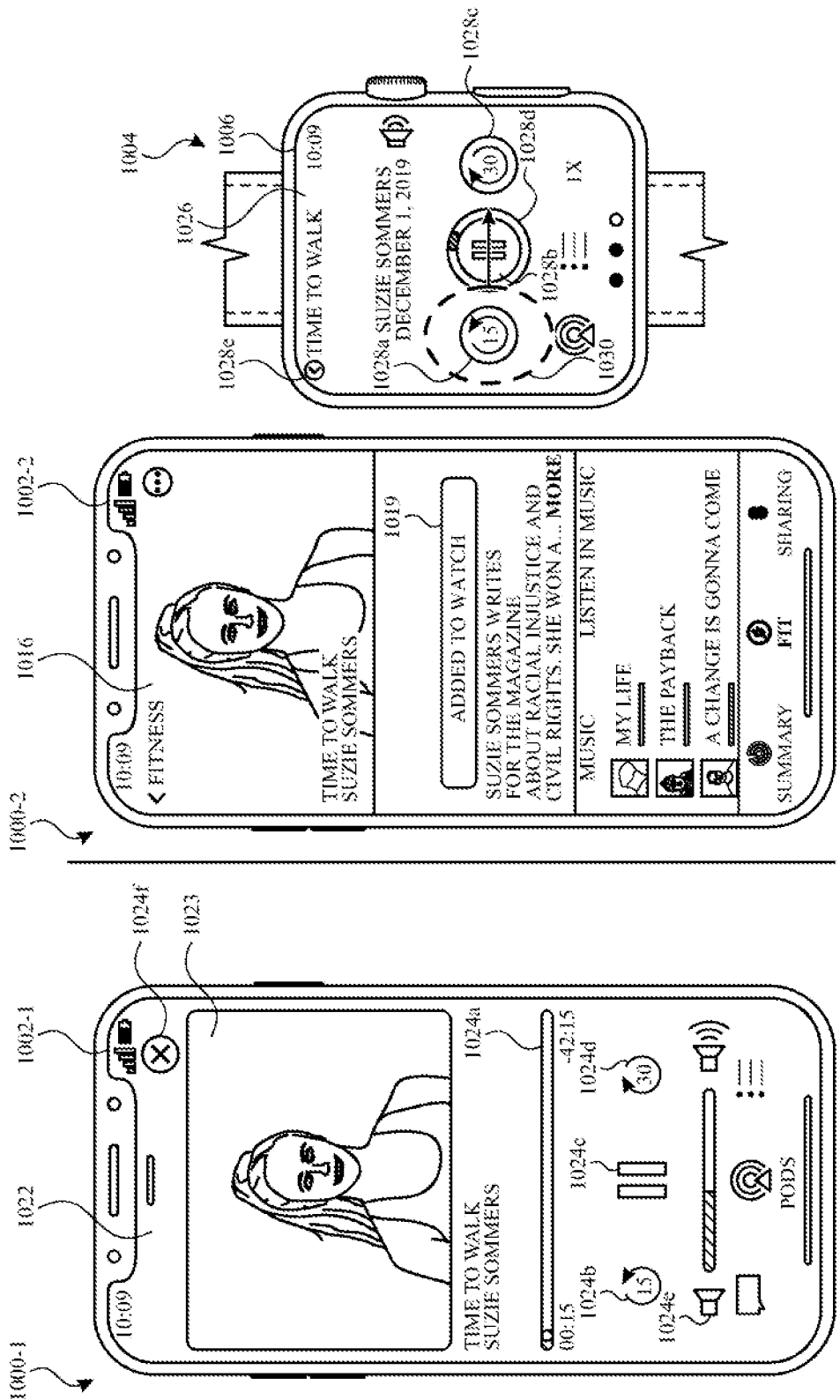

At FIG. 10C, in response to user input 1020-1, electronic device 1000-1 displays workout session user interface 1022, indicative of an active workout session of the first workout. In contrast, in response to user input 1020-2, and in accordance with a determination that electronic device 1000-2 is associated with (e.g., paired with) external electronic device 1004, maintains display of user interface 1016, displays indication 1019 indicating that the first workout has been added to external electronic device 1004, and causes external electronic device 1004 to display workout session user interface 1026 (e.g., by transmitting one or more messages and/or signals to external electronic device 1004). In the depicted embodiments, because electronic device 1000-2 is associated with (e.g., paired with) electronic device 1004, electronic device 1000-2 does not display workout session user interface 1022. However, in some embodiments, in accordance with a determination that electronic device 1000-2 is associated with (e.g., paired with) electronic device 1004, electronic device 1000-2 displays workout session user interface 1022 and causes electronic device 1004 to display workout session user interface 1026.

In some embodiments, the first workout type primarily includes audio workout content for the user to listen to while walking outdoors. In some embodiments, the first workout type includes some visual content, such as images and/or videos, as will be discussed later, but does not include video content that continuously demonstrates a workout. Workout session user interface 1022 includes progress indication 1024a, and playback controls 1024b (selectable to rewind audio content by 15 seconds), 1024c (selectable to pause audio playback), 1024d (selectable to fast forward audio content by 30 seconds), 1024e (selectable to adjust volume of audio playback), and 1024f (selectable to cease display of user interface 1022 and cease output of audio content and/or workout content of the first workout). Workout session user interface 1026 includes similar controls 1028a (selectable to rewind audio content by 15 seconds), 1028b (selectable to pause audio content), 1028c (selectable to fast forward audio content by 30 seconds), progress indication 1028d, and 1028e (selectable to cease display of user interface 1026 and cease output of audio content and/or workout content of the first workout). At FIG. 10C, electronic device 1004 detects user input 1030 (e.g., a swipe right touch user input).

Figure 10D:
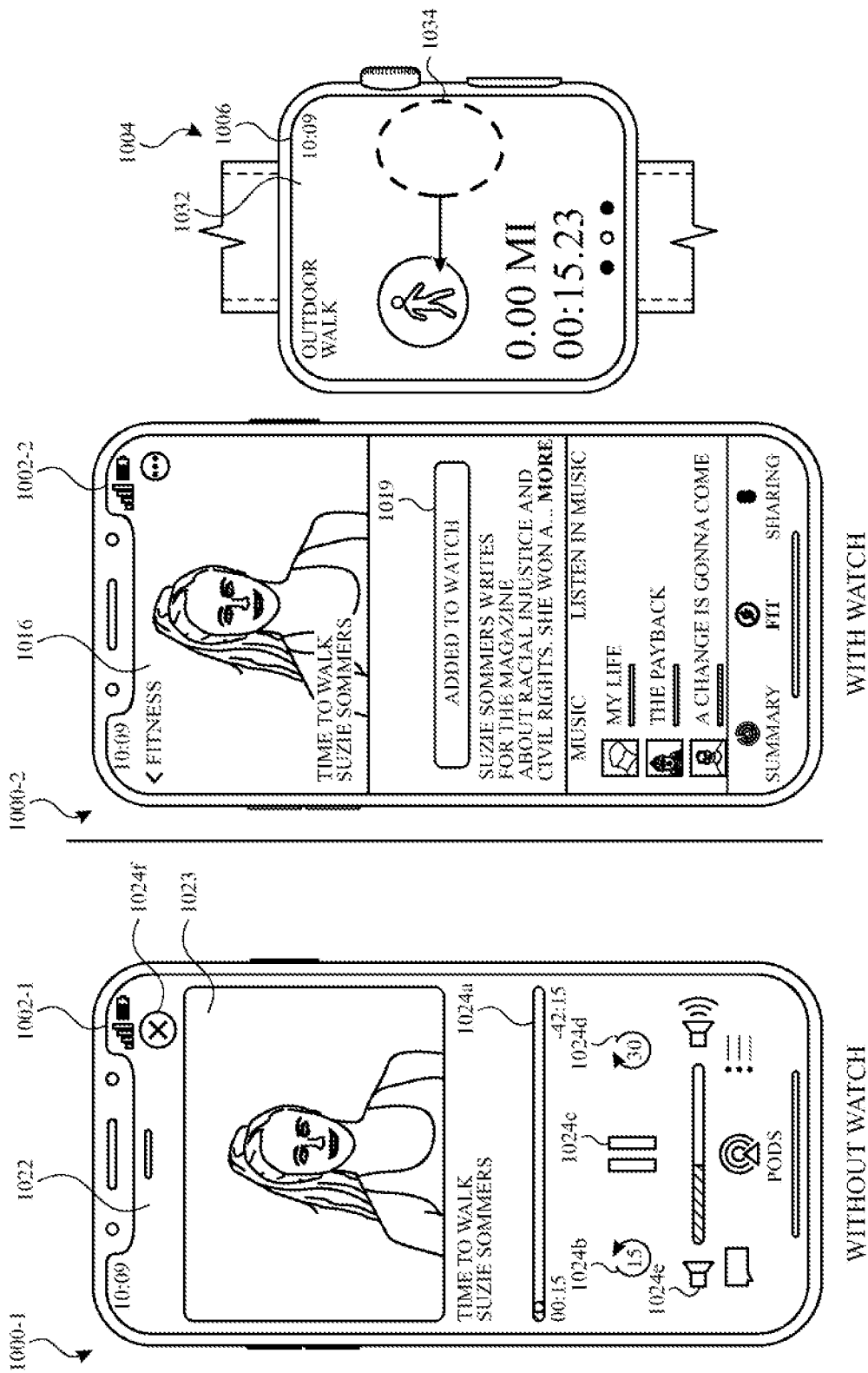

At FIG. 10D, in response to user input 1030, electronic device 1004 replaces display of workout session user interface 1026 with workout metrics user interface 1032, which displays one or more workout metrics corresponding to the current workout (e.g., distance traversed/walked and elapsed time). At FIG. 10D, electronic device 1004 detects user input 1034 (e.g., a swipe left touch user input), which would cause electronic device 1004 to replace display of workout metrics user interface 1032 with workout session user interface 1026.

Figure 10E:
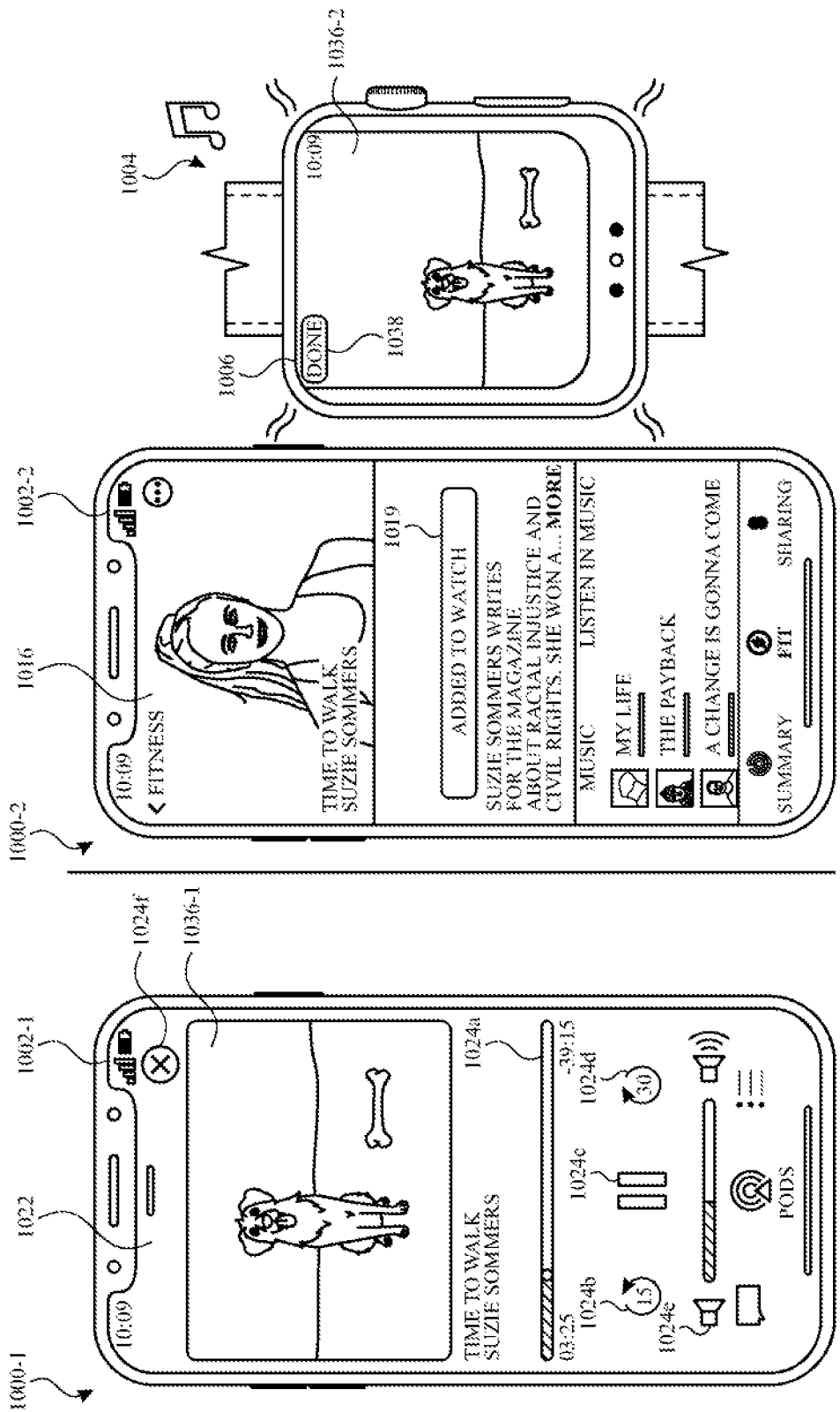

At FIG. 10E, electronic device 1000-1 and electronic device 1000-2 (and/or electronic device 1004) have detected a first "media moment" event. In some embodiments, as discussed above, the first workout includes audio content that is output for a user for the user to listen to while the user walks. In some embodiments, the first workout includes visual media content (e.g., photos and/or videos) that are configured to be displayed at predetermined positions (e.g., predetermined playback times and/or predetermined elapsed times) in the first workout. In FIG. 10E, at 3 minutes and 25 seconds into the first workout, an image 1036-1 of a dog is configured to be displayed. At FIG. 10E, in response to detecting the first media moment event, and in accordance with a determination that electronic device 1000-1 is not paired with an external electronic device, electronic device 1000-1 displays media item 1036-1. At FIG. 10E, in response to detecting the first media moment event, and in accordance with a determination that electronic device 1000-2 is paired with external electronic device 1004, electronic device 1000-1 does not display the media item, and electronic device 1004 displays media item 1036-2. In some embodiments, electronic device 1000-2 causes electronic device 1004 to display media item 1036-2 (e.g., by transmitting one or more messages and/or signals to electronic device 1004). In some embodiments, electronic device 1000-2 also displays media item 1036-1 and/or 1036-2 while electronic device 1004 displays media item 1036-2. In FIG. 10E, electronic device 1004 also outputs haptic and/or audio feedback in addition to displaying media item 1036-2, and also displays option 1038 that is selectable to cease display of media item 1036-2 (and cause display of user interface 1026). In some embodiments, electronic device 1000-1 ceases display of media item 1036-1 and/or electronic device 1004 automatically cease display of media item 1036-2 (and re-display user interface 1022 and/or 1026) after a threshold duration of time.

Figure 10F:
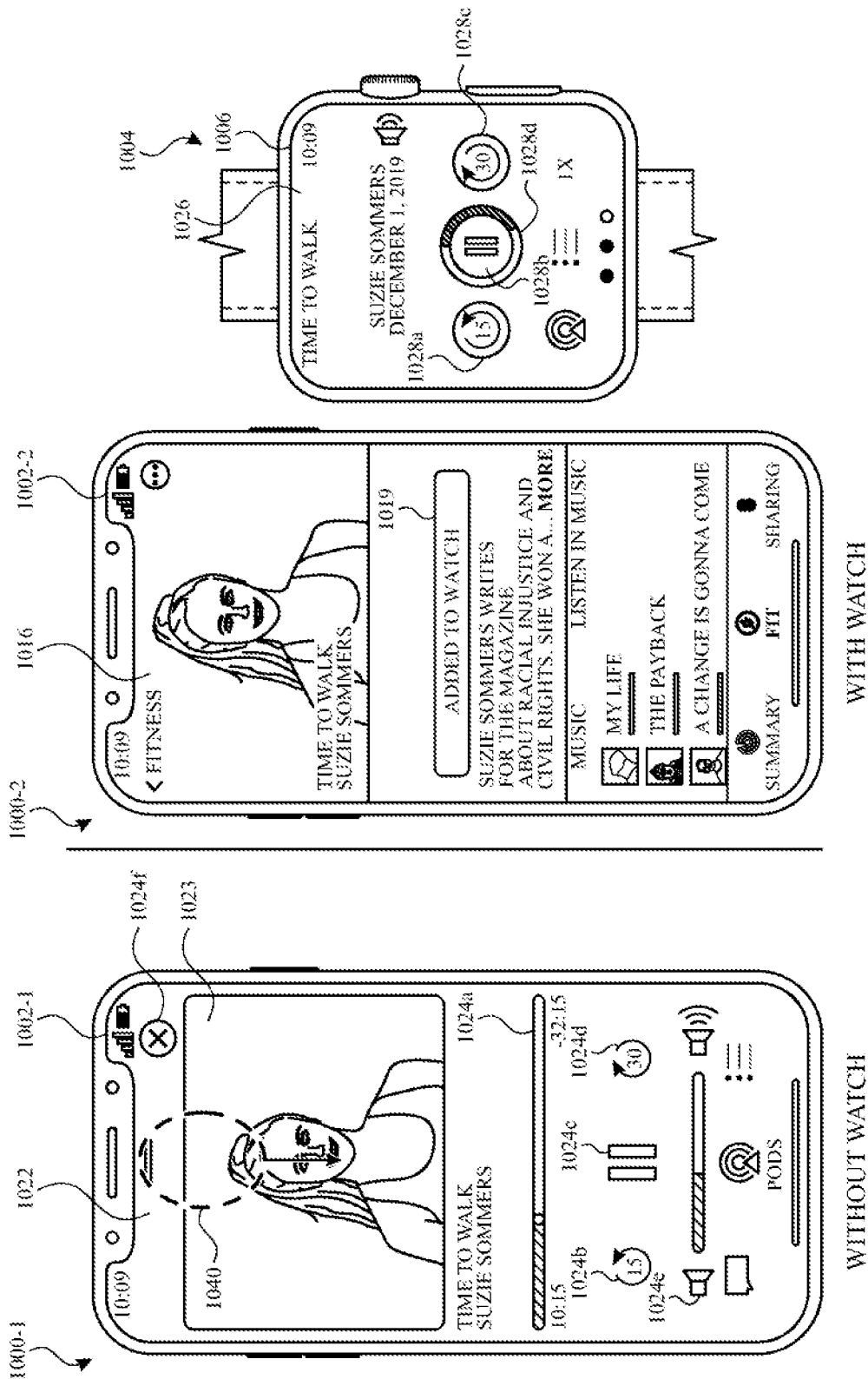
Figure 10G:
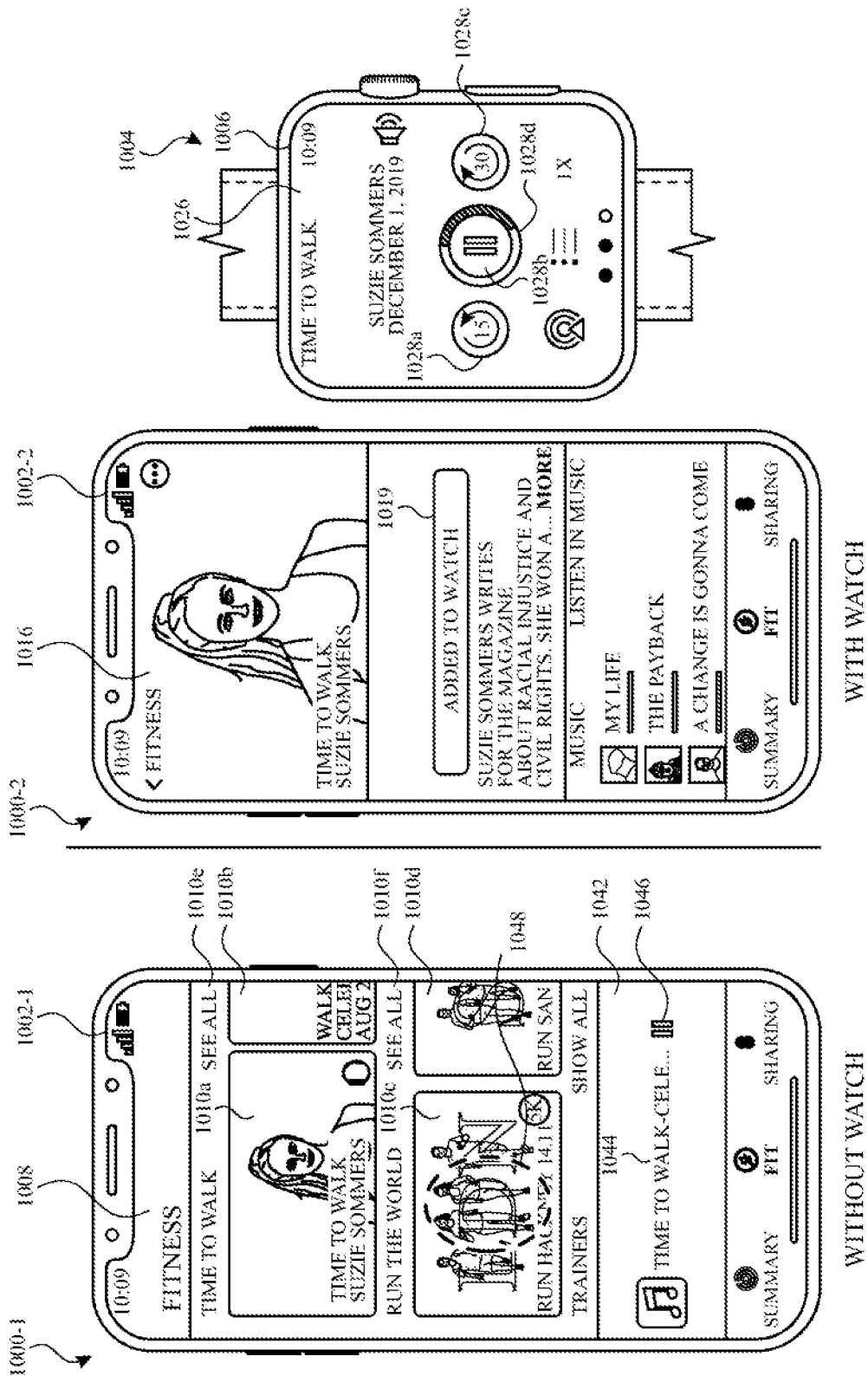

At FIG. 10F, while displaying user interface 1022, electronic device 1000-1 detects user input 1040 (e.g., a swipe down touch input). At FIG. 10G, in response to detecting user input 1040, electronic device 1000-1 ceases display of user interface 1022 and displays miniplayer user interface 1042 overlaid on workout selection user interface 1008. Miniplayer user interface 1042 includes title information 1044 corresponding to the first workout, and pause button 1046 that is selectable to pause audio playback of the first workout. At FIG. 10G, while displaying miniplayer user interface 1042 overlaid on workout selection user interface 1008, electronic device 1000-1 detects user input 1048 corresponding to selection of workout representation 1010c.

Figure 10H:
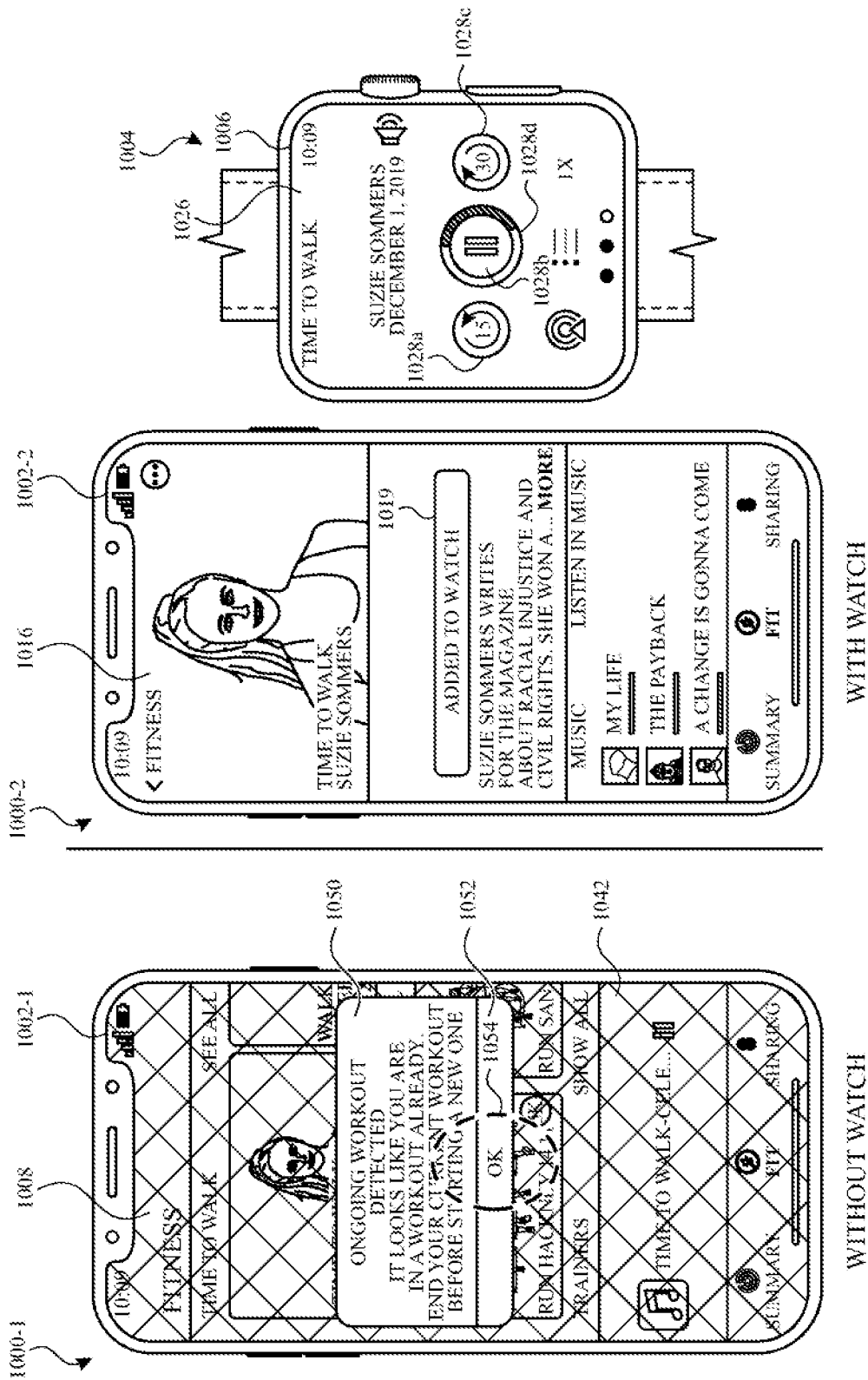

At FIG. 10H, in response to user input 1048, and in accordance with a determination that there is already an active workout session taking place, electronic device 1000-1 displays notification 1050 informing the user that the user must end their current workout before selecting a new workout. In some embodiments, in response to user input 1048, electronic device 1000-1 displays a user interface corresponding to the selected workout (e.g., similar to user interface 1016), that includes an option to initiate the selected workout (e.g., similar to option 1018a of FIG. 10B). In some such embodiments, while displaying the user interface corresponding to the selected workout, if electronic device 1000-1 detects user input corresponding to selection of the option to initiate the selected workout, electronic device 1000-1 displays notification 1050. Accordingly, in some embodiments, a user is able to interact with user interfaces and navigate content while miniplayer 1042 is displayed, but is not able to initiate and/or start a new workout. Notification 1050 includes option 1052 that is selectable to cease display of notification 1050. At FIG. 10H, electronic device 1000-1 detects user input 1054 (e.g., a tap input) corresponding to selection of option 1052.

Figure 10I:
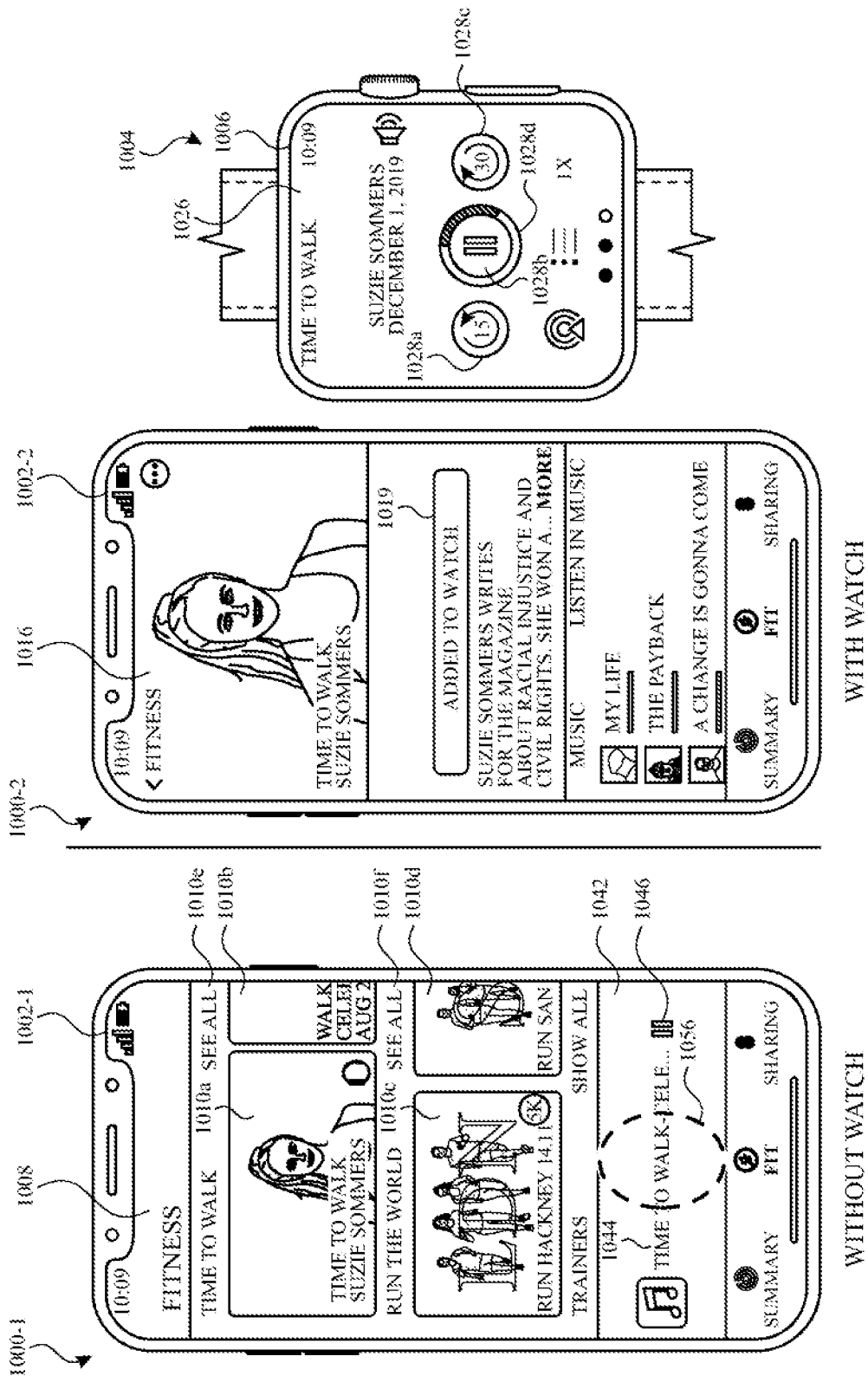

At FIG. 10I, in response to user input 1054, electronic device 1000-1 ceases display of notification 1050. At FIG. 10I, while displaying miniplayer user interface 1042, electronic device 1000-1 detects user inputs 1056 (e.g., a tap input) corresponding to selection of miniplayer user interface 1042.

Figure 10J:
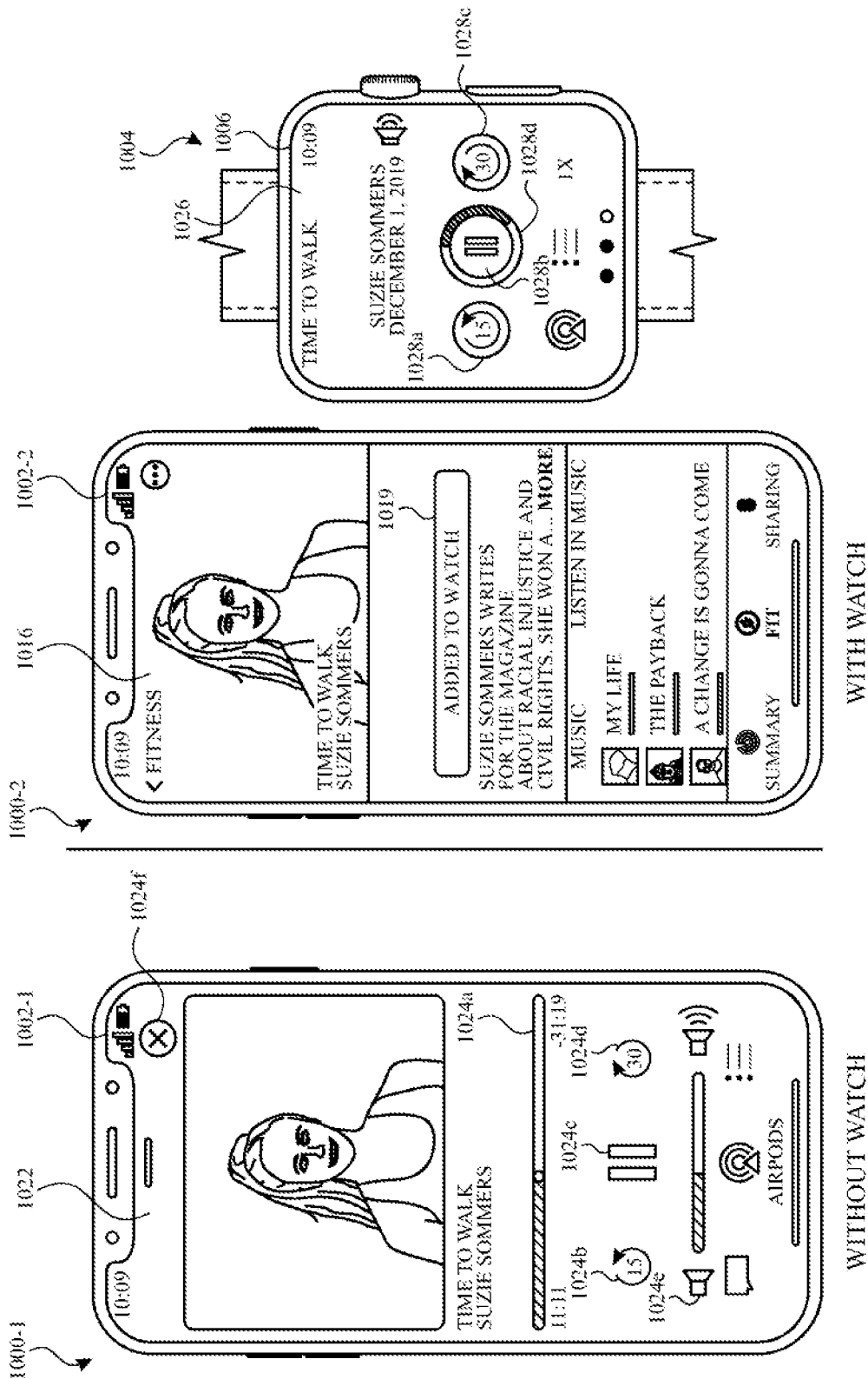

At FIG. 10J, in response to user input 1056, electronic device 1000-1 ceases display of miniplayer user interface 1042, and displays workout session user interface 1022.

Figure 10K:
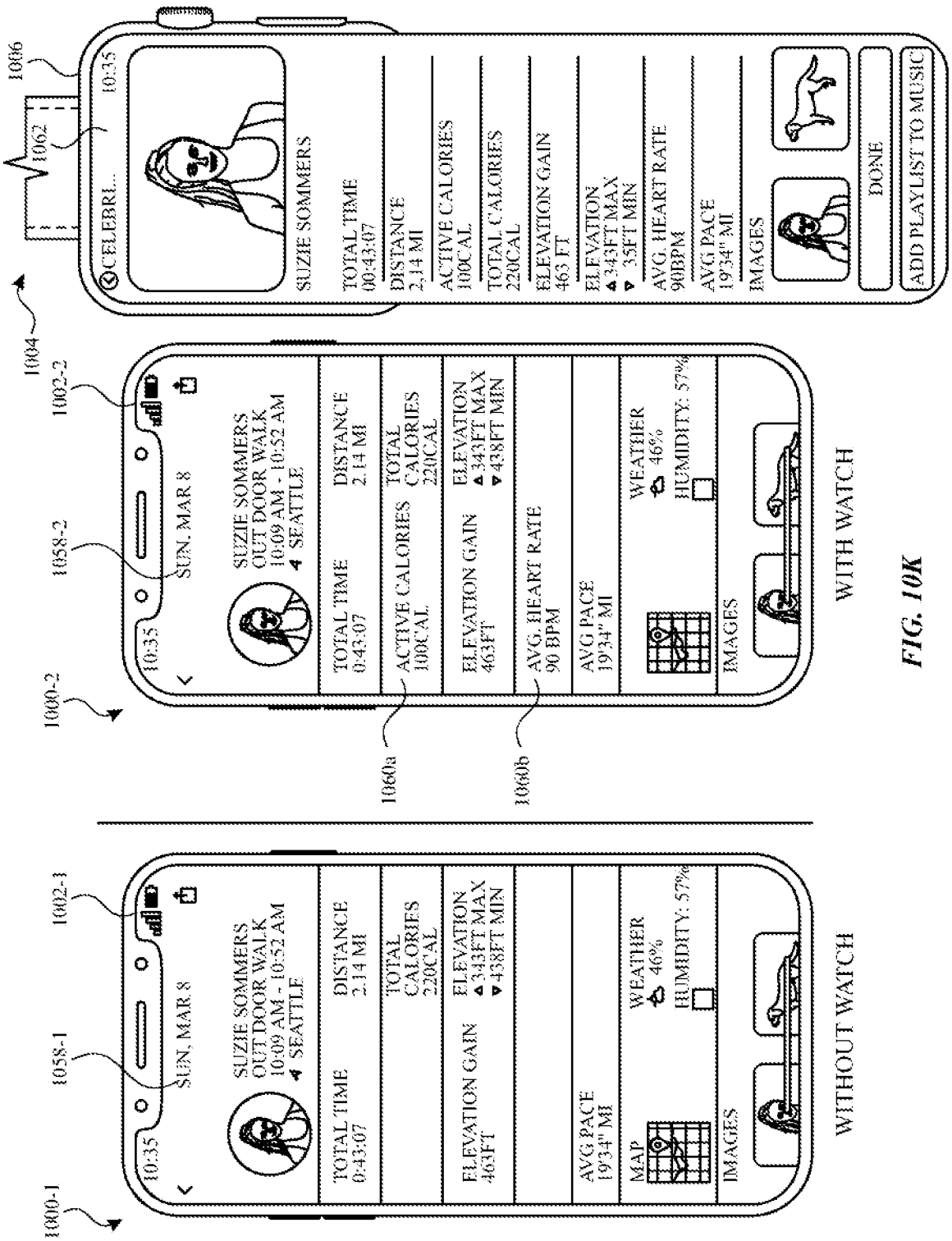

At FIG. 10K, the first workout has ended (e.g., has ended after a predetermined period of time and/or after audio content of the first workout completes playing). In response to detecting that the first workout has ended, electronic device 1000-1 displays workout summary user interface 1058-1, which includes information about the user's workout, including one or more physical activity metrics measured during the workout. Similarly, in response to detecting that the first workout has ended, electronic device 1000-2 displays workout summary user interface 1058-2 and electronic device 1004 displays workout summary user interface 1062. In FIG. 10K, it can be seen that workout summary user interfaces 1058-2 and 1062 include additional physical activity metrics and/or workout metrics that are not in workout summary user interface 1058-1, such as "Active Calories" and "Avg. Heart Rate." This is because electronic device 1000-2 is paired with electronic device 1004, and these physical activity metrics rely on one or more sensor readings from electronic device 1004 (e.g., heartrate measurement from electronic device 1004 and/or other sensor readings).

FIGS. 10L-10N depict an alternative scenario in which the first workout ends while miniplayer user interface 1042 is displayed. In some embodiments, when a workout ends while miniplayer user interface 1042 is displayed, miniplayer user interface 1042 ceases to be displayed and, in some embodiments, the electronic device does not display a workout summary user interface. In FIG. 10L, while displaying miniplayer user interface 1042 overlaid on workout selection user interface 1008, electronic device 1000-1 detects that the first workout has ended. In FIG. 10M, in response to this determination, electronic device 1000-1 displays miniplayer 1042 sliding downward, and in FIG. 10L, electronic device 1000-1 ceases display of miniplayer user interface 1042 and maintains display of workout selection user interface 1008.

FIG. 11 is a flow diagram illustrating a method for providing physical activity information including workout content using a computer system in accordance with some embodiments. Method 1100 is performed at a computer system (e.g., 100, 300, 500) (e.g., a wearable device, a smart watch, a smart phone, a tablet, a head-mounted device (HMD), and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 1100 are, optionally, combined, the orders of some operations are, optionally, changed, and some operations are, optionally, omitted.

As described below, method 1100 provides an intuitive way for providing and/or accessing physical activity information, including workout content. The method reduces the cognitive burden on a user for accessing physical activity information, thereby creating a more efficient human-machine interface. For battery-operated computing devices, enabling a user to access physical activity information, including workout content, faster and more efficiently conserves power and increases the time between battery charges.

The computer system (e.g., 1000-1, 1000-2) receives (1102), via the one or more input devices, a first user input (e.g., 1020-1, 1020-2) (e.g., a first set of user inputs and/or one or more user inputs) (e.g., one or more touch inputs, one or more non-touch inputs, and/or one or more gestures) corresponding to a request to initiate a workout session corresponding to a first workout (e.g., a first workout selected (e.g., by a user) from a plurality of available workouts). In some embodiments, initiating the workout session includes initiating recording of one or more physical activity metrics (e.g., heartrate and/or calories burned) for the workout session (e.g., via one or more sensors in communication with the computer system). In some embodiments, initiating the workout session includes recording one or more physical activity metrics at a greater frequency than prior to initiation of the workout session.

In some embodiments, in response to receiving the first user input (e.g., 1020-1, 1020-2) (1104) and in accordance with a determination that a first set of criteria are met, the computer system (e.g., 1000-1, 1000-2) displays (1106), via the display generation component (e.g., 1002-1, 1002-2), a first workout session user interface (e.g., 1022) (e.g., a user interface indicative of an active and/or in-progress workout session), corresponding to the first workout (in some embodiments, in accordance with a determination that the first set of criteria are not met, the computer system forgoes displaying the first workout session user interface (e.g., device 1000-2 in FIG. 10C) (e.g., displays a second user interface (e.g., 1016) different from the first workout session user interface (e.g., 1022))). In some embodiments, the first set of criteria includes a criterion that is met when the first user input is received at the computer system (e.g., received via the one or more input devices in communication with the computer system). In some embodiments, the first set of criteria includes a criterion that is met when an external device of a first type (e.g., 1004) (e.g., a wearable device and/or a smart watch) is not connected to and/or paired with the computer system (e.g., 1000-1) (e.g., at the time the first user input is received). In some embodiments, the first set of criteria includes a criterion that is met when an external device of the first type (e.g., 1004) is not worn by a user (e.g., at the time the first user input is received).

In some embodiments, in response to receiving the first input (e.g., 1020-1, 1020-2) (1104) and in accordance with a determination that external device criteria are met with respect to a first external device (e.g., 1004) (e.g., in accordance with a determination that a first external device of a first type is connected to and/or paired with the computer system (e.g., at the time of receiving the first user input and/or during the workout session); and/or in accordance with a determination that a first external device of a first type is connected to and/or paired with the computer system and is being worn by a user (e.g., at the time of receiving the first user input and/or during the workout session)), the computer system (e.g., 1000-2) causes (1108) the first external device (e.g., 1004) to display (e.g., via a display generation component (e.g., 1006) in communication with the first external device (e.g., 1004)) a second workout session user interface (e.g., 1026) corresponding to the first workout (e.g., a user interface indicative of an active and/or in-progress workout session) (e.g., a second workout session user interface different from the first workout session user interface). In some embodiments, in accordance with a determination that the external device criteria are not met, the computer system forgoes causing an external device to display the second workout session user interface. In some embodiments, the second workout session user interface is different than the first workout session user interface.

In some embodiments, if both the first set of criteria are met and the external device criteria are met, the computer system (e.g., 1000-1, 1000-2) displays, via the display generation component (e.g., 1002-1, 1002-2), the first workout session user interface (e.g., 1022) while also causing the first external device (e.g., 1004) to display the second workout session user interface (e.g., 1026). In some embodiments, the first set of criteria includes a criterion that is not met if the external device criteria are met, such that if the external device criteria are met and the computer system causes the first external device to display the second workout session user interface, the computer system does not display (e.g., forgoes displaying) the first workout session user interface. In some embodiments, in response to receiving the first user input (e.g., 1020-1, 1020-2): in accordance with a determination that the external device criteria are not met (e.g., in accordance with a determination that the computer system is not connected to and/or paired with an external device of the first type (e.g., at the time of receiving the first user input and/or during the workout session); and/or in accordance with a determination that the computer system is not connected to and/or paired with an external device of the first type that is being worn by a user (e.g., at the time of receiving the first user input and/or during the workout session), the computer system (e.g., 1000-1, 1000-2) displays, via the display generation component (e.g., 1002-1, 1002-2), the first workout session user interface (e.g., 1022) corresponding to the first workout and forgoes causing an external device to display the second workout session user interface corresponding to the first workout; and in accordance with a determination that the external device criteria are met with respect to a first external device (e.g., 1004) (e.g., in accordance with a determination that a first external device of a first type is connected to and/or paired with the computer system (e.g., at the time of receiving the first user input and/or during the workout session; and/or in accordance with a determination that a first external device of a first type is connected to and/or paired with the computer system and is being worn by a user (e.g., at the time of receiving the first user input and/or during the workout session)), the computer system (e.g., 1000-1, 1000-2) causes the first external device (e.g., 1004) to display (e.g., via a display generation component (e.g., 1006) in communication with the first external device) the second workout session user interface (e.g., 1026) corresponding to the first workout (e.g., a user interface indicative of an active and/or in-progress workout session) (e.g., a second workout session user interface different from the first workout session user interface) and forgoes displaying, via the display generation component, the first workout session user interface corresponding to the first workout. Causing the first external device to display the second workout session user interface in accordance with a determination that external device criteria are met with respect to the first external device provides the user with feedback about the state of the device (e.g., that the computer system has determined that external device criteria are met with respect to the first external device). Causing the first external device to display the second workout session user interface in accordance with a determination that external device criteria are met with respect to the first external device causes the device to automatically perform causing the first external device to display the second workout session user interface without further user inputs.

In some embodiments, the first set of criteria includes a first criterion that is met when a user input (e.g., 1020-1, 1020-2) corresponding to a request to initiate a workout session corresponding to the first workout is received. In some embodiments, the first set of criteria includes a first criterion that is satisfied and/or met when the user provides a user input corresponding to a request to initiate a workout session corresponding to the first workout. Displaying the first workout session user interface in response to receiving the first user input provides the user with feedback about the state of the device (e.g., that the computer system has detected the first user input).

In some embodiments, the first set of criteria includes a second criterion that is met when an external device of a first type (e.g., 1004) (e.g., a wearable device and/or a smart watch) is not connected to (e.g., is not paired with and/or registered on) the computer system (e.g., 1000-1, 1000-2) (e.g., at the time the first user input is received). In some embodiments, if an external device of the first type is connected to the computer system (e.g., at the time the first user input is received), the computer system forgoes displaying the first workout session user interface (and, optionally, in some embodiments, displays a different user interface)). Displaying the first workout session user interface in accordance with a determination that an external device of the first type is not connected to the computer system provides the user with feedback about the state of the device (e.g., that the computer system has determined that an external device of the first type is not connected to the computer system). Doing so also performs an operation (e.g., displaying the relevant interface) when a set of conditions (e.g., an external device of the first type is not connected to the computer system) has been met without requiring further user input.

In some embodiments, while displaying, via the display generation component (e.g., 1002-1, 1002-2), the first workout session user interface (e.g., 1022), the computer system receives, via the one or more input devices, a second user input (e.g., 1040) (e.g., a second set of user inputs and/or one or more user inputs) (e.g., one or more touch inputs, one or more non-touch inputs, and/or one or more gestures) (e.g., a swipe input (e.g., a swipe down input)). In some embodiments, in response to receiving the second user input, the computer system ceases display of the first workout session user interface (e.g., 1022). In some embodiments, in response to receiving the second user input (e.g., 1040), the computer system displays, via the display generation component, a third workout session user interface (e.g., 1042) different from the first workout session user interface and corresponding to the first workout, wherein the third workout session user interface (e.g., 1042) occupies a smaller area of the display generation component (e.g., 1002-1) than the first workout session user interface (e.g., 1022). Displaying the third workout session user interface in response to the second user input provides the user with feedback about the state of the device (e.g., that the computer system has detected the second user input). Furthermore, displaying the third workout session user that is smaller than the first workout session user interface avoids cluttering the display with user interface elements that the user does not need.

In some embodiments, while displaying, via the display generation component, the third workout session user interface (e.g., 1042), the computer system receives, via the one or more input devices, a third user input (e.g., 1056) (e.g., a third set of user inputs and/or one or more user inputs) (e.g., one or more touch inputs, one or more non-touch inputs, and/or one or more gestures) (e.g., a tap input (e.g., a tap input on the third workout session user interface)). In some embodiments, in response to receiving the third user input (e.g., 1056), the computer system ceases display of the third workout session user interface (e.g., 1042) and displays, via the display generation component, the first workout session user interface (e.g., 1022). Displaying the first workout session user interface in response to the third user input provides the user with feedback about the state of the device (e.g., that the computer system has detected the third user input).

In some embodiments, while displaying, via the display generation component, the third workout session user interface (e.g., 1042) corresponding to the first workout, the computer system detects that the first workout has ended (e.g., FIGS. 10L-10N). In some embodiments, in response to detecting that the first workout has ended, the computer system ceases display of the third workout session user interface (e.g., 1042) (e.g., FIGS. 10L-10N). In some embodiments, the third workout session user interface is displayed concurrently with a background user interface (e.g., 1008), and in response to detecting that the first workout has ended, the computer system ceases display of the third workout session user interface while maintaining display of the background user interface (e.g., FIG. 10N).

Ceasing display of the third workout session user interface in response to detecting that the first workout has ended provides the user with feedback about the state of the device (e.g., that the first workout has ended). Ceasing display of the third workout session user interface in response to detecting that the first workout has ended causes the device to automatically cease display of the third workout session user interface without further user input. Furthermore, automatically ceasing display of the third workout session user interface when the workout ends avoids cluttering the display with user interface elements that the user no longer needs.

In some embodiments, the computer system concurrently displays, via the display generation component, the third workout session user interface (e.g., 1042) and a workout selection user interface (e.g., 1008). In some embodiments, the workout selection user interface (e.g., 1008) includes a first selectable object (e.g., 1010a-1010d) (e.g., affordance) that is selectable to initiate a workout session corresponding to a second workout and a second selectable object (e.g., 1010a-1010d) (e.g., affordance) that is selectable to initiate a workout session corresponding to a third workout different from second workout. In some embodiments, displaying the workout selection user interface includes concurrently displaying the first selectable object and the second selectable object. In some embodiments, the workout selection user interface includes a third selectable object that is selectable to initiate a workout session corresponding to the first workout. In some embodiments, the first user input is received while displaying the workout selection user interface. Displaying the third workout session user interface in response to the second user input provides the user with feedback about the state of the device (e.g., that the computer system has detected the second user input).

In some embodiments, while concurrently displaying the third workout session user interface (e.g., 1042) and the workout selection user interface (e.g., 1008), the computer system receives, via the one or more input devices, a user input (e.g., 1048) (e.g., a first set of user inputs and/or one or more user inputs) (e.g., one or more touch inputs, one or more non-touch inputs, and/or one or more gestures) corresponding to selection of the first selectable object (e.g., 1010c). In some embodiments, in response to receiving the user input corresponding to selection of the first selectable object (and, optionally, in some embodiments, in accordance with a determination that the workout session corresponding to the first workout is active and/or ongoing), the computer system displays, via the display generation component, a visual indication (e.g., 1050) that another workout is active (e.g., a visual indication that the user cannot start a new workout while another workout is active). In some embodiments, if the user input corresponding to selection of the first selectable object had been received while the workout session corresponding to the first was not active and/or ongoing, the computer system would have initiated a workout session corresponding to the second workout and/or displayed a fourth workout session user interface corresponding to the second workout. Displaying the visual indication in response to the fourth user input provides the user with feedback about the state of the device (e.g., that the computer system has detected the fourth user input and/or that the user is not able to select an additional workout until the user ends the current workout). Doing so also makes the user-device interface more efficient by assisting the user in providing correct inputs.

In some embodiments, in response to receiving the first user input (e.g., 1020-1, 1020-2), the computer system initiates a workout session corresponding to the first workout. In some embodiments, initiating the workout session includes initiating recording of one or more physical activity metrics (e.g., heartrate and/or calories burned) for the workout session (e.g., via one or more sensors in communication with the computer system). In some embodiments, initiating the workout session includes recording one or more physical activity metrics at a greater frequency than prior to initiation of the workout session. In some embodiments, during the workout session corresponding to the first workout, the computer system detects that a predetermined condition has been met (e.g., a media moment event and/or a predetermined playback position within the first workout). In some embodiments, in response to detecting that the predetermined condition has been met and in accordance with a determination that a second set of criteria are met, the computer system displays, via the display generation component, a media item (e.g., 1036-1) (e.g., an image, a photo, and/or a video) corresponding to the predetermined condition (e.g., corresponding to the predetermined playback position within the first workout). In some embodiments, the second set of criteria includes a criterion that is met when the predetermined condition has been met. In some embodiments, the second set of criteria includes a criterion that is met when an external device of a first type (e.g., a wearable device and/or a smart watch) is not connected to and/or paired with the computer system (e.g., at the time the first user input is detected, at the time the predetermined condition has been met, and/or during the workout session). In some embodiments, the second set of criteria includes a criterion that is met when an external device of the first type is not worn by a user (e.g., at the time the first user input is detected, at the time the predetermined condition is met, and/or during the workout session).

In some embodiments, in response to detecting that the predetermined condition has been met and in accordance with a determination that second external device criteria are met with respect to the first external device (e.g., in accordance with a determination that a first external device of a first type is connected to and/or paired with the computer system (e.g., at the time of receiving the first user input, at the time the predetermined condition is met, and/or during the workout session); and/or in accordance with a determination that a first external device of a first type is connected to and/or paired with the computer system and is being worn by a user (e.g., at the time of receiving the first user input, at the time the predetermined condition is met, and/or during the workout session)) (in some embodiments, the second external device criteria are the same as the external device criteria), the computer system (e.g., 1000-2) causes the first external device (e.g., 1004) to display (e.g., via a display generation component in communication with the first external device) the media item (e.g., 1036-2) corresponding to the predetermined condition and generate tactile output (e.g., a sequence and/or a number of individual tactile outputs) (e.g., vibration and/or movement of the first external device). Causing the first external device to display the media item corresponding to the predetermined condition and generate tactile output in accordance with a determination that second external device criteria are met with respect to the first external device provides the user with feedback about the state of the device (e.g., that the computer system has determined that second external device criteria are met with respect to the first external device). Doing so also performs an operation (e.g., causing the first external device to display the media item) when a set of conditions (e.g., whether the second external device criteria are met) has been met without requiring further user input.

In some embodiments, in response to detecting that the predetermined condition has been met and in accordance with a determination that second external device criteria are met with respect to the first external device, the computer system (e.g., 1000-2) displays, via the display generation component (e.g., 1002-2), the media item corresponding to the predetermined condition (e.g., in FIG. 10E, electronic device 1000-2 would display media item 1036-1 and/or 1036-2). In some embodiments, the media item corresponding to the predetermined condition is concurrently displayed (e.g., displayed at the same time) on the computer system and on the first external device. In some embodiments, the second set of criteria is satisfied if the first type of event is detected. Causing the first external device and the computer system to display the media item corresponding to the predetermined condition in response to detecting the first type of event provides the user with feedback about the state of the device (e.g., that the computer system has detected that the predetermined condition has been met). Doing so also performs an operation (e.g., displaying the media item) when a set of conditions (e.g., whether the second external device criteria are met) has been met without requiring further user input.

In some embodiments, in response to detecting that the predetermined condition has been met and in accordance with a determination that second external device criteria are met with respect to the first external device (e.g., 1004), the computer system (e.g., 1000-2) forgoes display of the media item (e.g., 1036-2) corresponding to the predetermined condition on the computer system (e.g., on the display generation component) (e.g., displaying the media item corresponding to the predetermined condition on the first external device without displaying the media item corresponding to the predetermined condition on the computer system). In some embodiments, the second set of criteria includes a criterion that is met when an external device of a first type (e.g., a wearable device and/or a smart watch) is not connected to (e.g., is not paired with and/or registered on) the computer system (e.g., at the time the first user input is received and/or at the time the predetermined condition is met). In some embodiments, the second set of criteria are not met if an external device of the first type is connected to the computer system (e.g., at the time the first user input is received and/or at the time the predetermined condition is met). In some embodiments, if the second external device criteria are satisfied, the second set of criteria are not satisfied. Causing the first external device to display the media item corresponding to the predetermined condition and generate tactile output in accordance with a determination that second external device criteria are met with respect to the first external device provides the user with feedback about the state of the device (e.g., that the computer system has determined that second external device criteria are met with respect to the first external device). Furthermore, forgoing display of the media item if the second external device criteria are met avoids cluttering the display with unnecessary user interface elements.

In some embodiments, displaying, via the display generation component, the media item (e.g., 1036-1) corresponding to the predetermined condition includes displaying the media item (e.g., 1036-1) corresponding to the predetermined condition within the first workout session user interface (e.g., 1022) (and, optionally, in some embodiments, replacing display of a first media item within the first workout session user interface with display of the media item corresponding to the predetermined condition). In some embodiments, causing the first external device (e.g., 1004) to display the media item (e.g., 1036-2) corresponding to the predetermined condition includes causing the first external device (e.g., 1004) to, on a display generation component (e.g., 1006) in communication with the first external device, replace display of the second workout session user interface (e.g., 1026) with display of the media item (e.g., 1036-2) corresponding to the predetermined condition. Causing the first external device to display the media item corresponding to the predetermined condition in accordance with a determination that second external device criteria are met with respect to the first external device provides the user with feedback about the state of the device (e.g., that the computer system has determined that second external device criteria are met with respect to the first external device). Furthermore, replacing display of the second workout session user interface with display of the media item avoids cluttering the display with unnecessary user interface elements.

In some embodiments, in response to receiving the first user input (e.g., 1020-1, 1020-2), the computer system (e.g., 1000-1, 1000-2) initiates a workout session corresponding to the first workout. In some embodiments, initiating the workout session includes initiating recording of one or more physical activity metrics (e.g., heartrate and/or calories burned) for the workout session (e.g., via one or more sensors in communication with the computer system). In some embodiments, initiating the workout session includes recording one or more physical activity metrics at a greater frequency than prior to initiation of the workout session. In some embodiments, after initiating the workout session corresponding to the first workout, the computer system detects that the first workout has ended (e.g., FIG. 10K). In some embodiments, in response to detecting that the first workout has ended and in accordance with a determination that the computer system is associated with an external device of the first type (e.g., a smart watch and/or a wearable device) (e.g., in accordance with a determination that a first external device of a first type is connected to and/or paired with the computer system (e.g., at the time of receiving the first user input, at the time the first type of event is detected, and/or during the workout session)), the computer system (e.g., 1000-2) displays, via the display generation component, a first workout summary user interface (e.g., 1058-2). In some embodiments, in response to detecting that the first workout has ended and in accordance with a determination that the computer system is not associated with an external device of the first type (e.g., in accordance with a determination that a first external device of a first type is not connected to and/or paired with the computer system (e.g., at the time of receiving the first user input, at the time the first type of event is detected, and/or during the workout session) and/or in accordance with a determination that a user participating in the workout session is not wearing a first external device of the first type (e.g., at the time of receiving the first user input, at the time the first type of event is detected, and/or during the workout session)), the computer system (e.g., 1000-1) displays, via the display generation component (e.g., 1002-2), a second workout summary user interface (e.g., 1058-1) different from the first workout summary user interface (e.g., 1058-2), wherein the first workout summary user interface includes first workout information (e.g., average heart rate and/or active calories in FIG. 10K) that is not included in the second workout summary user interface.

In some embodiments, the second workout summary user interface displays a subset of the information that is displayed in the first workout summary user interface (e.g., without displaying additional information that is not displayed in the first workout summary user interface). In some embodiments, in response to detecting that the first workout has ended and in accordance with the determination that the computer system is associated with an external device of the first type, the external device of the first type displays a third workout summary user interface. Displaying the first workout summary user interface if the computer system is associated with an external device of the first type, and displaying the second workout summary user interface if the computer system is not associated with an external device of the first type, provides the user with feedback about the state of the device (e.g., whether or not the computer system is associated with an external device of the first type). Doing so also performs an operation (e.g., displaying the relevant interface) when a set of conditions (e.g., whether the user is associated with an external device of the first type) has been met without requiring further user input. Furthermore, displaying the second workout summary user interface if the user is not associated with an external device interface avoids cluttering the display with user interface elements that are not relevant to the particular user.

Note that details of the processes described above with respect to method 1100 (e.g., FIG. 11) are also applicable in an analogous manner to the methods described above. For example, methods 700 and/or 900 optionally include one or more of the characteristics of the various methods described above with reference to method 1100. For example, the computer system in method 1100 is, in some embodiments, the computer system in methods 700 and 900, and the external device in method 1100 is, in some embodiments, the external device in methods 700 and 900. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of workout content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, social network IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content that is of greater interest to the user. Accordingly, use of such personal information data enables users to have calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of physical activity information and/or workout content services, the present technology can be configured to allow users to select to "opt in" or "opt out" of participation in the collection of personal information data during registration for services or anytime thereafter. In another example, users can select not to provide physical activity information for targeted services. In yet another example, users can select to limit the length of time physical activity information is maintained or entirely prohibit the development of a physical activity profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. A computer system that is in communication with a display generation component and one or more input devices, comprising:
   one or more processors; and
   memory storing one or more programs configured to be executed by the one or more processors, the one or more programs including instructions for:
   receiving, via the one or more input devices, a first user input corresponding to a request to initiate a workout session corresponding to a first workout; and
   in response to receiving the first user input:
   in accordance with a determination that a user participating in the workout session is associated with an external device of a first type, displaying, via the display generation component, a first workout session user interface, wherein displaying the first workout session user interface includes concurrently displaying:
   visual content corresponding to the first workout;
   a representation of a first physical activity metric; and
   a representation of a second physical activity metric different from the first physical activity metric, wherein:
   the representation of the first physical activity metric and the representation of the second physical activity metric correspond to a predetermined amount of time that includes a period of time preceding playback of the visual content;
   the representation of the first physical activity metric is indicative of progress towards a first goal value for the first physical activity metric during the predetermined amount of time; and the representation of the second physical activity metric is indicative of progress towards a second goal value for the second physical activity metric during the predetermined amount of time; and in accordance with a determination that the user participating in the workout session is not associated with the external device of the first type, displaying, via the display generation component, a second workout session user interface different from first workout session user interface, wherein displaying the second workout session user interface includes concurrently displaying:

the visual content corresponding to the first workout, and the representation of the first physical activity metric, without displaying the representation of the second physical activity metric.

2. The computer system of claim 1, the one or more programs further including instructions for:

during a process for setting activity goals for one or more physical activity metrics:

displaying a set of selectable options for setting activity goal values, wherein:

in accordance with a determination that a user of the computer system is associated with an external device of the first type, the set of selectable options include a first selectable option for setting an activity goal value for the first physical activity metric and a second selectable option for setting an activity goal value for the second physical activity metric; and in accordance with a determination that the user of the computer system is not associated with an external device of the first type, the set of selectable options include the first selectable option for setting an activity goal value for the first physical activity metric without including the second selectable option for setting an activity goal value for the second physical activity metric.

3. The computer system of claim 1, the one or more programs further including instructions for:

at a first time, in accordance with a determination that a user of the computer system is not associated with an external device of the first type, displaying, via the display generation component, the second workout session user interface;

at a second time subsequent to the first time, detecting that the user of the computer system is now associated with a first external device of the first type; and after detecting that the user of the computer system is now associated with the first external device of the first type and in accordance with a determination that the user of the computer system is now associated with the first external device of the first type, displaying, via the display generation component, a goal setting user interface prompting the user to provide user input to define a goal value corresponding to the second physical activity metric.

4. The computer system of claim 1, the one or more programs further including instructions for:

at a third time, in accordance with a determination that a user of the computer system is not associated with an external device of the first type, displaying, via the display generation component, the second workout session user interface;

at a fourth time subsequent to the third time, detecting that the user of the computer system is now associated with a second external device of the first type; and after detecting that the user of the computer system is now associated with the second external device of the first type and in accordance with a determination that the user of the computer system is now associated with the second external device of the first type, initiating a process to cause the second external device of the first type to display, via a display generation component corresponding to the second external device of the first type, a third goal setting user interface prompting the user to provide user input to define a goal value corresponding to the second physical activity metric.

5. The computer system of claim 1, the one or more programs further including instructions for:

at a fifth time, in accordance with a determination that a user of the computer system is not associated with an external device of the first type, displaying, via the display generation component, the second workout session user interface;

at a sixth time subsequent to the fifth time, detecting that the user of the computer system is now associated with a third external device of the first type;

after detecting that the user of the computer system is now associated with the third external device of the first type, receiving, via the one or more input devices, a third user input corresponding to a request to initiate a workout session corresponding to the first workout; and in response to receiving the third user input:

in accordance with a determination that the user of the computer system is now associated with the third external device of the first type, displaying, via the display generation component, the first workout session user interface.

6. The computer system of claim 1, wherein the representation of the first physical activity metric is indicative of a number of calories burned by the user.

7. The computer system of claim 1, wherein:

the representation of the first physical activity metric is indicative of a number of calories burned by the user;

the representation of the first physical activity metric in the second workout session user interface is determined without input by an external device of the first type; and the representation of the first physical activity metric in the first workout session user interface is determined based on at least information received from an external device of the first type.

8. The computer system of claim 1, wherein the representation of the second physical activity metric is indicative of a duration of time during which the user surpassed a threshold physical activity level, wherein the representation of the second physical activity metric is determined based on at least information received from an external device of the first type.

9. The computer system of claim 1, wherein the representation of the second physical activity metric is indicative of a duration of time during which the user was in a predetermined posture for at least a threshold duration of time, wherein the representation of the second physical activity metric is determined based on at least information received from an external device of the first type.

10. The computer system of claim 1, the one or more programs further including instructions for:

while displaying the second workout session user interface:

detecting that a user has satisfied goal criteria pertaining to the first physical activity metric; and
in response to detecting that the user has satisfied the goal criteria pertaining to the first physical activity metric, displaying, via the display generation component, a first animation; and
while displaying the first workout session user interface:
detecting that the user has satisfied the goal criteria pertaining to the first physical activity metric; and
in response to detecting that the user has satisfied the goal criteria pertaining to the first physical activity metric, displaying, via the display generation component, a second animation different from the first animation.

11. The computer system of claim 1, the one or more programs further including instructions for:
while displaying the second workout session user interface:
detecting a first type of event has occurred; and
in response to detecting that the first type of event has occurred, displaying, via the display generation component, a first visual indication that the first type of event has occurred; and
while displaying the first workout session user interface:
detecting that the first type of event has occurred; and
in response to detecting that the first type of event has occurred, displaying, via the display generation component, the first visual indication that the first type of event has occurred.

12. The computer system of claim 11, wherein:
the first workout session user interface and the second workout session user interface are indicative of an active workout session; and
the first visual indication includes one or more instructions for the user pertaining to the workout session.

13. A non-transitory computer-readable storage medium storing one or more programs configured to be executed by one or more processors of a computer system that is in communication with a display generation component and one or more input devices, the one or more programs including instructions for:
receiving, via the one or more input devices, a first user input corresponding to a request to initiate a workout session corresponding to a first workout; and
in response to receiving the first user input:
in accordance with a determination that a user participating in the workout session is associated with an external device of a first type, displaying, via the display generation component, a first workout session user interface, wherein displaying the first workout session user interface includes concurrently displaying:
visual content corresponding to the first workout;
a representation of a first physical activity metric; and
a representation of a second physical activity metric different from the first physical activity metric, wherein:
the representation of the first physical activity metric and the representation of the second physical activity metric correspond to a predetermined amount of time that includes a period of time preceding playback of the visual content;
the representation of the first physical activity metric is indicative of progress towards a first goal value for the first physical activity metric during the predetermined amount of time; and
the representation of the second physical activity metric is indicative of progress towards a second goal value for the second physical activity metric during the predetermined amount of time; and
in accordance with a determination that the user participating in the workout session is not associated with the external device of the first type, displaying, via the display generation component, a second workout session user interface different from first workout session user interface, wherein displaying the second workout session user interface includes concurrently displaying:
the visual content corresponding to the first workout, and
the representation of the first physical activity metric, without displaying the representation of the second physical activity metric.

14. The non-transitory computer-readable storage medium of claim 13, the one or more programs further including instructions for:
during a process for setting activity goals for one or more physical activity metrics:
displaying a set of selectable options for setting activity goal values, wherein:
in accordance with a determination that a user of the computer system is associated with an external device of the first type, the set of selectable options include a first selectable option for setting an activity goal value for the first physical activity metric and a second selectable option for setting an activity goal value for the second physical activity metric; and
in accordance with a determination that the user of the computer system is not associated with an external device of the first type, the set of selectable options include the first selectable option for setting an activity goal value for the first physical activity metric without including the second selectable option for setting an activity goal value for the second physical activity metric.

15. The non-transitory computer-readable storage medium of claim 13, the one or more programs further including instructions for:
at a first time, in accordance with a determination that a user of the computer system is not associated with an external device of the first type, displaying, via the display generation component, the second workout session user interface;
at a second time subsequent to the first time, detecting that the user of the computer system is now associated with a first external device of the first type; and
after detecting that the user of the computer system is now associated with the first external device of the first type and in accordance with a determination that the user of the computer system is now associated with the first external device of the first type, displaying, via the display generation component, a goal setting user interface prompting the user to provide user input to define a goal value corresponding to the second physical activity metric.

16. The non-transitory computer-readable storage medium of claim 13, the one or more programs further including instructions for:

at a third time, in accordance with a determination that a user of the computer system is not associated with an external device of the first type, displaying, via the display generation component, the second workout session user interface;

at a fourth time subsequent to the third time, detecting that the user of the computer system is now associated with a second external device of the first type; and after detecting that the user of the computer system is now associated with the second external device of the first type and in accordance with a determination that the user of the computer system is now associated with the second external device of the first type, initiating a process to cause the second external device of the first type to display, via a display generation component corresponding to the second external device of the first type, a third goal setting user interface prompting the user to provide user input to define a goal value corresponding to the second physical activity metric.

17. The non-transitory computer-readable storage medium of claim 13, the one or more programs further including instructions for:

at a fifth time, in accordance with a determination that a user of the computer system is not associated with an external device of the first type, displaying, via the display generation component, the second workout session user interface;

at a sixth time subsequent to the fifth time, detecting that the user of the computer system is now associated with a third external device of the first type;

after detecting that the user of the computer system is now associated with the third external device of the first type, receiving, via the one or more input devices, a third user input corresponding to a request to initiate a workout session corresponding to the first workout; and in response to receiving the third user input:
in accordance with a determination that the user of the computer system is now associated with the third external device of the first type, displaying, via the display generation component, the first workout session user interface.

18. The non-transitory computer-readable storage medium of claim 13, wherein the representation of the first physical activity metric is indicative of a number of calories burned by the user.

19. The non-transitory computer-readable storage medium of claim 13, wherein:
the representation of the first physical activity metric is indicative of a number of calories burned by the user;
the representation of the first physical activity metric in the second workout session user interface is determined without input by an external device of the first type; and
the representation of the first physical activity metric in the first workout session user interface is determined based on at least information received from an external device of the first type.

20. The non-transitory computer-readable storage medium of claim 13, wherein the representation of the second physical activity metric is indicative of a duration of time during which the user surpassed a threshold physical activity level, wherein the representation of the second physical activity metric is determined based on at least information received from an external device of the first type.

21. The non-transitory computer-readable storage medium of claim 13, wherein the representation of the second physical activity metric is indicative of a duration of time during which the user was in a predetermined posture for at least a threshold duration of time, wherein the representation of the second physical activity metric is determined based on at least information received from an external device of the first type.

22. The non-transitory computer-readable storage medium of claim 13, the one or more programs further including instructions for:

while displaying the second workout session user interface:
detecting that a user has satisfied goal criteria pertaining to the first physical activity metric; and
in response to detecting that the user has satisfied the goal criteria pertaining to the first physical activity metric, displaying, via the display generation component, a first animation; and while displaying the first workout session user interface:
detecting that the user has satisfied the goal criteria pertaining to the first physical activity metric; and
in response to detecting that the user has satisfied the goal criteria pertaining to the first physical activity metric, displaying, via the display generation component, a second animation different from the first animation.

23. The non-transitory computer-readable storage medium of claim 13, the one or more programs further including instructions for:

while displaying the second workout session user interface:
detecting a first type of event has occurred; and
in response to detecting that the first type of event has occurred, displaying, via the display generation component, a first visual indication that the first type of event has occurred; and while displaying the first workout session user interface:
detecting that the first type of event has occurred; and
in response to detecting that the first type of event has occurred, displaying, via the display generation component, the first visual indication that the first type of event has occurred.

24. The non-transitory computer-readable storage medium of claim 23, wherein:
the first workout session user interface and the second workout session user interface are indicative of an active workout session; and
the first visual indication includes one or more instructions for the user pertaining to the workout session.

25. A method, comprising:
at a computer system that is in communication with a display generation component and one or more input devices:
receiving, via the one or more input devices, a first user input corresponding to a request to initiate a workout session corresponding to a first workout; and
in response to receiving the first user input:
in accordance with a determination that a user participating in the workout session is associated with an external device of a first type, displaying, via the display generation component, a first workout session user interface, wherein displaying the first workout session user interface includes concurrently displaying:
visual content corresponding to the first workout;
a representation of a first physical activity metric; and a representation of a second physical activity metric different from the first physical activity metric, wherein:
the representation of the first physical activity metric and the representation of the second physical activity metric correspond to a predetermined amount of time that includes a period of time preceding playback of the visual content;
the representation of the first physical activity metric is indicative of progress towards a first goal value for the first physical activity metric during the predetermined amount of time; and
the representation of the second physical activity metric is indicative of progress towards a second goal value for the second physical activity metric during the predetermined amount of time; and
in accordance with a determination that the user participating in the workout session is not associated with the external device of the first type, displaying, via the display generation component, a second workout session user interface different from first workout session user interface, wherein displaying the second workout session user interface includes concurrently displaying:
the visual content corresponding to the first workout, and
the representation of the first physical activity metric, without displaying the representation of the second physical activity metric.

26. The method of claim 25, further comprising:
during a process for setting activity goals for one or more physical activity metrics:
displaying a set of selectable options for setting activity goal values, wherein:
in accordance with a determination that a user of the computer system is associated with an external device of the first type, the set of selectable options include a first selectable option for setting an activity goal value for the first physical activity metric and a second selectable option for setting an activity goal value for the second physical activity metric; and
in accordance with a determination that the user of the computer system is not associated with an external device of the first type, the set of selectable options include the first selectable option for setting an activity goal value for the first physical activity metric without including the second selectable option for setting an activity goal value for the second physical activity metric.

27. The method of claim 25, further comprising:
at a first time, in accordance with a determination that a user of the computer system is not associated with an external device of the first type, displaying, via the display generation component, the second workout session user interface;
at a second time subsequent to the first time, detecting that the user of the computer system is now associated with a first external device of the first type; and
after detecting that the user of the computer system is now associated with the first external device of the first type and in accordance with a determination that the user of the computer system is now associated with the first external device of the first type, displaying, via the display generation component, a goal setting user interface prompting the user to provide user input to define a goal value corresponding to the second physical activity metric.

28. The method of claim 25, further comprising:
at a third time, in accordance with a determination that a user of the computer system is not associated with an external device of the first type, displaying, via the display generation component, the second workout session user interface;
at a fourth time subsequent to the third time, detecting that the user of the computer system is now associated with a second external device of the first type; and
after detecting that the user of the computer system is now associated with the second external device of the first type and in accordance with a determination that the user of the computer system is now associated with the second external device of the first type, initiating a process to cause the second external device of the first type to display, via a display generation component corresponding to the second external device of the first type, a third goal setting user interface prompting the user to provide user input to define a goal value corresponding to the second physical activity metric.

29. The method of claim 25, further comprising:
at a fifth time, in accordance with a determination that a user of the computer system is not associated with an external device of the first type, displaying, via the display generation component, the second workout session user interface;
at a sixth time subsequent to the fifth time, detecting that the user of the computer system is now associated with a third external device of the first type;
after detecting that the user of the computer system is now associated with the third external device of the first type, receiving, via the one or more input devices, a third user input corresponding to a request to initiate a workout session corresponding to the first workout; and
in response to receiving the third user input:
in accordance with a determination that the user of the computer system is now associated with the third external device of the first type, displaying, via the display generation component, the first workout session user interface.

30. The method of claim 25, wherein the representation of the first physical activity metric is indicative of a number of calories burned by the user.

31. The method of claim 25, wherein:
the representation of the first physical activity metric is indicative of a number of calories burned by the user;
the representation of the first physical activity metric in the second workout session user interface is determined without input by an external device of the first type; and
the representation of the first physical activity metric in the first workout session user interface is determined based on at least information received from an external device of the first type.

32. The method of claim 25, wherein the representation of the second physical activity metric is indicative of a duration of time during which the user surpassed a threshold physical activity level, wherein the representation of the second physical activity metric is determined based on at least information received from an external device of the first type.

33. The method of claim 25, wherein the representation of the second physical activity metric is indicative of a duration of time during which the user was in a predetermined posture for at least a threshold duration of time, wherein the representation of the second physical activity metric is determined based on at least information received from an external device of the first type.

34. The method of claim 25, further comprising:
while displaying the second workout session user interface:
 detecting that a user has satisfied goal criteria pertaining to the first physical activity metric; and
 in response to detecting that the user has satisfied the goal criteria pertaining to the first physical activity metric, displaying, via the display generation component, a first animation; and
while displaying the first workout session user interface:
 detecting that the user has satisfied the goal criteria pertaining to the first physical activity metric; and
 in response to detecting that the user has satisfied the goal criteria pertaining to the first physical activity metric, displaying, via the display generation component, a second animation different from the first animation.

35. The method of claim 25, further comprising:
while displaying the second workout session user interface:
 detecting a first type of event has occurred; and
 in response to detecting that the first type of event has occurred, displaying, via the display generation component, a first visual indication that the first type of event has occurred; and
while displaying the first workout session user interface:
 detecting that the first type of event has occurred; and
 in response to detecting that the first type of event has occurred, displaying, via the display generation component, the first visual indication that the first type of event has occurred.

36. The method of claim 35, wherein:
the first workout session user interface and the second workout session user interface are indicative of an active workout session; and
the first visual indication includes one or more instructions for the user pertaining to the workout session.

* * * * *